（12) United States Patent
Decrescenzo et al.

(10) Patent No.: US 12,384,757 B2
(45) Date of Patent: Aug. 12, 2025

(54) METHODS OF SYNTHESIZING SUBSTITUTED PYRIDINONE-PYRIDINYL COMPOUNDS

(71) Applicant: ACLARIS THERAPEUTICS, INC., Wayne, PA (US)

(72) Inventors: Gary A. Decrescenzo, Parkville, MO (US); John Robert Springer, Wentzville, MO (US)

(73) Assignee: Aclaris Therapeutics, Inc., Wayne, PA (US)

( * ) Notice: Subject to any disclaimer, the term of this patent is extended or adjusted under 35 U.S.C. 154(b) by 4 days.

(21) Appl. No.: 18/232,651

(22) Filed: Aug. 10, 2023

(65) Prior Publication Data

US 2024/0043398 A1    Feb. 8, 2024

Related U.S. Application Data

(63) Continuation of application No. 17/533,931, filed on Nov. 23, 2021, now Pat. No. 11,767,309.

(60) Provisional application No. 63/275,111, filed on Nov. 3, 2021, provisional application No. 63/239,596, filed on Sep. 1, 2021, provisional application No. 63/139,553, filed on Jan. 20, 2021, provisional application No. 63/117,053, filed on Nov. 23, 2020.

(51) Int. Cl.
  *C07D 401/04*    (2006.01)
  *C07D 401/14*    (2006.01)
  *C07D 405/12*    (2006.01)

(52) U.S. Cl.
  CPC ......... *C07D 401/04* (2013.01); *C07D 401/14* (2013.01); *C07D 405/12* (2013.01)

(58) Field of Classification Search
  CPC ... C07D 401/04; C07D 401/14; C07D 405/12
  See application file for complete search history.

(56) References Cited

U.S. PATENT DOCUMENTS 11,767,309 B2    9/2023  Decrescenzo et al.
2015/0352092 A1  12/2015 Hockerman et al.

FOREIGN PATENT DOCUMENTS

WO    WO-2014197846 A1 *  12/2014  ........... A61K 31/444

OTHER PUBLICATIONS

D. McNamara et al. J Med Chem. Jul. 1990;33(7):2006-11. doi: 10.1021/jm00169a032. PMID: 2163455. (Year: 1990).*
Z. Hyder, et al. Chemistry—A European Journal, (2008), 14: 5555-5566. https://doi.org/10.1002/chem.200800411. (Year: 2008).*

* cited by examiner

*Primary Examiner* — James H Alstrum-Acevedo
*Assistant Examiner* — Manahil Mirghani Ali Abdalhameed
(74) *Attorney, Agent, or Firm* — DLA Piper LLP

(57) ABSTRACT

The present disclosure provides methods of synthesizing a compound of Formula (P)-I. The method proceeds through several different pathways including several novel chiral separations, a Sonogashira coupling, a zinc mediated reductive cyanation, as well as through various halide containing intermediates. Also disclosed is the multi-kilogram preparation of several novel intermediates.

10 Claims, No Drawings

METHODS OF SYNTHESIZING SUBSTITUTED PYRIDINONE-PYRIDINYL COMPOUNDS

CROSS-REFERENCE TO RELATED APPLICATIONS

This application is a continuation of U.S. patent application Ser. No. 17/533,931, filed Nov. 23, 2021, issued as U.S. Pat. No. 11,767,309, which claims the benefit of U.S. Provisional Application No. 63/275,111 filed Nov. 3, 2021, U.S. Provisional Application No. 63/239,596 filed Sep. 1, 2021, U.S. Provisional Application No. 63/139,553 filed Jan. 20, 2021, and U.S. Provisional Application No. 63/117,053 filed Nov. 23, 2020. The disclosures of each of these applications are incorporated herein by reference.

SUMMARY

The present disclosure includes embodiments directed to methods of synthesizing a compound of Formula (P)-I, having the structure:

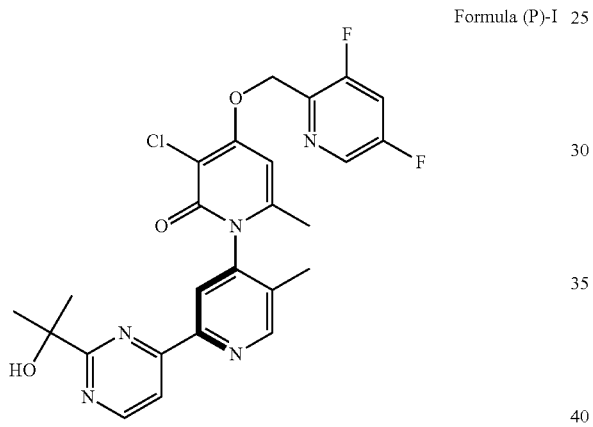

Formula (P)-I

The methods include the chiral resolution to produce the compound of Formula (P)-I or, in the alternative, several different intermediates in the synthesis of Formula (P)-I. Also disclosed are alternative syntheses of several intermediates.

Definitions

Before the present compositions and methods are described, it is to be understood that this invention is not limited to the particular processes, formulations, compositions, or methodologies described, as these may vary. It is also to be understood that the terminology used in the description is for the purpose of describing the particular versions or embodiments only, and is not intended to limit the scope of embodiments herein which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of embodiments herein, the preferred methods, devices, and materials are now described. All publications mentioned herein are incorporated by reference in their entirety. Nothing herein is to be construed as an admission that embodiments herein are not entitled to antedate such disclosure by virtue of prior invention.

It must also be noted that as used herein and in the appended claims, the singular forms "a," "an," and "the" include plural reference unless the context clearly dictates otherwise.

The transitional term "comprising," which is synonymous with "including," "containing," or "characterized by," is inclusive or open-ended and does not exclude additional, unrecited elements or method steps.

In embodiments or claims where the term "comprising" is used as the transition phrase, such embodiments can also be envisioned with replacement of the term "comprising" with the terms "consisting of" or "consisting essentially of."

As used herein, the term "consists of" or "consisting of" means that the composition, formulation or the method includes only the elements, steps, or ingredients specifically recited in the particular claimed embodiment or claim.

As used herein, the term "consisting essentially of" or "consists essentially of" means that the composition, formulation or the method includes only the elements, steps or ingredients specifically recited in the particular claimed embodiment or claim and may optionally include additional elements, steps or ingredients that do not materially affect the basic and novel characteristics of the particular embodiment or claim. For example, the only active ingredient(s) in the formulation or method that treats the specified condition (e.g., nutrient depletion) is the specifically recited therapeutic(s) in the particular embodiment or claim.

As used herein, two embodiments are "mutually exclusive" when one is defined to be something which is different from the other. For example, an embodiment wherein two groups combine to form a cycloalkyl is mutually exclusive with an embodiment in which one group is ethyl the other group is hydrogen. Similarly, an embodiment wherein one group is $CH_2$ is mutually exclusive with an embodiment wherein the same group is NH.

When ranges of values are disclosed, and the notation "from n1 . . . to n2" or "between n1 . . . and n2" is used, where n1 and n2 are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean plus or minus 10% of the numerical value of the number with which it is being used. Therefore, about 50% means in the range of 45%-55%.

In embodiments or claims the "X" in the term "MeMgX" is a halogen.

The term "chiral separation," as used herein, refers to the separation of racemic compounds into their single or enriched atropisomers or enantiomers.

The term "substantially free" as used herein, is used interchangeably with, the term "substantially pure", refers to a compound which is free from all other compounds within the limits of detection as measured by any means including nuclear magnetic resonance (NMR), gas chromatography/mass spectroscopy (GC/MS), or liquid chromatography/mass spectroscopy (LC/MS). In some embodiments, substantially free may be less than about 1.0%, less than about 0.5%, less than about 0.4%, less than about 0.3%, less than about 0.2%, less than about 0.1%, less than about 0.05%, or less than about 0.01%.

The term "interconversion" or "conformational interconversion" refers to any change between the atropisomers of this disclosure, including but not limited to equilibration.

The term "equilibration" refers to a chemical reaction in which the forward and reverse ratio rates cancel out. Equilibration can be dynamic or static. A reaction in equilibrium need not contain equal parts reactant and product. When referring to atropisomeric compounds, the term "equilibration" refers to when the rate of interconversion cancels out. Atropisomers in equilibrium need not contain equal parts of each single atropisomer and encompasses racemic mixtures of atropisomers, enriched mixtures of atropismers, as well as single atropisomers.

Also provided are embodiments wherein any embodiment herein may be combined with any one or more of the other embodiments, unless otherwise stated and provided the combination is not mutually exclusive.

Atropisomers are stereoisomers resulting from hindered rotation about single bonds where the steric strain barrier to rotation is high enough to allow for the isolation of the conformers. Oki (Oki, M; Topics in Stereochemistry 1983, 1) defined atropisomers as conformers that interconvert with a half-life of more than 1000 seconds at a given temperature. The scope of embodiments herein as described and claimed encompasses the racemic forms of the compounds as well as the individual atropisomers (an atropisomer "substantially free" of its corresponding atropisomer) and stereoisomer-enriched mixtures, i.e. mixtures of atropisomers.

Separation of atropisomers is possibly by chiral resolution methods such as selective crystallization. In an atropo-enantioselective or atroposelective synthesis one atropisomer is formed at the expense of the other. Atroposelective synthesis may be carried out by use of chiral auxiliaries like a Corey-Bakshi-Shibata (CBS) catalyst (asymmetric catalyst derived from proline) in the total synthesis of knipholone or by approaches based on thermodynamic equilibration when an isomerization reaction favors one atropisomer over the other.

The term "atropisomerism" refers to a type of isomerism resulting from hindered rotation around a single bond due to steric strain of the substituents. This phenomenon creates stereoisomers which display axial chirality.

The following scheme illustrates "atropisomerism" with reference to specific pyridinone-pyridine compounds of the invention:

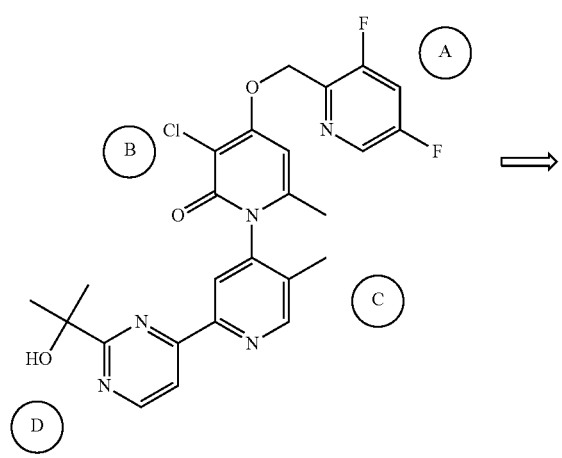

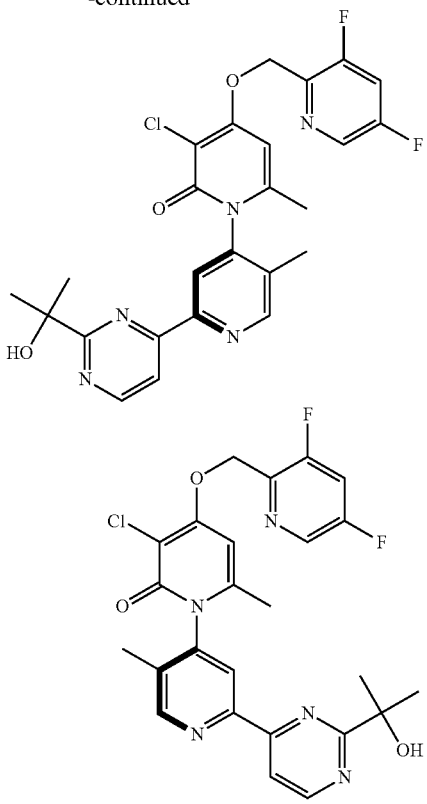

The bond between the B and C rings of the title compounds is hindered and does not allow for facile rotation. The steric strain barrier to rotation is sufficiently high such that individual conformers can be isolated. The compounds of the invention may also exist as atropisomers, i.e., chiral rotational isomers. The invention encompasses racemates, resolved atropisomers, and mixtures thereof. Atropisomers may be separated by a variety of chromatographic methods, including by not limited to supercritical fluid chromatography using a mobile phase of carbon dioxide and ethanol/methanol as well as simulated moving bed (SMB) chromatography with a chiral stationary phase and a mobile phase.

Atropisomers are generally stable but can often be equilibrated thermally. Atropisomers will have the same but opposite optical rotation. Each atropisomers may have different properties when bound to an enzyme or receptor with one isomer often being more potent than the other. Atropisomers are frequently used as pharmaceutical agents. Known examples include Vancomycin and derivatives.

The configuration of atropisomers can be described using the nomenclature (M)- and (P)- to describe the relative position of substituents as described in Bringmann, G. et. al., Angew. Chem. Int. Ed. 2005, 44, 5384 and references cited therein. Structures are designated as drawn but it is understood that either (P)- or (M)-isomers may be desirable and the methods described would be useful for the interconversion of either (P)- or (M)-stereoisomers.

DETAILED DESCRIPTION

The present disclosure includes embodiments directed to methods of synthesizing a compound of Formula (P)-I, having the structure:

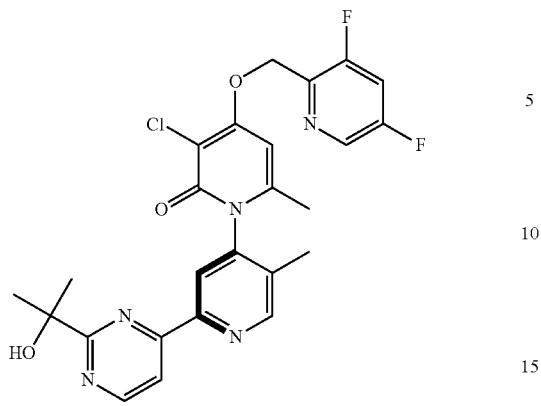

(P)-3-chloro-4-((3,5-difluoro pyridin-2-yl)methoxy)-2'-(2-(2-hydroxypropan-2-yl) pyrimidin-4-yl)-5',6-dimethyl-2H-[1,4'-bipyridin]-2-one Scheme 1 outlines Routes A, B, C, D, and H for synthesizing a compound of Formula (P)-I. Each of these routes feature chiral separation of an intermediate and then carrying forward a single or enriched atropisomer through the remainder of the synthesis of a compound of Formula (P)-I.

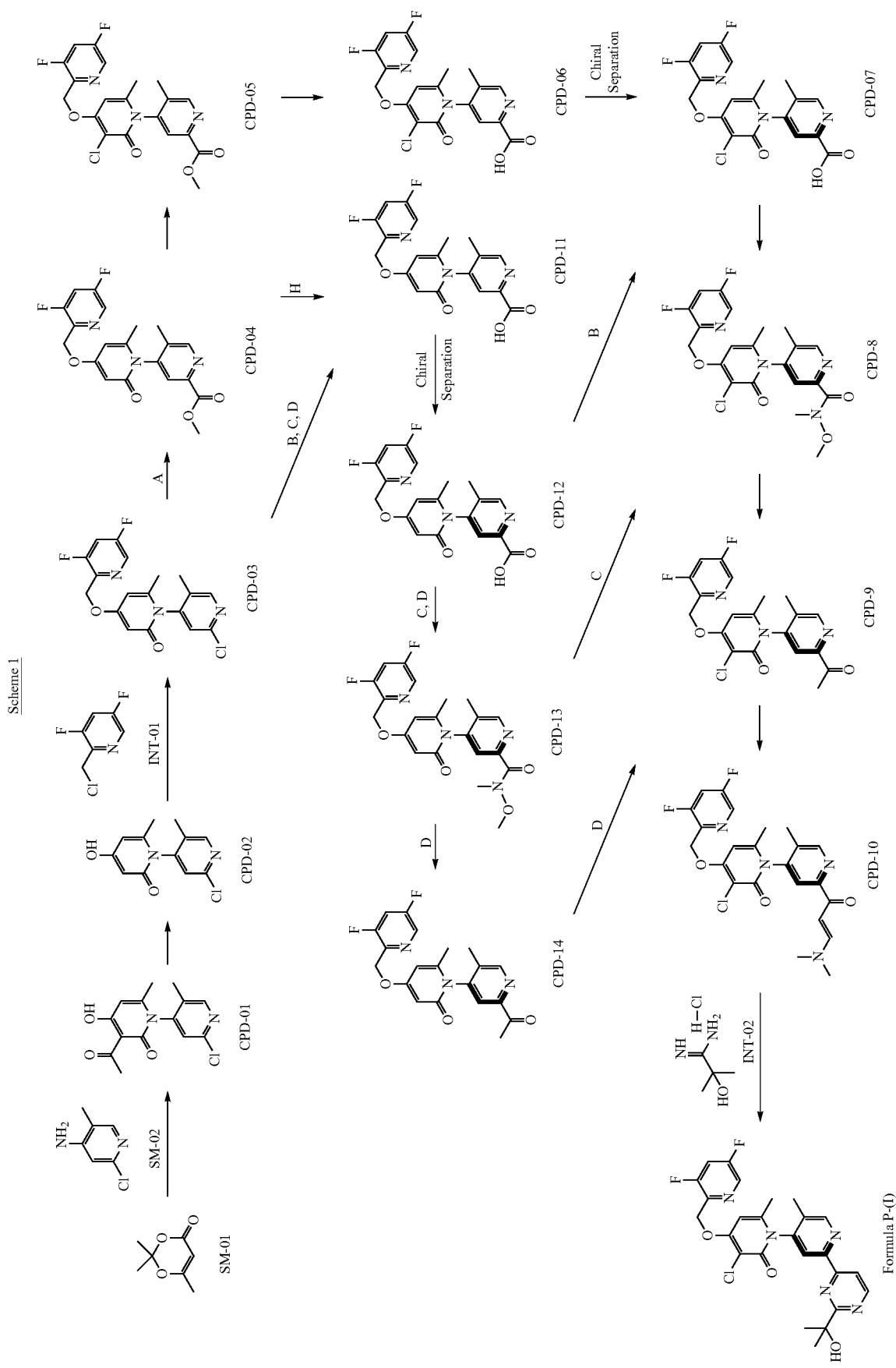
Scheme 1

In some embodiments, the process for the preparation of the compound of Formula (P)-I proceeds through Route A as follows: contacting SM-01 and SM-02 to give CPD-01, converting CPD-01 to CPD-02, contacting CPD-02 and INT-01 to give CPD-03, converting CPD-03 to CPD-04, converting CPD-04 to CPD-05, converting CPD-05 to CPD-06, subjecting CPD-06 to chiral separation to give CPD-07, converting CPD-07 to CPD-08, converting CPD-08 to CPD-09, converting CPD-09 to CPD-10, then contacting CPD-10 and NT-02 to give Formula P-(I).

In some embodiments, the process for the preparation of the compound of Formula (P)-I proceeds through Route B as follows: contacting SM-01 and SM-02 to give CPD-01, converting CPD-01 to CPD-02, contacting CPD-02 and INT-01 to give CPD-03, converting CPD-03 to CPD-11, subjecting CPD-11 to chiral separation to give CPD-12, converting CPD-12 to CPD-07, converting CPD-07 to CPD-08, converting CPD-08 to CPD-09, converting CPD-09 to CPD-10, then contacting CPD-10 and INT-02 to give Formula P-(I).

In some embodiments, the process for the preparation of the compound of Formula (P)-I proceeds through Route C as follows: contacting SM-01 and SM-02 to give CPD-01, converting CPD-01 to CPD-02, contacting CPD-02 and INT-01 to give CPD-03, converting CPD-03 to CPD-11, subjecting CPD-11 to chiral separation to give CPD-12, converting CPD-12 to CPD-13, converting CPD-13 to CPD-08, converting CPD-08 to CPD-09, converting CPD-09 to CPD-10, then contacting CPD-10 and INT-02 to give Formula P-(I).

In some embodiments, the process for the preparation of the compound of Formula (P)-I proceeds through Route D as follows: contacting SM-01 and SM-02 to give CPD-01, converting CPD-01 to CPD-02, contacting CPD-02 and INT-01 to give CPD-03, converting CPD-03 to CPD-11, subjecting CPD-11 to chiral separation to give CPD-12, converting CPD-12 to CPD-13, converting CPD-13 to CPD-14, converting CPD-14 to CPD-09, converting CPD-09 to CPD-10, then contacting CPD-10 and INT-02 to give Formula P-(I).

In some embodiments, the process for the preparation of the compound of Formula (P)-I proceeds through Route H as follows: contacting SM-01 and SM-02 to give CPD-01, converting CPD-01 to CPD-02, contacting CPD-02 and INT-01 to give CPD-03, converting CPD-03 to CPD-04, converting CPD-04 to CPD-11, subjecting CPD-11 to chiral separation to give CPD-12. CMP-12 is then carried forward to Formula P-(I) through the synthetic sequences described in Route B, Route C, or Route D.

Scheme 2 outlines Routes E, F, and G for synthesizing a compound of Formula (P)-I. Each of these routes feature chiral separation as the last step of the synthesis of a compound of Formula (P)-I.

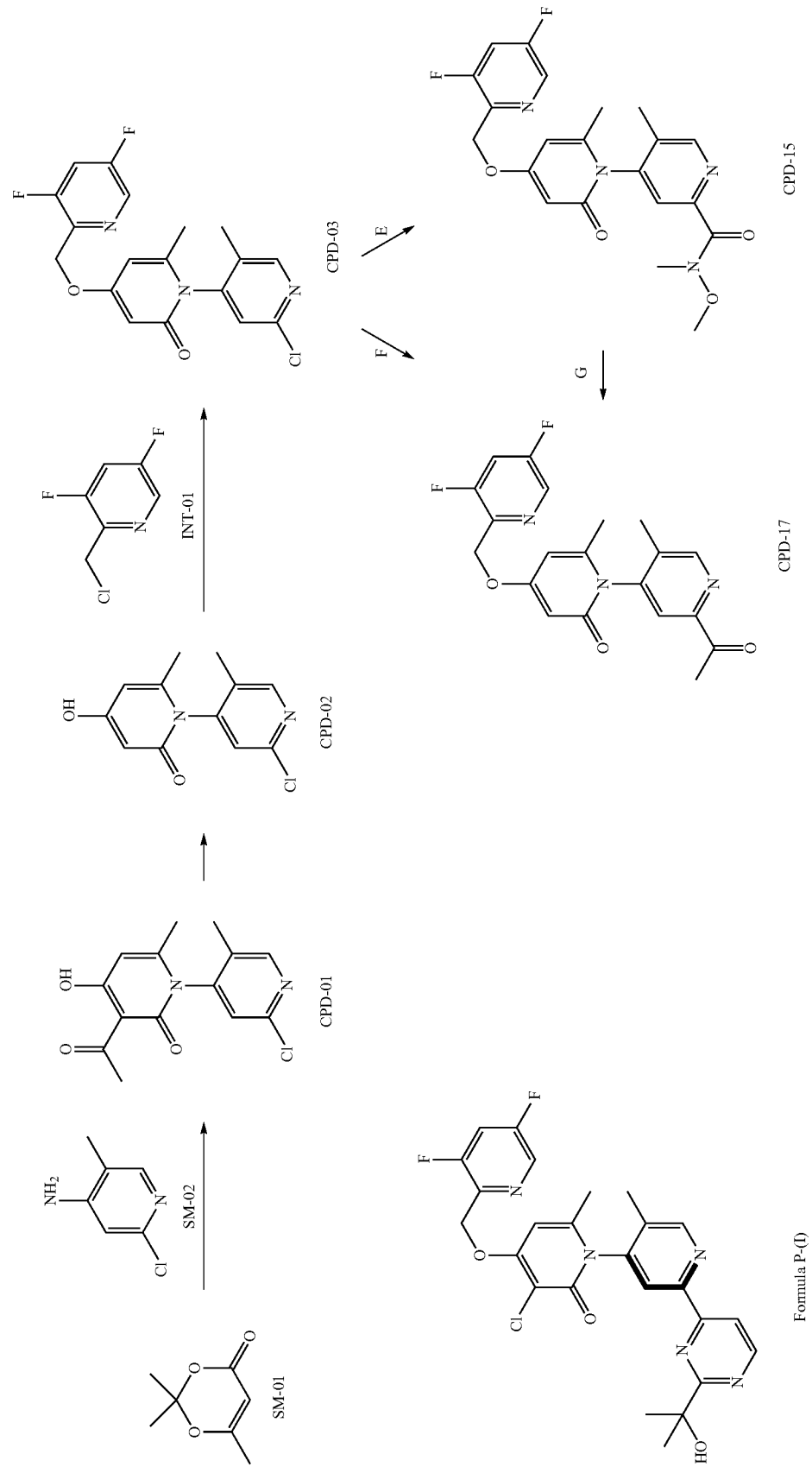

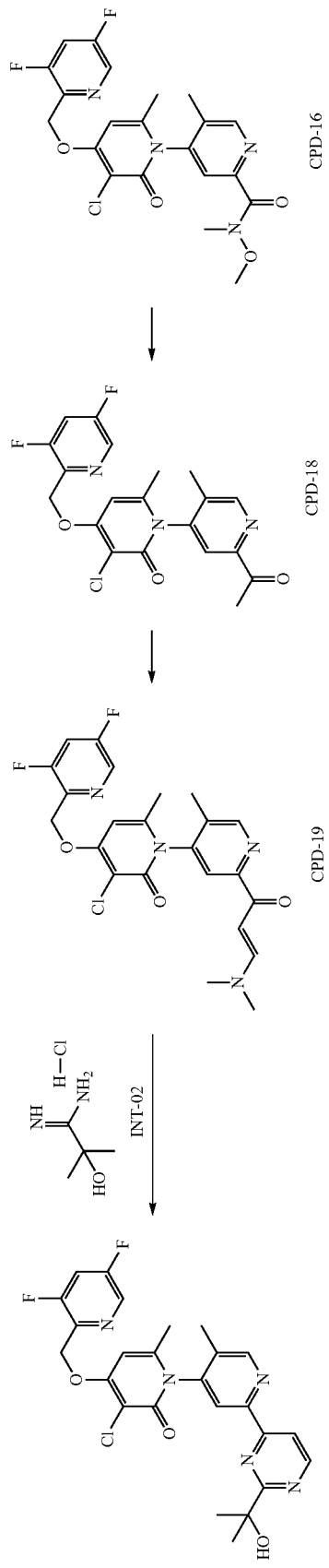

In some embodiments, the process for the preparation of the compound of Formula (P)-I proceeds through Route E as follows: contacting SM-01 and SM-02 to give CPD-01, converting CPD-01 to CPD-02, contacting CPD-02 and INT-01 to give CPD-03, converting CPD-03 to CPD-15, converting CPD-15 to CPD-16, converting CPD-16 to CPD-18, converting CPD-18 to CPD-19, contacting CPD-19 and INT-02 to give CPD-20, then subjecting CPD-20 to chiral separation to give Formula P-(I).

In some embodiments, the process for the preparation of the compound of Formula (P)-I proceeds through Route F as follows: contacting SM-01 and SM-02 to give CPD-01, converting CPD-01 to CPD-02, contacting CPD-02 and INT-01 to give CPD-03, converting CPD-03 to CPD-17, converting CPD-17 to CPD-18, converting CPD-18 to CPD-19, contacting CPD-19 and INT-02 to give CPD-20, then subjecting CPD-20 to chiral separation to give Formula P-(I).

In some embodiments, the process for the preparation of the compound of Formula (P)-I proceeds through Route G as follows: contacting SM-01 and SM-02 to give CPD-01, converting CPD-01 to CPD-02, contacting CPD-02 and INT-01 to give CPD-03, converting CPD-03 to CPD-15, converting CPD-15 to CPD-17, converting CPD-17 to CPD-18, converting CPD-18 to CPD-19, contacting CPD-19 and INT-02 to give CPD-20, then subjecting CPD-20 to chiral separation to give Formula P-(I).

Scheme 3 outlines a method of synthesizing a compound of Formula (P)-I.

Scheme 3

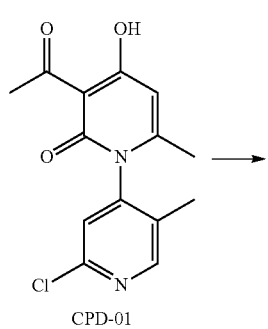

SM-01    SM-02

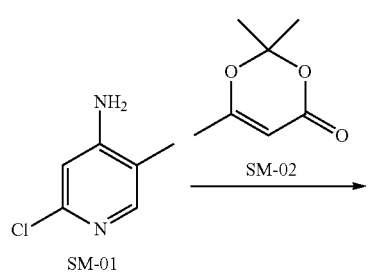

CPD-01

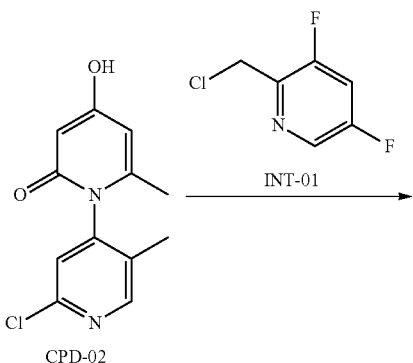

CPD-02    INT-01

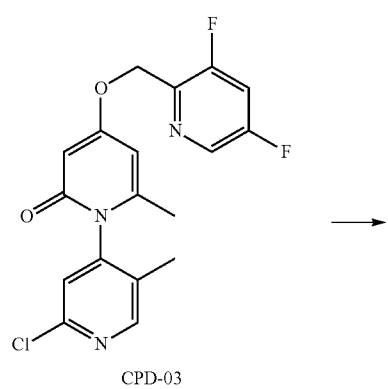

CPD-03

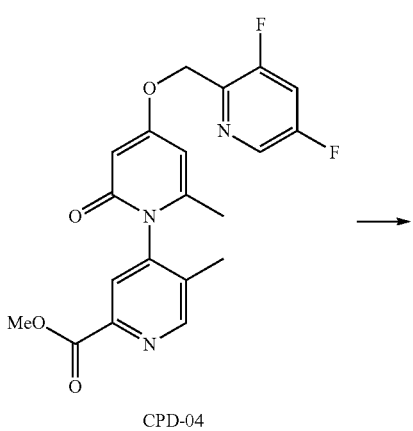

CPD-04

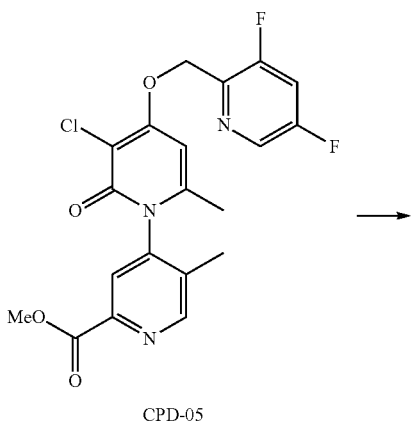

CPD-05

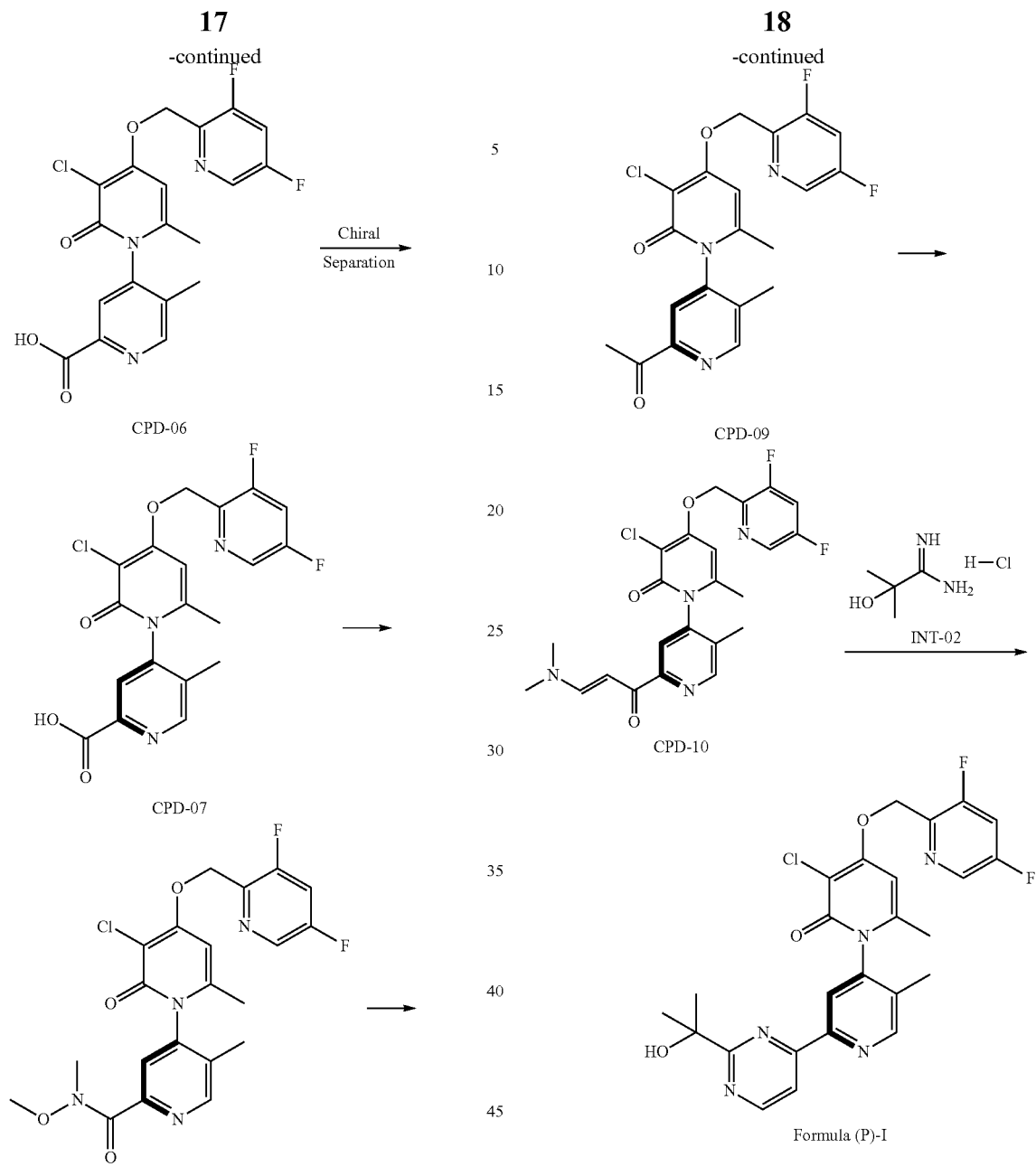
Scheme Alpha outlines a method of synthesizing a compound of Formula (P)-I.

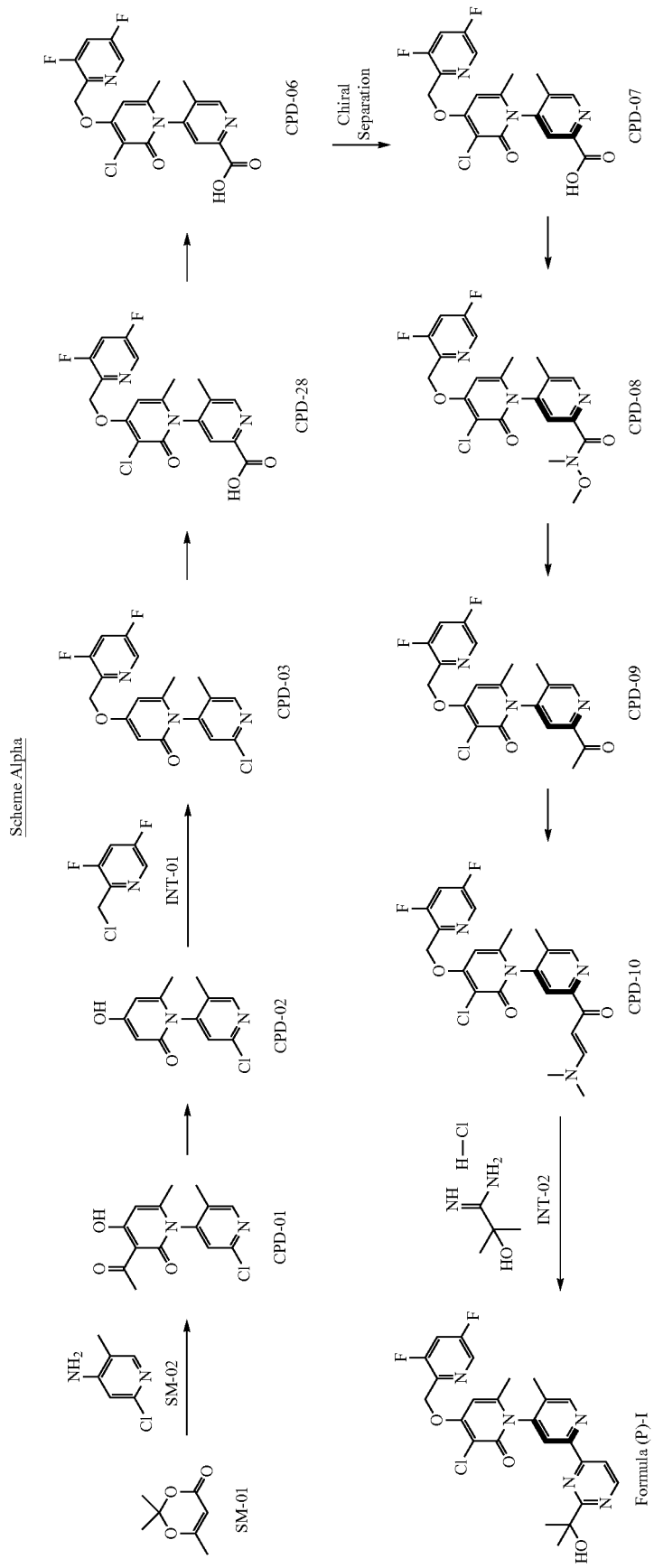

Another embodiment of the present disclosure is directed to a compound of Formula (P)-I as prepared according to Routes A, B, C, D, and H as shown in Scheme 1; Routes E, F, and G as shown in Scheme 2; the route as shown in Scheme 3, and the route as shown in Scheme Alpha.

Some embodiments of the present application describe a process for the preparation of compound of Formula (P)-I having the structure:

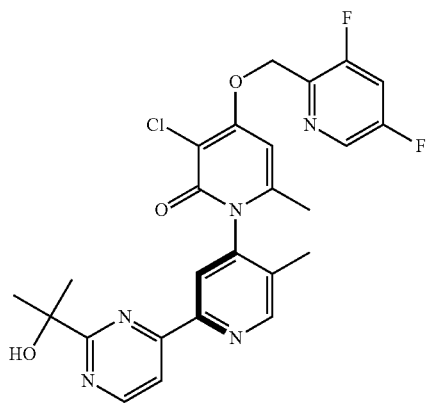

Formula (P)-I comprising the steps of:

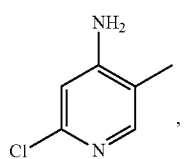

SM-01

(a) contacting the compound SM-01, with the compound SM-02 in the presence of dimethylacetemide (DMAc) to form a mixture; and

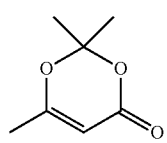

SM-02

(b) contacting the mixture of (a) with an alcoholic HCl solution to form the compound

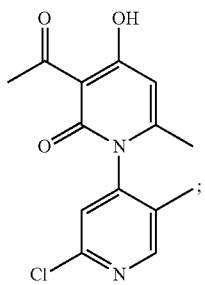

CPD-01 and (c) converting CPD-01 to Formula (P)-I.

In some embodiments of the forming of CPD-01, the alcoholic HCl solution is selected from the group consisting of an isopropyl alcohol HCl solution or p-toluenesulfonic acid in dimethylacetamide (DMAc).

In some embodiments of the forming of CPD-01, the alcoholic HCl solution is an isopropyl alcohol HCl solution.

In another embodiment of the process for the preparation of Formula (P)-I, the process further comprises contacting the compound CPD-01 with $H_2SO_4$ to form the compound

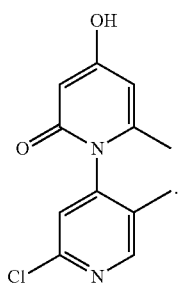

CPD-02

In another embodiment of the process for the preparation of Formula (P)-I, the process further comprises contacting the compound CPD-02 with the compound

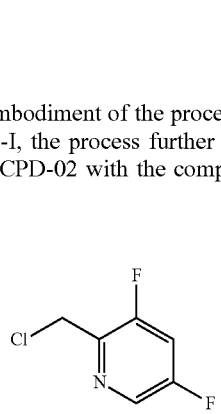

INT-01 and a base to form the compound

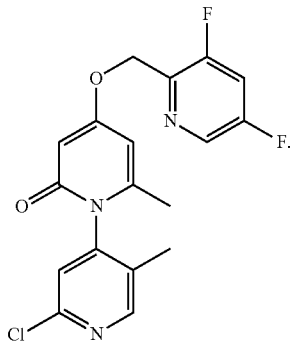
CPD-03

In some embodiments of forming CPD-03, the base is selected from the group consisting of $K_2CO_3$, NaOH, $Cs_2CO_3$, and $NaHCO_3$.

In some embodiments, the base used to form CPD-03 is selected from the group consisting of $K_2CO_3$ and $Cs_2CO_3$.

In some embodiments of forming CPD-03, the base is $K_2CO_3$.

In some embodiments, the base used to form CPD-03 is $Cs_2CO_3$.

In some embodiments of the process for the preparation of Formula (P)-I, the process further comprises contacting the compound CPD-03 with CO in the presence of a palladium catalyst, an amine base, and methanol to form the compound

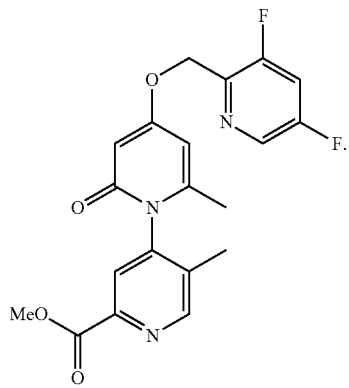
CPD-04

In some embodiments of the forming of CPD-04, the palladium catalyst is selected from the group consisting of Pd(dppf)Cl$_2$, Pd(OAc)$_2$/Bis(diphenylphosphino)propane (DPPP), Pd(PPh$_3$)Cl$_2$, Pd(OAc)$_2$/Xphos, Pd(OAc)$_2$/Ruphos, Pd (DTBPF)Cl$_2$, and (BINAP)PdCl$_2$.

In some embodiments of the forming of CPD-04, the palladium catalyst is Pd(dppf)Cl$_2$.

In some embodiments of the forming of CPD-04, the amine base is selected from the group consisting of triethylamine, iPr$_2$NEt, and tetramethylethylenediamine, In some embodiments of the forming of CPD-04, the amine base is triethylamine.

In some embodiments of the process for the preparation of Formula (P)-I, the process further comprises contacting the compound CPD-04 with a chlorination reagent to form the compound

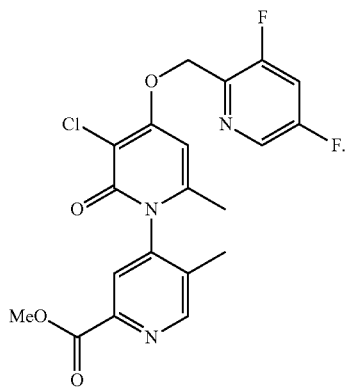
CPD-05

In some embodiments of the forming of CPD-05, the chlorination reagent is N-chlorosuccinimide.

In some embodiments, the forming of CPD-05 further comprises contacting CPD-04 with dichloroacetic acid.

In some embodiments of the process for the preparation of Formula (P)-I, the process further comprises hydrolyzing and desalting the compound CPD-05 to form the compound CPD-06

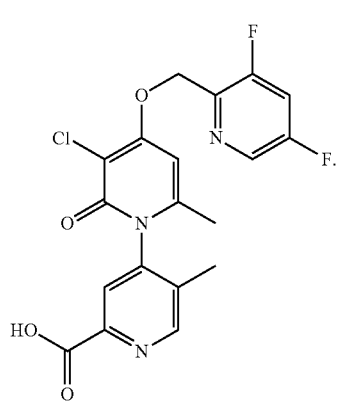
CPD-06

In some embodiments of the process for the preparation of Formula (P)-I, the process further comprises subjecting the compound CPD-06 to chiral separation with a chiral amine and a solvent to obtain the compound

CPD-07

In some embodiments of the chiral separation of the compound CPD-06, the chiral amine is selected from the group consisting of (S)-1-(naphthalen-2-yl)ethan-1-amine and (1S,2R)-2-amino-1,2-diphenylethan-1-ol.

In some embodiments of the chiral separation of the compound CPD-06, the chiral amine is (S)-1-(naphthalen-2-yl)ethan-1-amine.

In some embodiments of the chiral separation of the compound CPD-06, the chiral amine is (1S,2R)-2-amino-1,2-diphenylethan-1-ol.

In some embodiments of the chiral separation of the compound CPD-06, the solvent is selected from the group consisting of toluene, ethylbenzene, n-butanol, anisole, DMSO, or a combination thereof.

In some embodiments of the chiral separation of the compound CPD-06, the solvent is toluene.

In some embodiments of the chiral separation of the compound CPD-06, the solvent is ethylbenzene.

In some embodiments of the chiral separation of the compound CPD-06, the solvent is n-butanol.

In some embodiments of the chiral separation of the compound CPD-06, the solvent is anisole.

In some embodiments of the chiral separation of the compound CPD-06, the solvent is anisole and DMSO.

In some embodiments of the process for the preparation of Formula (P)-I, the process further comprises contacting the compound CPD-07 with a solvent, MeNHOMe, an amine base, and a coupling reagent to obtain the compound

CPD-08

In some embodiments of contacting the compound CPD-07, the solvent is selected from DMF, dichloromethane, or a combination thereof.

In some embodiments of contacting the compound CPD-07, the solvent is DMF.

In some embodiments of contacting the compound CPD-07, the solvent is dichloromethane.

In some embodiments of the contacting the compound CPD-07, the amine base is triethylamine.

In some embodiments of the contacting the compound CPD-07, the coupling reagent is N-(3-Dimethylaminopropyl)-N'-ethylcarbodiimide hydrochloride.

In some embodiments of the process for the preparation of Formula (P)-I, the process further comprises contacting the compound CPD-08 with MeMgX to obtain the compound

CPD-09

In some embodiments of the contacting the compound CPD-07, the MeMgX is selected from the group consisting of MeMgBr and MeMgCl.

In some embodiments of the contacting the compound CPD-07, the MeMgX is MeMgBr.

In some embodiments of the contacting the compound CPD-07, the MeMgX is MeMgCl.

In some embodiments of the process for the preparation of Formula (P)-I, the process further comprises condensing compound CPD-09 with N,N-dimethyl-formamide dimethyl acetal to obtain the compound

CPD-10

In some embodiments of the process for the preparation of Formula (P)-I, the process further comprises contacting the compound CPD-10 with

INT-02 in the presence of a base, and forming the compound of Formula (P)-I.

In some embodiments of forming the compound of Formula (P)-I, the base is selected from the group consisting of K$_2$CO$_3$, N,N-diisopropylethylamine (DIPEA), triethylamine (TEA), tBuOK, tBuONa, and Cs$_2$CO$_3$.

In some embodiments of forming the compound of Formula (P)-I, the base is K$_2$CO$_3$.

Scheme 4 outlines another method of synthesizing CPD-07, CPD-08, and CPD-09 starting from CPD-03. CPD-07, CPD-08, and CPD-09 may each then be carried forward through the rest of the sequence outlined in Scheme 3 to result in the production of the compound of Formula P-(I).

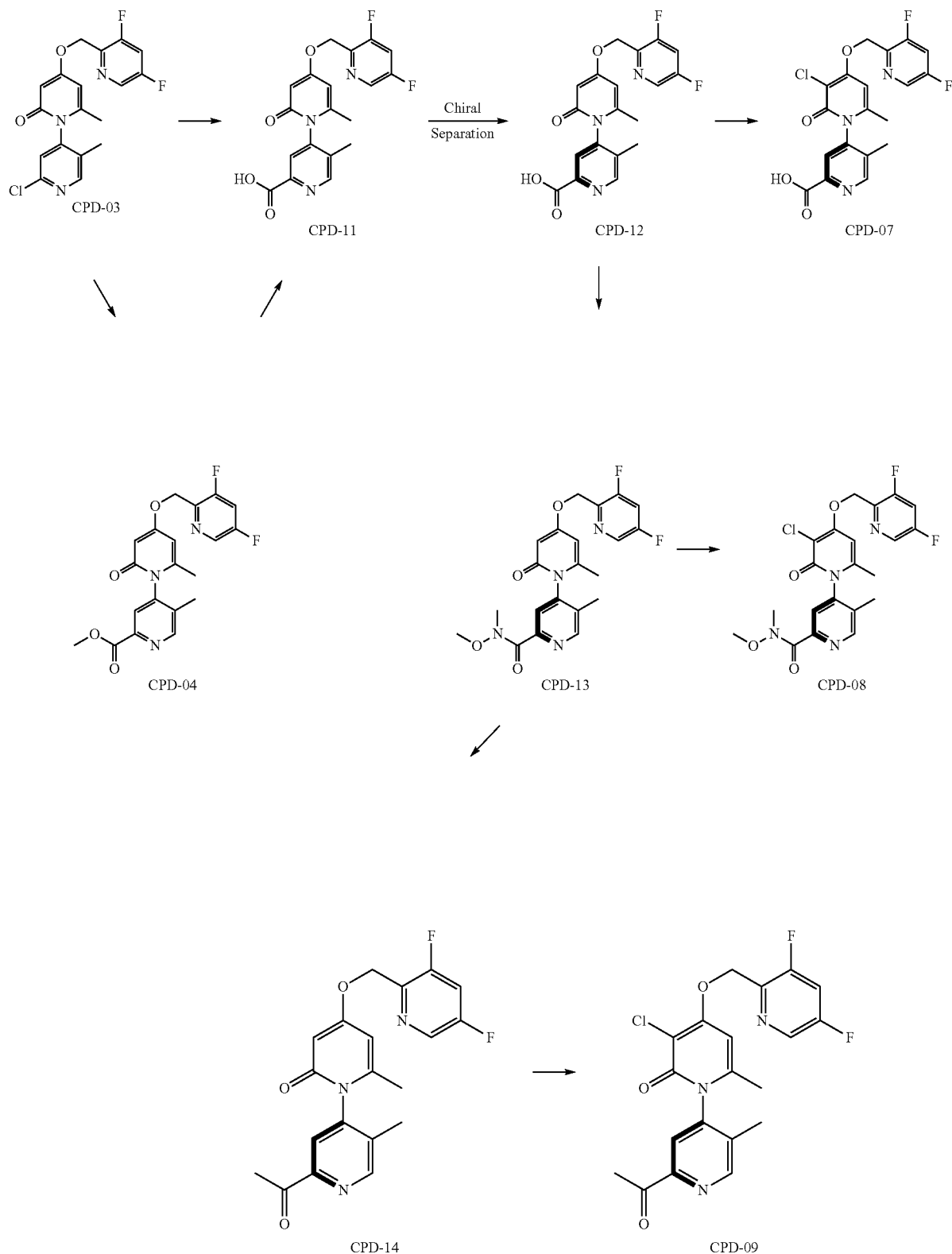
Scheme 4
Forming CPD-04 from CPD-03 is as disclosed above.
In accordance with Scheme 4, in some embodiments, the process for the preparation of Formula (P)-I comprises contacting the compound CPD-03 with CO in the presence of a palladium catalyst, an amine base and DMF/H$_2$O to form the compound

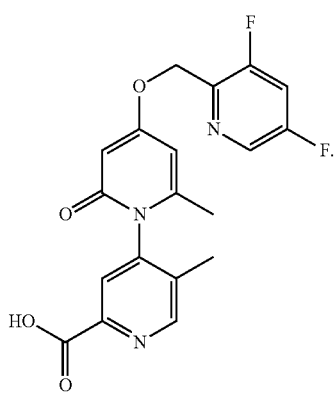

CPD-11

In some embodiments of forming CPD-11, the palladium catalyst is (BINAP)PdCl$_2$.

In some embodiments of forming CPD-11, the amine base is triethylamine.

In accordance with Scheme 4, in some embodiments, the process for the preparation of Formula (P)-I, comprises the steps of:
(a) contacting the compound CPD-03 with CO in the presence of a palladium catalyst, an amine base, a first base, and MeOH/H$_2$O to form a mixture; and
(b) contacting the mixture of (a) with a second base to form the compound

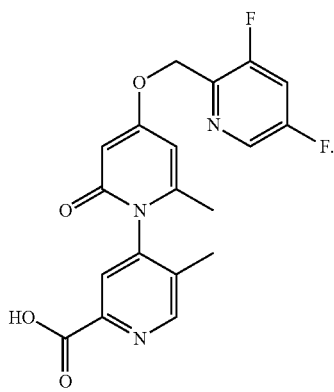

CPD-11

In some embodiments of forming CPD-11, the palladium catalyst is Pd(dppf)Cl$_2$·DCM.

In some embodiments of forming CPD-11, the amine base is triethylamine.

In some embodiments of forming CPD-11, the first base is Na$_2$CO$_3$.

In some embodiments of forming CPD-11, the second base is NaOH.

In some embodiments of the process for the preparation of Formula (P)-I, the process further comprises contacting the compound CPD-04 with a base to form the compound

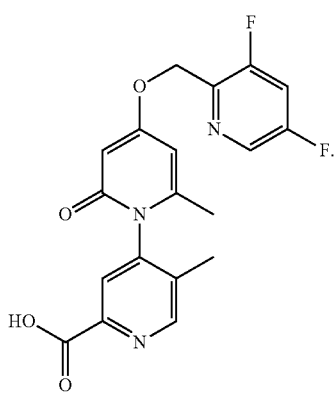

CPD-11

In some embodiments of forming CPD-11, the base is selected from LiOH or NaOH.

In some embodiments of forming CPD-11, the base is LiOH.

In some embodiments of forming CPD-11, the base is NaOH.

In some embodiments of the process for the preparation of Formula (P)-I, the process further comprises subjecting the compound CPD-11 to chiral separation with a chiral amine and a solvent to obtain the compound

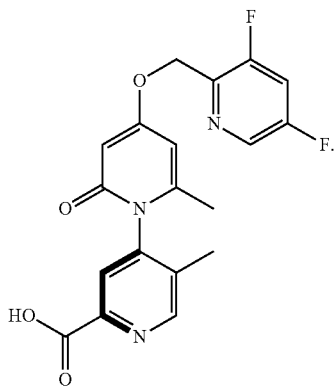

CPD-12

In some embodiments of the chiral separation of the compound CPD-11, the chiral amine is selected from the group consisting of (S)-1-(naphthalen-2-yl)ethan-1-amine and (1S,2R)-2-amino-1,2-diphenylethan-1-ol.

In some embodiments of the chiral separation of the compound CPD-11, the chiral amine is (S)-1-(naphthalen-2-yl)ethan-1-amine.

In some embodiments of the chiral separation of the compound CPD-11, the chiral amine is (1S,2R)-2-amino-1,2-diphenylethan-1-ol.

In some embodiments of the chiral separation of the compound CPD-11, the solvent is selected from the group consisting of toluene, ethylbenzene, n-butanol, anisole, DMSO, or a combination thereof.

In some embodiments of the chiral separation of the compound CPD-11, the solvent is toluene.

In some embodiments of the chiral separation of the compound CPD-11, the solvent is ethylbenzene.

In some embodiments of the chiral separation of the compound CPD-11, the solvent is n-butanol.

In some embodiments of the chiral separation of the compound CPD-11, the solvent is anisole.

In some embodiments of the chiral separation of the compound CPD-11, the solvent is anisole and DMSO.

In some embodiments of the process for the preparation of Formula (P)-I, the process further comprises contacting the compound CPD-12 with a chlorination reagent to form the compound

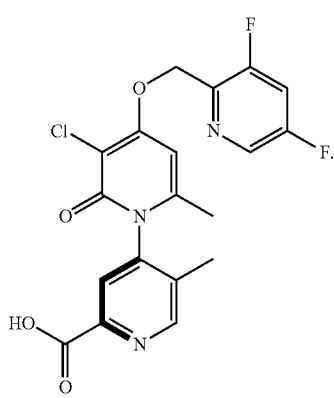

CPD-07

In some embodiments of forming CPD-07, the chlorination reagent is N-chlorosuccinimide.

In some embodiments, the forming of CPD-07 further comprises contacting CPD-12 with dichloroacetic acid.

In another embodiment of the process for the preparation of Formula (P)-I, the process further comprises contacting the compound CPD-12 with a solvent, MeNHOMe, an amine base, and a coupling reagent to obtain the compound

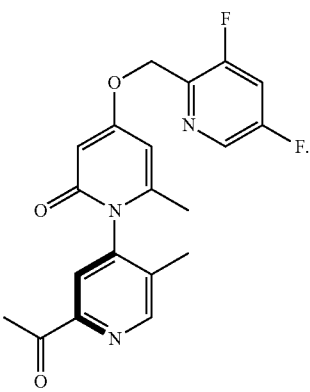

CPD-13

In some embodiments of contacting the compound CPD-12, the solvent is selected from DMF, dichloromethane, or a combination thereof.

In some embodiments of contacting the compound CPD-12, the solvent is DMF.

In some embodiments of contacting the compound CPD-12, the solvent is dichloromethane.

In some embodiments of contacting the compound CPD-12, the amine base is triethylamine.

In some embodiments of contacting the compound CPD-12, the coupling reagent is N-(3-Dimethylaminopropyl)-N'-ethylcarbodiimide hydrochloride.

In some embodiments of the process for the preparation of Formula (P)-I, the process further comprises contacting the compound CPD-13 with a chlorination reagent to form the compound

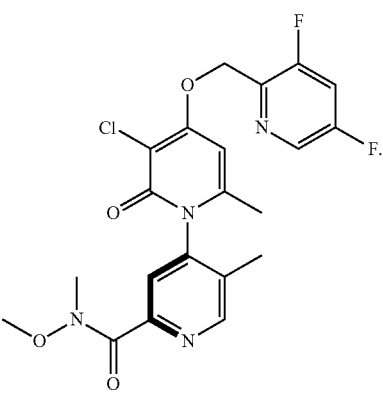

CPD-08

In some embodiments of the forming of CPD-08, the chlorination reagent is N-chlorosuccinimide.

In some embodiments, the forming of CPD-08 further comprises contacting CPD-13 with dichloroacetic acid.

In another embodiment of the process for the preparation of Formula (P)-I, the process further comprises contacting the compound CPD-13 with MeMgX to obtain the compound

CPD-14

In some embodiments of the contacting the compound CPD-13, the MeMgX is selected from the group consisting of MeMgBr and MeMgCl.

In some embodiments of the contacting the compound CPD-13, the MeMgX is MeMgBr.

In some embodiments of the contacting the compound CPD-13, the MeMgX is MeMgCl.

In some embodiments of the process for the preparation of Formula (P)-I, the process further comprises contacting the compound CPD-14 with a chlorination reagent to form the compound CPD-09
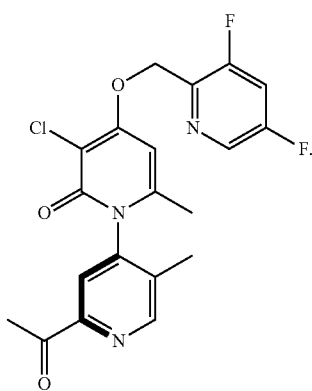
In some embodiments of the forming of CPD-09, the chlorination reagent is N-chlorosuccinimide.
In some embodiments, the forming of CPD-09 further comprises contacting CPD-14 with dichloroacetic acid.
Scheme 5 outlines another method of synthesizing a Formula (P)-I via either CPD-15 or CPD-17 starting from CPD-03. Chiral separation is utilized to produce Formula (P)-I.
Scheme 5
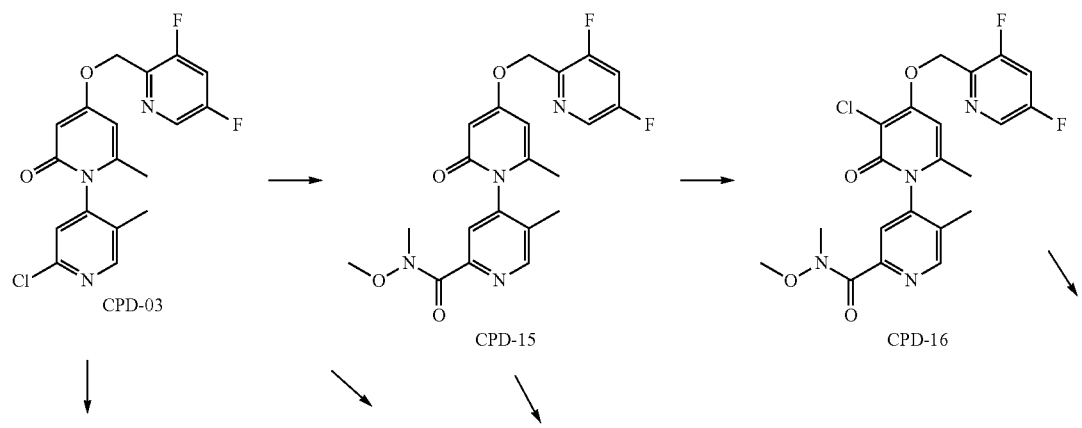
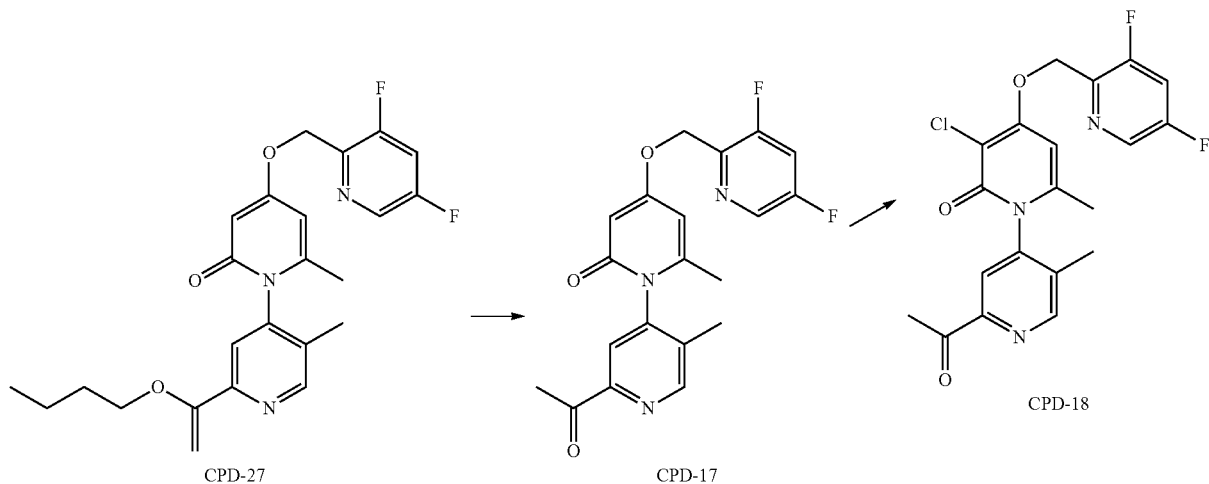

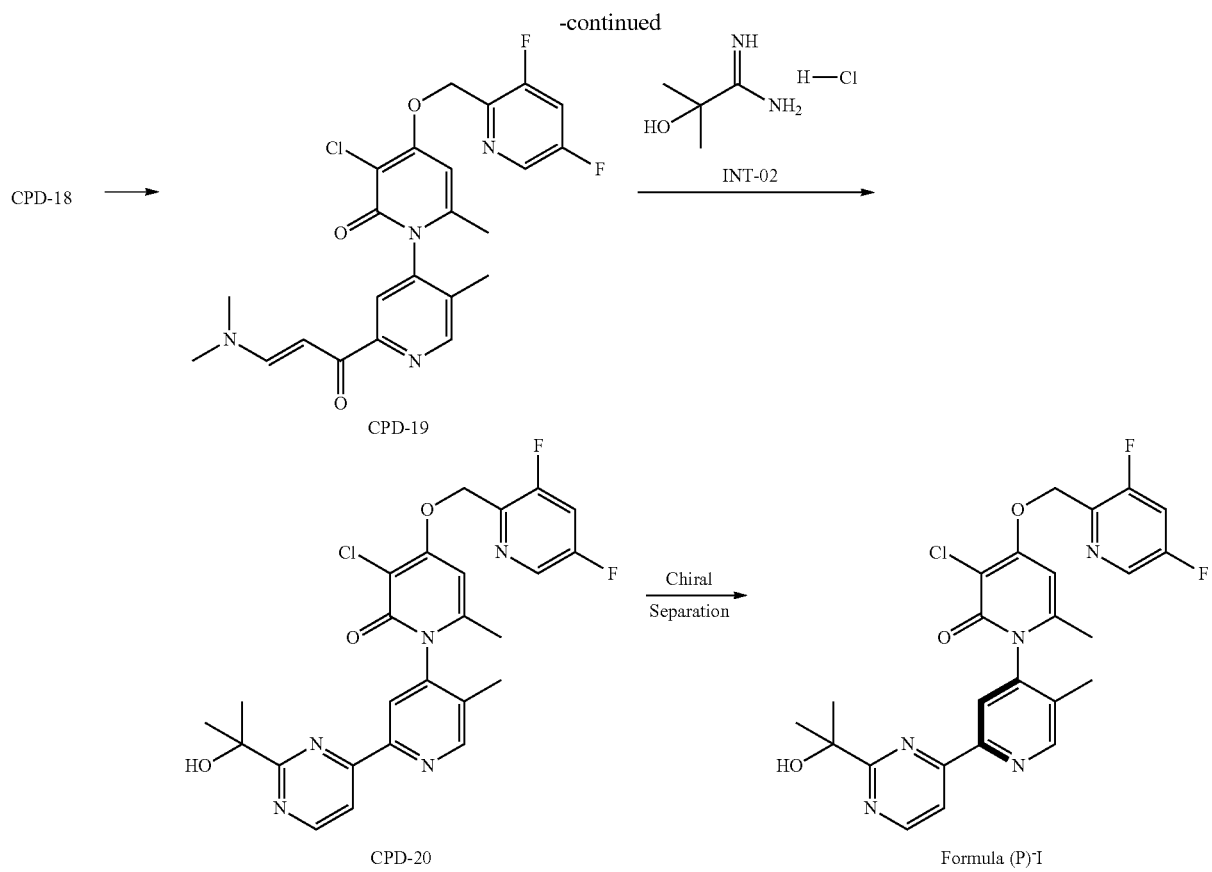

In accordance with the process set forth in Scheme 5, the process for the preparation of Formula (P)-I comprises contacting the compound CPD-03 with MeNH(OMe)-HCl in the presence of a palladium catalyst, a phosphorus reagent, CO, and a base to form the compound In some embodiments of the process for the preparation of Formula (P)-I, the process further comprises contacting the compound CPD-15 with MeMgX to obtain the compound

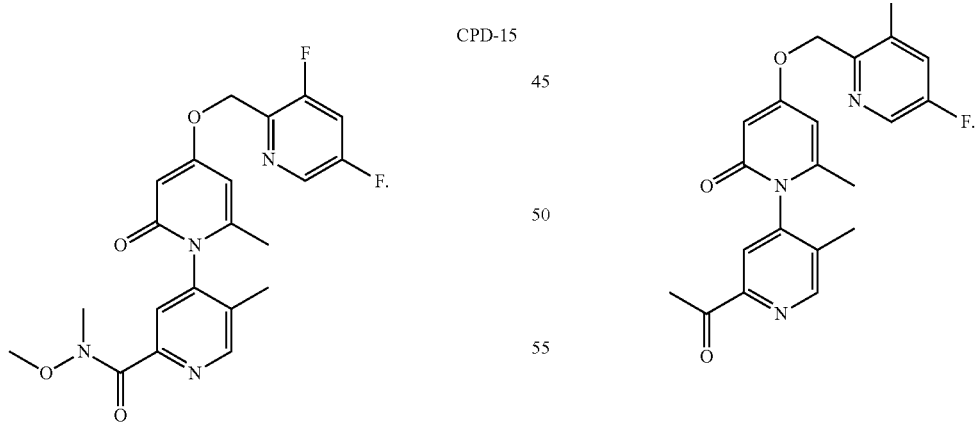

In some embodiments of forming CPD-15, the palladium catalyst is Pd(OAc)$_2$.

In some embodiments of forming CPD-15, the phosphorus reagent is Xantphos.

In some embodiments of forming CPD-15, the base is Na$_2$CO$_3$.

In some embodiments of the contacting the compound CPD-15, the MeMgX is selected from the group consisting of MeMgBr and MeMgCl.

In some embodiments of the contacting the compound CPD-15, the MeMgX is MeMgBr.

In some embodiments of the contacting the compound CPD-15, the MeMgX is MeMgCl.

In another embodiment of the process for the preparation of Formula (P)-I, the process further comprises contacting the compound CPD-15 with a chlorination reagent to form the compound

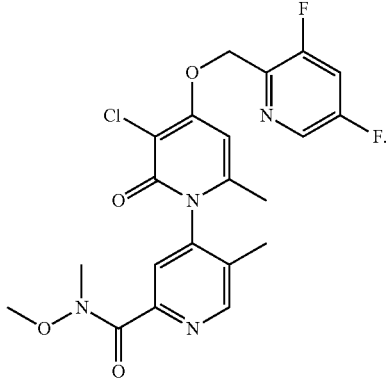

CPD-16

In some embodiments of the forming of CPD-16, the chlorination reagent is N-chlorosuccinimide.

In some embodiments, the forming of CPD-16 further comprises contacting CPD-15 with dichloroacetic acid.

In another embodiment of the process for the preparation of Formula (P)-I, the process further comprises contacting the compound CPD-16 with MeMgX to obtain the compound

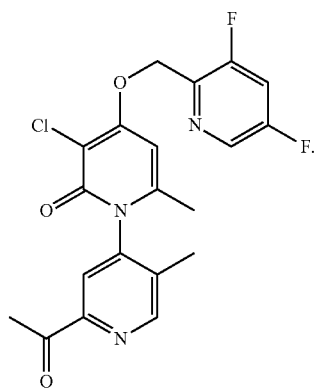

CPD-18

In some embodiments of the contacting the compound CPD-16, the MeMgX is selected from the group consisting of MeMgBr and MeMgCl.

In some embodiments of the contacting the compound CPD-16, the MeMgX is MeMgBr.

In some embodiments of the contacting the compound CPD-16, the MeMgX is MeMgCl.

Also in accordance with Scheme 5, in another embodiment of the process for the preparation of Formula (P)-I, the process further comprises the steps of:

(a) contacting the compound CPD-03 with a vinyl tin reagent in the presence of a palladium catalyst to form a mixture; and (b) contacting the mixture of (a) with HCl to form the compound

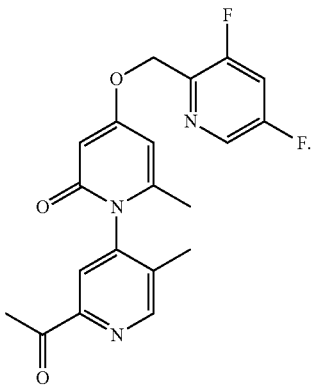

CPD-17

In some embodiments of forming CPD-17, the vinyl tin reagent is

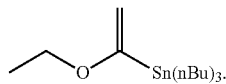

In some embodiments of forming CPD-17, the palladium catalyst is PdCl$_2$(PPh$_3$)$_2$.

Also in accordance with the process set forth in Scheme 5, the process for the preparation of Formula (P)-I comprises another method of converting CPD-03 to CPD-17. The process comprises contacting the compound CPD-03 with butyl vinyl ether in the presence of a palladium catalyst, a phosphorus reagent, and a base to form the compound

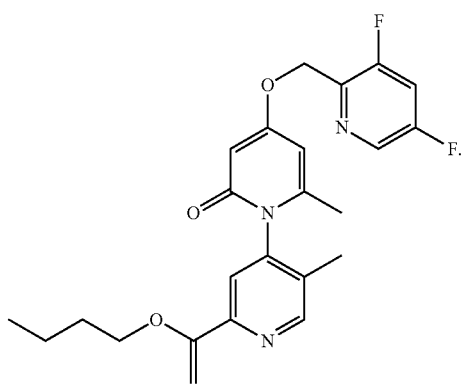

CPD-27

In some embodiments of forming CPD-27, the palladium catalyst is Pd(OAc)$_2$.

In some embodiments of forming CPD-27, the phosphorus reagent is 1,1'-Ferrocenediyl-bis(diphenylphosphine) (dppf).

In some embodiments of forming CPD-27, the base is iPr$_2$NEt.

In some embodiments of the process for the preparation of Formula (P)-I, the process further comprises contacting the compound CPD-27 with an acid to form the compound

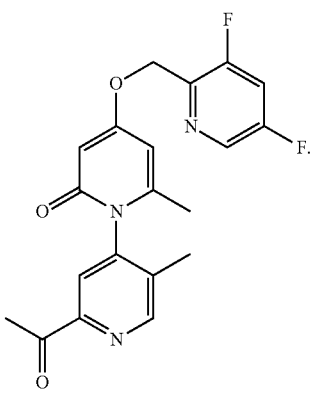

CPD-17

In some embodiments of forming CPD-17, the acid is HCl.

In some embodiments of the process for the preparation of Formula (P)-I, the process further comprises contacting the compound CPD-17 with a chlorination reagent to form the compound

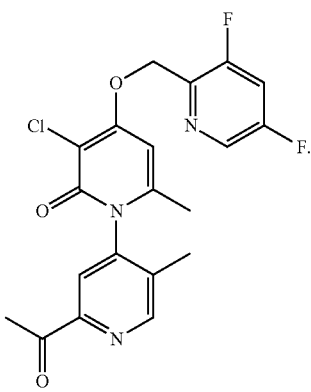

CPD-18

In some embodiments of the forming of CPD-18, the chlorination reagent is N-chlorosuccinimide.

In some embodiments, the forming of CPD-18 further comprises contacting CPD-17 with dichloroacetic acid.

In accordance with Scheme 5, whether the process proceeds via the formation of CPD-17 or CPD-15 as described supra the process for the preparation of Formula (P)-I further comprises condensing the compound CPD-18 with N,N-dimethyl-formamide dimethyl acetal to obtain the compound

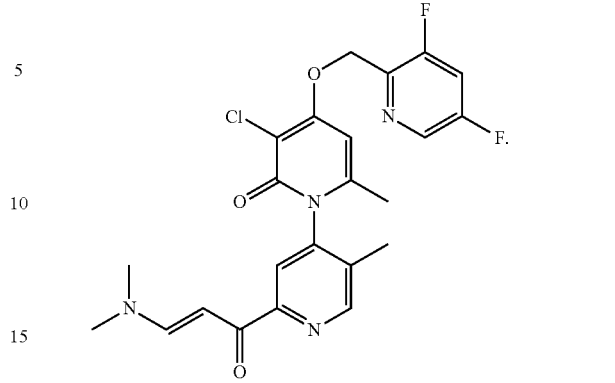

CPD-19

In some embodiments of the condensation of the compound CPD-18, wherein the condensing further comprises L-proline.

In another embodiment of the process for the preparation of Formula (P)-I, the process further comprises contacting the compound CPD-19 with

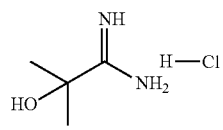

INT-02 in the presence of a base, and forming the compound

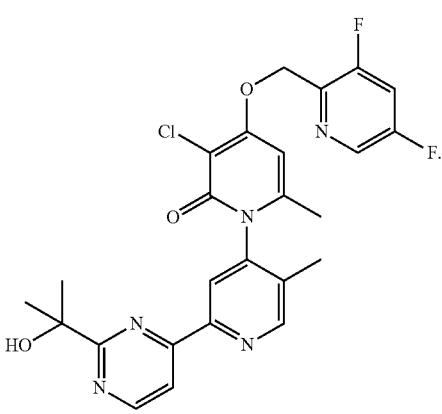

CPD-20

In some embodiments of forming the compound of CPD-20, the base is selected from the group consisting of K$_2$CO$_3$, N,N-diisopropylethylamine (DIPEA), triethylamine (TEA), tBuOK, tBuONa, and Cs$_2$CO$_3$.

In some embodiments of the forming of CPD-20, the base is K$_2$CO$_3$.

In another embodiment of the process for the preparation of Formula (P)-I, the process further comprises subjecting the compound CPD-20 to a chromatographic separation to obtain the compound of Formula (P)-I.

In some embodiments of the process for the preparation of Formula (P)-I, the chromatographic separation comprises simulated moving bed (SMB) chromatography with a chiral stationary phase and a mobile phase.

In some embodiments of the process for the preparation of Formula (P)-I, the chiral stationary phase is selected from the group consisting of Chiralpak® AD, Chiralpak® AS, Chiralpak® AY, Chiralpak® AZ, Chiralpak® OD, Chiralpak® OZ, Chiralpak® IA, Chiralpak® IB-N, Chiralpak® IC, Chiralpak® ID, Chiralpak® IE, Chiralpak® IF, Chiralpak® IG, and Chiralpak® IH.

In some embodiments of the process for the preparation of Formula (P)-I, the chiral stationary phase is Chiralpak® IB-N.

In some embodiments of the process for the preparation of Formula (P)-I, the mobile phase is selected from the group consisting of acetonitrile, methanol, acetonitrile and methanol, n-heptane and ethanol, n-heptane and dichloromethane, n-heptane and ethylacetate, dichloromethane and methanol, and dichloromethane and acetonitrile.

In some embodiments of the process for the preparation of Formula (P)-I, the mobile phase is dichloromethane and acetonitrile.

In some embodiments of the process for the preparation of Formula (P)-I, when the mobile phase is in the form of a mixture the mixtures may be in a volumetric ratio of about 1:1, about 2:1, about 3:1, about 4:1, about 5:1, about 6:1, about 7:1, about 8:1, about 9:1, about 10:1, about 7:3, about 1:2, about 1:3, about 1:4, about 1:5, about 1:6, about 1:7, about 1:8, about 1:9, about 1:10, about 3:7, or any ratio in between any two ratios.

A process for the preparation of the compound

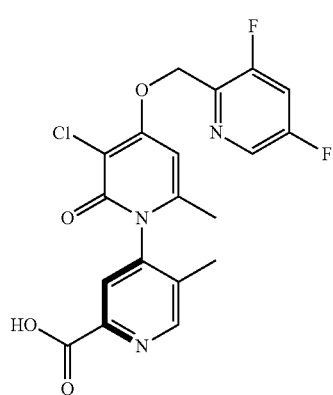

CPD-07 comprising subjecting the compound

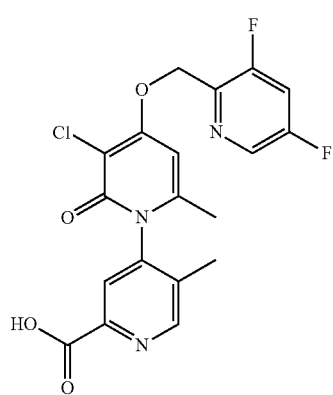

CPD-06 to chiral separation with a chiral amine and a solvent to obtain the compound CPD-07.

In some embodiments of the chiral separation of the compound CPD-06, the chiral amine is selected from the group consisting of (S)-1-(naphthalen-2-yl)ethan-1-amine and (1S,2R)-2-amino-1,2-diphenylethan-1-ol.

In some embodiments of the chiral separation of the compound CPD-06, the chiral amine is (S)-1-(naphthalen-2-yl)ethan-1-amine.

In some embodiments of the chiral separation of the compound CPD-06, the chiral amine is (1S,2R)-2-amino-1,2-diphenylethan-1-ol.

In some embodiments of the chiral separation of the compound CPD-06, the solvent is selected from the group consisting of toluene, ethylbenzene, n-butanol, anisole, DMSO, or a combination thereof.

In some embodiments of the chiral separation of the compound CPD-06, the solvent is toluene.

In some embodiments of the chiral separation of the compound CPD-06, the solvent is ethylbenzene.

In some embodiments of the chiral separation of the compound CPD-06, the solvent is n-butanol.

In some embodiments of the chiral separation of the compound CPD-06, the solvent is anisole.

In some embodiments of the chiral separation of the compound CPD-06, the solvent is anisole and DMSO.

A process for the preparation of the compound

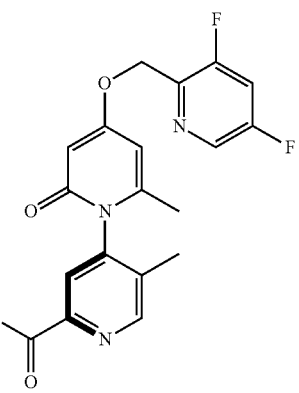

CPD-12 comprising subjecting the compound

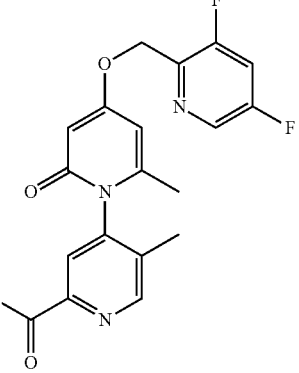

CPD-11 to chiral separation with a chiral amine and a solvent to obtain the compound CPD-12.

In some embodiments of the chiral separation of the compound CPD-11, the chiral amine is selected from the group consisting of (S)-1-(naphthalen-2-yl)ethan-1-amine and (1S,2R)-2-amino-1,2-diphenylethan-1-ol.

In some embodiments of the chiral separation of the compound CPD-11, the chiral amine is (S)-1-(naphthalen-2-yl)ethan-1-amine.

In some embodiments of the chiral separation of the compound CPD-11, the chiral amine is (1S,2R)-2-amino-1,2-diphenylethan-1-ol.

In some embodiments of the chiral separation of the compound CPD-11, the solvent is selected from the group consisting of toluene, ethylbenzene, n-butanol, anisole, DMSO, or a combination thereof.

In some embodiments of the chiral separation of the compound CPD-11, the solvent is toluene.

In some embodiments of the chiral separation of the compound CPD-11, the solvent is ethylbenzene.

In some embodiments of the chiral separation of the compound CPD-11, the solvent is n-butanol.

In some embodiments of the chiral separation of the compound CPD-11, the solvent is anisole.

In some embodiments of the chiral separation of the compound CPD-11, the solvent is anisole and DMSO.

Scheme 6 outlines another route of synthesizing a Formula (P)-I starting from CPD-03 utilizing a Sonogashira coupling. Chiral separation is utilized to produce Formula (P)-I.

Scheme 6

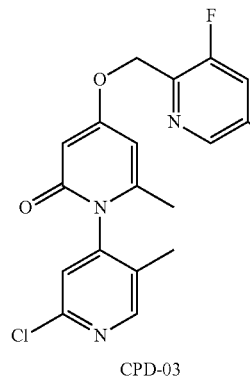

CPD-03

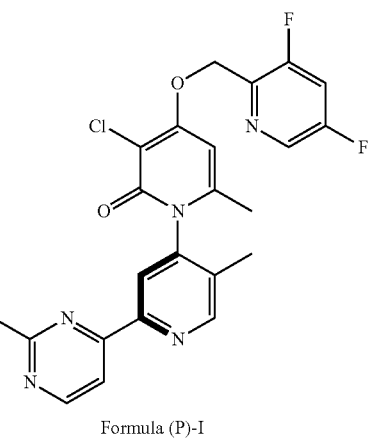

CPD-21

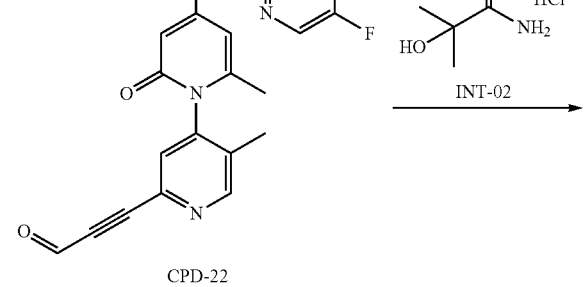

CPD-22

CPD-23

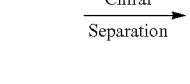

CPD-20

Formula (P)-I

In accordance with Scheme 6, some embodiments of the present application involves a process for the preparation of compound of Formula (P)-I having the structure:

Formula (P)-I

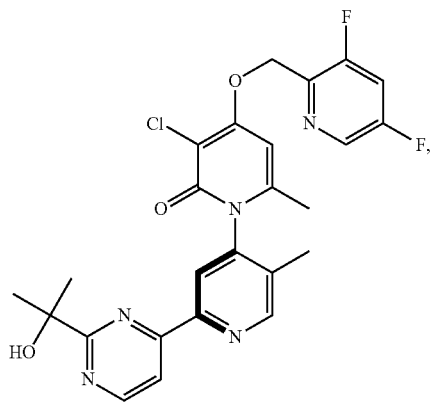

said process comprising:
subjecting

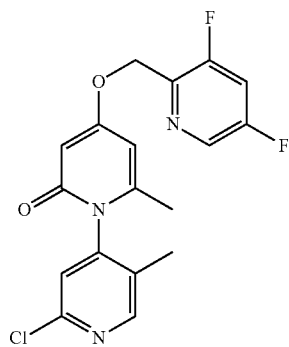

CPD-03 and propargyl alcohol to a Sonogashira coupling reaction in the presence of a palladium catalyst and a base to form the compound

CPD-21

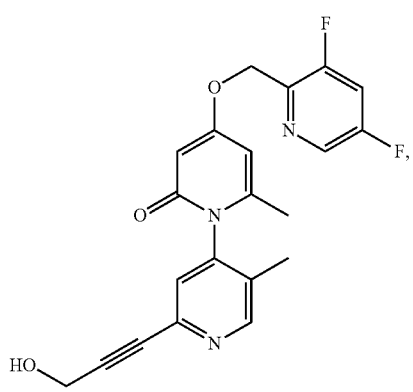

and converting CPD-21 to Formula (P)-I.

In some embodiments of the Sonogashira coupling of CPD-03, the palladium catalyst is Pd(PPh₃)₄.

In some embodiments of the Sonogashira coupling of CPD-03, the amine base is triethylamine.

In some embodiments of the process for the preparation of Formula (P)-I, the process further comprises oxidizing the compound CPD-21 with an oxidizing agent to form the compound

CPD-22

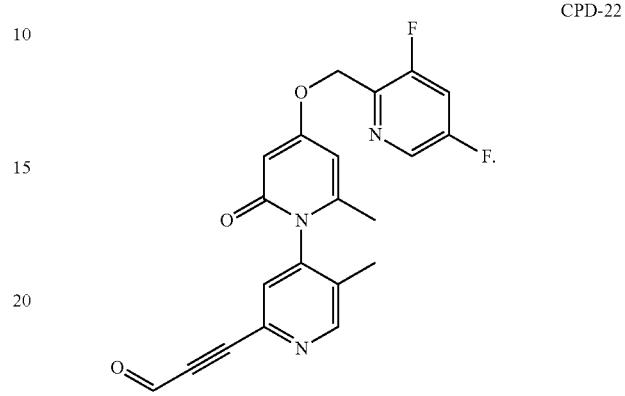

In some embodiments of the oxidation of CPD-21, the oxidizing agent is Dess-Martin periodinane.

In some embodiments of the process for the preparation of Formula (P)-I, the process further comprises comprising contacting the compound CPD-22 with

INT-02

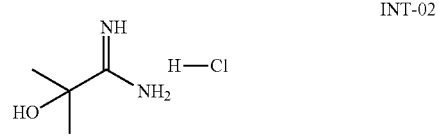

in the presence of a base, and
forming the compound

CPD-23

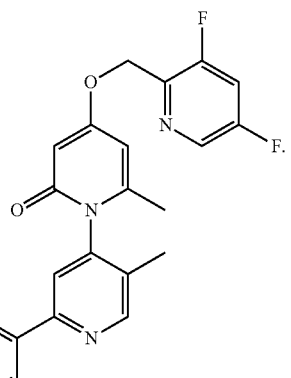

In some embodiments of the forming of CPD-23, the base is Na₂CO₃.

In some embodiments of the process for the preparation of Formula (P)-I, the process further comprises contacting the compound CPD-23 with a chlorination reagent to form the compound

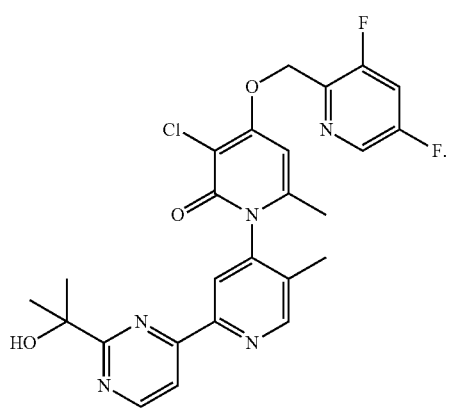

CPD-20

In some embodiments of the chlorination of CPD-23, the chlorination reagent is N-chlorosuccinimide.

In some embodiments, the forming of CPD-20 further comprises contacting CPD-23 with dichloroacetic acid.

In some embodiments of the process for the preparation of Formula (P)-I, the process further comprises subjecting the compound CPD-20 to chiral chromatography to obtain the compound of Formula (P)-I.

Scheme 7 depicts another method of synthesizing CPD-17 starting from CPD-03. CPD-03 utilized in this manner may be from any of the embodiments described herein that produce CPD-03. CPD-17 produced in this manner may be used in any of the embodiments disclosed herein that utilizes CPD-17.

Scheme 7

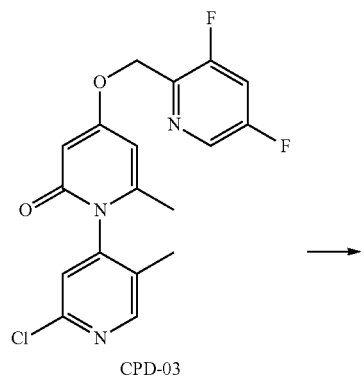

CPD-03

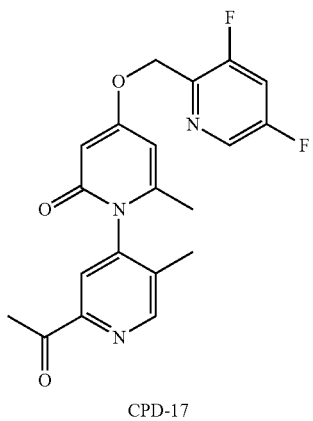

CPD-17

Accordingly, some embodiments of the present application involve a process for the preparation of the compound

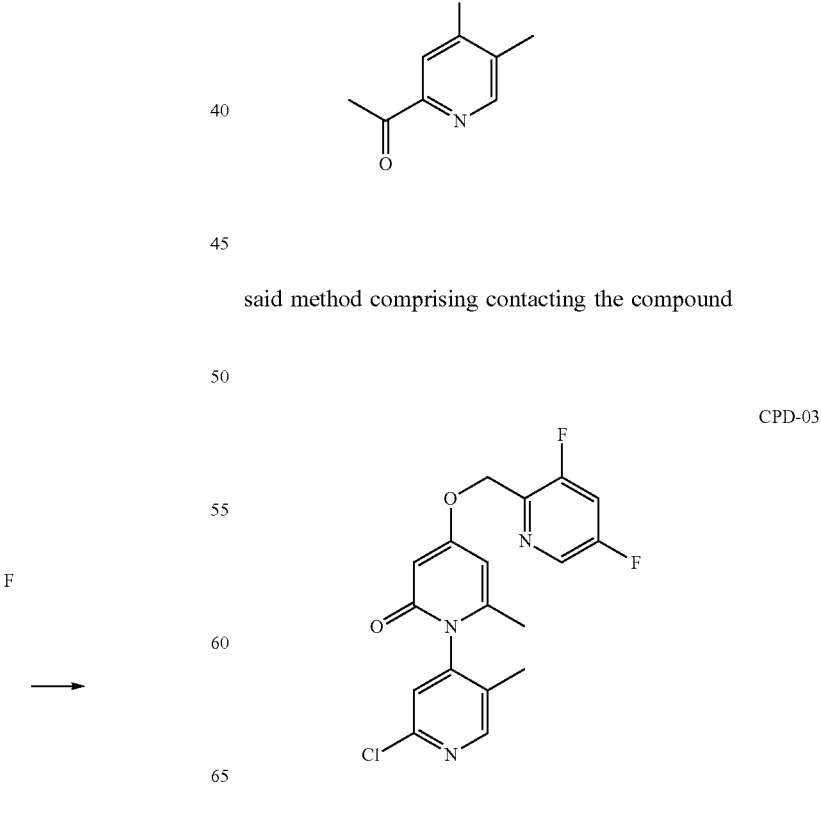

said method comprising contacting the compound with Pd$_2$(dba)$_3$ and Zn(CN)$_2$ to form the compound

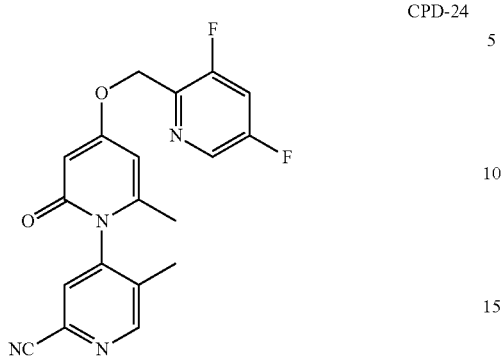

CPD-24 and converting CPD-24 to CPD-17.

In another embodiment of the process for the preparation of the compound CPD-17, the process comprises contacting the compound CPD-24 with MeMgX to obtain the compound CPD-17.

In some embodiments of the contacting the compound CPD-17, the MeMgX is selected from the group consisting of MeMgBr, MeMgCl, and MeMgI.

In some embodiments of the contacting the compound CPD-17, the MeMgX is MeMgBr.

In some embodiments of the contacting the compound CPD-17, the MeMgX is MeMgCl.

In some embodiments of the contacting the compound CPD-17, the MeMgX is MeMgI.

Scheme 8 depicts another method of synthesizing CPD-04 starting from CPD-02 via bromine containing intermediates. CPD-02 utilized in this manner may be from any of the embodiments described herein that produce CPD-02. CPD-04 produced in this manner may be used in any of the embodiments disclosed herein that utilizes CPD-04.

Scheme 8

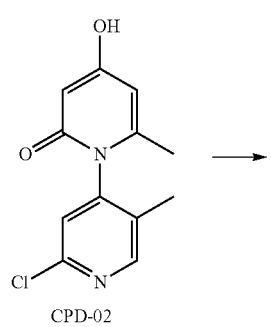

CPD-02

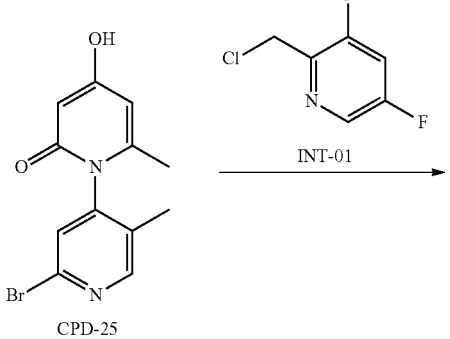

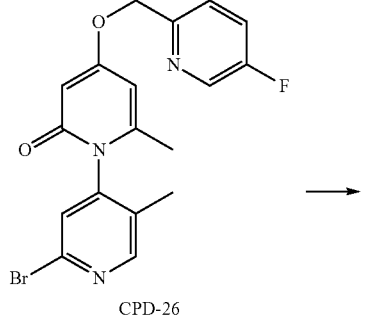

CPD-26

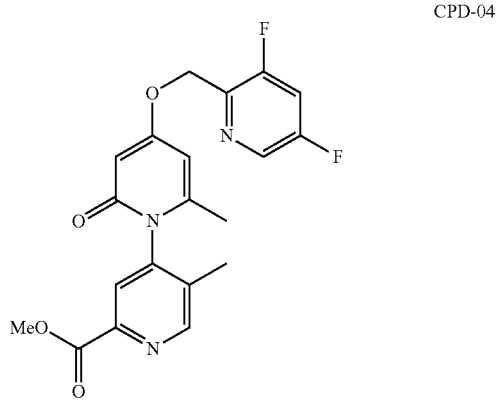 [SMILES: COC(=O)c1cc(-n2c(C)cc(OCc3ncc(F)cc3F)cc2=O)c(C)cn1]

CPD-04

In accordance with Scheme 8, some embodiments of the present application involve a process for the preparation of the compound

CPD-04 comprising contacting the compound

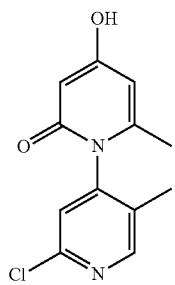
CPD-02 with HBr to form the compound

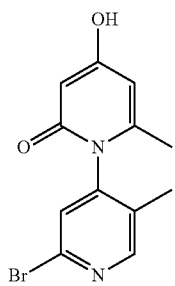
CPD-25 and converting CPD-25 to CPD-04.

In some embodiments of the process for the preparation of the compound CPD-04, the process further comprises contacting the compound CPD-25 with the compound

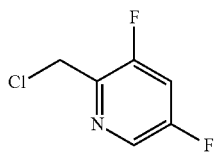
INT-01 and a base to form the compound

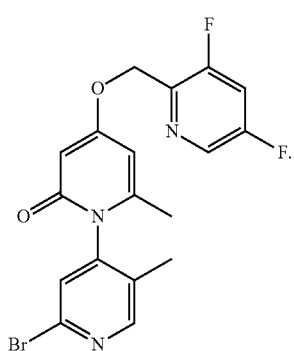
CPD-26

In some embodiments, the base used to form CPD-26 is selected from the group consisting of $K_2CO_3$ and $Cs_2CO_3$.

In some embodiments, the base used to form CPD-26 is $K_2CO_3$.

In some embodiments, the base used to form CPD-26 is $Cs_2CO_3$.

In some embodiments of the process for the preparation of the compound CPD-04, the process further comprises contacting the compound CPD-26 with CO in the presence of a palladium catalyst, an amine base, and methanol to form the compound

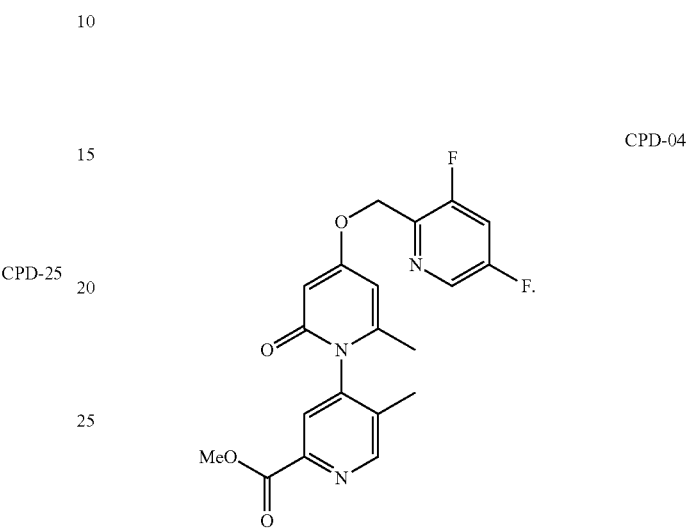
CPD-04

In some embodiments of the process for the preparation of the compound CPD-26, the palladium catalyst is Pd(dppf)Cl₂•DCM.

In some embodiments of the process for the preparation of the compound CPD-26, the amine base is triethylamine.

Scheme 9 depicts another method of synthesizing CPD-17 starting from CPD-26. CPD-26 utilized in this manner may be from any of the embodiments described herein that produce CPD-26. CPD-17 produced in this manner may be used in any of the embodiments disclosed herein that utilizes CPD-17.

Scheme 9

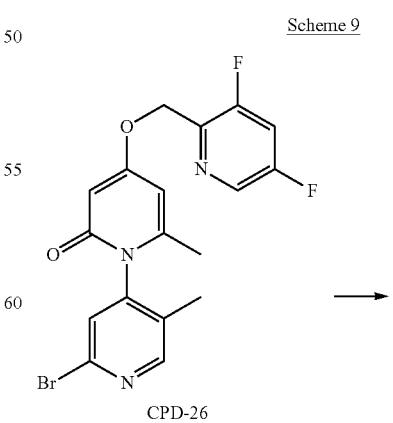
CPD-26

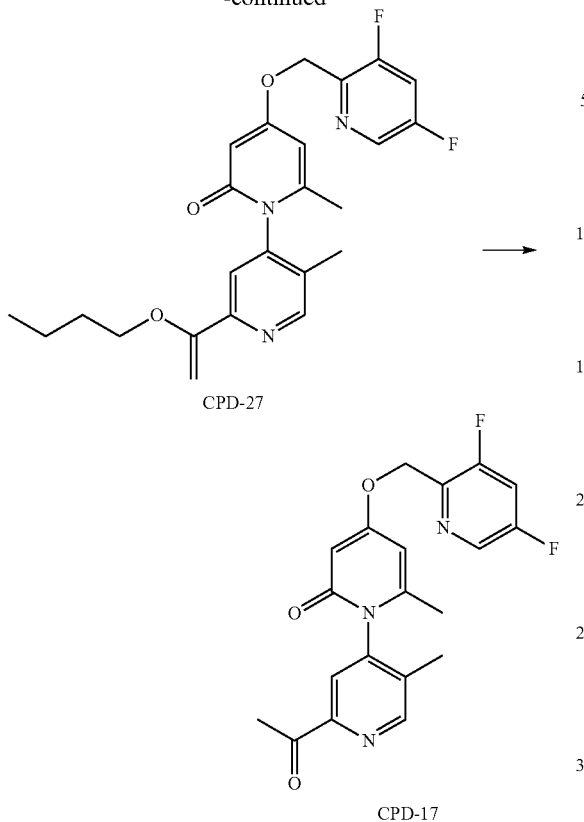

In accordance with Scheme 9, some embodiments of the present application involve a process for the preparation of the compound CPD-17 comprising contacting the compound CPD-26 with butyl vinyl ether in the presence of a palladium catalyst, a phosphorus reagent, and a base to form the compound

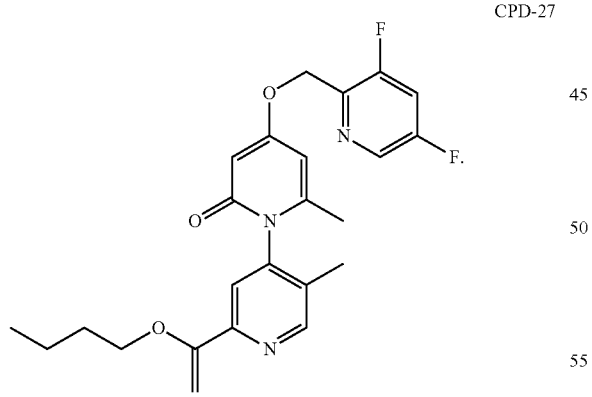

In some embodiments of forming CPD-27, the palladium catalyst is Pd(OAc)$_2$.

In some embodiments of forming CPD-27, the phosphorus reagent is 1,1'-Ferrocenediyl-bis(diphenylphosphine) (dppf).

In some embodiments of forming CPD-27, the base is iPr$_2$NEt.

In some embodiments of the process for the preparation of CPD-17, the process further comprises contacting the compound CPD-27 with an acid to form the compound

CPD-17

In some embodiments of forming CPD-17, the acid is HCl.

Scheme 10 depicts another method of synthesizing CPD-17 starting from CPD-26. CPD-26 utilized in this manner may be from any of the embodiments described herein that produce CPD-26. CPD-17 produced in this manner may be used in any of the embodiments disclosed herein that utilizes CPD-17.

Scheme 10

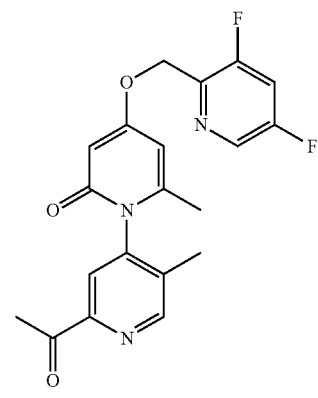

In accordance with Scheme 10, some embodiments of the present application involve a process for the preparation of the compound CPD-17 comprising the steps of:

CPD-26

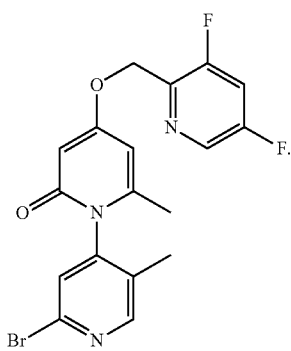

(a) contacting the compound CPD-26 with hydroxyethyl vinyl ether in the presence of a palladium catalyst, a phosphorus reagent, and a base to form a mixture; and
(b) contacting the mixture of (a) with an acid to form the compound

CPD-17

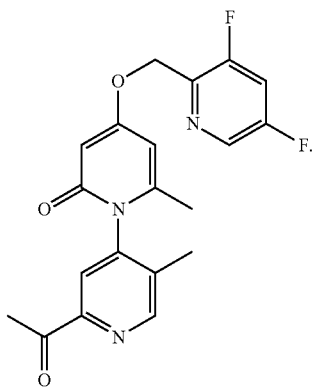

In some embodiments of forming CPD-17, the palladium catalyst is Pd(OAc)₂.

In some embodiments of forming CPD-17, the phosphorus reagent is 1,3-bis(diphenylphosphino)propane (dppp).

In some embodiments of forming CPD-17, the base is iPr₂NEt.

In some embodiments of forming CPD-17, the acid is HCl.

Scheme 11 depicts another method of synthesizing CPD-18 starting from CPD-28. CPD-28 utilized in this manner may be from any of the embodiments described herein that produce CPD-28. CPD-18 produced in this manner may be used in any of the embodiments disclosed herein that utilizes CPD-18.

Scheme 11

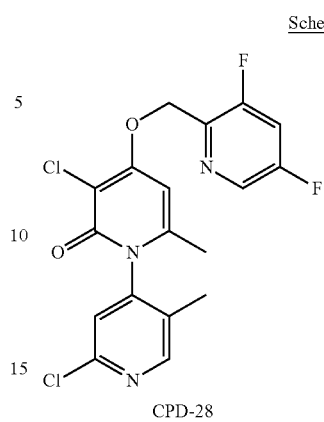

CPD-28

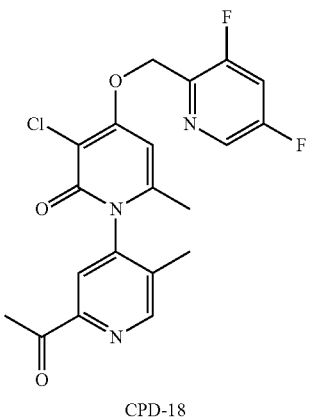

CPD-18

In accordance with Scheme 11, some embodiments of the present application involve a process for the preparation of the compound CPD-18 comprising the steps of:

(a) contacting the compound

CPD-28

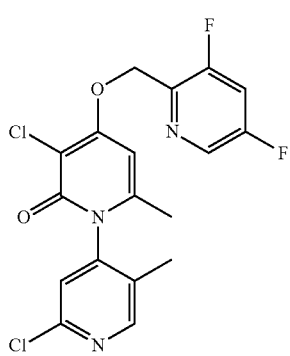

with a vinyl tin reagent in the presence of a palladium catalyst to form a mixture; and (b) contacting the mixture of (a) with an acid

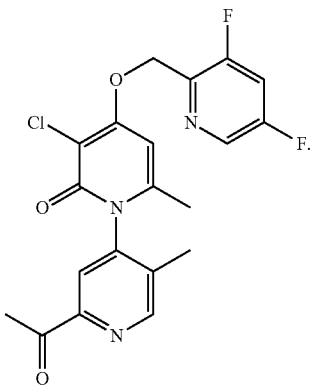
CPD-18 to form the compound

In some embodiments of forming CPD-18, the vinyl tin reagent is

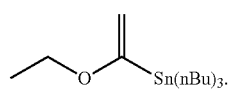

In some embodiments of forming CPD-18, the palladium catalyst is Pd(dppf)Cl$_2$.

In some embodiments of forming CPD-18, the acid is HCl.

Scheme 12 depicts another method of synthesizing CPD-18 starting from CPD-29. CPD-29 utilized in this manner may be from any of the embodiments described herein that produce CPD-29. CPD-18 produced in this manner may be used in any of the embodiments disclosed herein that utilizes CPD-18.

Scheme 12

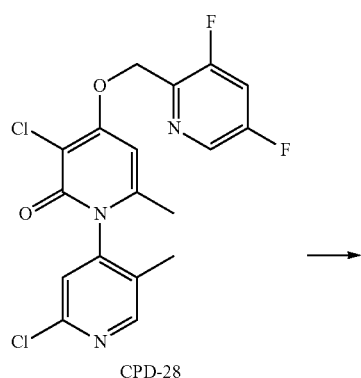
CPD-28

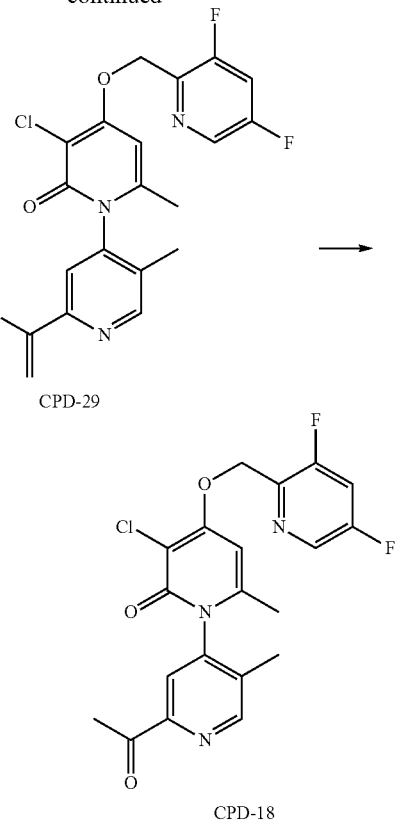

In accordance with Scheme 12, some embodiments of the present application involve a process for the preparation of the compound CPD-18 comprising contacting the compound CPD-28 with butyl vinyl ether in the presence of a palladium catalyst, a phosphorus reagent, and a base to form the compound

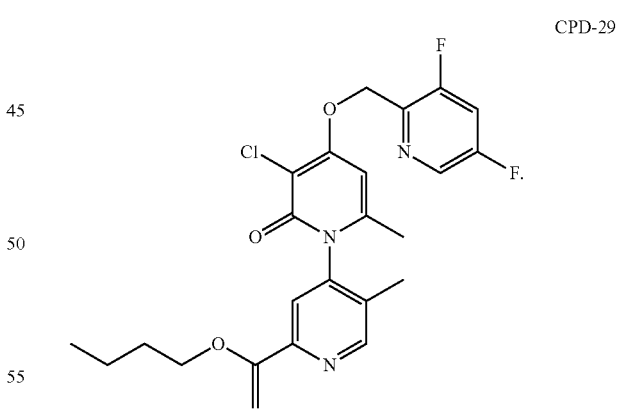

In some embodiments of forming CPD-18, the palladium catalyst is Pd(OAc)$_2$.

In some embodiments of forming CPD-18, the phosphorus reagent is 1,1'-Ferrocenediyl-bis(diphenylphosphine) (dppf).

In some embodiments of forming CPD-18, the base is iPr$_2$NEt.

In some embodiments of the process for the preparation of CPD-18, the process further comprises contacting the compound CPD-29 with an acid to form the compound

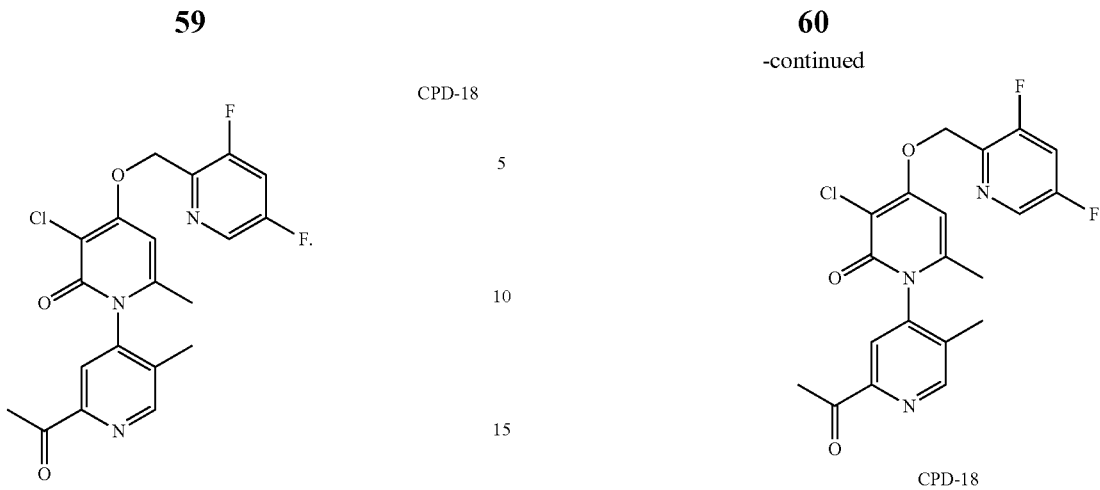

CPD-18

In some embodiments of forming CPD-18, the acid is HCl.

Scheme 13 depicts another method of synthesizing CPD-18 starting from CPD-30. CPD-30 utilized in this manner may be from any of the embodiments described herein that produce CPD-30. CPD-18 produced in this manner may be used in any of the embodiments disclosed herein that utilizes CPD-18.

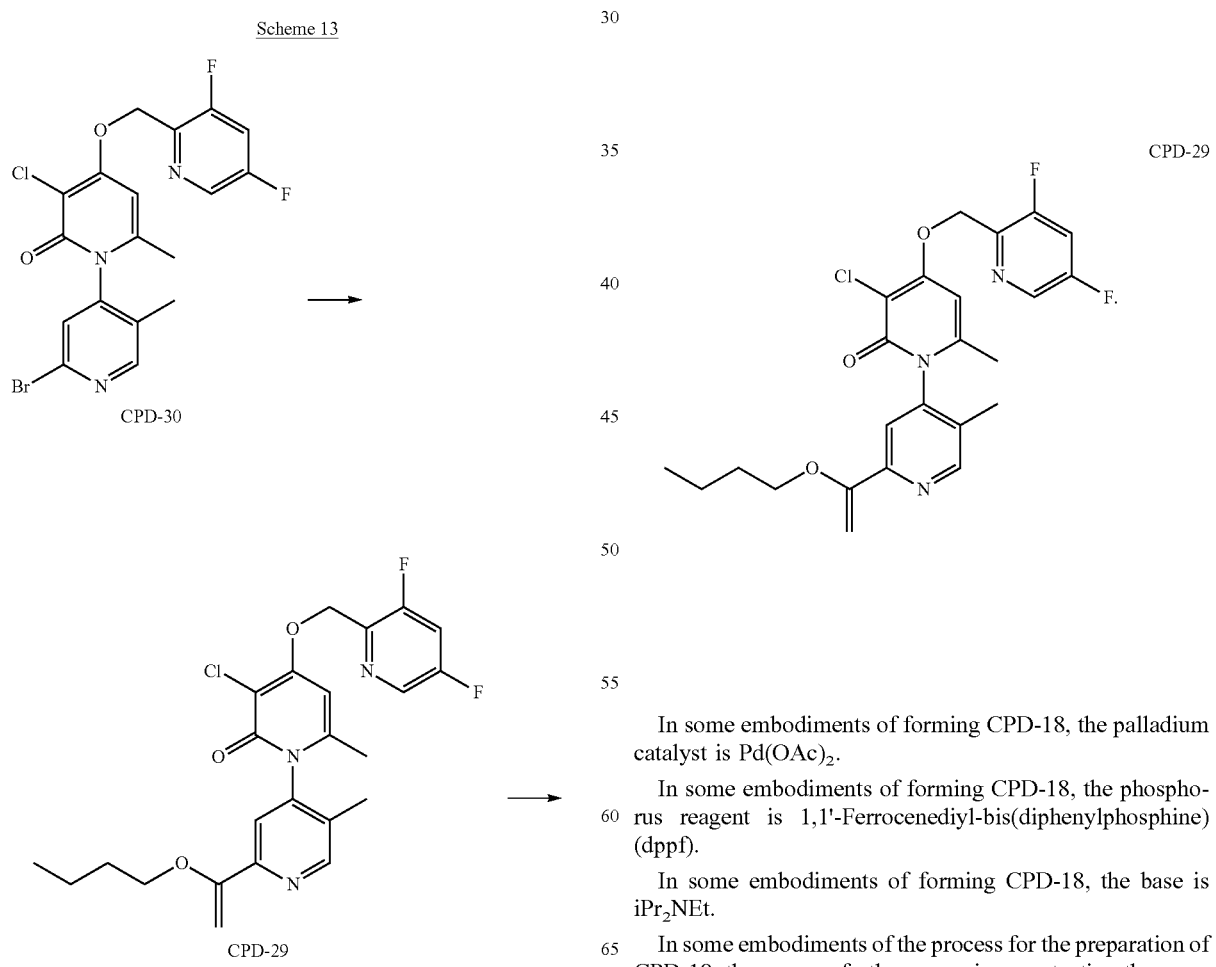

Scheme 13

In accordance with Scheme 13, some embodiments of the present application involve a process for the preparation of compound CPD-18 comprising contacting the compound CPD-30 with butyl vinyl ether in the presence of a palladium catalyst, a phosphorus reagent, and a base to form the compound In some embodiments of forming CPD-18, the palladium catalyst is Pd(OAc)$_2$.

In some embodiments of forming CPD-18, the phosphorus reagent is 1,1'-Ferrocenediyl-bis(diphenylphosphine) (dppf).

In some embodiments of forming CPD-18, the base is iPr$_2$NEt.

In some embodiments of the process for the preparation of CPD-18, the process further comprises contacting the compound CPD-29 with an acid to form the compound

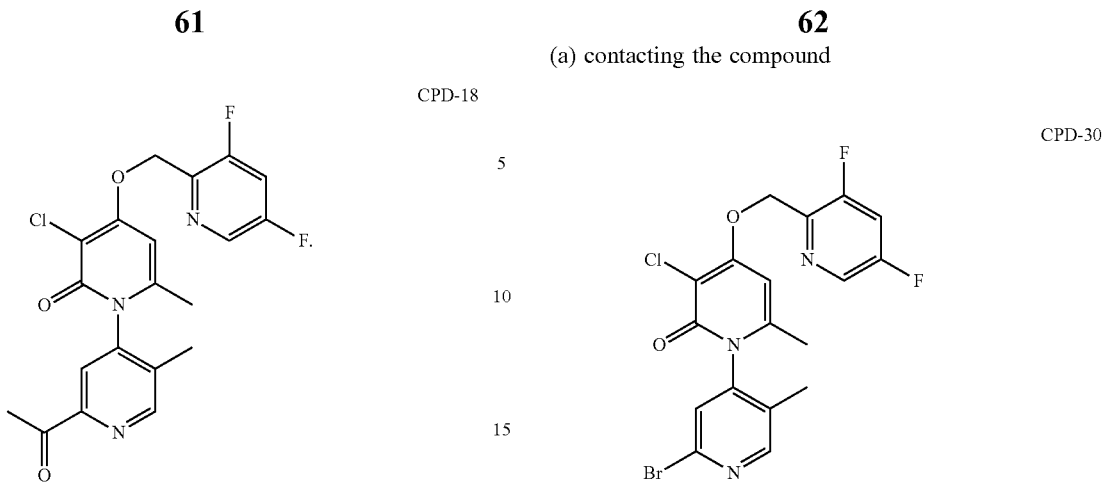

In some embodiments of forming CPD-18, the acid is HCl.

Scheme 14 depicts another method of synthesizing CPD-18 starting from CPD-30. CPD-30 utilized in this manner may be from any of the embodiments described herein that produce CPD-30. CPD-18 produced in this manner may be used in any of the embodiments disclosed herein that utilizes CPD-18.

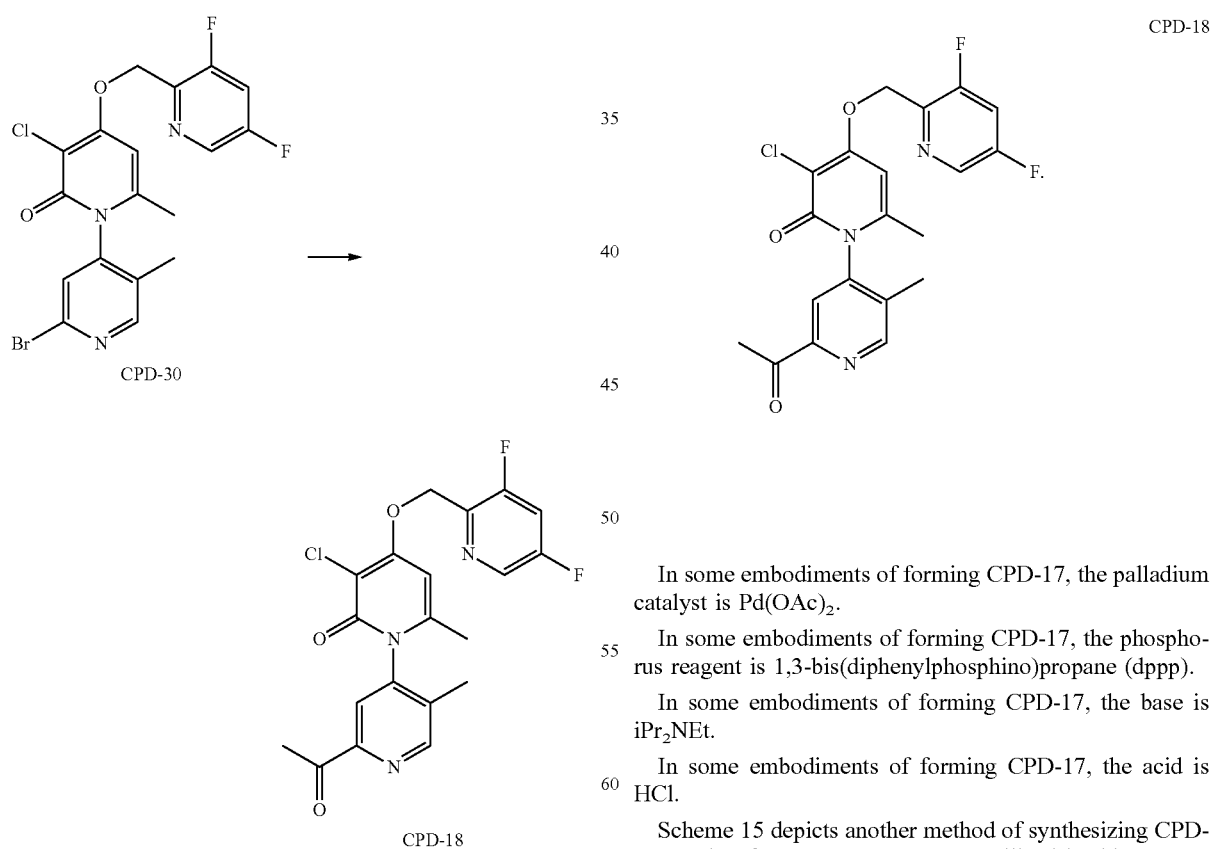

In accordance with Scheme 14, some embodiments of the present application involve a process for the preparation of the compound CPD-18 comprising the steps of:

(a) contacting the compound with hydroxyethyl vinyl ether in the presence of a palladium catalyst, a phosphorus reagent, and a base to form a mixture; and (b) contacting the mixture of (a) with an acid to form the compound In some embodiments of forming CPD-17, the palladium catalyst is Pd(OAc)$_2$.

In some embodiments of forming CPD-17, the phosphorus reagent is 1,3-bis(diphenylphosphino)propane (dppp).

In some embodiments of forming CPD-17, the base is iPr$_2$NEt.

In some embodiments of forming CPD-17, the acid is HCl.

Scheme 15 depicts another method of synthesizing CPD-18 starting from CPD-28. CPD-28 utilized in this manner may be from any of the embodiments described herein that produce CPD-28. CPD-18 produced in this manner may be used in any of the embodiments disclosed herein that utilizes CPD-18.

Scheme 15

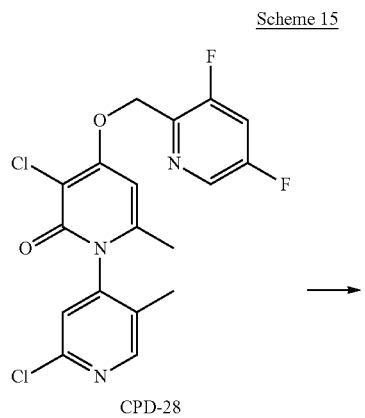

CPD-28

→

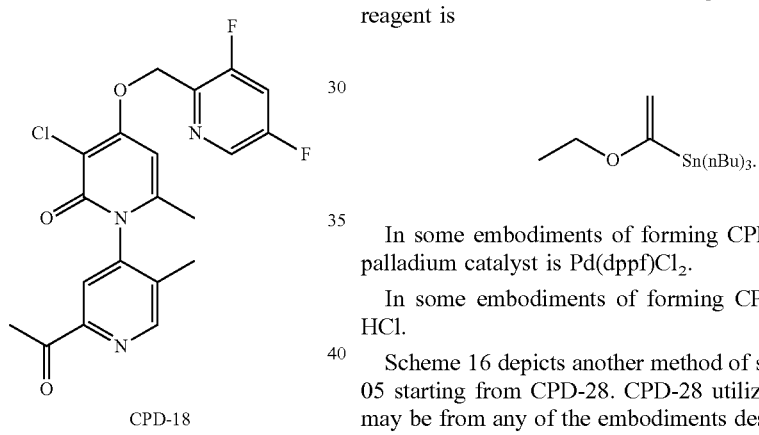

CPD-18

In accordance with Scheme 15, some embodiments of the present application involve a process for the preparation of the compound CPD-18 comprising the steps of:
(a) contacting the compound

CPD-28

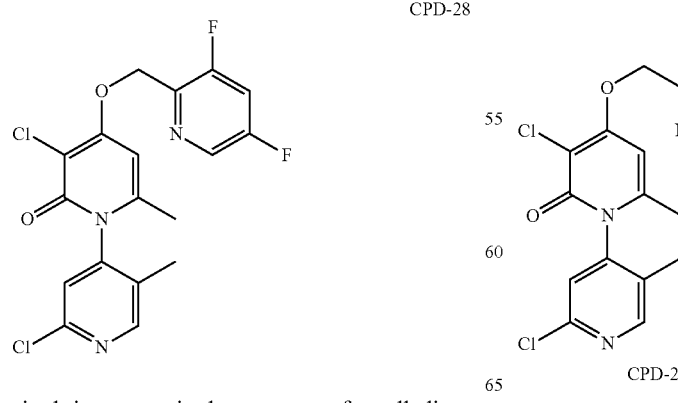

with a vinyl tin reagent in the presence of a palladium catalyst to form a mixture; and (b) contacting the mixture of (a) with an acid to form the compound

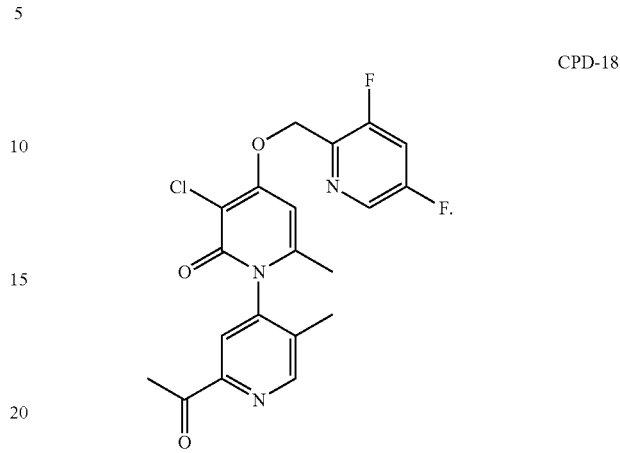

CPD-18

In some embodiments of forming CPD-18, the vinyl tin reagent is $$\text{EtO-C(=CH}_2\text{)-Sn(nBu)}_3$$

In some embodiments of forming CPD-18, wherein the palladium catalyst is Pd(dppf)Cl$_2$.

In some embodiments of forming CPD-18, the acid is HCl.

Scheme 16 depicts another method of synthesizing CPD-05 starting from CPD-28. CPD-28 utilized in this manner may be from any of the embodiments described herein that produce CPD-28. CPD-05 produced in this manner may be used in any of the embodiments disclosed herein that utilizes CPD-05.

Scheme 16

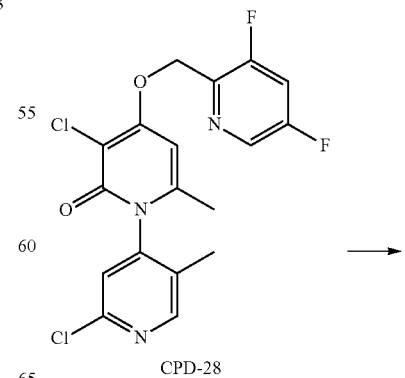

CPD-28

→

-continued

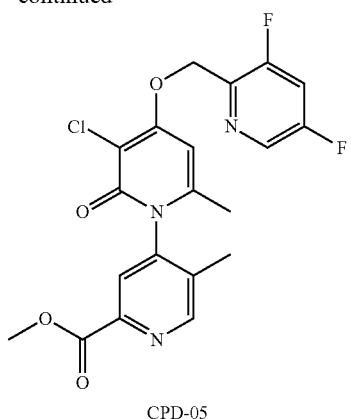

CPD-05

In accordance with Scheme 16, some embodiments of the present application involve a process for the preparation of the compound CPD-05 comprising contacting the compound CPD-28 with CO in the presence of a palladium catalyst, an amine base, and methanol to form the compound

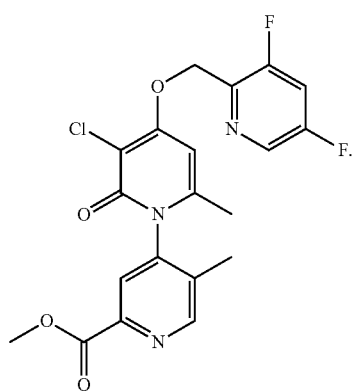

CPD-05

In some embodiments of forming CPD-05, the palladium catalyst is Pd(dppf)Cl$_2$.

In some embodiments of forming CPD-05, the amine base is triethylamine.

Scheme 17 depicts another method of synthesizing CPD-05 starting from CPD-30. CPD-30 utilized in this manner may be from any of the embodiments described herein that produce CPD-30. CPD-05 produced in this manner may be used in any of the embodiments disclosed herein that utilizes CPD-05.

Scheme 17

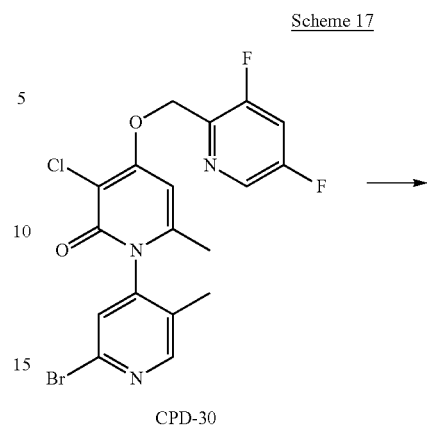

CPD-30

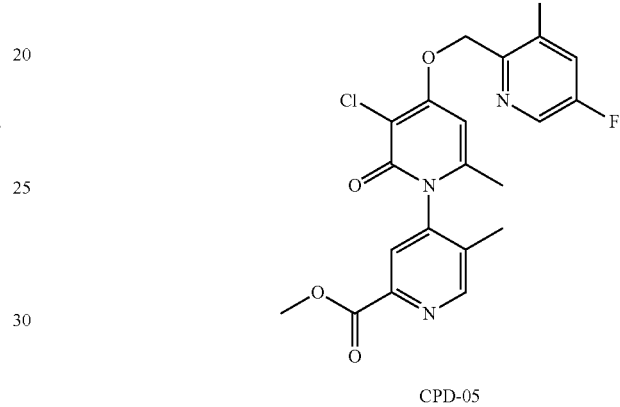

CPD-05

In accordance with Scheme 17, some embodiments of the present application involve a process for the preparation of the compound CPD-05 comprising contacting the compound CPD-30 with CO in the presence of a palladium catalyst, a phosphorus reagent, an amine base, and methanol to form the compound CPD-05

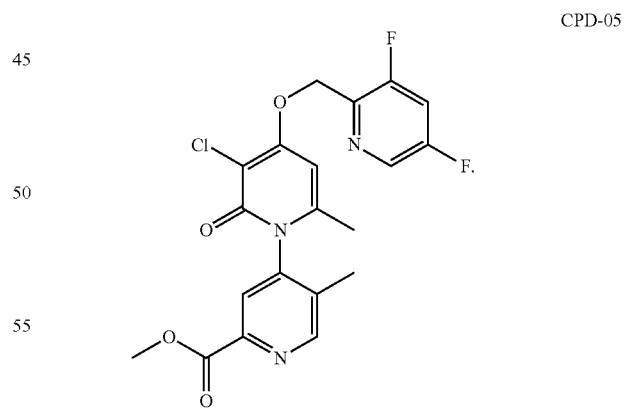

CPD-05

In some embodiments of forming CPD-05, the palladium catalyst is Pd(OAc)$_2$.

In some embodiments of forming CPD-05, the phosphorus reagent is 1,1'-Ferrocenediyl-bis(diphenylphosphine) (dppf).

In some embodiments of forming CPD-05, the amine base is triethylamine.

Scheme 18 depicts another method of synthesizing CPD-16 starting from CPD-28. CPD-28 utilized in this manner may be from any of the embodiments described herein that produce CPD-28. CPD-16 produced in this manner may be used in any of the embodiments disclosed herein that utilizes CPD-16.

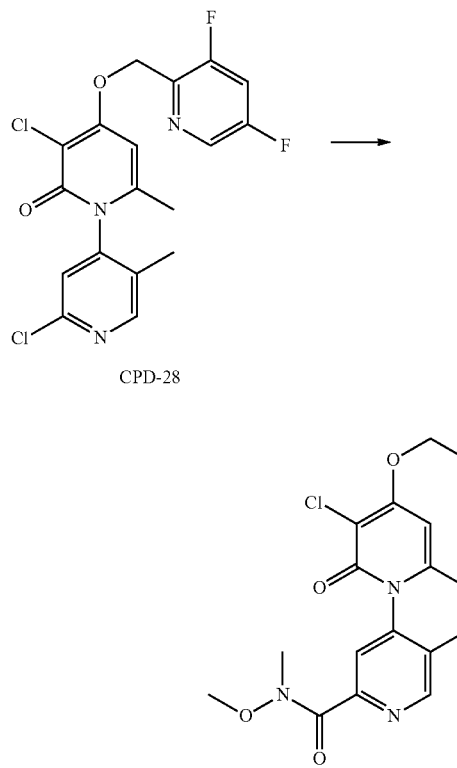

Scheme 18

CPD-28

CPD-16

In accordance with Scheme 18, some embodiments of the present application involve a process for the preparation of the compound CPD-16 comprising contacting the compound CPD-28 with MeNH(OMe)-HCl in the presence of a palladium catalyst, a phosphorus reagent, CO, and a base to form the compound

CPD-16

In some embodiments of forming CPD-16, the palladium catalyst is Pd(OAc)$_2$.

In some embodiments of forming CPD-16, the phosphorus reagent is Xantphos.

In some embodiments of forming CPD-16, the base is K$_3$PO$_4$.

Scheme 19 depicts another method of synthesizing CPD-16 starting from CPD-30. CPD-30 utilized in this manner may be from any of the embodiments described herein that produce CPD-30. CPD-16 produced in this manner may be used in any of the embodiments disclosed herein that utilizes CPD-16.

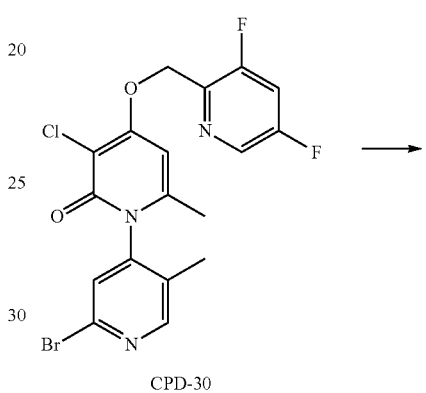

Scheme 19

CPD-30

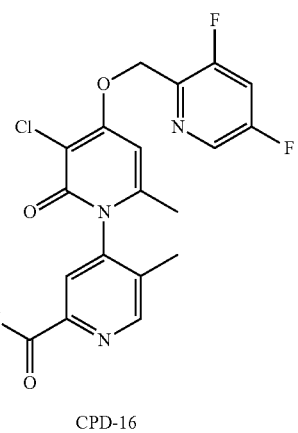

CPD-16

In accordance with Scheme 19, some embodiments of the present application involve a process for the preparation of the compound CPD-16 comprising contacting the compound CPD-30 with MeNH(OMe)-HCl in the presence of a palladium catalyst, a phosphorus reagent, CO, and a base to form the compound

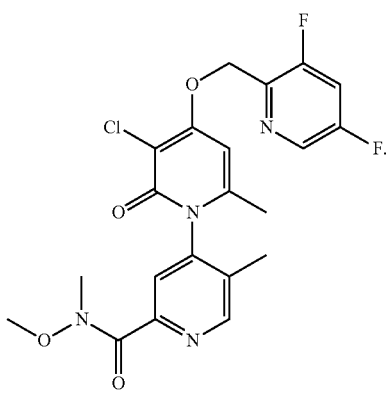

CPD-16

In some embodiments of forming CPD-16, the palladium catalyst is Pd(OAc)$_2$.

In some embodiments of forming CPD-16, the phosphorus reagent is Xantphos.

In some embodiments of forming CPD-16, the base is K$_3$PO$_4$.

Scheme 20 depicts another method of synthesizing CPD-11 starting from CPD-26. CPD-26 utilized in this manner may be from any of the embodiments described herein that produce CPD-26. CPD-11 produced in this manner may be used in any of the embodiments disclosed herein that utilizes CPD-11.

Scheme 20

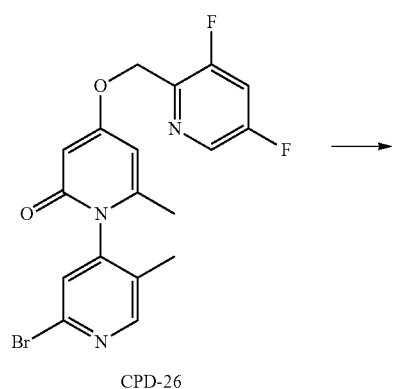

In accordance with Scheme 20, some embodiments of the present application involve a process for the preparation of the compound CPD-16 that comprises the steps of:

(a) contacting the compound CPD-26 with CO in the presence of a palladium catalyst, an amine base, a phosphorus reagent, and MeOH/H$_2$O to form a mixture; and (b) contacting the mixture of (a) with a base to form the compound

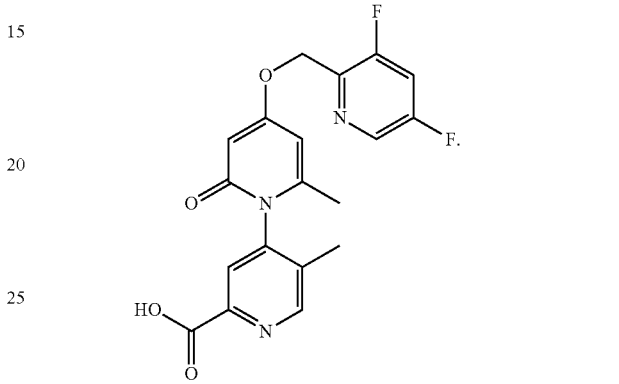

CPD-11

In some embodiments of forming CPD-11, the palladium catalyst is Pd(OAc)$_2$.

In some embodiments of forming CPD-11, the amine base is triethylamine.

In some embodiments of forming CPD-11, the phosphorus reagent is 1,1'-Ferrocenediyl-bis(diphenylphosphine) (dppf).

In some embodiments of forming CPD-11, the base is NaOH.

Scheme 21 depicts another method of synthesizing CPD-06 starting from CPD-28. CPD-28 utilized in this manner may be from any of the embodiments described herein that produce CPD-28. CPD-06 produced in this manner may be used in any of the embodiments disclosed herein that utilize CPD-06.

Scheme 21

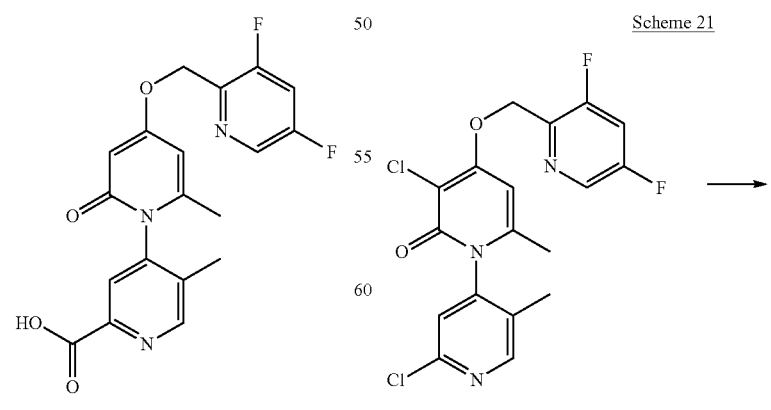

-continued

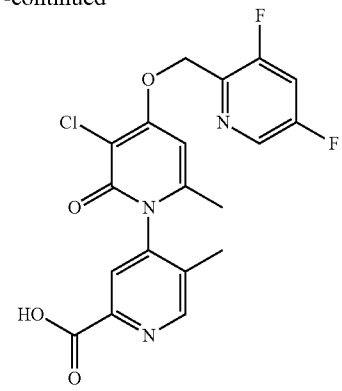

CPD-06

In accordance with Scheme 21, some embodiments of the present application involve a process for the preparation of the compound CPD-06 comprising contacting the compound CPD-28 with CO in the presence of a palladium catalyst, a base, and a solvent mixture to form the compound CPD-06

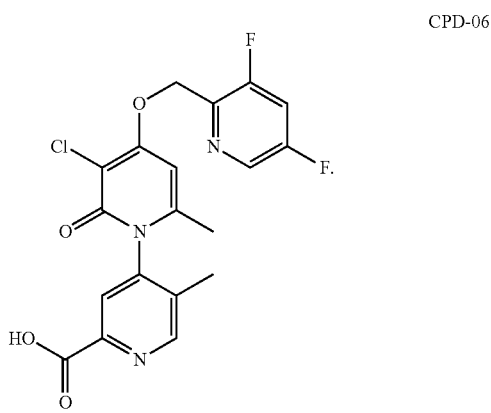 [SMILES: Cc1cnc(C(=O)O)cc1-n1c(C)cc(OCc2ncc(F)cc2F)c(Cl)c1=O]

CPD-06

In some embodiments of forming CPD-06, the palladium catalyst is Pd(dppf)Cl$_2$.

In some embodiments of forming CPD-06, the base is Na$_2$CO$_3$.

In some embodiments of forming CPD-06, the base is K$_2$CO$_3$.

In some embodiments of forming CPD-06, the base is Li$_2$CO$_3$.

In some embodiments of forming CPD-06, the forming of CPD-06 further comprising contacting CPD-28 with triethylamine.

In some embodiments of forming CPD-06, the solvent mixture is MeOH/H$_2$O.

In some embodiments of forming CPD-06, the solvent mixture is acetonitrile/H$_2$O.

Scheme 22 depicts another method of synthesizing CPD-06 starting from CPD-30. CPD-30 utilized in this manner may be from any of the embodiments described herein that produce CPD-30. CPD-06 produced in this manner may be used in any of the embodiments disclosed herein that utilizes CPD-06.

Scheme 22

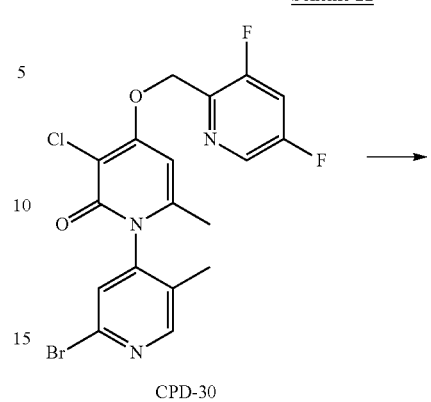

CPD-30

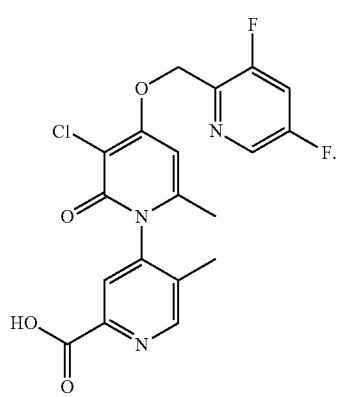

CPD-06

In accordance with Scheme 22, some embodiments of the present application involve a process for the preparation of the compound CPD-06 comprising contacting the compound CPD-30 with CO in the presence of a palladium catalyst, an amine base, a phosphorus reagent, a base, and DMF to form the compound

CPD-06

In some embodiments of forming CPD-06, the palladium catalyst is Pd(OAc)$_2$.

In some embodiments of forming CPD-06, the amine base is triethylamine.

In some embodiments of forming CPD-06, the phosphorus reagent is 1,1'-Ferrocenediyl-bis(diphenylphosphine) (dppf).

In some embodiments of forming CPD-06, the base is K₂CO₃.

Scheme 23 depicts another method of synthesizing CPD-06 starting from CPD-11. CPD-11 utilized in this manner may be from any of the embodiments described herein that produce CPD-11. CPD-06 produced in this manner may be used in any of the embodiments disclosed herein that utilizes CPD-06.

Scheme 23

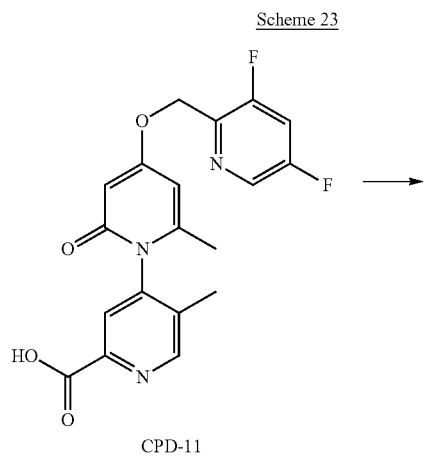

CPD-11

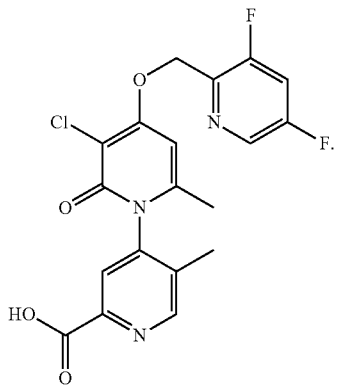

CPD-06

In some embodiments of forming CPD-06, the chlorination reagent is N-chlorosuccinimide.

In some embodiments, the forming of CPD-06 further comprises contacting CPD-11 with dichloroacetic acid.

Scheme 24 depicts another method of synthesizing CPD-15 starting from CPD-26. CPD-26 utilized in this manner may be from any of the embodiments described herein that produce CPD-26. CPD-15 produced in this manner may be used in any of the embodiments disclosed herein that utilizes CPD-15.

Scheme 24

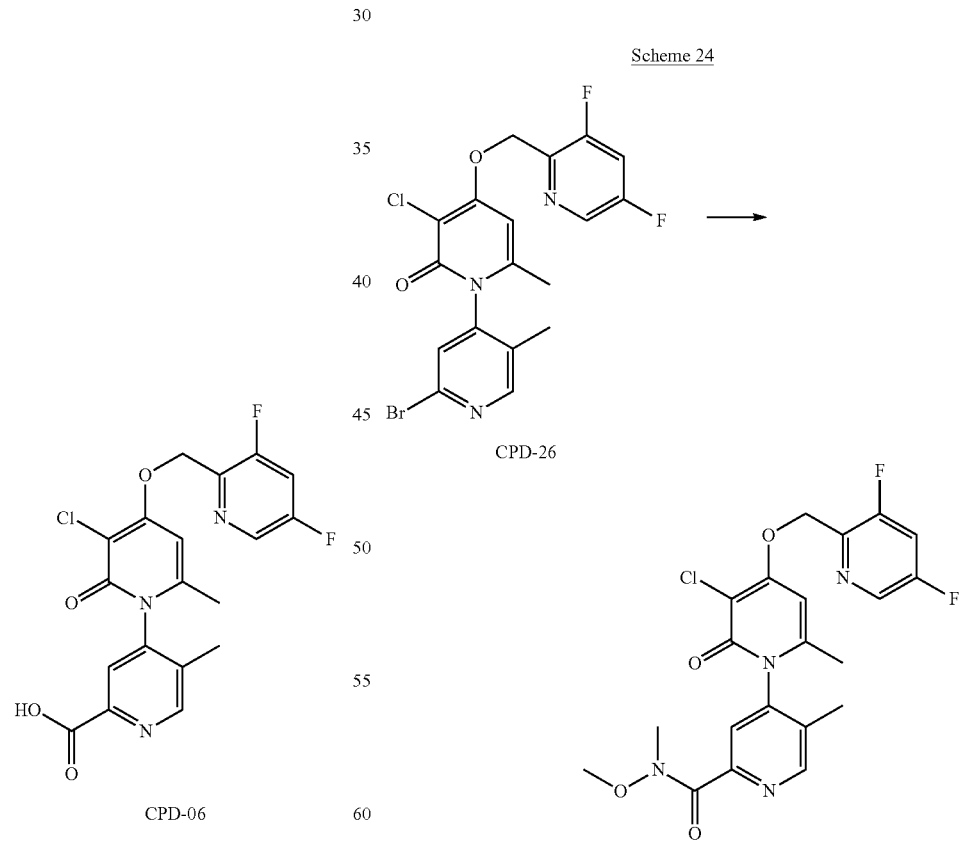

In accordance with Scheme 23, some embodiments of the present application involve a process for the preparation of the compound CPD-06 comprising contacting the compound CPD-11 with a chlorination reagent to form the compound In accordance with Scheme 24, some embodiments of the present application involve a process for the preparation of the compound CPD-15 comprising contacting the compound CPD-26 with MeNH(OMe)·HCl in the presence of a palladium catalyst, a phosphorus reagent, CO, and a base to form the compound

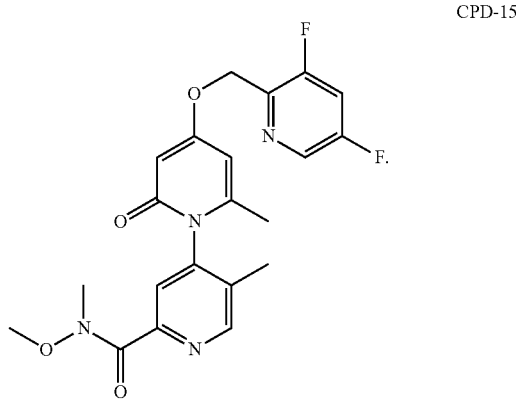 [SMILES: CON(C)C(=O)c1cc(-n2c(C)cc(OCc3ncc(F)cc3F)cc2=O)c(C)cn1]

CPD-15

In some embodiments of forming CPD-15, the palladium catalyst is Pd(OAc)$_2$.

In some embodiments of forming CPD-15, the phosphorus reagent is Xantphos.

In some embodiments of forming CPD-15, the base is K$_3$PO$_4$.

Scheme 25 depicts another method of synthesizing CPD-30 starting from CPD-26. CPD-26 utilized in this manner may be from any of the embodiments described herein that produce CPD-26. CPD-30 produced in this manner may be used in any of the embodiments disclosed herein that utilizes CPD-30.

In accordance with Scheme 25, some embodiments of the present application involve a process for the preparation of the compound CPD-30 comprising contacting the compound CPD-26 with a chlorination reagent to form the compound

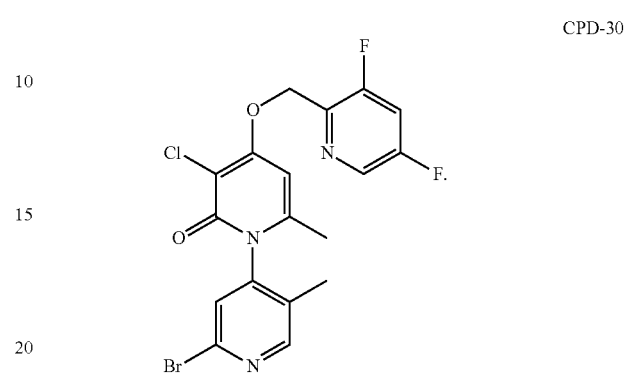

CPD-30

In some embodiments of forming CPD-30, the chlorination reagent is N-chlorosuccinimide.

In some embodiments, the forming of CPD-30 further comprises contacting CPD-26 with dichloroacetic acid.

Scheme 26 depicts another method of synthesizing CPD-30 starting from CPD-31. CPD-31 utilized in this manner may be from any of the embodiments described herein that produce CPD-31. CPD-30 produced in this manner may be used in any of the embodiments disclosed herein that utilizes CPD-30.

Scheme 25

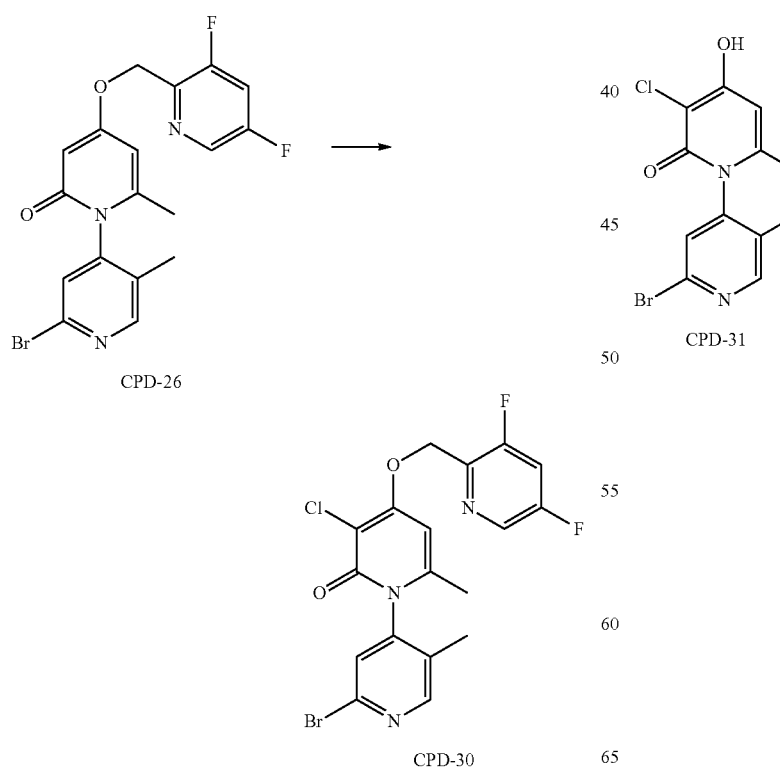

Scheme 26

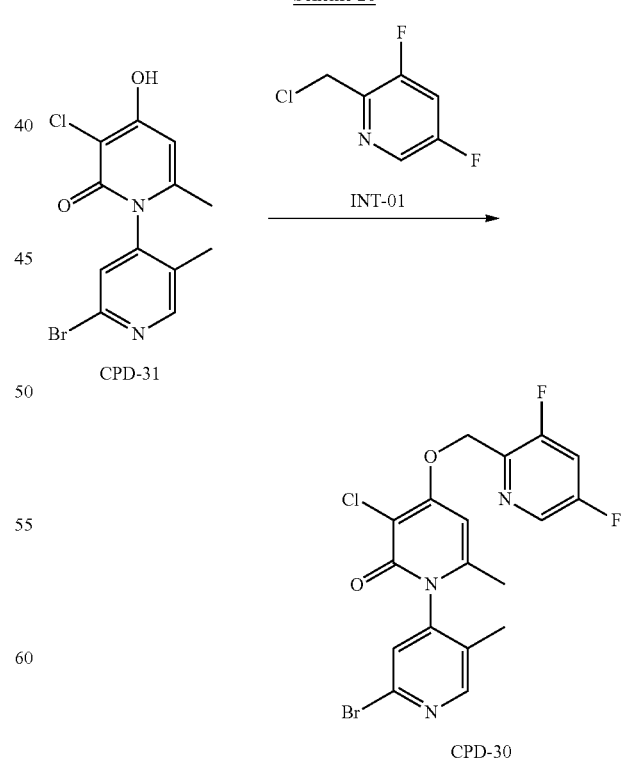

In accordance with Scheme 26, some embodiments of the present application involve a process for the preparation of the compound CPD-30 comprising contacting the compound CPD-31 with the compound

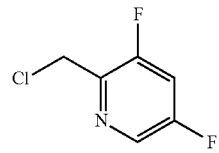

INT-01 and a base to form the compound

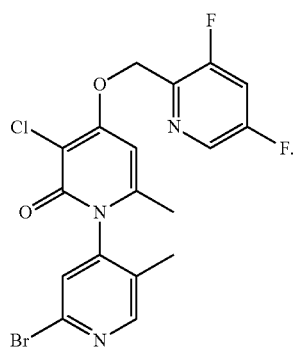

CPD-30

In some embodiments, the base used to form CPD-30 is selected from the group consisting of $K_2CO_3$ and $Cs_2CO_3$.

In some embodiments, the base used to form CPD-30 is $K_2CO_3$.

In some embodiments, the base used to form CPD-30 is $Cs_2CO_3$.

Scheme 27 depicts another method of synthesizing CPD-31 starting from CPD-25. CPD-25 utilized in this manner may be from any of the embodiments described herein that produce CPD-25. CPD-31 produced in this manner may be used in any of the embodiments disclosed herein that utilizes CPD-31.

Scheme 27

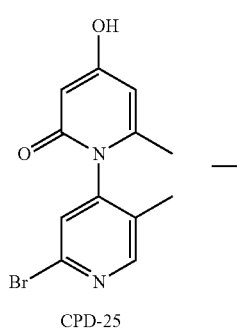 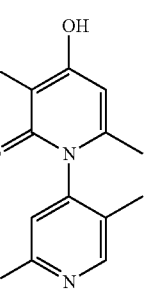

CPD-25　　　　CPD-31

In accordance with Scheme 27, some embodiments of the present application involve a process for the preparation of the compound CPD-31 comprising contacting the compound CPD-25 with a chlorination reagent to form the compound

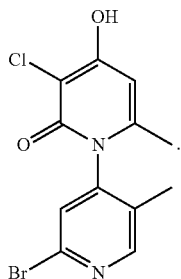

CPD-31

In some embodiments of forming CPD-31, the chlorination reagent is N-chlorosuccinimide.

In some embodiments, the forming of CPD-31 further comprises contacting CPD-25 with dichloroacetic acid.

Scheme 28 depicts another method of synthesizing CPD-28 starting from CPD-03. CPD-03 utilized in this manner may be from any of the embodiments described herein that produce CPD-03. CPD-28 produced in this manner may be used in any of the embodiments disclosed herein that utilizes CPD-28.

Scheme 28

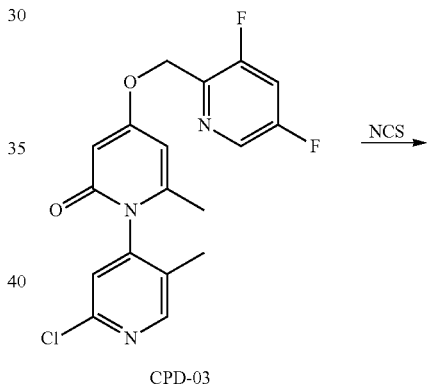

CPD-03

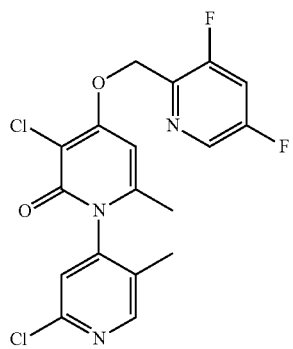

CPD-28

In accordance with Scheme 28, some embodiments of the present application involve a process for the preparation of the compound CPD-28 comprising contacting the compound CPD-03 with a chlorination reagent to form the compound

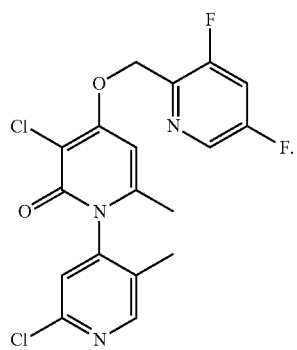

CPD-28

In some embodiments of forming CPD-28, the chlorination reagent is N-chlorosuccinimide.

In some embodiments, the forming of CPD-28 further comprises contacting CPD-03 with dichloroacetic acid.

Some embodiments of the present application describe a process for the preparation of TAUT-01 having the structure:

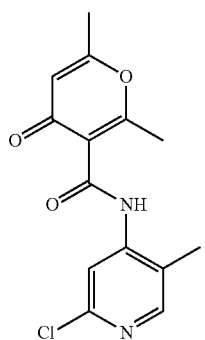

TAUT-01 comprising:
contacting the compound

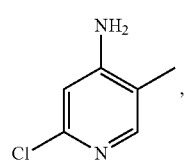

SM-01

, with the compound

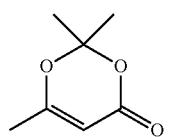

SM-02 in the presence of dimethylacetemide (DMAc) to form the compound TAUT-01.

Some embodiments are directed a method of obtaining the single or enriched atropisomers of CPD-02, said method comprising subjecting CPD-02 to a chromatographic separation to obtain

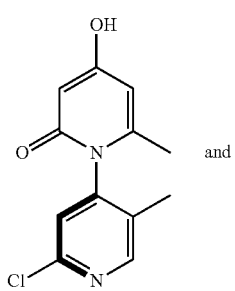

CPD-32 and

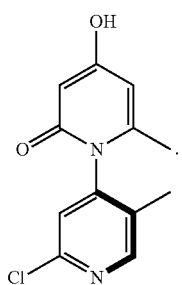

CPD-33

In some embodiments of obtaining the single or enriched atropisomers of CPD-02, the chromatographic separation comprises simulated moving bed (SMB) chromatography with a chiral stationary phase and a mobile phase.

In some embodiments of obtaining the single or enriched atropisomers of CPD-02, the chiral stationary phase is selected from the group consisting of Chiralpak® AD, Chiralpak® AS, Chiralpak® AY, Chiralpak® AZ, Chiralpak® OD, Chiralpak® OZ, Chiralpak® IA, Chiralpak® IB-N, Chiralpak® IC, Chiralpak® ID, Chiralpak® IE, Chiralpak® IF, Chiralpak® IG, and Chiralpak® IH.

In some embodiments of obtaining the single or enriched atropisomers of CPD-02, the chiral stationary phase is Chiralpak® IB-N.

In some embodiments of obtaining the single or enriched atropisomers of CPD-02, the mobile phase is selected from the group consisting of acetonitrile, methanol, acetonitrile and methanol, n-heptane and ethanol, n-heptane and dichloromethane, n-heptane and ethylacetate, dichloromethane and methanol, and dichloromethane and acetonitrile.

In some embodiments of obtaining the single or enriched atropisomers of CPD-02, the mobile phase is dichloromethane and acetonitrile.

Some embodiments are directed a method of obtaining the single or enriched atropisomers of CPD-03, said method comprising subjecting CPD-03 to a chromatographic separation to obtain

CPD-34

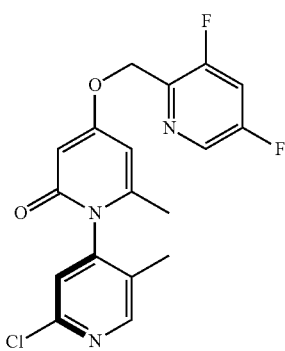

and

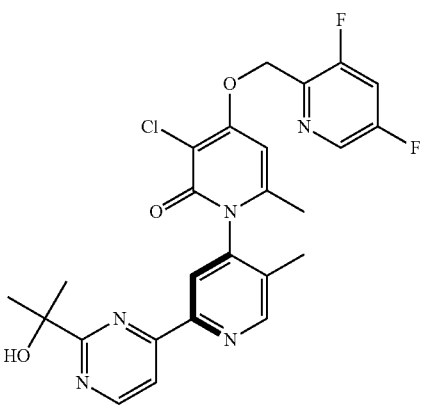

Formula (P)-I and

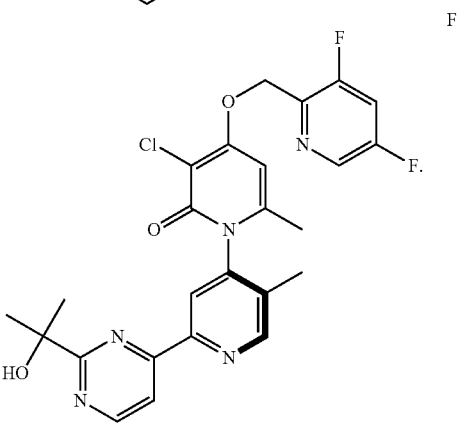

Formula (M)-I

CPD-35

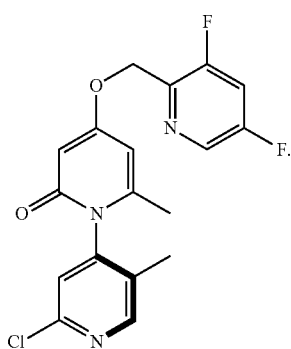

In some embodiments of obtaining the single or enriched atropisomers of CPD-03, the chromatographic separation comprises simulated moving bed (SMB) chromatography with a chiral stationary phase and a mobile phase.

In some embodiments of obtaining the single or enriched atropisomers of CPD-03, the chiral stationary phase is selected from the group consisting of Chiralpak® AD, Chiralpak® AS, Chiralpak® AY, Chiralpak® AZ, Chiralpak® OD, Chiralpak® OZ, Chiralpak® IA, Chiralpak® IB-N, Chiralpak® IC, Chiralpak® ID, Chiralpak® IE, Chiralpak® IF, Chiralpak® IG, and Chiralpak® IH.

In some embodiments of obtaining the single or enriched atropisomers of CPD-03, the chiral stationary phase is Chiralpak® IB-N.

In some embodiments of obtaining the single or enriched atropisomers of CPD-03, the mobile phase is selected from the group consisting of acetonitrile, methanol, acetonitrile and methanol, n-heptane and ethanol, n-heptane and dichloromethane, n-heptane and ethylacetate, dichloromethane and methanol, and dichloromethane and acetonitrile.

In some embodiments of obtaining the single or enriched atropisomers of CPD-03, the mobile phase is dichloromethane and acetonitrile.

Some embodiments are directed a method of obtaining the single or enriched atropisomers of CPD-20, said method comprising subjecting CPD-20 to a chromatographic separation to obtain In some embodiments of obtaining the single or enriched atropisomers of CPD-20, the chromatographic separation comprises simulated moving bed (SMB) chromatography with a chiral stationary phase and a mobile phase.

In some embodiments of obtaining the single or enriched atropisomers of CPD-20, the chiral stationary phase is selected from the group consisting of Chiralpak® AD, Chiralpak® AS, Chiralpak® AY, Chiralpak® AZ, Chiralpak® OD, Chiralpak® OZ, Chiralpak® IA, Chiralpak® IB-N, Chiralpak® IC, Chiralpak® ID, Chiralpak® IE, Chiralpak® IF, Chiralpak® IG, and Chiralpak® IH.

In some embodiments of obtaining the single or enriched atropisomers of CPD-20, the chiral stationary phase is Chiralpak® IB-N.

In some embodiments of obtaining the single or enriched atropisomers of CPD-20, the mobile phase is selected from the group consisting of acetonitrile, methanol, acetonitrile and methanol, n-heptane and ethanol, n-heptane and dichloromethane, n-heptane and ethylacetate, dichloromethane and methanol, and dichloromethane and acetonitrile.

In some embodiments of obtaining the single or enriched atropisomers of CPD-20, the mobile phase is dichloromethane and acetonitrile.

In any of the foregoing, when the mobile phase is in the form of a mixture the mixtures may be in a volumetric ratio of about 1:1, about 2:1, about 3:1, about 4:1, about 5:1, about 6:1, about 7:1, about 8:1, about 9:1, about 10:1, about 7:3, about 1:2, about 1:3, about 1:4, about 1:5, about 1:6, about 1:7, about 1:8, about 1:9, about 1:10, about 3:7, or any ratio in between any two ratios.

In some embodiments of the present application, the salts disclosed herein may be co-crystals.

Some embodiments of the present application relate to a compound, or a salt thereof, or a co-crystal thereof, selected from the group consisting of:
CPD-01
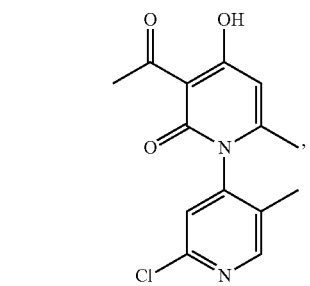
CPD-21
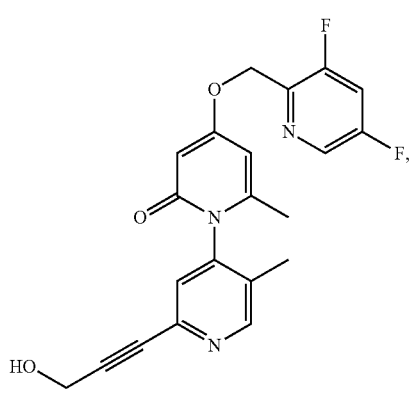
CPD-22
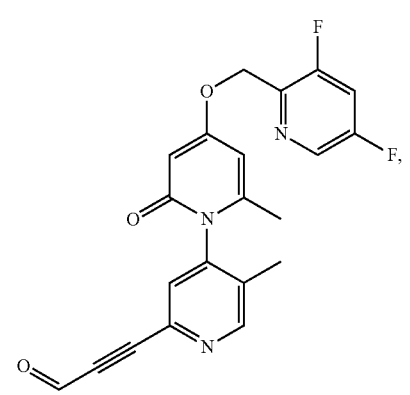
CPD-24
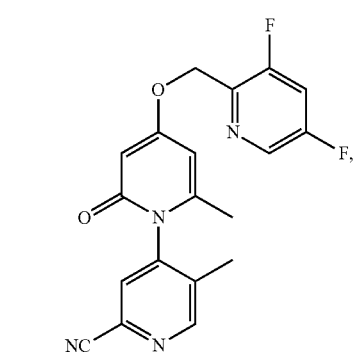
CPD-25
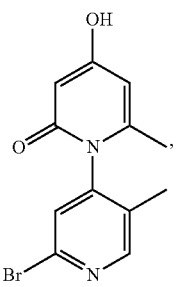
CPD-26
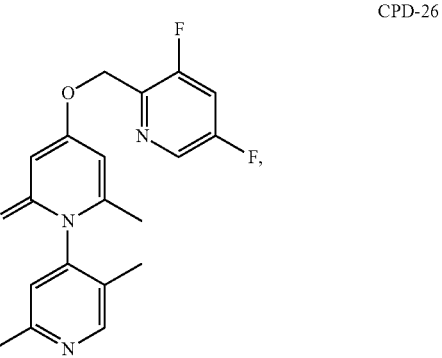
Isomer 1
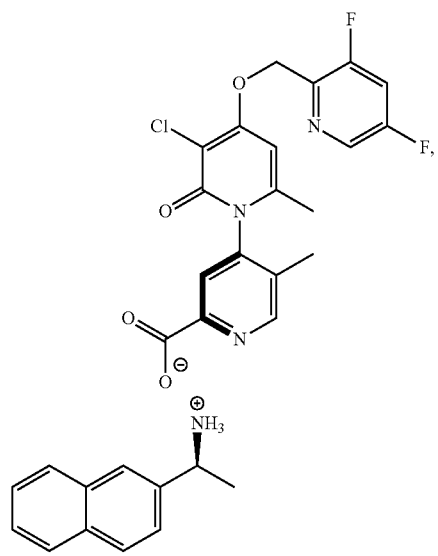
Salt A Isomer 2
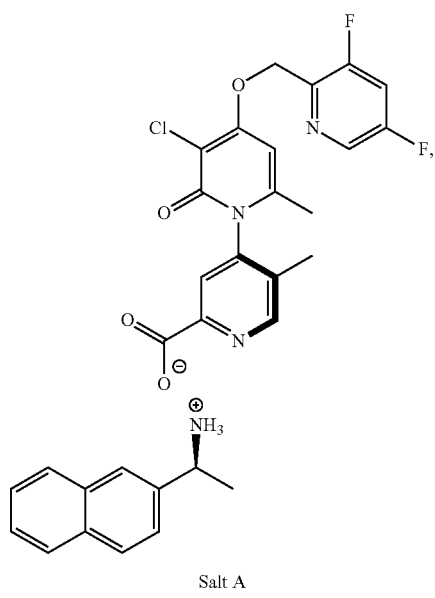
Salt A
Isomer 1
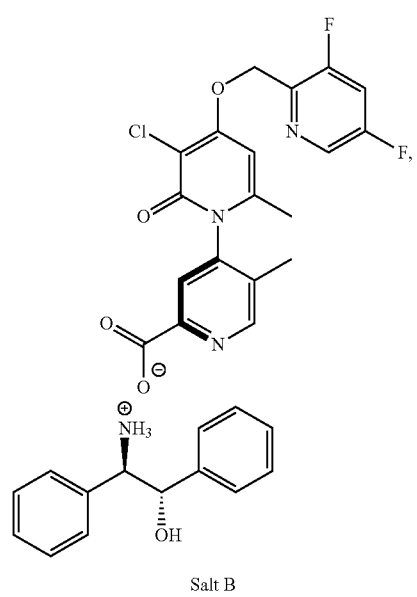
Salt B
Isomer 2
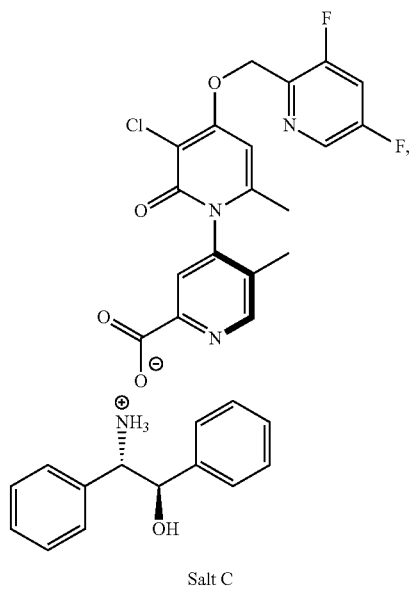
Salt C
CPD-27
CPD-28
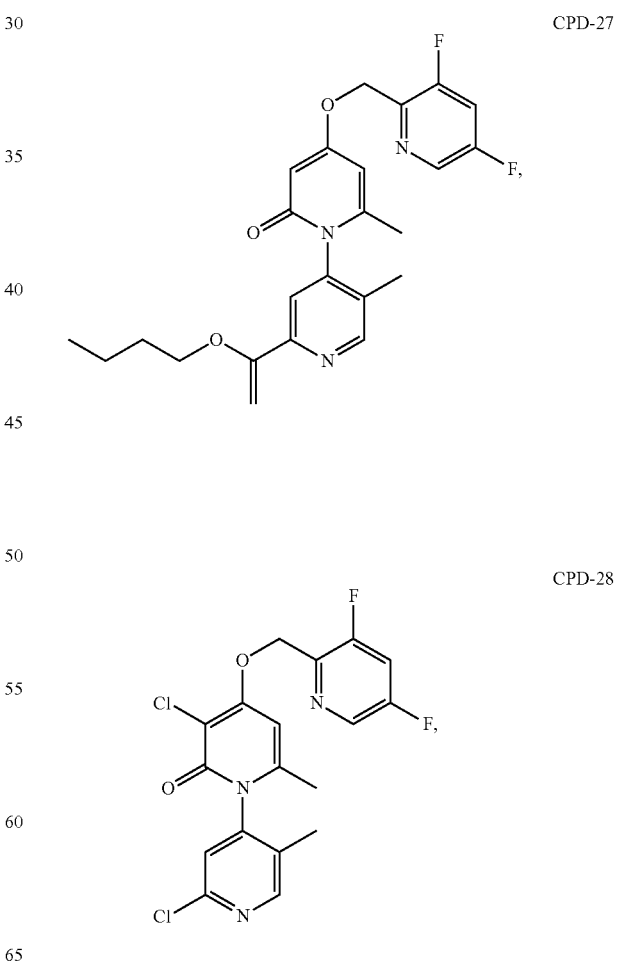

CPD-29

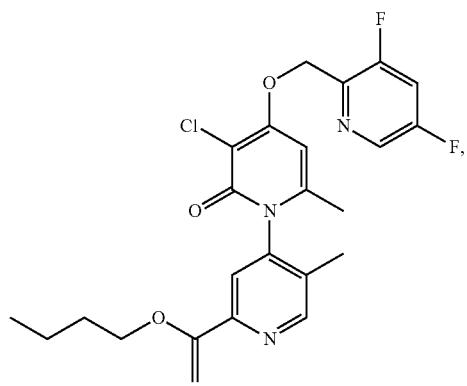

CPD-30

CPD-31

CPD-32

CPD-33

CPD-34

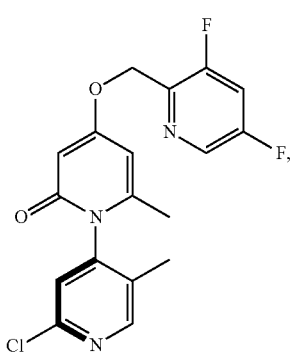

CPD-35

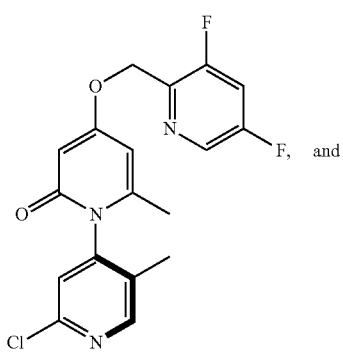

and

TAUT-01

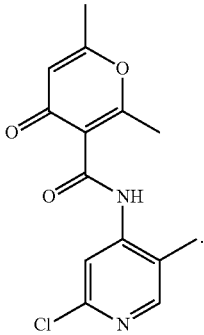

Experimental Section

The compound of the present invention can, but are not limited to being prepared using the methods illustrated in the experimental procedures detailed below. The starting materials used to prepare the compounds of the present invention are commercially available or can be prepared using routine methods known in the art. Solvents and reagents, whose synthetic preparations are not described below, can be purchased at Sigma-Aldrich or Fisher Scientific.

Representative procedures for the preparation of compounds of this disclosure are outlined below.

Example 1: General Resolution Screening Procedure

A stock solution of the racemate was made in pure MeOH or, in case of low solubility, in a mixture of MeOH and CHCl$_3$. 15 μmol of racemate was pipetted in 96 tube plates. To these solutions stock solutions of the resolving agents (24 basic or 36 acidic resolving agents) were added, each containing 15 μmol of resolving agent (or 7.5 μmol in case of half an equivalent of some double acids). The transfer solvents were allowed to evaporate in a circulation oven at 45° C. for two days. The dry solids were treated with 0.5 mL of the 8 solvent systems. The tubes were capped and heated to 70° C. for 15 minutes whilst being sonicated. The resulting mixtures were allowed to cool to RT over a couple of days. At least one and a maximum of two samples per resolving agents were worked up. The suspension was filtered and the solid and filtrate were each dissolved in MeOH (1.5 mL) and analyzed by chiral HPLC or chiral UPC as such. If the filtrate contained water, it was first concentrated to dryness with a flow of $N_2$ at 50° C. before the MeOH was added as the chiral methods are not compatible with water. The optical purities of solid and filtrate of a given experiment were used to determine the yield. Results of various resolving agents for isolating CPD-07 are shown in Table 1, entries A and B are further elaborated in Examples 9 and 10. Results of various resolving agents for isolating Formula P-(I).

The yield of precipitated material was calculated as follows:

$$\text{Crystallization yield} = -\frac{ee_{soln} - ee_0}{ee_{cryst} - ee_{soln}} \times 100\%$$

In which:

$ee_{soln}$=Optical purity of the solution $ee_0$=Optical purity of the material before the resolution $ee_{cryst}$=Optical purity of the precipitated material

TABLE 1

Screening Results for isolating CPD-07

| Entry | Resolving agent | Solvent | ee solid[a] | ee filtrate[a] | calc. yield |
|---|---|---|---|---|---|
| A | (S)-1-(naphthalen-2-yl)ethan-1-amine | EtOH | 99.86% | | |
| B | (1S, 2R)-2-amino-1,2-diphenylethan-1-ol | MeCN | 99.19% | | |
| 1 | (S)-2-amino-1-propanol (L-alaninol) | MeCN | −7% | +5% | 40% |
| 2 | (S)-2-amino-1-propanol (L-alaninol) | MEK | −6% | +7% | 55% |
| 3 | (R)-(+)-1-Phenylethylamine | MeCN | −5% | +5% | 46% |
| 4 | (R)-(+)-1-phenylethylamine | EtOH | Racemic | −6% | — |
| 5 | L-(−)-2-amino-1-butanol | MeCN | Racemic | −37% | — |
| 6 | L-(−)-2-amino-1-butanol | IPA | Racemic | −20% | — |
| 7 | (1R, 2S)-(−)-ephedrine | MeCN | −6% | Racemic | — |
| 8 | (1R, 2S)-(−)-ephedrine | EtOH | +26% | −24% | 48% |
| 9 | (S)-(+)-2-amino-3-methyl-1-butanol (L-valinol) | MeCN | −8% | +6% | 43% |
| 10 | (S)-(+)-2-amino-3-methyl-1-butanol (L-valinol) | IPA | −5% | Racemic | — |
| 11 | (S)-(−)-N-benzyl-α-methylbenzylamine | iPrOAc | −7% | Racemic | — |
| 12 | (+)-dehydroabietylamine (60% purity) | $H_2O$ | −25% | +11% | 30% |
| 13 | (+)-dehydroabietylamine (60% purity) | MeCN | −51% | +5% | 9% |
| 14 | (1S,2S)-(+)-2-amino-1-phenyl-1,3-propanediol | $H_2O$ | Racemic | −7% | — |
| 15 | (R)-(+)-3-pyrrolidinol | MeCN | Racemic | −19% | — |
| 16 | (R)-(+)-3-pyrrolidinol | MEK | Racemic | −9% | — |
| 17 | (S)-(+)-2-pyrrolidinemethanol (L-prolinol) | MeCN | Racemic | −10% | — |
| 18 | (S)-(+)-2-pyrrolidinemethanol (L-prolinol) | IPA | −15% | +34% | 69% |
| 19 | (S)-(−)-1-(1-naphthyl)ethylamine | MeCN | −15% | +17% | 52% |
| 20 | (S)-(−)-1-(1-naphthyl)ethylamine | IPA | Racemic | −8% | — |
| 21 | (R)-1-amino-2-propanol | MeCN | Racemic | −9% | — |
| 22 | (R)-1-amino-2-propanol | MEK | −20% | +33% | 62% |
| 23 | L-proline amide | MEK | −6% | +12% | 67% |
| 24 | L-proline amide | Dioxane | Racemic | −34% | — |
| 25 | (1R,2R)-(−)-pseudoephedrine | MeCN | Racemic | −6% | — |
| 26 | (1R,2R)-(−)-pseudoephedrine | EtOH | Racemic | Racemic | — |
| 27 | L-phenylalaninol | IPA | Racemic | −5% | — |
| 28 | (1R,2R)-2-amino-1-(4-nitrophenyl)propane-1,3-diol | IPA | −8% | Racemic | — |
| 29 | cinchonine | MeCN | −6% | Racemic | — |
| 30 | cinchonine | iPrOAc | −17% | Racemic | — |
| 31 | quinidine | iPrOAc | Racemic | −6% | — |
| 32 | quinine | Dioxane | Racemic | −16% | — |
| 33 | cinchonidine | iPrOAc | Racemic | −33% | — |
| 34 | (R)-(−)-2-phenylglycine amide | MeCN | Racemic | −22% | — |
| 35 | (R)-(−)-2-phenylglycine amide | MEK | Racemic | −10% | — |
| 36 | (R)-(+)-2-phenylpropylamine | MeCN | Racemic | −17% | — |

TABLE 2

Screening Results for isolating Formula P-(I)

| Entry | Resolving agent | Solvent | ee solid[a] | ee filtrate[a] | calc yield |
|---|---|---|---|---|---|
| 1 | dibenzoyl-L-tartaric acid hydrate (1 eq) | IPA | Racemic | Racemic | — |
| 2 | (R)-phencyphos hydrate (1 eq) | MeCN | Racemic | Racemic | — |
| 3 | (R)-phencyphos hydrate (1 eq) | 1:1 $H_2O$:EtOH | Racemic | Racemic | — |

TABLE 2-continued

Screening Results for isolating Formula P-(I)

| Entry | Resolving agent | Solvent | ee solid$^a$ | ee filtrate$^a$ | calc yield |
|---|---|---|---|---|---|
| 4 | (R)-chlocyphos (1 eq) | MeCN | Racemic | Racemic | — |
| 5 | (R)-chlocyphos (1 eq) | IPA | Racemic | Racemic | — |
| 6 | (−)-tartaric acid (1 eq) | 1:1 H$_2$O:EtOH | Racemic | Racemic | — |
| 7 | (+)-camphorsulfonic acid (1 eq) | 1:1 H$_2$O:EtOH | Racemic | Racemic | — |
| 8 | (+)-camphorsulfonic acid (1 eq) | iPrOAc | Racemic | Racemic | — |
| 9 | D-camphoric acid (1 eq) | 1:1 H$_2$O:EtOH | Racemic | Racemic | — |
| 10 | D-camphoric acid (1 eq) | iPrOAc | Racemic | Racemic | — |
| 11 | L-malic acid (1 eq) | 1:1 H$_2$O:EtOH | Racemic | Racemic | — |
| 12 | L-malic acid (1 eq) | iPrOAc | Racemic | Racemic | — |
| 13 | (S)-mandelic acid (1 eq) | 1:1 H$_2$O:EtOH | Racemic | Racemic | — |
| 14 | (S)-mandelic acid (1 eq) | EtOH | Racemic | Racemic | — |
| 15 | L-(−)-di-p-anisoyltartaric acid (1 eq) | 1:1 H$_2$O:EtOH | Racemic | Racemic | — |
| 16 | L-(−)-di-p-toluoyltartaric acid (1 eq) | IPA | Racemic | Racemic | — |
| 17 | (R)-anisyphos (1 eq) | 1:1 H$_2$O:EtOH | Racemic | Racemic | — |
| 18 | (R)-anisyphos (1 eq) | IPA | Racemic | Racemic | — |
| 19 | (R)-BINAP phosphate (1 eq) | iPrOAc | Racemic | Racemic | — |
| 20 | (R)-(−)-2-chloromandelic acid (1 eq) | 1:1 H$_2$O:EtOH | Racemic | Racemic | — |
| 21 | N-acetyl-L-phenylalanine (1 eq) | IPA | Racemic | Racemic | — |
| 22 | N-acetyl-D-leucine (1 eq) | 1:1 H$_2$O:EtOH | Racemic | Racemic | — |
| 23 | N-acetyl-D-leucine (1 eq) | iPrOAc | Racemic | Racemic | — |
| 24 | (R)-(−)-2-phenylpropionic acid (1 eq) | 1:1 H$_2$O:EtOH | Racemic | Racemic | — |
| 25 | (R)-(−)-2-phenylpropionic acid (1 eq) | IPA | Racemic | Racemic | — |
| 26 | (S)-naproxen (1 eq) | 1:1 H$_2$O:EtOH | Racemic | Racemic | — |
| 27 | (S)-naproxen (1 eq) | IPA | Racemic | Racemic | — |
| 28 | D-(+)-3-phenyllactic acid (1 eq) | 1:1 H$_2$O:EtOH | Racemic | Racemic | — |
| 29 | D-(+)-3-phenyllactic acid (1 eq) | IPA | Racemic | Racemic | — |
| 30 | N-acetyl-L-proline (1 eq) | H$_2$O | Racemic | Racemic | — |
| 31 | N-acetyl-L-proline (1 eq) | IPA | Racemic | Racemic | — |
| 32 | L-α-hydroxyisovaleric acid (1 eq) | 1:1 H$_2$O:EtOH | Racemic | Racemic | — |
| 33 | L-α-hydroxyisovaleric acid (1 eq) | iPrOAc | Racemic | Racemic | — |
| 34 | dibenzoyl-L-tartaric acid hydrate (0.5 eq) | EtOH | Racemic | Racemic | — |
| 35 | (−)-tartaric acid (0.5 eq) | 1:1 H$_2$O:EtOH | Racemic | Racemic | — |
| 36 | (−)-tartaric acid (0.5 eq) | IPA | Racemic | Racemic | — |
| 37 | L-(−)-di-p-anisoyltartaric acid (0.5 eq) | 1:1 H$_2$O:EtOH | Racemic | Racemic | — |
| 38 | L-(−)-di-p-anisoyltartaric acid (0.5 eq) | IPA | Racemic | Racemic | — |
| 39 | L-(−)-di-p-toluoyltartaric acid (0.5 eq) | 1:1 H$_2$O:EtOH | Racemic | Racemic | — |
| 40 | L-(−)-di-p-toluoyltartaric acid (0.5 eq) | IPA | Racemic | Racemic | — |
| 41 | (2S,3S)-2'-methoxytartranilic acid (1 eq) | MeCN | Racemic | Racemic | — |
| 42 | (2S,3S)-2'-methoxytartranilic acid (1 eq) | 1:1 H$_2$O:EtOH | Racemic | Racemic | — |
| 43 | (R)-phenylsuccinic acid (1 eq) | 1:1 H$_2$O:EtOH | Racemic | Racemic | — |
| 44 | (R)-phenylsuccinic acid (1 eq) | iPrOAc | Racemic | Racemic | — |
| 45 | (S)-(α-methyl-benzyl)phthalamic acid (1 eq) | 1:1 H$_2$O:EtOH | Racemic | Racemic | — |
| 46 | (S)-(α-methylbenzyl)phthalamic acid (1 eq) | IPA | Racemic | Racemic | — |
| 47 | (S)-4-bromomandelic acid (1 eq) | 1:1 H$_2$O:EtOH | Racemic | Racemic | — |
| 48 | (S)-4-bromomandelic acid (1 eq) | iPrOAc | Racemic | Racemic | — |
| 49 | Boc-D-phenylalanine (1 eq) | 1:1 H$_2$O:EtOH | Racemic | Racemic | — |
| 50 | Boc-D-phenylalanine (1 eq) | IPA | Racemic | Racemic | — |
| 51 | (2R,3R)-2'-chlorotartranilic acid (1 eq) | 1:1 H$_2$O:EtOH | Racemic | Racemic | — |
| 52 | (2R,3R)-2'-chlorotartranilic acid (1 eq) | IPA | Racemic | Racemic | — |
| 53 | Boc-D-homophenylalanine (1 eq) | 1:1 H$_2$O:EtOH | Racemic | Racemic | — |
| 54 | Boc-D-homophenylalanine (1 eq) | IPA | Racemic | Racemic | — |
| 55 | (S)-O'-acetyl mandelic acid (1 eq) | IPA | Racemic | Racemic | — |
| 56 | D-pyroglutamic acid (1 eq) | 1:1 H$_2$O:EtOH | Racemic | Racemic | |
| 57 | D-pyroglutamic acid (1 eq) | IPA | Racemic | Racemic | — |
| 58 | (2R,3R)-tartranilic acid | 1:1 H$_2$O:EtOH | Racemic | Racemic | — |
| 59 | (2R,3R)-tartranilic acid (1 eq) | MEK | Racemic | Racemic | — |
| 60 | (R)-4-methylmandelic acid (1 eq) | 1:1 H$_2$O:EtOH | Racemic | Racemic | — |
| 61 | (R)-4-methylmandelic acid (1 eq) | iPrOAc | Racemic | Racemic | — |
| 62 | (R)-α-methoxy-phenylacetic acid (1 eq) | 1:1 H$_2$O:EtOH | Racemic | Racemic | — |
| 63 | (R)-α-methoxy-phenylacetic acid (1 eq) | iPrOAc | Racemic | Racemic | — |

Example 2: Preparation of 3-acetyl-2'-chloro-4-hydroxy-5',6-dimethyl-2H-[1,4'-bipyridin]-2-one (CPD-01)

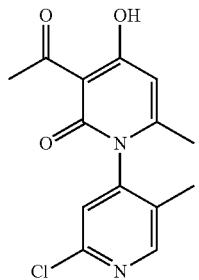

CPD-01

To a round bottom flask with a short path distillation head with a receiving flask was added 2-Chloro-5-methyl pyridine-4-amine (SM-01) (42.0 kg, 1.0 eq), 2,2,6-trimethyl-4H-1,3-dioxin-4-one (SM-02) (3.7 eq.) and DMAc (5.0 vol.). The reaction mass was slowly warmed to 115-120° C., and the reaction mass was maintained at that temperature for 4-6 hours. (Note: Acetone was collected in a receiving flask during this operation). The reaction was monitored by TLC and HPLC. After the reaction was completed, the mass was cooled to 50-60° C. Water (15.0 vol.) was slowly added into the reaction mass at 50-60° C. The mass was then cooled first to 25-30° C. and then to 5-10° C. After stirring for 1-2 hrs. the solids were filtered and washed with cold water (15.0 vol.). The solid was dried in a hot air oven to afford 79.5 kg (yield: 92.3%) of 3-acetyl-2'-chloro-4-hydroxy-5',6-dimethyl-2H-[1,4'-bipyridin]-2-one with HPLC purity 96.45%. $^1$H-NMR (400 MHz, DMSO-$d_6$): δ ppm 15.74 (s, 1H), 8.52 (s, 1H), 7.67 (s, 1H), 6.25 (s, 1H), 2.55 (s, 3H), 2.02 (s, 3H), 1.94 (s, 3H). MS (ES) m/z 293.62 (M+H).

Example 3: Preparation of 2'-chloro-4-hydroxy-5',6-dimethyl-2H-[1,4'-bipyridin]-2-one (CPD-02)

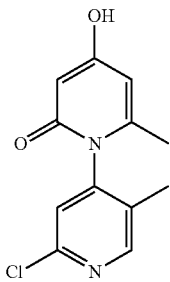

CPD-02

To a round bottom flask was added 3-acetyl-2'-chloro-4-hydroxy-5',6-dimethyl-2H-[1,4'-bipyridin]-2-one (CPD-01, Example 2) (65 kg, 1.0 eq), water (12.0 vol.), and IPA·HCl (20-25% solution) (3.5 vol.) at 25-30° C. The reaction mass was heated to 80-85° C. and maintained for 14-15 hours at this temperature. The reaction was monitored by TLC. After reaction was completed, the reaction mass was cooled to 5-10° C. and stirred for 2-3 hours. The solids were filtered, washed with cold water, and dried for 1-2 hours. The material was then dried at 50-55° C. in an oven to afford 63.3 kg (yield: 72.3%) of 2'-chloro-4-hydroxy-5',6-dimethyl-2H-[1,4'-bipyridin]-2-one with HPLC purity 83.7%. $^1$H-NMR (400 MHz, DMSO-$d_6$): δ ppm 10.8 (br s, 1H), 8.47 (s, 1H), 7.55 (s, 1H), 5.97-5.96 (m, 1H), 5.57 (d, J=2.4 Hz, 1H), 1.96 (s, 3H), 1.83 (s, 3H). MS (ES) m/z 251.52 (M+H).

Example 4: Preparation of 2-chloromethyl-3,5-difluoro-pyridine (INT-01)

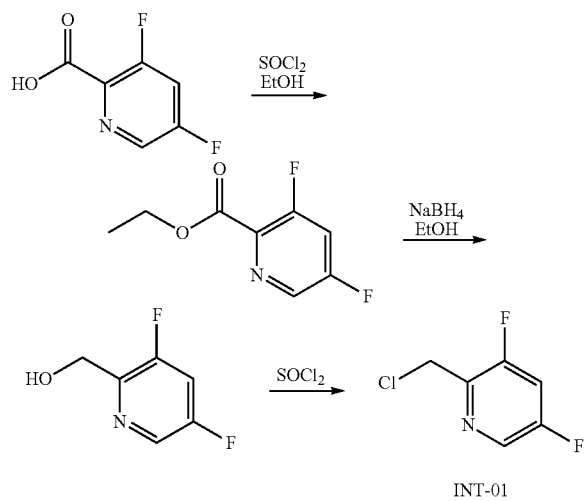

Step A: Preparation of 3,5-difluoro-pyridine-2-carboxylic Acid Ethyl Ester

To a cooled suspension (using an ice water bath) of 3,5-difluoropyridine-2-carboxylic acid (2.0 g, 12.6 mmol) in ethanol (5 mL), was added thionyl chloride (2 mL) in a dropwise manner. The solution was then heated to 60° C. for 3 h. The reaction was cooled to ambient temperature and was concentrated in vacuo to provide the ethyl ester, hydrochloride salt as a yellow oil (2.5 g).

Step B: Preparation of (3,5-difluoro-pyridin-2-yl)-methanol

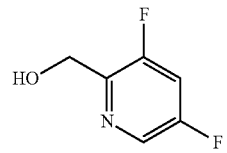

To a cooled (using an ice water bath) solution of 3,5-difluoro-pyridine-2-carboxylic acid ethyl ester of part A (2.5 g, 12.6 mmol) in ethanol (10 mL) was added sodium borohydride (1.43 g, 37.8 mmol) in a portion wise manner. The solution was stirred at 0° C. for thirty minutes and at ambient temperature for 2 h. The reaction mixture was cooled to 0° C. and saturated ammonium chloride was added dropwise. The solvent was removed in vacuo, and the resulting residue was partitioned between ethyl acetate and water. The organic layer was washed with saturated ammonium chloride, water, and brine, and dried over magnesium sulfate. The slurry was filtered and concentrated to provide the alcohol as a yellow oil (1.8 g): MS (ES) m/e 146 (M+H).

Step C: Preparation of 2-chloromethyl-3,5-difluoro-pyridine

INT-01

To a solution of (3,5-difluoro-pyridin-2-yl)-methanol from part B (1.8 g, 12.3 mmol) in dichloromethane (20 mL) was added three drops of N,N-dimethylformamide and cooled using an ice water bath. Thionyl chloride (2 mL) was added dropwise and the solution was stirred at ambient temperature for one hour. The solution was concentrated in vacuo to provide the chloro compound as a light brown liquid (1.75 g).

Example 5: Preparation of 2'-Chloro-4-((3,5-difluoropyridin-2-yl)methoxy)-5',6-dimethyl-2H-[1,4'-bipyridin]-2-one (CPD-03)

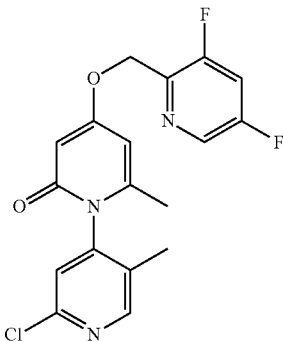

CPD-03

To a stirred solution of 2'-chloro-4-hydroxy-5',6-dimethyl-2H-[1,4'-bipyridin]-2-one (CPD-02, Example 3) (200.0 g, 1.0 eq.), in DMF (4 vol.) was added $K_2CO_3$ (1.5 eq.) at RT. It was stirred for 10-15 min. and then 2-(chloromethyl)-3,5-difluoro-pyridine (INT-01, Example 4) (1.2 eq.) in DMF (1 vol.) was added slowly at 25-35° C. The reaction mass was stirred for 16-18 h at 25-35° C. Progress of the reaction was monitored by TLC and IPC-HPLC. After completion of the reaction (Not More Than (NMT) 5.0% a/a), ice-cold water (20 vol.) was charged. The mixture was stirred for 1 h, and it was then extracted with EtOAc (3×10 vol.). The combined EtOAc layer was washed with water (1×5 vol.) and brine solution (1×5 vol.), and then it was dried over anhydrous Sodium sulphate. The EtOAc layer was distilled-off under reduced pressure at 45-50° C. MTBE was added (1-2 vol.) and the mixed solvent was co-distilled. Additional MTBE (3 vol.) was added at 25-35° C. to precipitate the solid. After filtration, the wet solid was dried under reduced pressure at 45-50° C. to afford 244 g (yield: 80.9%) of 2'-Chloro-4-((3,5-difluoropyridin-2-yl)methoxy)-5',6-dimethyl-2H-[1,4'-bipyridin]-2-one with HPLC purity 96.45%. $^1$H-NMR (400 MHz, DMSO-$d_6$): δ ppm 8.58 (d, 1H, J=2.4 Hz); 8.49 (s, 1H); 8.03-8.10 (m, 1H), 7.60 (s, 1H), 6.11-6.14 (m, 1H), 6.02 (d, 1H, J=2.4 Hz), 5.24 (d, 2H, J=1.6 Hz), 1.98 (s, 3H), 1.85 (s, 3H), MS (ES) m/z 378.19 (M+H).

Example 6: Preparation of Methyl 4-((3,5-difluoropyridin-2-yl)methoxy)-5',6-dimethyl-2-oxo-2H-[1,4'-bipyridine]-2'-carboxylate (CPD-04)

CPD-04

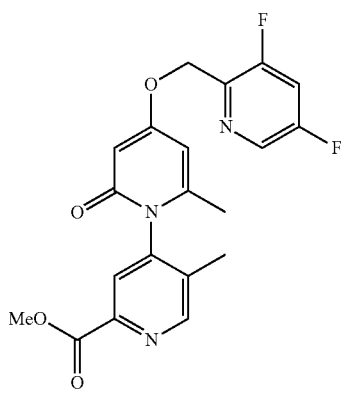

To a stirred suspension of 2'-Chloro-4-((3,5-difluoropyridin-2-yl)methoxy)-5',6-dimethyl-2H-[1,4'-bipyridin]-2-one (CPD-03, Example 5) (100.0 g, 1.0 eq.) in methanol (8 vol.), was added triethylamine (TEA (3.0 eq.). The reaction was purged with argon gas for 30 min. Then the reaction mass was transferred into an autoclave under argon atmosphere and Pd(dppf)Cl$_2$ (0.05 eq.) was added. The reactor was pressurized with CO gas (15 PSI (1 Kg)). The pressure was released and the reactor was re-pressurized with CO pressure (75 PSI (5 Kg)). The temperature was raised to 95-100° C. and maintained for 16 h. Progress of the reaction was monitored by TLC. After completion of reaction, the reaction mass was cooled to 25-35° C. The pressure was released and the reactor was purged with nitrogen. The contents of the reactor were filtered through a Celite bed. The filtrate was distilled under reduced pressure at below 45° C. and co-distilled with EtOAc (1-2 vol.). A crude solid was obtained. It was diluted with EtOAc (5 vol.) and was stirred for 1-2 h at 25-35° C. The mixture was filtered to afford 85 g (yield: 80%) of Methyl 4-((3,5-difluoropyridin-2-yl)methoxy)-5',6-dimethyl-2-oxo-2H-[1,4'-bipyridine]-2'-carboxylate with HPLC purity 99.37%. $^1$H-NMR (400 MHz, DMSO-$d_6$): δ ppm 8.78 (s, 1H), 8.59 (d, 1H, J=2.4 Hz), 8.04-8.11 (m, 1H), 7.90 (s, 1H), 6.12-6.15 (m, 1H), 6.03 (d, 1H, J=2.4 Hz), 5.24 (d, 2H, J=1.6 Hz), 3.88 (s, 3H), 2.09 (s, 3H), 1.81 (s, 3H); MS (ES) m/z 402.44 (M+H).

Example 7: Preparation of Methyl 3-chloro-4-((3,5-difluoropyridin-2-yl)methoxy)-5',6-dimethyl-2-oxo-2H-[1,4'-bipyridine]-2'-carboxylate (CPD-05)

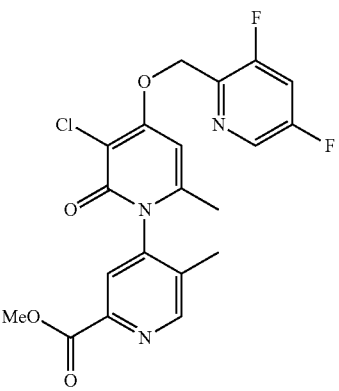

CPD-05

To a stirred suspension of Methyl 4-((3,5-difluoropyridin-2-yl)methoxy)-5',6-dimethyl-2-oxo-2H-[1,4'-bipyridine]-2'-carboxylate (CPD-04, Example 6) (100.0 g, 1.0 eq.) in IPA (15.0 vol.) was added dichloroacetic acid (0.25 eq.) at 25-35° C. Slowly, the temperature was raised to 45-50° C. and N-chlorosuccinimide (0.95 eq.) was added. Then the temperature was raised to 60-65° C., and it was maintained for 1 h. Progress of the reaction was monitored by TLC. After completion of reaction, the heating was stopped and the reaction mass was allowed to cool to 25-35° C., and then to 0-5° C. The solid was filtered and washed with IPA. The wet solid was dried at 45-50° C., to afford 70 g (yield: 64.5%) Methyl 3-chloro-4-((3,5-difluoropyridin-2-yl)methoxy)-5',6-dimethyl-2-oxo-2H-[1,4'-bipyridine]-2'-carboxylate with HPLC purity 96.46%. $^1$H-NMR (400 MHz, DMSO-$d_6$): δ ppm 8.82 (s, 1H), 8.60 (d, 1H, J=2.4 Hz), 8.07-8.13 (m, 1H), 8.03 (s, 1H), 6.79 (d, 1H, J=0.4 Hz), 5.47 (d, 2H, J=1.2 Hz), 3.89 (s, 3H), 2.08 (s, 3H), 1.92 (s, 3H), MS (ES) m/z 436.36 (M+H).

Example 8: Preparation of 3-Chloro-4-((3,5-difluoropyridin-2-yl)methoxy)-5',6-dimethyl-2-oxo-2H-[1,4'-bipyri-dine]-2'-carboxylic acid (CPD-06)

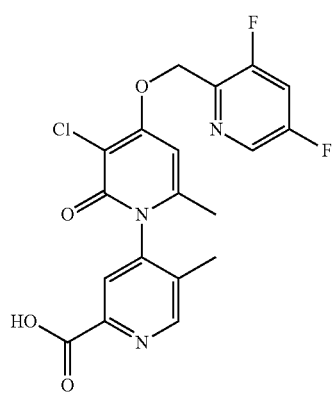

CPD-06

To a stirred solution of Methyl 3-chloro-4-((3,5-difluoropyridin-2-yl)methoxy)-5',6-dimethyl-2-oxo-2H-[1,4'-bipyridine]-2'-carboxylate (CPD-05, Example 7) (34 g, 1.0 eq.) in THF (5 vol.) was added LiOH·H$_2$O (3.0 eq.) in water (5 vol.) at 25-35° C. The mixture was then stirred for 2-4 h. After completion of the reaction, EtOAc (5.0 vol.) was added. After stirring for 10-15 min., the aqueous layer and the organic layers were separated. The pH of the aqueous was adjusted to 3-5 with dil. HCl (4M solution) at 25-35° C. The solid was filtered and washed with n-heptane (2-3 vol.). The obtained wet solid was dried at 45-50° C. for 3-4 h to afford 23.0 g (yield: 70.0%) of 3-Chloro-4-((3,5-difluoropyridin-2-yl)methoxy)-5',6-dimethyl-2-oxo-2H-[1,4'-bipyri-dine]-2'-carboxylic acid with HPLC purity 97.93%, Chiral HPLC purity, Isomer 1: Isomer 2 (48.75%:51.25%). $^1$H-NMR (400 MHz, DMSO-d6): δ ppm 13.35 (br s, 1H), 8.80 (s, 1H), 8.60 (d, 1H, J=2.4 Hz), 8.01-8.13 (m, 1H), 7.97 (s, 1H), 6.79 (s, 1H), 5.47 (d, 2H, J=1.6 Hz), 2.08 (s, 3H), 1.92 (s, 3H), MS (ES) m/z 422.36 (M+H).

Example 9: Preparation of (P)-3-Chloro-4-((3,5-difluoropyridin-2-yl)methoxy)-5',6-dimethyl-2-oxo-2H-[1,4'-bipyri-dine]-2'-carboxylic acid (CPD-07) via chiral separation with (S)-1-(naphthalen-2-yl)ethan-1-amine

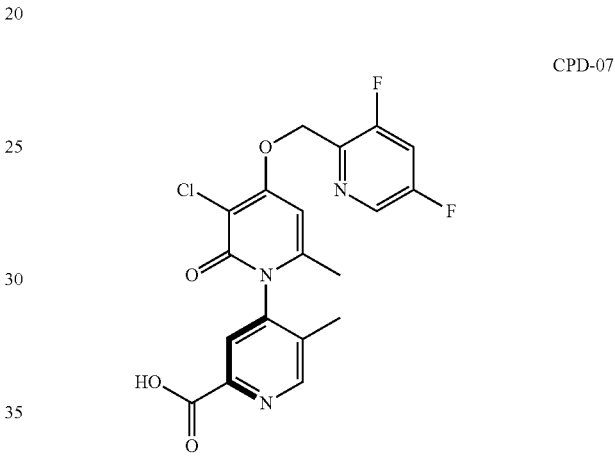

CPD-07

Step 1: Synthesis of (P)-3-Chloro-4-((3,5-difluoropyridin-2-yl)methoxy)-5',6-dimethyl-2-oxo-2H-[1,4'-bipyridine]-2'-carboxylate (S)-1-(naphthalen-2-yl)ethan-1-aminium (Isomer 1 Salt A)

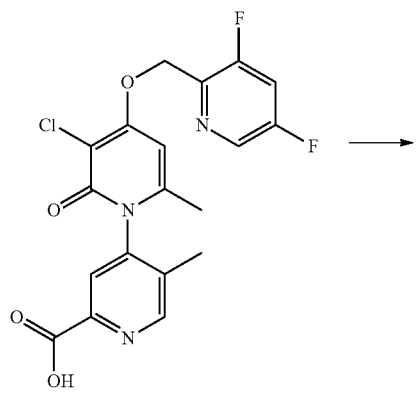

CPD-06

-continued

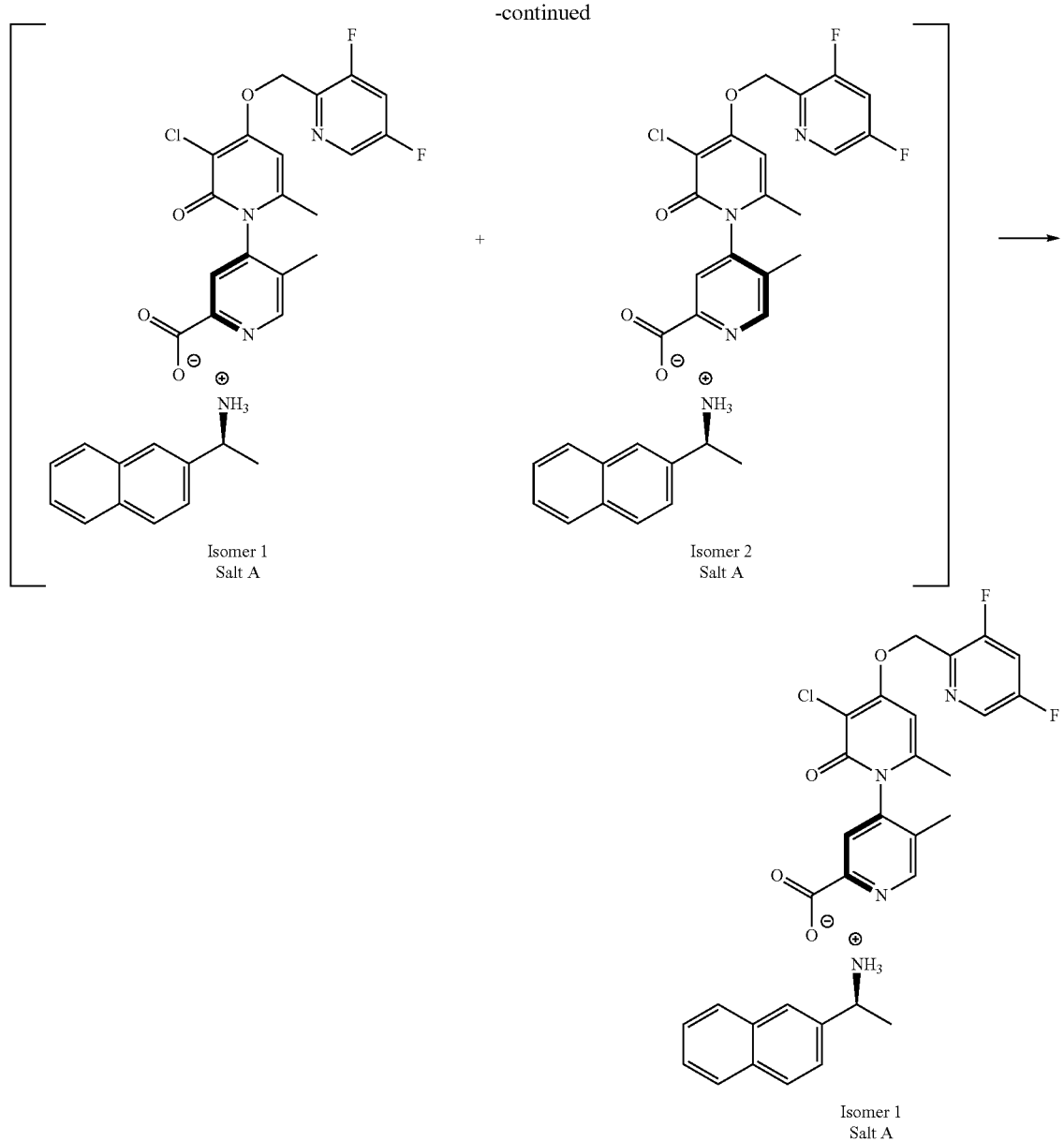

Isomer 1
Salt A

Isomer 2
Salt A

Isomer 1
Salt A

Step 1: To a stirred suspension of 3-Chloro-4-((3,5-difluoropyridin-2-yl)methoxy)-5',6-dimethyl-2-oxo-2H-[1,4'-bipyri-dine]-2'-carboxylic acid (CPD-06, Example 8, Isomer 1: Isomer 2, 48.75%:51.25%) (10 g, 1.0 eq.) in ethanol (200 mL, 20 vol.) (250 mL RBF) was added 0.9 eq. of (S)-1-(naphthalen-2-yl)ethan-1-amine at 60-65° C. (Observation: After addition of (S)-1-(naphthalen-2-yl)ethan-1-amine, a clear solution was observed). Then stirring was continued at 60-65° C. for 1-2 h. The stirred solution was allowed to cool to 25-35° C. for 24 h. The solid was filtered to afford 15 g of (P)-3-Chloro-4-((3,5-difluoropyridin-2-yl)methoxy)-5',6-dimethyl-2-oxo-2H-[1,4'-bipyri-dine]-2'-carboxylate (S)-1-(naphthalen-2-yl)ethan-1-aminium (Isomer 1 Salt A) with enhanced HPLC chiral purity (Isomer 1: Isomer 2, 55.36%:44.64%). $^1$H-NMR (400 MHz, DMSO-d$_6$): δ ppm 8.58-8.62 (m, 2H), 8.58-8.62 (m, 2H), 8.04-8.14 (m, 1H), 7.82-8.02 (m, 4H), 7.72 (s, 1H), 7.62-7.70 (m, 1H), 7.45-7.57 (m, 2H), 6.11-6.14 (m, 1H), 6.77 (s, 1H), 5.45 (d, 2H, J=10.8 Hz), 4.43-4.55 (m, 1H), 2.04 (s, 3H), 2.00 (s, 3H), 1.45-1.60 (m, 3H); MS (ES) m/z 422 (M+H).

Step 2: First purification of (P)-3-Chloro-4-((3,5-difluoropyridin-2-yl)methoxy)-5',6-dimethyl-2-oxo-2H-[1,4'-bipyridine]-2'-carboxylate (S)-1-(naphthalen-2-yl)ethan-1-aminium (Isomer 1 Salt A). The wet solid, (P)-3-Chloro-4-((3,5-difluoropyridin-2-yl)methoxy)-5',6-dimethyl-2-oxo-2H-[1,4'-bipyridine]-2'-carboxylate (S)-1-(naphthalen-2-yl)ethan-1-aminium (Isomer 1 Salt A), (Example 9, Step 1, 15 g, Isomer 1: Isomer 2, 55.36%:44.64) in methanol (10 vol.) was heated with stirring to 60-65° C. for 1-2 h to afford a clear solution. Then the heating was stopped and the solution was allowed to cool to 25-35° C. The mixture was stirred for 24 h and filtered. This afforded 11.5 g of (P)-3-Chloro-4-((3,5-difluoropyridin-2-yl)methoxy)-5',6-dimethyl-2-oxo-2H-[1,4'-bipyridine]-2'-carboxylate (S)-1-(naphthalen-2-yl)ethan-1-aminium with enhanced HPLC chiral purity (Isomer 1: Isomer 2, 83.06%:16.94%).

Step 3: Second purification of (P)-3-Chloro-4-((3,5-difluoropyridin-2-yl)methoxy)-5',6-dimethyl-2-oxo-2H-[1,4'-bipyridine]-2'-carboxylate (S)-1-(naphthalen-2-yl)ethan-1-aminium (Isomer 1 Salt A). The wet solid, (P)-3-Chloro-4-((3,5-difluoropyridin-2-yl)methoxy)-5',6-dimethyl-2-oxo-2H-[1,4'-bipyridine]-2'-carboxylate (S)-1-(naphthalen-2-yl)ethan-1-aminium (Isomer 1 Salt A), (Example 9, Step 2, 11.5 g, Isomer 1: Isomer 2, 83.06%:16.94%) in methanol (10 vol.) was heated to 60-65° C. with stirring for 1-2 h. Then the heating was stopped and the solution was allowed to cool to 25-35° C. The mixture was stirred for 24 h and then filtered. This afforded 8.9 g of (P)-3-Chloro-4-((3,5-difluoropyridin-2-yl)methoxy)-5',6-dimethyl-2-oxo-2H-[1,4'-bipyridine]-2'-carboxylate (S)-1-(naphthalen-2-yl)ethan-1-aminium (Isomer 1 Salt A) with enhanced HPLC chiral purity (Isomer 1: Isomer 2, 92.48%:7.52%).

Step 4: Third purification of (P)-3-Chloro-4-((3,5-difluoropyridin-2-yl)methoxy)-5',6-dimethyl-2-oxo-2H-[1,4'-bipyridine]-2'-carboxylate (S)-1-(naphthalen-2-yl)ethan-1-aminium (Isomer 1 Salt A). The wet solid, (P)-3-Chloro-4-((3,5-difluoropyridin-2-yl)methoxy)-5',6-dimethyl-2-oxo-2H-[1,4'-bipyridine]-2'-carboxylate (S)-1-(naphthalen-2-yl)ethan-1-aminium (Isomer 1 Salt A), (Example 9, Step 3, 8.9 g, Isomer 1: Isomer 2, 92.48%:7.52%) in methanol (10 vol.) was heated to 60-65° C. with stirring for 1-2 h. Then the heating was stopped and the solution was allowed to cool to 25-35° C. The mixture was stirred for 24 h and then filtered. This afforded 8.0 g of (P)-3-Chloro-4-((3,5-difluoropyridin-2-yl)methoxy)-5',6-dimethyl-2-oxo-2H-[1,4'-bipyridine]-2'-carboxylate (S)-1-(naphthalen-2-yl)ethan-1-aminium (Isomer 1 Salt A) with enhanced HPLC chiral purity (Isomer 1: Isomer 2, 95.26%:4.74%).

Step 5: Fourth purification of (P)-3-Chloro-4-((3,5-difluoropyridin-2-yl)methoxy)-5',6-dimethyl-2-oxo-2H-[1,4'-bipyridine]-2'-carboxylate (S)-1-(naphthalen-2-yl)ethan-1-aminium (Isomer 1 Salt A). The wet solid, (P)-3-Chloro-4-((3,5-difluoropyridin-2-yl)methoxy)-5',6-dimethyl-2-oxo-2H-[1,4'-bipyridine]-2'-carboxylate (S)-1-(naphthalen-2-yl)ethan-1-aminium (Isomer 1 Salt A), (Example 9, Step 4, 8.0 g, Isomer 1: Isomer 2, 95.26%:4.74%) in methanol (10 vol.) was heated to 60-65° C. with stirring for 1-2 h. Then the heating was stopped and the solution was allowed to cool to 25-35° C. The mixture was stirred for 24 h and then filtered. This afforded 6.0 g of (P)-3-Chloro-4-((3,5-difluoropyridin-2-yl)methoxy)-5',6-dimethyl-2-oxo-2H-[1,4'-bipyridine]-2'-carboxylate (S)-1-(naphthalen-2-yl)ethan-1-aminium (Isomer 1 Salt A) with enhanced HPLC chiral purity (Isomer 1: Isomer 2, 98.29%:1.71%).

Step 6: Fifth purification of (P)-3-Chloro-4-((3,5-difluoropyridin-2-yl)methoxy)-5',6-dimethyl-2-oxo-2H-[1,4'-bipyridine]-2'-carboxylate (S)-1-(naphthalen-2-yl)ethan-1-aminium (Isomer 1 Salt A). The wet solid, (P)-3-Chloro-4-((3,5-difluoropyridin-2-yl)methoxy)-5',6-dimethyl-2-oxo-2H-[1,4'-bipyridine]-2'-carboxylate (S)-1-(naphthalen-2-yl)ethan-1-aminium (Isomer 1 Salt A), (Example 9, Step 5, 6.0 g, Isomer 1: Isomer 2, 98.29%:1.71) in methanol (10 vol.) was heated to 60-65° C. with stirring for 1-2 h. Then the heating was stopped and the solution was allowed to cool to 25-35° C. The mixture was stirred for 24 h and then filtered. This afforded 6.0 g of (P)-3-Chloro-4-((3,5-difluoropyridin-2-yl)methoxy)-5',6-dimethyl-2-oxo-2H-[1,4'-bipyridine]-2'-carboxylate (S)-1-(naphthalen-2-yl)ethan-1-aminium (Isomer 1 Salt A) with enhanced HPLC chiral purity (Isomer 1: Isomer 2, 98.29%:4.74%).

Step 7: Synthesis of (P)-3-Chloro-4-((3,5-difluoropyridin-2-yl)methoxy)-5',6-dimethyl-2-oxo-2H-[1,4'-bipyridine]-2'-carboxylic acid (CPD-07)

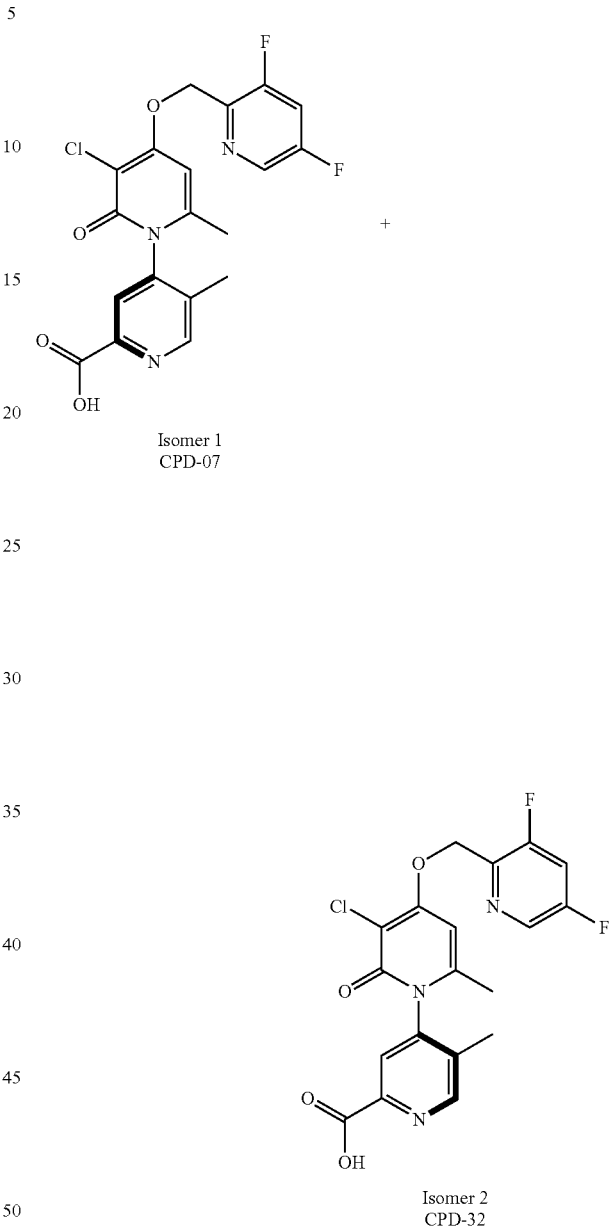

Isomer 1
CPD-07

Isomer 2
CPD-32

(P)-3-Chloro-4-((3,5-difluoropyridin-2-yl)methoxy)-5',6-dimethyl-2-oxo-2H-[1,4'-bipyridine]-2'-carboxylate (S)-1-(naphthalen-2-yl)ethan-1-aminium (Isomer 1 Salt A) (Example 9, Step 6, 4.2 g, Isomer 1: Isomer 2, 98.29%:4.74%) was dissolved in water (42 mL, 10 vol.) and basified with 2N NaOH to pH ~12. It was extracted three times with EtOAc (42 mL, 10 vol.). The EtOAc extract contained (S)-1-(naphthalen-2-yl)ethan-1-amine. The aq. layer was acidified with 2N HCl (pH 2) to precipitate the solid, The solid was filtered and washed with n-heptane (2 vol.) to afford chiral, (P)-3-Chloro-4-((3,5-difluoropyridin-2-yl)methoxy)-5',6-dimethyl-2-oxo-2H-[1,4'-bipyri-dine]-2'-carboxylic acid (2.3 g, Dry) HPLC chiral purity (Isomer I, Isomer 2, 99.86%:0.14%).

Example 10: Preparation of (P)-3-Chloro-4-((3,5-difluoropyridin-2-yl)methoxy)-5',6-dimethyl-2-oxo-2H-[1,4'-bipyri-dine]-2'-carboxylic acid (CPD-07) via chiral separation with (1S,2R)-2-amino-1,2-diphenylethan-1-ol
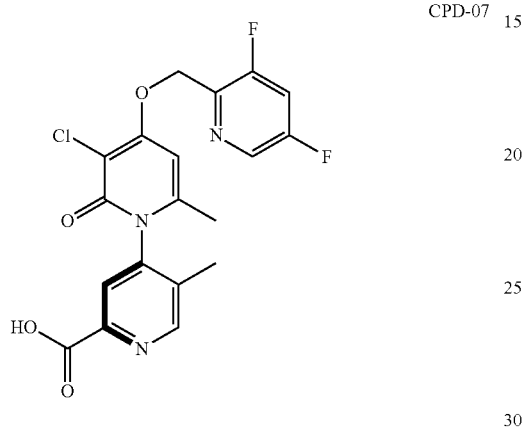
CPD-07
Step 1: Synthesis of (P)-3-Chloro-4-((3,5-difluoropyridin-2-yl)methoxy)-5',6-dimethyl-2-oxo-2H-[1,4'-bipyridine]-2'-carboxylate (1R,2S)-2-hydroxy-1,2-diphenylethan-1-aminium (Isomer 1 Salt B)
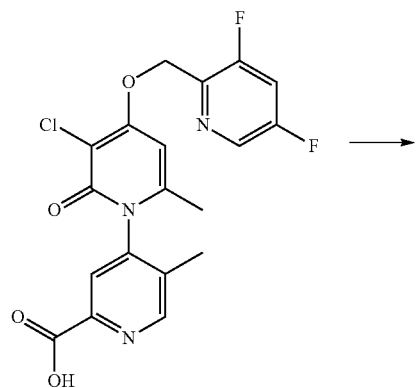
CPD-06

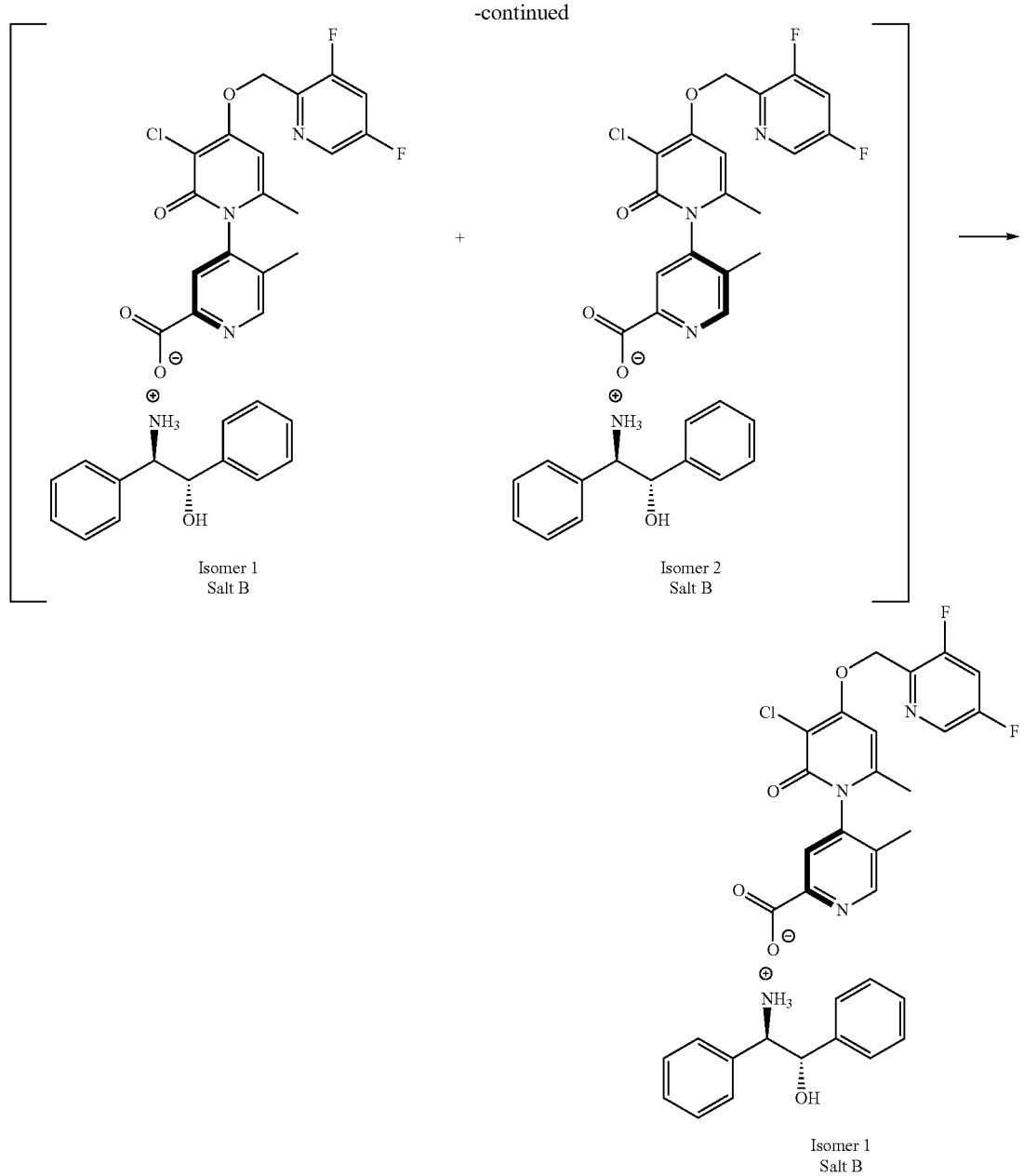

To a stirred suspension of 3-Chloro-4-((3,5-difluoropyridin-2-yl)methoxy)-5',6-dimethyl-2-oxo-2H-[1,4'-bipyridine]-2'-carboxylic acid (CPD-06, Example 8) (5 g, 1.0 eq.) in acetonitrile (100 mL, 20 vol.) (250 mL RBF) was added 1.0 eq. of (1S,2R)-2-amino-1,2-diphenylethan-1-ol at 60-65° C. (Observation: After addition of (1S,2R)-2-amino-1,2-diphenylethan-1-ol, a clear solution was observed). Stirring was continued at 60-65° C. for 1-2 h. The stirred solution was allowed to cool to 25-35° C. for 24 h. The solid was filtered to afford 4 g of (P)-3-Chloro-4-((3,5-difluoropyridin-2-yl)methoxy)-5',6-dimethyl-2-oxo-2H-[1,4'-bipyridine]-2'-carboxylate (1R,2S)-2-hydroxy-1,2-diphenylethan-1-aminium (Isomer 1 Salt B) with enhanced HPLC chiral purity (Isomer 1: Isomer 2, 58.98%:41.02%). $^1$H-NMR (400 MHz, DMSO-$d_6$): δ ppm 8.68 (s, 1H), 8.59 (d, 1H, J=2.4 Hz), 8.05-8.14 (m, 1H), 7.45-7.57 (m, 2H), 7.81 (s, 1H), 7.08-7.25 (m, 11H), 6.77 (s, 1H), 5.47 (d, 2H, J=1.6 Hz), 4.8-4.95 (m, 1H), 4.16-4.24 (m, 1H), 2.08 (s, 3H), 2.06 (s, 3H), 1.91 (d, 3H, J=7.2 Hz); MS (ES) m/z 422.28 (M+H).

Step 2: First purification of (P)-3-Chloro-4-((3,5-difluoropyridin-2-yl)methoxy)-5',6-dimethyl-2-oxo-2H-[1,4'-bipyridine]-2'-carboxylate (1R,2S)-2-hydroxy-1,2-diphenylethan-1-aminium (Isomer 1 Salt B). The wet solid, (P)-3-Chloro-4-((3,5-difluoropyridin-2-yl)methoxy)-5',6-dimethyl-2-oxo-2H-[1,4'-bipyridine]-2'-carboxylate (1R,2S)-2-hydroxy-1,2-diphenylethan-1-aminium (Isomer 1 Salt B), (Example 10, Step 1, 4 g, Isomer 1: Isomer 2, 58.98%:41.02%) in methanol (10 vol.) was heated with stirring to 60-65° C. for 1-2 h to afford a clear solution. Then the heating was stopped, and the solution was allowed to cool to 25-35° C. The mixture was stirred for 24 h and filtered. This afforded 3.1 g (P)-3-Chloro-4-((3,5-difluoropyridin-2-yl)methoxy)-5',6-dimethyl-2-oxo-2H-[1,4'-bipyridine]-2'-carboxylate (1R, 2S)-2-hydroxy-1,2-diphenylethan-1-aminium (Isomer 1 Salt B) with enhanced HPLC chiral purity (Isomer 1: Isomer 2, 75.72%:24.28%).

Step 3: Second purification of (P)-3-Chloro-4-((3,5-difluoropyridin-2-yl)methoxy)-5',6-dimethyl-2-oxo-2H-[1,4'-bipyridine]-2'-carboxylate (1R,2S)-2-hydroxy-1,2-diphenylethan-1-aminium (Isomer 1 Salt B). The wet solid, (P)-3-Chloro-4-((3,5-difluoropyridin-2-yl)methoxy)-5',6-dimethyl-2-oxo-2H-[1,4'-bipyridine]-2'-carboxylate (1R, 2S)-2-hydroxy-1,2-diphenylethan-1-aminium (Isomer 1 Salt B), (Example 10. Step 2, 3.1 g, Isomer 1: Isomer 2, 75.72%: 24.28%) in methanol (10 vol.) was heated with stirring to 60-65° C. for 1-2 h to afford a clear solution. Then the heating was stopped, and the solution was allowed to cool to 25-35° C. The mixture was stirred for 24 h and filtered. This afforded 2.0 g of (P)-3-Chloro-4-((3,5-difluoropyridin-2-yl)methoxy)-5',6-dimethyl-2-oxo-2H-[1,4'-bipyridine]-2'-carboxylate (1R,2S)-2-hydroxy-1,2-diphenylethan-1-aminium (Isomer 1 Salt B) with enhanced HPLC chiral purity (Isomer 1: Isomer 2, 81.27%:18.73%).

Step 4: Third purification of (P)-3-Chloro-4-((3,5-difluoropyridin-2-yl)methoxy)-5',6-dimethyl-2-oxo-2H-[1,4'-bipyridine]-2'-carboxylate (1R,2S)-2-hydroxy-1,2-diphenylethan-1-aminium (Isomer 1 Salt B). The wet solid, (P)-3-Chloro-4-((3,5-difluoropyridin-2-yl)methoxy)-5',6-dimethyl-2-oxo-2H-[1,4'-bipyridine]-2'-carboxylate (1R, 2S)-2-hydroxy-1,2-diphenylethan-1-aminium (Isomer 1 Salt B), (Step 3, 2 g, Isomer 1: Isomer 2, 81.27%:18.73%) in methanol (10 vol.) was heated to 60-65° C. with stirring for 1-2 h. Then the heating was stopped and the solution was allowed to cool to 25-35° C. The mixture was stirred for 24 h and then filtered. This afforded 0.5 g of (P)-3-Chloro-4-((3,5-difluoropyridin-2-yl)methoxy)-5',6-dimethyl-2-oxo-2H-[1,4'-bipyridine]-2'-carboxylate (1R,2S)-2-hydroxy-1,2-diphenylethan-1-aminium (Isomer 1 Salt B) with enhanced HPLC chiral purity (Isomer 1: Isomer 2, 99.19%:0.81%).

Step 5: Synthesis of (P)-3-Chloro-4-((3,5-difluoropyridin-2-yl)methoxy)-5',6-dimethyl-2-oxo-2H-[1,4'-bipyridine]-2'-carboxylic acid (CPD-07)

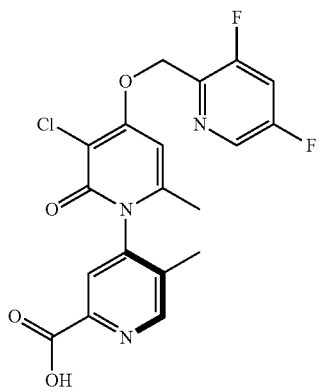

Isomer 2
CPD-32

(P)-3-Chloro-4-((3,5-difluoropyridin-2-yl)methoxy)-5',6-dimethyl-2-oxo-2H-[1,4'-bipyridine]-2'-carboxylate (1R, 2S)-2-hydroxy-1,2-diphenylethan-1-aminium (Isomer 1 Salt B) (Step 4, 0.5 g, Isomer 1: Isomer 2, 99.19%:0.81%) was dissolved in water (5 mL, 10 vol.) and basified with 2N NaOH to pH ~12. It was extracted three times with EtOAc (5 mL, 10 vol.). The EtOAc extract contained (1S,2R)-2-amino-1,2-diphenylethan-1-ol. The aq. layer was acidified with 2N HCl (pH 2) to precipitate the solid, The solid was filtered and washed with n-heptane (2 vol.) to afford chiral, (P)-3-Chloro-4-((3,5-difluoropyridin-2-yl)methoxy)-5',6-dimethyl-2-oxo-2H-[1,4'-bipyri-dine]-2'-carboxylic acid (0.25 g, Dry) HPLC chiral purity (Isomer 1: Isomer 2, 99.19%:0.81%).

Example 11: Preparation of (M)-3-Chloro-4-((3,5-difluoropyridin-2-yl)methoxy)-5',6-dimethyl-2-oxo-2H-[1,4'-bipyri-dine]-2'-carboxylic acid via chiral separation with (1R,2S)-2-amino-1,2-diphenylethan-1-ol (CPD-32)

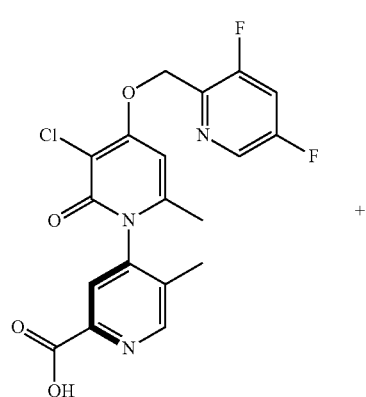

Isomer 1
CPD-07

+

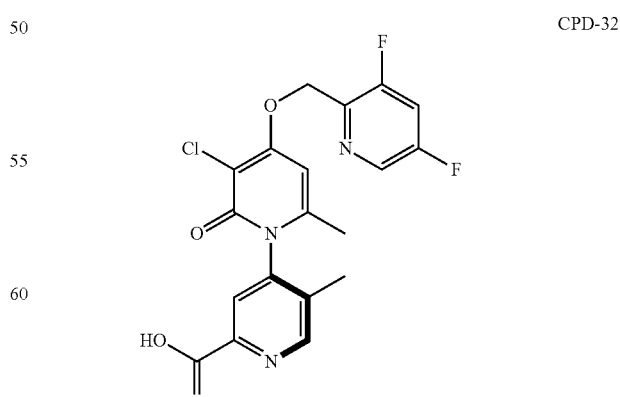

CPD-32

Step 1: Synthesis of (M)-3-Chloro-4-((3,5-difluoropyridin-2-yl)methoxy)-5',6-dimethyl-2-oxo-2H-[1,4'-bipyridine]-2'-carboxylate (1S,2R)-2-hydroxy-1,2-diphenylethan-1-aminium (Isomer 2 Salt C).

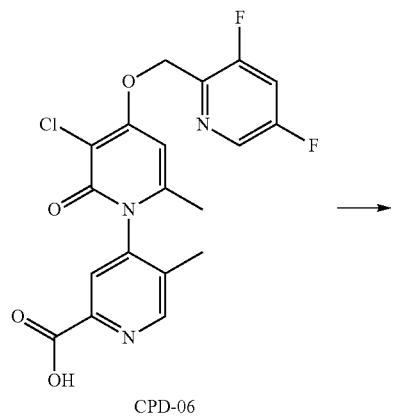

CPD-06

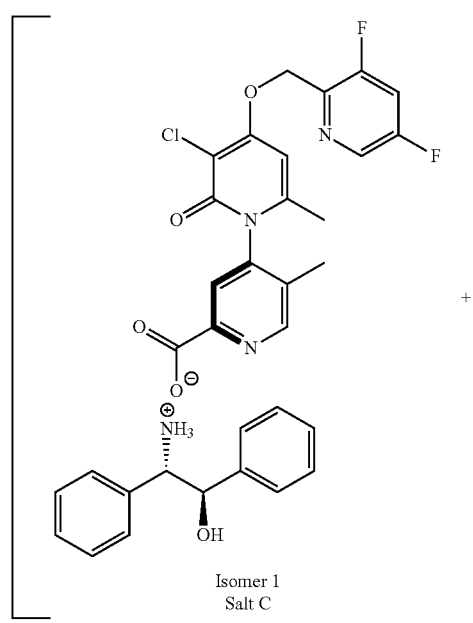

Isomer 1
Salt C

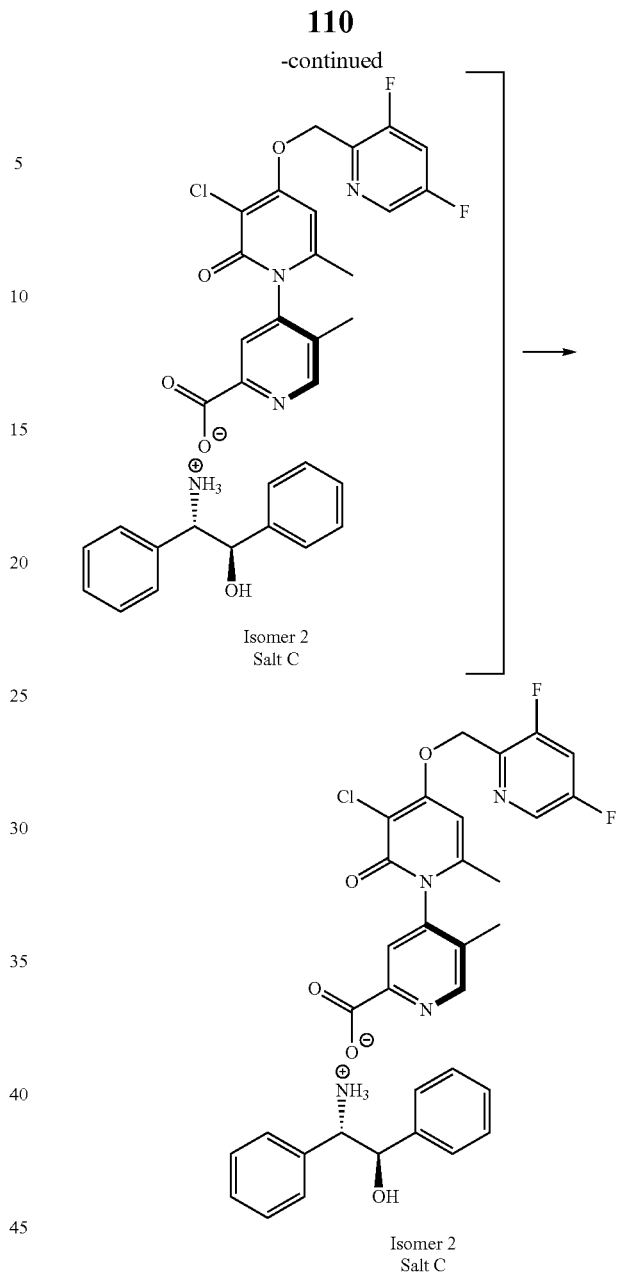

To a stirred suspension of 3-Chloro-4-((3,5-difluoropyridin-2-yl)methoxy)-5',6-dimethyl-2-oxo-2H-[1,4'-bipyridine]-2'-carboxylic acid (CPD-06, Example 8) (5.0 g, 1.0 eq.) in acetonitrile (100 mL, 20 vol.) (250 mL RBF) was added 1.0 eq. of (1R,2S)-2-amino-1,2-diphenylethan-1-ol at 60-65° C. (Observation: After addition of (1R,2S)-2-amino-1,2-diphenylethan-1-ol, a clear solution was observed). Then stirring was stirred at 60-65° C. for 1-2 h. The stirred solution was allowed to cool to 25-35° C. for 24 h. The solid was filtered to afford 6.0 g of (M)-3-Chloro-4-((3,5-difluoropyridin-2-yl)methoxy)-5',6-dimethyl-2-oxo-2H-[1,4'-bipyrid-ine]-2'-carboxylate (1S,2R)-2-hydroxy-1,2-diphenylethan-1-aminium (Isomer 2 Salt C) with enhanced HPLC chiral purity (Isomer 1: Isomer 2, 18.86%:81.14%).
$^1$H-NMR (400 MHz, DMSO-d6): δ ppm 8.68 (s, 1H), 8.59 (d, 1H, J=2.4 Hz), 8.04-8.12 (m, 1H), 7.81 (s, 1H), 7.16-7.29 (m, 9H), 7.08-7.15 (m, 2H), 6.77 (s, 1H), 5.47 (d, 2H, J=1.2 Hz), 4.90 (s, 1H), 4.21 (d, 1H), 2.03 (s, 3H), 1.91 (s, 3H); MS (ES) m/z 422 (M+H).

Step 2: First purification of (M)-3-Chloro-4-((3,5-difluoropyridin-2-yl)methoxy)-5',6-dimethyl-2-oxo-2H-[1,4'-bipyridine]-2'-carboxylate (1S,2R)-2-hydroxy-1,2-diphenylethan-1-aminium (Isomer 2 Salt C). The wet solid, (M)-3-Chloro-4-((3,5-difluoropyridin-2-yl)methoxy)-5',6-dimethyl-2-oxo-2H-[1,4'-bipyridine]-2'-carboxylate (1S,2R)-2-hydroxy-1,2-diphenylethan-1-aminium (Isomer 2 Salt C), (Step 1, 6.0 g, Isomer 1: Isomer 2, 18.86%:81.14%) in methanol (10 vol.) was heated with stirring to 60-65° C. for 1-2 h to afford a clear solution. Then the heating was stopped and the solution was allowed to cool to 25-35° C. The mixture was stirred for 24 h and filtered. This afforded 4.0 g (M)-3-Chloro-4-((3,5-difluoropyridin-2-yl)methoxy)-5',6-dimethyl-2-oxo-2H-[1,4'-bipyridine]-2'-carboxylate (1S,2R)-2-hydroxy-1,2-diphenylethan-1-aminium (Isomer 2 Salt C) with enhanced HPLC chiral purity (Isomer 1: Isomer 2, 15.487%:84.52%).

Step 3: Second purification of (M)-3-Chloro-4-((3,5-difluoropyridin-2-yl)methoxy)-5',6-dimethyl-2-oxo-2H-[1,4'-bipyridine]-2'-carboxylate (1S,2R)-2-hydroxy-1,2-diphenylethan-1-aminium (Isomer 2 Salt C). The wet solid, (M)-3-Chloro-4-((3,5-difluoropyridin-2-yl)methoxy)-5',6-dimethyl-2-oxo-2H-[1,4'-bipyridine]-2'-carboxylate (1S,2R)-2-hydroxy-1,2-diphenylethan-1-aminium (Isomer 2 Salt C), (Step 2, 4.0 g, Isomer 1: Isomer 2, 15.487%:84.52%) in methanol (10 vol.) was heated with stirring to 60-65° C. for 1-2 h to afford a clear solution. Then the heating was stopped and the solution was allowed to cool to 25-35° C. The mixture was stirred for 24 h and filtered. This afforded 2.0 g of (M)-3-Chloro-4-((3,5-difluoropyridin-2-yl)methoxy)-5',6-dimethyl-2-oxo-2H-[1,4'-bipyridine]-2'-carboxylate (1S,2R)-2-hydroxy-1,2-diphenylethan-1-aminium (Isomer 2 Salt C) with enhanced HPLC chiral purity (Isomer 1: Isomer 2, 12.567%:87.44%).

Step 4: Third purification of (P)-3-Chloro-4-((3,5-difluoropyridin-2-yl)methoxy)-5',6-dimethyl-2-oxo-2H-[1,4'-bipyridine]-2'-carboxylate (1S,2R)-2-hydroxy-1,2-diphenylethan-1-aminium (Isomer 2 Salt C). The wet solid, (M)-3-Chloro-4-((3,5-difluoropyridin-2-yl)methoxy)-5',6-dimethyl-2-oxo-2H-[1,4'-bipyridine]-2'-carboxylate (1S,2R)-2-hydroxy-1,2-diphenylethan-1-aminium (Isomer 2 Salt C), (Step 3, 2.0 g, Isomer 1: Isomer 2, 12.567%:87.44) in methanol (10 vol.) was heated to 60-65° C. with stirring for 1-2 h. Then the heating was stopped and the solution was allowed to cool to 25-35° C. The mixture was stirred for 24 h and then filtered. This afforded 1.5 g of (M)-3-Chloro-4-((3,5-difluoropyridin-2-yl)methoxy)-5',6-dimethyl-2-oxo-2H-[1,4'-bipyridine]-2'-carboxylate (1S,2R)-2-hydroxy-1,2-diphenylethan-1-aminium (Isomer 2 Salt C) with enhanced HPLC chiral purity (Isomer 1: Isomer 2, 0.137%:99.87%).

Step 5: Synthesis of (M)-3-Chloro-4-((3,5-difluoropyridin-2-yl)methoxy)-5',6-dimethyl-2-oxo-2H-[1,4'-bipyridine]-2'-carboxylic acid

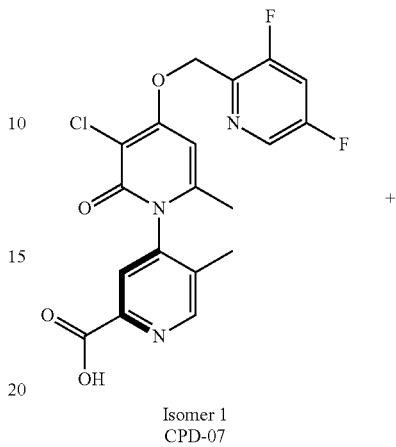

Isomer 1
CPD-07

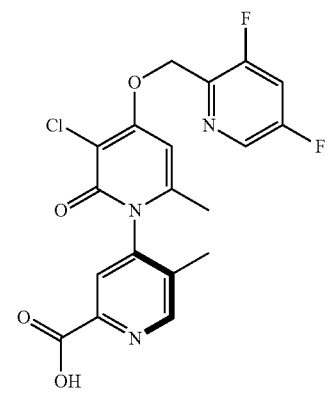

Isomer 2
CPD-32

(M)-3-Chloro-4-((3,5-difluoropyridin-2-yl)methoxy)-5',6-dimethyl-2-oxo-2H-[1,4'-bipyridine]-2'-carboxylate (1S,2R)-2-hydroxy-1,2-diphenylethan-1-aminium (Isomer 2 Salt C) (Step 4, 1.5 g, Isomer 1: Isomer 2, 0.137%:99.87) was dissolved in water (5 mL, 10 vol.) and basified with 2N NaOH to pH ~12. It was extracted three times with EtOAc (5 mL, 10 vol.). The EtOAc extract contained (1R,2S)-2-amino-1,2-diphenylethan-1-ol. The aq. layer was acidified with 2N HCl (pH 2) to precipitate the solid, The solid was filtered and washed with n-heptane (2 vol.) to afford chiral, (M)-3-Chloro-4-((3,5-difluoropyridin-2-yl)methoxy)-5',6-dimethyl-2-oxo-2H-[1,4'-bipyri-dine]-2'-carboxylic acid (0.25 g, Dry), HPLC chiral purity (Isomer 1: Isomer 2, 0.137%:99.87%).

Example 12: Preparation of (P)-3-Chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one (Formula P-(I))

Formula (P)-I

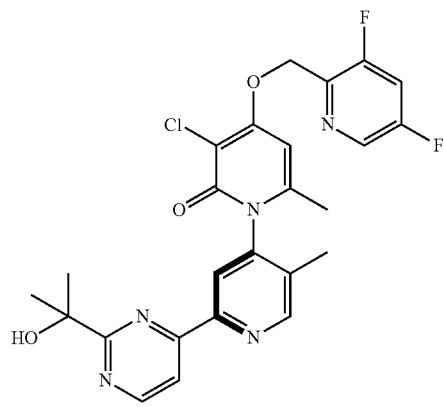

Step 1: Synthesis of (P)-3-Chloro-4-((3,5-difluoropyridin-2-yl)methoxy)-N-methoxy-N,5',6-trimethyl-2-oxo-2H-[1,4'-bipyridine]-2'-carboxamide (CPD-08)

CPD-08

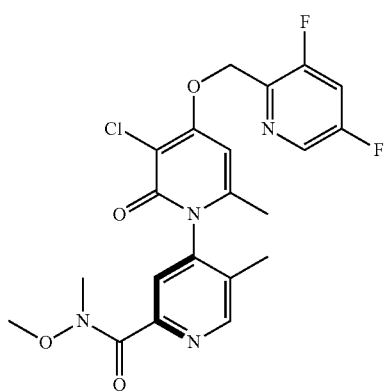

To a stirred solution of (P)-3-Chloro-4-((3,5-difluoropyridin-2-yl)methoxy)-5',6-dimethyl-2-oxo-2H-[1,4'-bipyridine]-2'-carboxylic acid (CPD-07, Example 9, Step 7) (6.0 g, 1.0 eq, Isomer I, Isomer 2, 99.86%:0.14%) in DMF (8 vol.) was added N-(3-Dimethylaminopropyl)-N'-ethylcarbodiimide hydrochloride (EDC•HCl (1.0 eq.)) at 0-5° C., and it was stirred for 5-10 min. TEA (1.0 eq.) was added at 0-5° C., and the mixture was stirred for 10-20 min. Then N, O-dimethyl hydroxylamine hydrochloride (1.5 eq.) was added at 0-5° C. The mixture was stirred for 1-2 h, and the progress of the reaction was monitored by TLC. After completion of the reaction, the reaction was allowed to cool to 25-35° C. Ice-cold water (20.0 vol.) was added and stirring as continued for 30-45 min. The mixture was then extracted with EtOAc (3×10 vol.). The combined EtOAc layers were washed with ice-cold water (10 vol.) and dried over anhydrous sodium sulphate. After filtration, the EtOAc distilled-off completely and MTBE (2 vol.) was added, and it was stirred for 1-2 h. The solid was filtered and dried at below 45° C. to afford 5.0 g (yield: 75%) of (P)-3-Chloro-4-((3,5-difluoropyridin-2-yl)methoxy)-N-methoxy-N,5',6-trimethyl-2-oxo-2H-[1,4'-bipyridine]-2'-carboxamide with HPLC purity 99.0% along with HPLC Chiral purity (Isomer 1: Isomer 2, 99.56%:0.44%). $^1$H-NMR (400 MHz, DMSO-d6): δ ppm 8.70 (s, 1H), 8.59 (d, 1H, J=2.4 Hz), 8.04-8.12 (m, 1H), 7.63 (s, 1H), 6.79 (s, 1H), 5.47 (d, 2H, J=1.6 Hz), 3.67 (s, 3H), 3.29 (s, 3H), 2.04 (s, 3H), 1.93 (s, 3H); MS (ES) m/z 465.31 (M+H).

Step 2: Synthesis of (P)-2'-Acetyl-3-chloro-4-((3,5-difluoropyridin-2-yl)methoxy)-5',6-dimethyl-2H-[1,4'-bipyridin]-2-one (CPD-09)

CPD-09

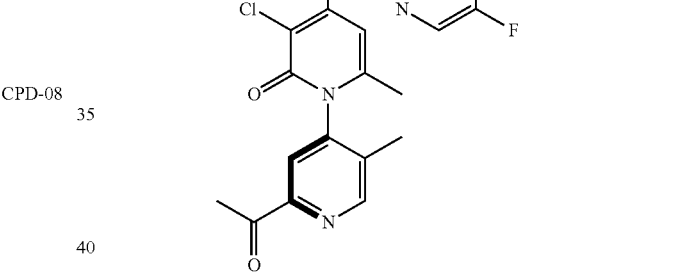

To a stirred solution of (P)-3-Chloro-4-((3,5-difluoropyridin-2-yl)methoxy)-N-methoxy-N,5',6-trimethyl-2-oxo-2H-[1,4'-bipyridine]-2'-carboxamide (CPD-08, Example 12, Step 1) (5.0 g, Isomer 1: Isomer 2 (99.56%:0.44%) in dry THF (42 vol.) was slowly added MeMgBr (9.5 eq.; 2M solution in THF) at 0-10° C. Then the reaction mass temperature was raised to 0-5° C. and maintained for 1 h. The reaction mass was quenched with 15% aq. ammonium chloride solution (10 vol.) and extracted with EtOAc (2×10 vol.). The combined EtOAc layers were distilled-off completely to afford a crude solid. The solid was dissolved in dichloromethane (DCM (1 vol.)) and then precipitated by adding hexanes (9 vol.) The solid was filtered to afford 3.0 g (yield: 66%) of (P)-2'-Acetyl-3-chloro-4-((3,5-difluoropyridin-2-yl)methoxy)-5',6-dimethyl-2H-[1,4'-bipyridin]-2-one with HPLC purity 98.80% and HPLC chiral purity (Isomer 1: Isomer 2, 99.86%:0.14%). $^1$H-NMR (400 MHz, DMSO-d6): δ ppm 8.83 (s, 1H), 8.59 (d, 1H, J=2.4 Hz), 8.05-8.14 (m, 1H), 7.89 (s, 1H), 6.79 (s, 1H), 5.47 (d, 2H, J=1.6 Hz), 2.66 (s, 3H), 2.09 (s, 3H), 1.91 (s, 3H); MS (ES) m/z 420.08 (M+H).

Step 3: Synthesis of (P)-(E)-3-Chloro-4-((3,5-difluoropyridin-2-yl)methoxy)-2'-(3-(dimethyl-amino)acryloyl)-5',6-dimethyl-2H-[1,4'-bipyridin]-2-one (CPD-10)

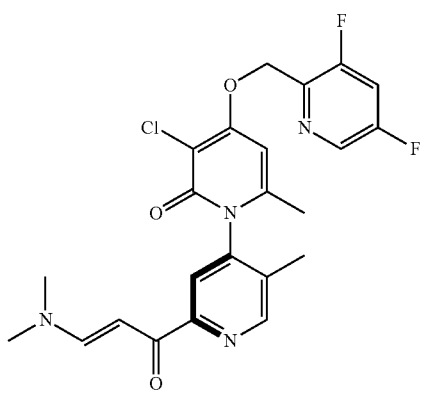

CPD-10

To a stirred solution of (P)-2'-Acetyl-3-chloro-4-((3,5-difluoropyridin-2-yl)methoxy)-5',6-dimethyl-2H-[1,4'-bipyridin]-2-one (CPD-09, Example 12, Step 2) (2.0 g, 1.0 eq., Isomer 1: Isomer 2, 99.86%:0.14%), was added N,N-dimethyl-formamide dimethyl acetal (DMF-DMA (8.0 eq.)) and DMF (1.0 vol.) at 25-35° C. The reaction mass was slowly heated to 50-55° C. and maintained for at that temperature for 24 h. Progress of the reaction was monitored by TLC. After completion of reaction, heating was stopped and the mixture was cooled to 25-35° C. Then dichloromethane (DCM) (10.0 vol.), and water (10.0 vol.) were added. The mixture was stirred for 10-15 min, and the phases were separated. The aqueous layer was extracted with DCM (2×10 vol.). The combined DCM layers were washed with ice cold water (2×10 vol.) and were dried with anhydrous sodium sulphate. The DCM layer was concentrated at below 35° C. to afford a crude solid. EtOAc (2.0 vol.) was added and the mixture was stirred for 1-2 h at 25-35° C. The solid was filtered to afford 1.8 g (yield: 79.6%) of (P)-(E)-3-Chloro-4-((3,5-difluoropyridin-2-yl)methoxy)-2'-(3-(dimethyl-amino)acryloyl)-5',6-dimethyl-2H-[1,4'-bipyridin]-2-one with HPLC 97.05%, and HPLC chiral purity (Isomer 1: Isomer 2 (99.96% 0.04%). $^1$H-NMR (400 MHz, DMSO-d6): δ ppm 8.71 (s, 1H), 8.60 (d, 1H, J=2.4 Hz), 8.04-8.12 (m, 1H), 7.80-7.86 (m, 2H), 6.78 (s, 1H), 6.37 (d, 1H, J=12.8 Hz), 5.47 (d, 2H, J=1.6 Hz), 3.19 (s, 3H), 2.94 (s, 3H), 2.05 (s, 3H), 1.91 (s, 3H); MS (ES) m/z 475.36 (M+H).

Step 4: Synthesis of (P)-3-Chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one (Formula P-(I))

Formula (P)-I

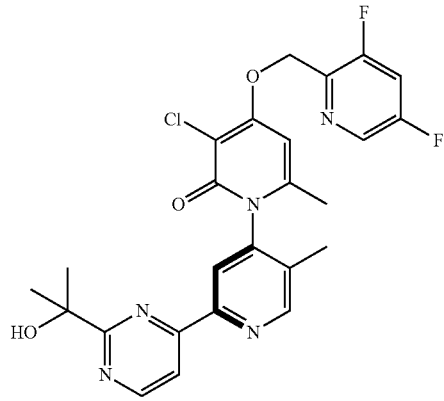

Isomer 1

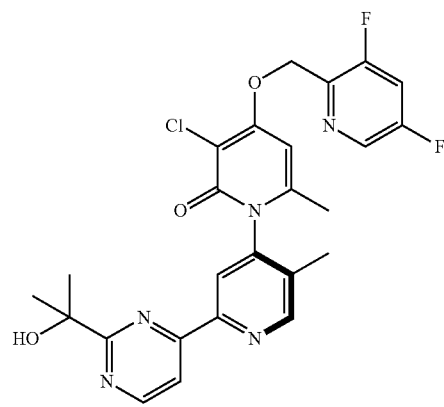

Isomer 2

To a stirred solution of (P)-(E)-3-Chloro-4-((3,5-difluoropyridin-2-yl)methoxy)-2'-(3-(dimethyl-amino)acryloyl)-5',6-dimethyl-2H-[1,4'-bipyridin]-2-one (CPD-10, Example 12, Step 3) (5.4 g, 1.0 eq., Isomer 1: Isomer 2, 99.96%: 0.04%) in DMF (6.0 vol.) was added K$_2$CO$_3$ (2.5 eq.). After stirring for 5-10 min at 25-35° C., 2-hydroxy-2-methylpropionamidine HCl (INT-02) (3.0 eq.) at 25-35° C. was added. The reaction mass was slowly warmed to 45-50° C. and was stirred at that temperature for 7 h. Progress of the reaction was monitored by TLC/IPC HPLC. After the reaction was completed, it was cooled to 10-15° C., diluted with water (20 vol.), and stirred for 1-2 h at 10-15° C. The solid was filtered and dried to afford 5.0 g of crude (P)-3-Chloro-4-((3,5-difluoropyridin-2-yl)methoxy)-2'-(2-(2-hydroxy-propan-2-yl)pyrimidin-4-yl)-5',6-dimethyl-2H-[1,4'-bipyridin]-2-one, HPLC chiral purity (Isomer 1: Isomer 2) (95% 5%).

Step 5: Purification of (P)-3-Chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one (Formula P-(I))

Formula (P)-I

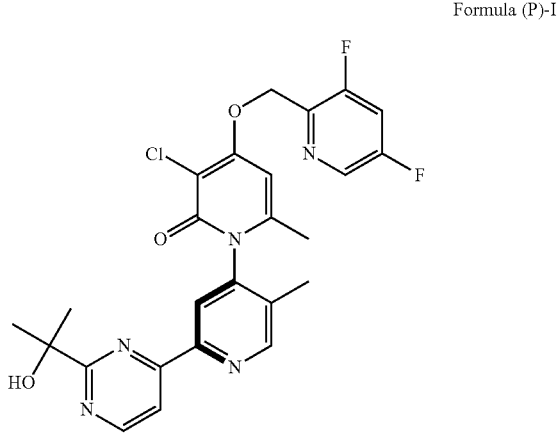

Crude (P)-3-Chloro-4-((3,5-difluoropyridin-2-yl)methoxy)-2'-(2-(2-hydroxy-propan-2-yl)-pyrim-idin-4-yl)-5',6-dimethyl-2H-[1,4'-bipyridin]-2-one (Formula P-(I), Example 12, Step 4) (5.0 g, 1.0 eq., Isomer 1: Isomer 2 (95%:5%) in IPA (19.0 vol.) was stirred for 1 h at 72-75° C. Seed material (Formula P-(I), Example 12, Step 4) (0.25 g, 0.05 w/w times, Seed Crystal's Assay is 98.4%) was then added at 72-75° C. Heating was stopped and the mixture was allowed to cool to 25-35° C. After stirring for 24 h the solid was filtered. The solid was washed with IPA (2.0 vol.), and it was dried at below 40° C. to afford 4.4 g (yield: 75%) of (P)-3-Chloro-4-((3,5-difluoropyridin-2-yl)methoxy)-2'-(2-(2-hydroxypropan-2-yl)-pyrimidin-4-yl)-5',6-dimethyl-2H-[1,4'-bipyridin]-2-one with HPLC purity 99.52% and HPLC chiral purity (Isomer 1: Isomer 2, 99.65%:0.35%). $^1$H-NMR (400 MHz, DMSO-$d_6$): δ ppm 8.97 (d, 1H, J=5.2 Hz), 8.86 (s, 1H), 8.69 (s, 1H), 8.61 (d, 1H, J=2.4 Hz), 8.24 (d, 1H, J=5.2 Hz), 8.06-8.14 (m, 1H), 6.84 (s, 1H), 5.49 (d, 2H, J=1.2 Hz), 5.25 (s, 1H), 2.10 (s, 3H), 1.98 (s, 3H), 1.04 (s, 3H), 1.03 (s, 3H); MS (ES) m/z 514.37 (M+H).

Example 13: Preparation of 3-chloro-4-((3,5-difluoropyridin-2-yl)methoxy)-2'-(2-(2-hydroxypropan-2-yl)pyrimidin-4-yl)-5', 6-dimethyl-2H-[1,4'-bipyridin]-2-one (CPD-20) Via Sonogashira Coupling

CPD-20

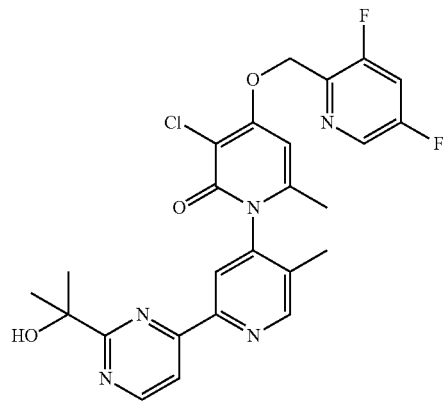

Step 1: Synthesis of Preparation of 4-((3,5-difluoropyridin-2-yl)methoxy)-2'-(3-hydroxyprop-1-yn-1-yl)-5',6-dimethyl-2H-[1,4'-bipyridin]-2-one (CPD-21)

CPD-21

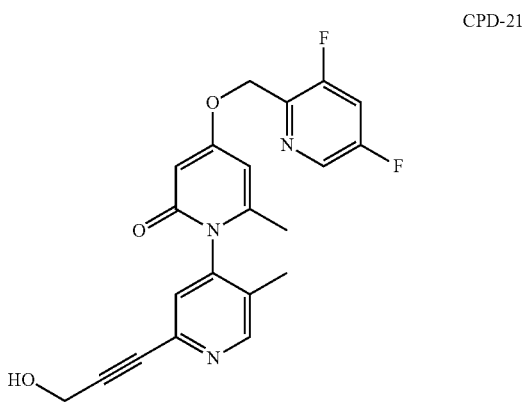 [SMILES: Cc1cnc(C#CCO)cc1-n1c(C)cc(OCc2ncc(F)cc2F)cc1=O]

To a pre-cleaned RBF was added water (5 vol, 200 mL) and 1,4-Dioxane (5 vol, 200 mL). The solvent was then degassed with argon for 10 min. 2'-Chloro-4-((3,5-difluoropyridin-2-yl)methoxy)-5',6-dimethyl-2H-[1,4'-bipyridin]-2-one (CPD-03, Example 5) (40.0 g, 106 mmol, 1 eq.), TPP (5.55 g, 21.2 mmol, 0.2 eq.), TEA (73.8 mL, 530.0 mmol, 5 eq.), CuI (1.0 g, 5.3 mmol, 0.05 eq.), and 10% Pd/C (11.29 g, 5.3 mmol, 0.05 eq.) were then added to the RBF. The mixture was degassed with argon for 10 min, and propargyl alcohol (24.7 mL, 424.4 mmol, 4 eq.) was added to the reaction mixture. The mixture was stirred for 10 min at room temperature. The reaction mixture was then heated to 90° C. for 62 h and monitored by LC-MS. After completion, the reaction mixture was cooled to RT and filtered and washed with EtOAc. The filtrate was extracted with EtOAc and was washed with brine solution. The organic layer was dried over $Na_2SO_4$ and it was concentrated under reduced pressure to obtain crude 4-((3,5-difluoropyridin-2-yl)methoxy)-2'-(3-hydroxyprop-1-yn-1-yl)-5',6-dimethyl-2H-[1,4'-bipyridin]-2-one (CPD-21). Crude compound (CPD-21) was purified by column chromatography over silica gel (230-400 mesh), eluted with 2-4% MeOH in DCM to obtain desired 4-((3,5-difluoropyridin-2-yl)methoxy)-2'-(3-hydroxyprop-1-yn-1-yl)-5',6-dimethyl-2H-[1,4'-bipyridin]-2-one (CPD-21) as yellow solid (18.5 g, 44%) with HPLC purity 93%. $^1$H-NMR (300 MHz, CDCl$_3$) δ ppm: 8.59 (s, 1H), 8.41 (d, J=2.1 Hz, 1H), 7.29 (s, 1H), 7.22 (s, 1H), 6.03 (d, J=2.4 Hz, 1H), 5.96 (m, 1H), 5.19 (d, J=1.8 Hz, 2H), 4.50 (d, J=6.0 Hz, 2H), 2.13 (s, 3H), and 1.85 (s, 3H). MS(ES), m/z 398.79 (M+H).

Step 2: Synthesis of Preparation of 3-(4-(4-((3,5-difluoropyridin-2-yl)methoxy)-6-methyl-2-oxopyridin-1(2H)-yl)-5-methylpyridin-2-yl)propiolaldehyde (CPD-22)

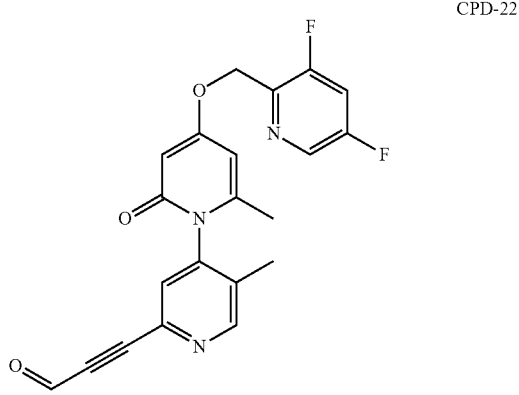 [SMILES: Cc1cnc(C#CC=O)cc1-n1c(C)cc(OCc2ncc(F)cc2F)cc1=O]

CPD-22

A stirred solution of 4-((3,5-difluoropyridin-2-yl)methoxy)-2'-(3-hydroxyprop-1-yn-1-yl)-5',6-dimethyl-2H-[1,4'-bipyridin]-2-one (CPD-21, Example 13, Step 1) (18.0 g, 45.3 mmol, 1 eq.) in DCM (360 mL) under nitrogen atmosphere was cooled (ice-bath). Dess-Martin periodinane (9.0 g, 68.0 mmol, and 1.5 eq.) was added portion wise at 0° C. The resulting reaction mixture was allowed to stir at room temperature for 3 h. Progress of the reaction was monitored by TLC. After completion, the reaction mixture was cooled to 0° C. and it was treated with 10% aq. sodium thiosulfate, then extracted with DCM (180 mL×3). The organic layer was washed with water, followed by brine, concentrated under reduced pressure to obtain 3-(4-(4-((3,5-difluoropyridin-2-yl)methoxy)-6-methyl-2-oxopyridin-1(2H)-yl)-5-methylpyridin-2-yl)propiolaldehyde (CPD-22) as yellow liquid (16 g, 83%). The crude compound was used for next step without further purification.

Step 3: Synthesis of 4-((3,5-difluoropyridin-2-yl)methoxy)-1-(2-(2-(2-hydroxypropan-2-yl)pyrimidin-4-yl)-5-methylpyridin-4-yl)-6-methylpyridin-2(1H)-one (CPD-23)

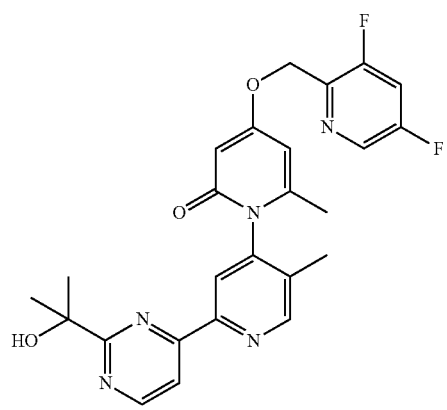

CPD-23

To a stirred solution of 3-(4-(4-((3,5-difluoropyridin-2-yl)methoxy)-6-methyl-2-oxopyridin-1(2H)-yl)-5-methylpyridin-2-yl)propiolaldehyde (CPD-22, Example 13, Step 2) (3.0 g, 7.59 mmol, 1 eq) in ACN (30 mL) were added $Na_2CO_3$ (2.3 g, 22.78 mmol, 3 eq) and 2-hydroxy-2-methylpropionamidine HCl (INT-02, 1.17 g, 11.39 mmol, 1.5 eq) at rt. The reaction mixture was heated at 80° C.-85° C. for 2 h. The reaction progress was monitored by TLC and LC-MS. After completion, the reaction mixture was cooled to room temperature. It was filtered and washed with ACN. The filtrate was concentrated under reduced pressure to obtain 4-((3,5-difluoropyridin-2-yl)methoxy)-1-(2-(2-(2-hydroxypropan-2-yl)pyrimidin-4-yl)-5-methylpyridin-4-yl)-6-methylpyridin-2(1H)-one (CPD-23) as a brown solid (3.6 g, 97%) with HPLC purity of 66%. The crude compound was used for next step without further purification. $^1$H-NMR (300 MHz, $CDCl_3$) δ ppm: 8.86 (d, J=5.1 Hz, 1H), 8.74 (s, 1H), 8.42-8.41 (m, 1H), 8.27-8.25 (m, 2H), 7.30-7.33 (m, 1H), 6.08 (d, J=2.1 Hz, 1H), 6.03 (d, J=0.9 Hz, 1H), 5.22 (s, 2H), 5.19 (br-s, 1H), 2.22 (s, 3H), 1.90 (s, 3H), 1.64 (s, 3H), and 1.63 (s, 3H). MS (ES) m/z=480.89 (M+H).

Step 4: Synthesis of 3-chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one (CPD-20)

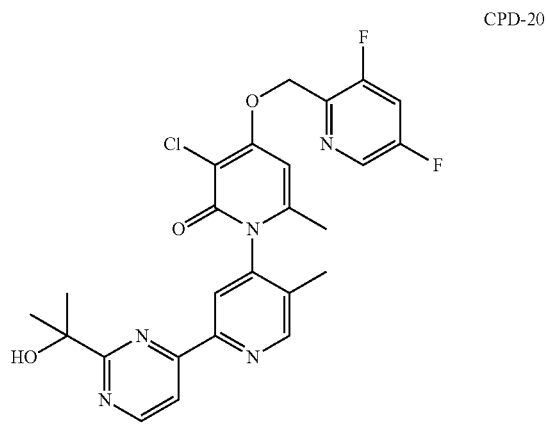 [SMILES: Cc1cnc(-c2ccnc(C(C)(C)O)n2)cc1-n1c(C)cc(OCc2ncc(F)cc2F)c(Cl)c1=O]

CPD-20

A mixture of 4-((3,5-difluoropyridin-2-yl)methoxy)-1-(2-(2-(2-hydroxypropan-2-yl)pyrimidin-4-yl)-5-methyl-pyridin-4-yl)-6-methylpyridin-2(1H)-one (CPD-23, Example 13, Step 3) (3.6 g, 7.515 mmol), N-chlorosuccinimide (1.19 g, 9.018 mmol, 1.2 eq) in DCM (108 mL) containing dichloroacetic acid (0.387 g, 3.006 mmol, 0.4 eq.) was heated at 60° C. under nitrogen for 2 h. The reaction mixture was cooled to room temperature and diluted with DCM. It was then basified with aq. $NaHCO_3$ solution. The layers were separated. The aqueous layer was extracted with DCM. The combined extracts were washed with brine, dried over anhydrous sodium sulfate and concentrated under reduced pressure. The crude compound was purified by column chromatography over silica-gel (230-400 mesh), using 2-4% MeOH as eluent to obtain 3-chloro-4-((3,5-difluoropyridin-2-yl)methoxy)-2'-(2-(2-hydroxy-propan-2-yl)pyrimidin-4-yl)-5', 6-dimethyl-2H-[1,4'-bipyridin]-2-one (CPD-20) as yellow solid (1.2 g, 31% yield) with HPLC purity 92%, $^1$H-NMR (400 MHz, DMSO-d6) δ ppm: 8.97 (d, J=5.2 Hz, 1H), 8.86 (s, 1H), 8.69 (s, 1H), 8.61 (d, J=2.0 Hz, 1H), 8.24

(d, J=5.4 Hz, 1H), 8.13-8.07 (m, 1H), 6.84 (s, 14H), 5.49 (d, J=1.2 Hz, 2H), 5.25 (br-s, 1H), 2.17 (s, 3H), 1.98 (s, 3H), 1.54 (s, 3H), 1.53 (s, 3H). MS (ES) m/z 514.89 (M+H).

Example 14: Preparation of 2'-acetyl-4-((3,5-difluoropyridin-2-yl)methoxy)-5',6-dimethyl-2H-[1,4'-bipyridin]-2-one (CPD-17) Via Reductive Cyanation

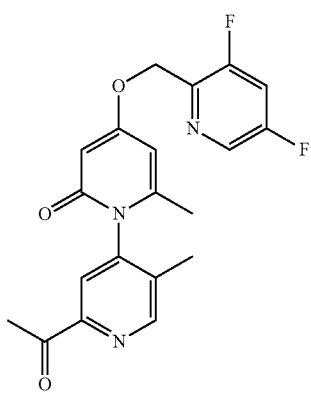

CPD-17

Step 1: Synthesis of 4-((3,5-Difluoropyridin-2-yl)methoxy)-5',6-dimethyl-2-oxo-2H-[1,4'-bipyridine]-2'-carbonitrile (CPD-24)

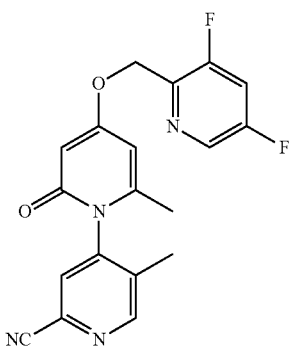

CPD-24

To a solution of 2'-Chloro-4-((3,5-difluoropyridin-2-yl)methoxy)-5',6-dimethyl-2H-[1,4'-bipyridin]-2-one (CPD-03, Example 5) (1 g, 2.65 mmol), zinc cyanide (186.2 mg, 1.59 mmol, 0.6 eq), Pd$_2$(dba)$_3$ (48.54 mmol, 0.05 mmol, 0.02 eq), zinc powder (6.94 mg, 0.11 mmol, 0.04 eq) and diphenylphopshinoferrocene (176.4 mg, 0.32 mmol, 0.12 eq.) were sequentially added, and the reaction mass was degassed with nitrogen for 30 minutes. The reaction mixture was heated to 120° C. for 18 h. The reaction was monitored by LCMS which showed ~59% desired mass and ~5-% of 4-((3,5-difluoropyridin-2-yl)methoxy)-5',6-dimethyl-2-oxo-2H-[1,4'-bipyridine]-2'-carboxylic acid. The reaction mixture was cooled to RT, diluted with ethyl acetate, and washed with water. The organic layer was dried over anhydrous sodium sulfate, and it was concentrated under reduced pressure. The crude product was purified by column chromatography over silica-gel using 1:1 ethyl acetate-hexanes mixture to afford the desired product 4-((3,5-Difluoropyridin-2-yl)methoxy)-5',6-dimethyl-2-oxo-2H-[1,4'-bipyridine]-2'-carbonitrile (CPD-24) (400 mg, 41%) with purity of 75%. $^1$H-NMR (300 MHz, DMSO-d6) δ ppm: 8.84 (brs, 1H), 8.59 (d, 1H, J=2.1 Hz), 8.12 (s, 1H), 8.11-8.04 (m, 1H), 6.12 (d, 1H, J=1.5 Hz), 6.05 (d, 1H, 2.4 Hz), 5.25 (2, 2H), 2.10 (s, 3H), 1.84 (s, 1H). MS (ES) m/z 369.20 (M+H).

Step 2: Synthesis of 2'-acetyl-4-((3,5-difluoropyridin-2-yl)methoxy)-5',6-dimethyl-2H-[1,4'-bipyridin]-2-one (CPD-17)

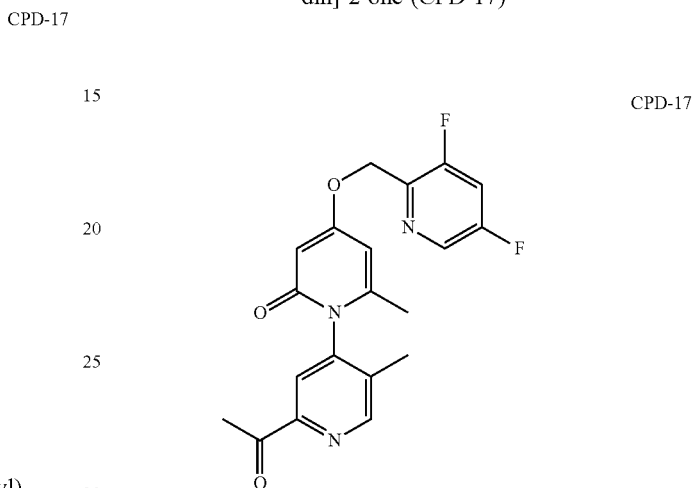

CPD-17

To a solution 4-((3,5-Difluoropyridin-2-yl)methoxy)-5',6-dimethyl-2-oxo-2H-[1,4'-bipyridine]-2'-carbonitrile (CPD-24, Example 14, Step 1) (50 mg, 0.136 mmol) in THF (5 mL) was added 3M methylmagnesium iodide in THF (0.0.2 mL, 0.6 mmol, 4.4 eq) at RT. The reaction mixture was stirred at room temperature for 12 h. It was quenched with saturated ammonium chloride solution (0.5 mL). The organic layer was separated and concentrated. The crude 2'-acetyl-4-((3,5-difluoropyridin-2-yl)methoxy)-5',6-dimethyl-2H-[1,4'-bipyridin]-2-one (CPD-17) was isolated and analyzed by MS (ES) m/z 386.29 (M+H).

Example 15: Preparation of Methyl 4-((3, 5-difluoropyridin-2-yl)methoxy)-5', 6-dimethyl-2-oxo-2H-[1,4'-bipyridine]-2'-carboxylate (CPD-04) Via Brominated Intermediates

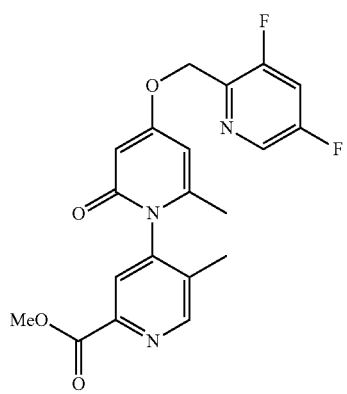

CPD-04

Step 1: Synthesis of 2'-bromo-4-hydroxy-5',6-dimethyl-2H-[1,4'-bipyridine]-2-one (CPD-25)

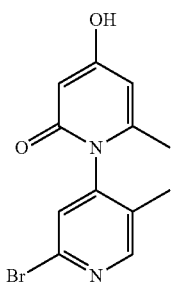

CPD-25

A stirred mixture of 2'-chloro-4-hydroxy-5',6-dimethyl-2H-[1,4'-bipyridin]-2-one (CPD-02, Example 3) (10.0 g, 40 mmol, 1 eq.) 33% HBr in AcOH (150 mL, 15 vol.) and NaBr (4.115 g, 40 mmol, 1 eq.) was heated to 90° C. for 36 h. After completion, the reaction mixture was cooled to room temperature. The solid was filtered and dried to obtain 2'-bromo-4-hydroxy-5',6-dimethyl-2H-[1,4'-bipyridine]-2-one (CPD-25) as light grey color solid (14 g, crude) with a crude HPLC purity of 88%. $^1$H-NMR (400 MHz), DMSO-$d_6$ δ: 10.78 (brs, 1H), 8.48 (s, 1H), 7.69 (s, 1H), 6.03-6.02 (m, 1H), 5.65 (d, J=2.4 Hz, 1H), 1.96 (s, 3H), 1.84 (s, 3H). MS (ES) m/z 296 (M+H).

Step 2: Synthesis of 2'-bromo-4-((3,5-difluoropyridin-2-yl)methoxy)-5',6-dimethyl-2H-[1,4'-bipyridin]-2-one (CPD-26)

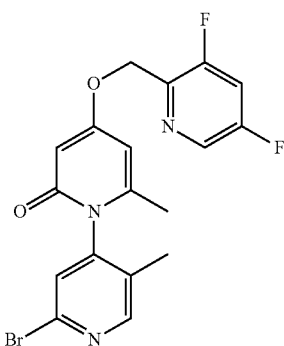

CPD-26

To a stirred suspension of 2'-bromo-4-hydroxy-5',6-dimethyl-2H-[1,4'-bipyridine]-2-one (CPD-25, Example 15, Step 1) (14 g, 37.4 mmol, 1 eq.) in DMF (56 mL, 4 vol.) was added $K_2CO_3$ (12.9 g, 93.5 mmol, 2.5 eq.) followed by a solution of 2-(chloromethyl)-3,5-difluoro-pyridine (INT-01, Example 4) (6.73 g, 41.1 mmol, 1.1 eq.) in DMF (14 mL, 1 vol). The resulting reaction mixture was stirred at room temperature for 32 h (reaction mixture became light greenish color after 10 min). Progress of the reaction was monitored by TLC. After completion, the reaction mixture was quenched with ice cold water (140 mL) and extracted with EtOAc (140 ml×2). The combined organic layer was washed with water (70 mL), followed by brine (70 mL). It was concentrated under reduced pressure to obtain 2'-bromo-4-((3,5-difluoropyridin-2-yl)methoxy)-5',6-dimethyl-2H-[1, 4'-bipyridin]-2-one (CPD-26) as dark liquid (12.5 g, 79%) with HPLC purity of 81%. $^1$H-NMR (400 MHz, DMSO-$d_6$) δ ppm: 8.59 (d, J=2.4 Hz, 1H), 8.47 (s, 1H), 8.09-8.04 (m, 1H), 7.72 (s, 1H), 6.13-6.12 (d, 1H, J=2.4 Hz), 6.03 (d, J=2.4 Hz, 1H), 5.24 (d, J=1.6 Hz, 2H), 1.96 (s, 3H), 1.85 (s, 3H). MS (ES) m/z 423.91 (M+2H).

Step 3: Synthesis of Methyl 4-((3,5-difluoropyridin-2-yl)methoxy)-5',6-dimethyl-2-oxo-2H-[1,4'-bipyridine]-2'-carboxylate (CPD-04)

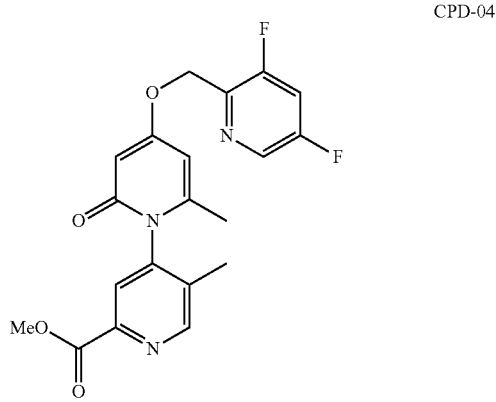

CPD-04

In a pre-cleaned 600 mL autoclave, 2'-bromo-4-((3,5-difluoropyridin-2-yl)methoxy)-5',6-dimethyl-2H-[1,4'-bipyridin]-2-one (CPD-26, Example 15, Step 2) (4 g, 9.5 mmol) was taken followed by methanol (64 mL, 16 vol.) and DMF (64 mL, 16 vol.) under argon atmosphere. The reaction mixture was de-gassed with argon for 15 minutes. Triethylamine (2.61 mL, 19.0 mmol, 2 eq.) was added and the mixture was degassed with argon for another 15 min. Pd(dppf)$Cl_2$•DCM complex (0.775 g, 0.95 mmol, 0.1 eq) was added, and the autoclave was closed. Carbon monoxide gas was charged at 100 psi and the pressure was released. It was again pressurized with CO gas at 200 psi, and the reaction mass was stirred and heated at 100° C. for 16 h. The reaction was monitored by TLC and LCMS. The reaction mixture was distilled to remove volatiles. It was filtered through a celite pad, and the pad was washed with EtOAc (40 mL×2). The filtrate was stirred with ice cold water (640 mL) and was extracted with EA (3×500 mL). The combined extract was washed with water, dried over $Na_2SO_4$, and concentrated under reduced pressure to obtain crude CPD-04. The crude compound was suspended in MTBE, stirred for 1 h, and filtered to obtain Methyl 4-((3,5-difluoropyridin-2-yl)methoxy)-5',6-dimethyl-2-oxo-2H-[1,4'-bipyridine]-2'-carboxylate (CPD-04) as a brown solid (3.1 g, 81%) with HPLC purity of 77%. $^1$H-NMR (400 MHz, DMSO-$d_6$) δ ppm: 8.79 (s, 1H), 8.59 (d, J=2.0 Hz, 1H), 8.10-8.05 (m, 1H), 7.92 (s, 1H), 6.14-6.13 (m, 1H), 6.04 (d, J=2.4 Hz, 1H), 5.25 (d, J=2.0 Hz, 2H), 3.89 (s, 3H), 2.09 (s, 3H), 1.81 (s, 3H). MS (ES) m/z 402.09 (M+H).

Example 16: Preparation of 4-((3,5-difluoropyridin-2-yl)methoxy)-5',6-dimethyl-2-oxo-2H-[1,4'-bipyridine]-2'-carboxylic acid (CPD-11) from Methyl 4-((3,5-difluoropyridin-2-yl)methoxy)-5',6-dimethyl-2-oxo-2H-[1,4'-bipyridine]-2'-carboxylate (CPD-04)

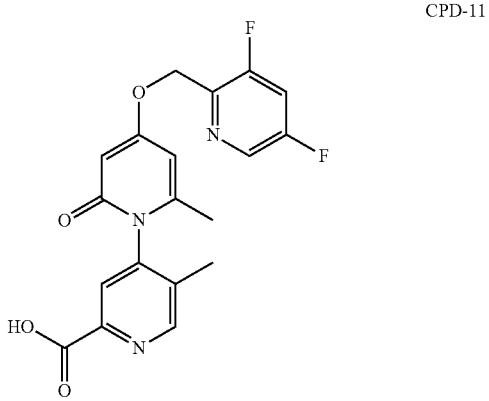 [SMILES: Cc1cnc(C(=O)O)cc1-n1c(C)cc(OCc2ncc(F)cc2F)cc1=O]

CPD-11

To a stirred suspension of Methyl 4-((3,5-difluoropyridin-2-yl)methoxy)-5',6-dimethyl-2-oxo-2H-[1,4'-bipyridine]-2'-carboxylate (CPD-04, Example 6) in THF (5 vol.) was added a solution of LiOH·H$_2$O (3.0 eq.) in water (5 vol.) at 25-35° C. and continued stirring the reaction mass for 2-4 h. The progress of the reaction was monitored by TLC. Then aq. layer was washed with EtOAc (5 vol.) and the pH of aq. layer was adjusted to 2-3 using 4M HCl solution. The aqueous layer was extracted with DCM (3×10 vol.). The combined DCM layer was dried over sodium sulphate and concentrated under reduced pressure at below 40° C. to afford 4-((3,5-difluoropyridin-2-yl)methoxy)-5',6-dimethyl-2-oxo-2H-[1,4'-bipyridine]-2'-carboxylic acid as a light brown colored solid with HPLC Purity 98.7% and having the ratio of atropisomers 51.5%: 48.5%. $^1$H-NMR (400 MHz, DMSO-d6) δ ppm: 13.26 (br s, 1H) 8.77 (s, 1H), 8.59 (s, 1H), 8.07-8.15 (m, 1H), 7.88 (s, 1H), 6.13 (s, 1H), 6.04 (d, J=2.4 Hz, 1H), 5.25 (d, J=1.6 Hz, 2H), 2.08 (s, 3H), 1.82 (s, 3H). MS (ES) m/z 388.17 (M+H).

Example 17: Preparation of (P)-4-((3,5-difluoro-pyridin-2-yl)methoxy)-5',6-dimethyl-2-oxo-2H-[1,4'-bipyri-dine]-2'-carboxylic Acid (CPD-12)

The racemic mixture of atropisomers 4-((3,5-difluoro-pyridin-2-yl)methoxy)-5',6-dimethyl-2-oxo-2H-[1,4'-bi-pyridine]-2'-carboxylic acid (Example 16) were separated using super critical fluid chromatography (SFC) (see Table 3). Fraction-1 ((P)-4-((3,5-difluoropyridin-2-yl)methoxy)-5',6-dimethyl-2-oxo-2H-[1,4'-bipyridine]-2'-carboxylic acid) after concentration afforded chiral purity Isomer 1: Isomer 2 (97.7%: 2.3%). $^1$H-NMR (400 MHz, DMSO-d6) δ ppm: 13.26 (br s, 1H) 8.75 (s, 1H), 8.59 (d, J=2.8 Hz, 1H), 8.12-8.05 (m, 1H), 7.91 (s, 1H), 6.13 (d, J=2.0 Hz, 1H), 6.03 (d, J=2.0 Hz, 1H), 5.24 (d, J=1.6 Hz, 2H), 2.08 (s, 3H), 1.82 (s, 3H). MS (ES) m/z 388.17 (M+H), and the separated Fraction-2 ((M)-4-((3,5-difluoropyridin-2-yl)methoxy)-5',6-dimethyl-2-oxo-2H-[1,4'-bipyridine]-2'-carboxylic acid) HPLC chiral purity is Isomer 1:Isomer 2 (2.7%:97.3%) respectively. $^1$H-NMR (400 MHz, DMSO-d6) δ ppm: 13.24 (br s, 1H) 8.76 (s, 1H), 8.59 (d, J=2.0 Hz, 1H), 8.13-8.05 (m, 1H), 7.91 (s, 1H), 6.13 (d, J=1.6 Hz, 1H), 6.03 (d, J=2.8 Hz, 1H), 5.24 (d, J=1.8 Hz, 2H), 2.08 (s, 3H), 1.82 (s, 3H). MS (ES) m/z 388.17 (M+H).

TABLE 3

| SFC Conditions | |
|---|---|
| Mobile Phase | 0.1% TFA in Methanol. |
| Column | Chiral pack IG 250 mm * 4.6 m * 5.0 μm |
| Flow Rate | 1.0 mL/min |
| Injection Volume | 10.0 μL |
| Run Time | 25.0 minutes |
| Column Temperature | 35° C. |
| Wavelength | 215 nm |
| Diluent | Methanol. |
| Sample Concentration | 0.7 mg/mL for all stages |

Example 18: Alternative Preparation of (P)-3-Chloro-4-((3,5-difluoropyridin-2-yl)methoxy)-5',6-dimethyl-2-oxo-2H-[1,4'-bipyri-dine]-2'-carboxylic acid (CPD-07) via chiral separation with (S)-1-(naphthalen-2-yl)ethan-1-amine

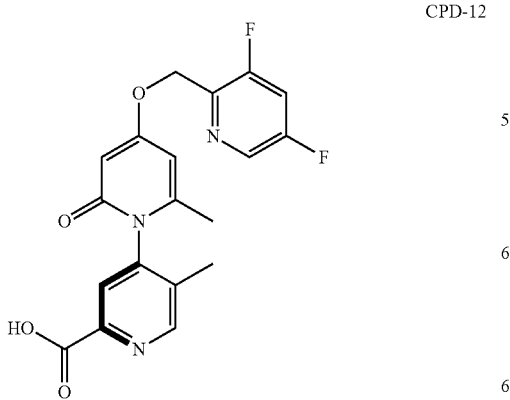

CPD-12

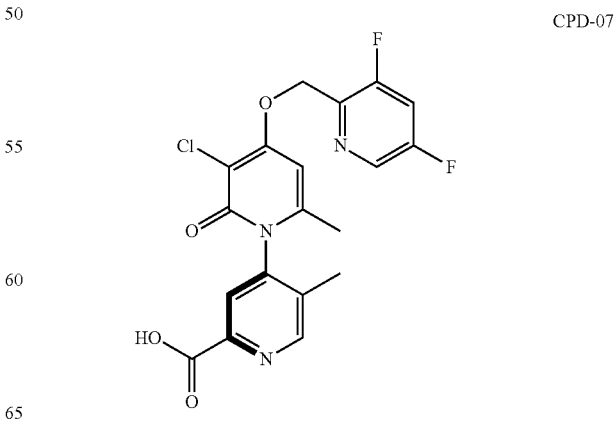

CPD-07

Step 1: Synthesis of (P)-3-Chloro-4-((3,5-difluoro-pyridin-2-yl)methoxy)-5',6-dimethyl-2-oxo-2H-[1,4'-bipyridine]-2'-carboxylate (S)-1-(naphthalen-2-yl)ethan-1-aminium (Isomer 1 Salt A)
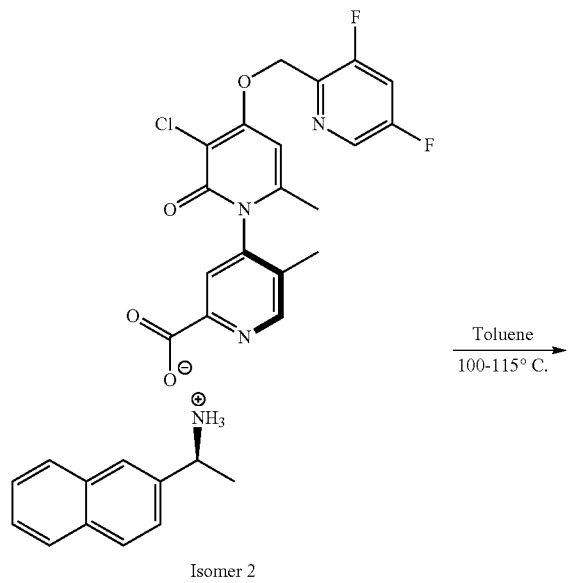
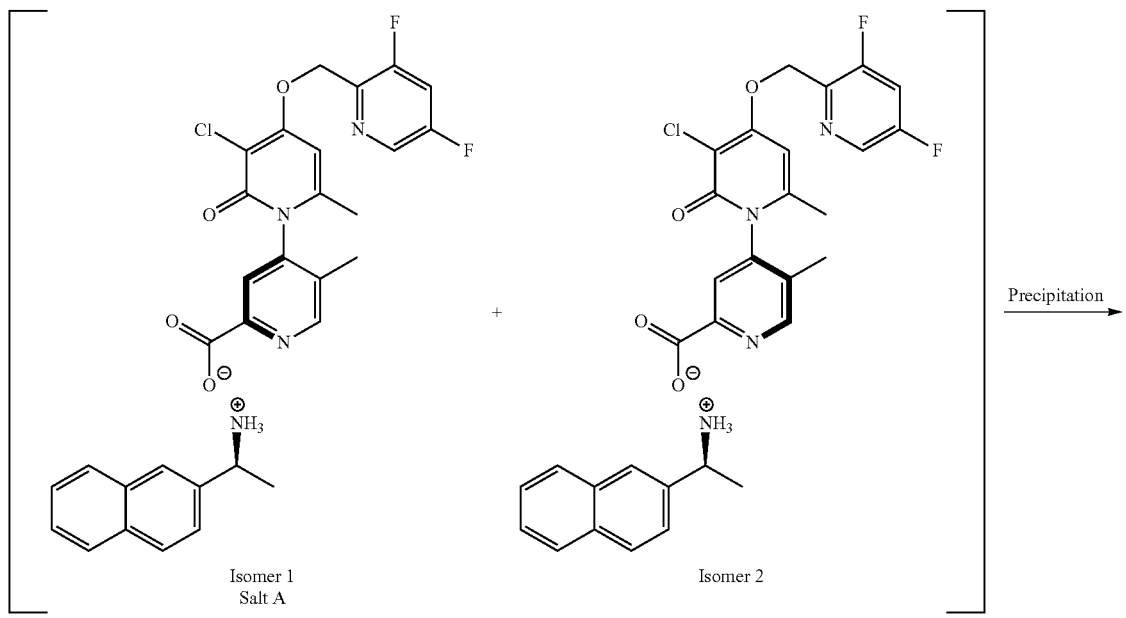

To the filtered mother liquors (FmL's) of Example 9, Step 3, (1 g, Isomer 1: Isomer 2, (8: 91)) was added toluene (10 vol.) at 25-35° C. Then the reaction mass temperature was raised to 110-115° C., and it was stirred at 110-115° C. for 48 h. An aliquot of the solid was removed from the heterogeneous mixture, and it was filtered. The solid was analyzed by chiral HPLC to confirm the configuration of the salt as the desired isomer. The reaction mass was filtered and dried under vacuum to afford chiral amine salt, Isomer 1, (P)-3-Chloro-4-((3,5-difluoropyridin-2-yl)methoxy)-5',6-dimethyl-2-oxo-2H-[1,4'-bipyridine]-2'-carboxylate (S)-1-(naphthalen-2-yl)ethan-1-aminium (Isomer 1 Salt A) with chiral purity of Isomer 1: Isomer 2 (96.1%:3.1%) and HPLC purity of 98.4%.

Step 2 Synthesis of (P)-3-Chloro-4-((3,5-difluoropyridin-2-yl)methoxy)-5',6-dimethyl-2-oxo-2H-[1,4'-bipyridine]-2'-carboxylic acid (CPD-07). The resulting chiral amine salt of Example 18, Step 1 ((P)-3-Chloro-4-((3,5-difluoropyridin-2-yl)methoxy)-5',6-dimethyl-2-oxo-2H-[1,4'-bipyridine]-2'-carboxylate (S)-1-(naphthalen-2-yl)ethan-1-aminium (Isomer 1 Salt A) (0.6 g, Isomer 1:Isomer 2 (96.1%:3.1%)) was dissolved in water (6.0 mL) and basified with 2N NaOH to pH ~12 and extracted with MTBE. The resulting MTBE layer containing the amine was discarded. The aqueous layer pH was adjusted up to pH=2 with 2N HCl. Solid precipitation was observed. The precipitated solid was washed and dried under vacuum to afford 0.4 g of (P)-3-Chloro-4-((3, 5-difluoropyridin-2-yl)methoxy)-5',6-dimethyl-2-oxo-2H-[1,4'-bipyridine]-2'-carboxylic acid with HPLC chiral purity Isomer 1:Isomer 2 (95.22%:4.78%) and 98.16% of HPLC purity. $^1$H-NMR (400 MHz, DMSO-d6): δ ppm 13.35 (br s, 1H), 8.80 (s, 1H), 8.60 (d, 1H, J=2.4 Hz), 8.07-8.12 (m, 1H), 7.97 (s, 1H), 6.80 (s, 1H), 5.47 (d, 2H, J=1.6 Hz), 2.08 (s, 3H), 1.93 (s, 3H). MS (ES) m/z 422.12 (M+H).

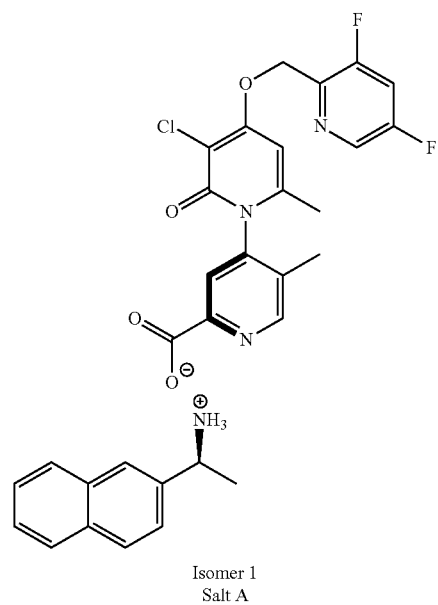

Isomer 1
Salt A

Example 19: Preparation of 2'-acetyl-4-((3,5-difluoropyridin-2-yl)methoxy)-5',6-dimethyl-2H-[1,4'-bipyridin]-2-one (CPD-17) from CPD-03

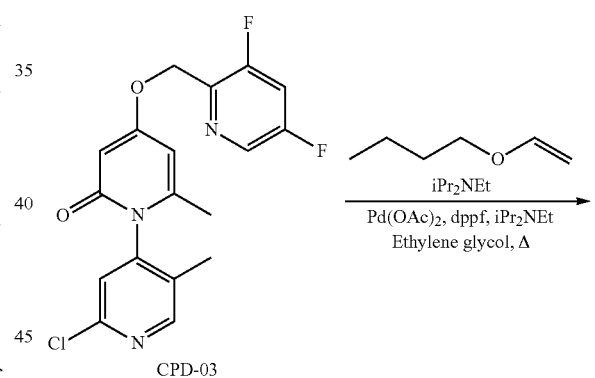

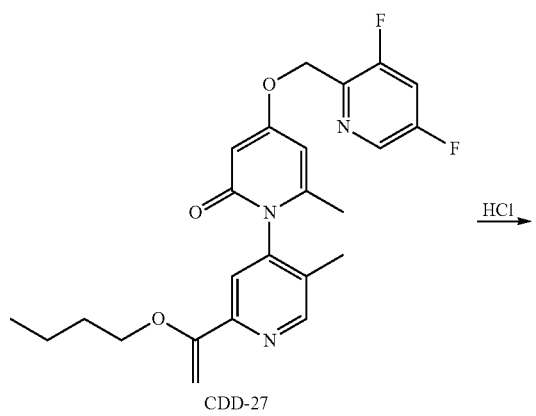

-continued

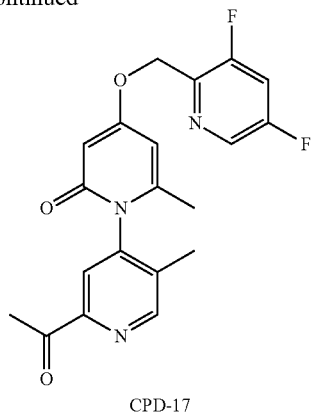

CPD-17

Step 1: Synthesis of 2'-(1-butoxyvinyl)-4-((3,5-difluoropyridin-2-yl)methoxy)-5',6-dimethyl-2H-[1,4'-bipyridin]-2-one (CPD-27). To a stirred suspension of 2'-chloro-4-((3,5-difluoropyridin-2-yl)methoxy)-5',6-dimethyl-2H-[1,4'-bipyridin]-2-one (CPD-03, Example 5) (3.0 g, 7.94 mmol) in iPr$_2$NEt (2.8 mL, 16.08 mmol), was added ethylene glycol (15 mL) and butyl vinyl ether (5.1 mL). The mixture was warmed in an oil bath to 35° C. with stirring while bubbling N$_2$ through mixture. Solid Pd(OAc)$_2$ (0.10 g, 0.397 mmol, 5 mol %) and 1,1'-Ferrocenediyl-bis(diphenylphosphine) (dppf) (0.44 g, 0.795 mmol, 10 mol %) were charged to the mixture sequentially, and the bath was heated to 110° C. After 3 h at 110° C. and 3 h more at 120° C., reaction was >95% complete by IPC-LCMS. The mixture was cooled and partitioned between water and EtOAc. The aq. phase was extracted again with EtOAc. The combined organic phase was washed with water and filtered through a pad of silica gel, eluting with EtOAc until all enol ether product was collected. The fractions containing product were evaporated to afford 2'-(1-butoxyvinyl)-4-((3,5-difluoropyridin-2-yl)methoxy)-5',6-dimethyl-2H-[1,4'-bipyridin]-2-one (CPD-27) as a tan solid, 0.310 g (yield: 10%), HPLC purity 80%. $^1$H-NMR (400 MHz, CDCl$_3$) δ ppm: 8.56 (s, 1H), 8.40 (s, 1H), 7.41 (s, 1H), 7.24-7.32 (m, 2H), 6.04 (s, 1H), 5.96 (s, 1H), 5.44 (s, 1H), 5.19 (s, 2H), 4.36 3.84-3.91 (m, 2H), 2.11 (s, 3H), 1.85 (s, 3H), 1.72-1.80 (m, 2H), 1.42-1.51 (m, 2H), 0.96 (t, J=7.3 Hz, 3H); MS (ES) m/z 386.29 (M+H).

Step 2: Synthesis of 2'-acetyl-4-((3,5-difluoropyridin-2-yl)methoxy)-5',6-dimethyl-2H-[1,4'-bipyridin]-2-one (CPD-17). 2'-(1-butoxyvinyl)-4-((3,5-difluoropyridin-2-yl)methoxy)-5',6-dimethyl-2H-[1,4'-bipyridin]-2-one (CPD-27 Example 19, Step 1) (0.250 g, 0.663 mmol) was treated with 8 mL of 3 N HCl at RT. After stirring vigorously for 30 min, the reaction was complete by IPC-HPLC. The mixture was transferred to a separatory funnel with EtOAc and water. A small amount of saturated aq. NaCl was added, and the mixture mixed well and allowed to separate. The phases were separated and the aq. extracted again w/EtOAc after neutralizing (K$_3$PO$_4$/aq. KOH). The combined organic extract was washed with water, and both aq. phases were back-extracted again with EtOAc. All of the organic phases were combined and vacuum filtered through a pad of silica gel. The filtrate was evaporated, and the residue chromatographed over silica gel with 0-30% 2-Methytetrahydrofuran in EtOAc. Pooled and evaporated all fractions containing desired product. The residue was dried further on a high vacuum line to get a tan foam of 2'-acetyl-4-((3,5-difluoropyridin-2-yl)methoxy)-5',6-dimethyl-2H-[1,4'-bipyridin]-2-one (CPD-17), 0.152 g (70% yield). $^1$H-NMR (400 MHz, DMSO-d6) δ ppm: 8.68 (s, 1H), 8.41 (s, 1H), 7.81 (s, 1H), 7.30-7.36 (m, 1H), 6.06 (s, 1H), 5.96 (s, 1H), 5.18 (s, 2H), 2.73 (s, 3H), 2.20 (s, 3H), 1.83 (s, 3H); MS (ES) m/z 385.15 (M+H).

Example 20: Alternative Preparation of 2'-acetyl-4-((3,5-difluoropyridin-2-yl)methoxy)-5',6-dimethyl-2H-[1,4'-bipyridin]-2-one (CPD-17) from CPD-26

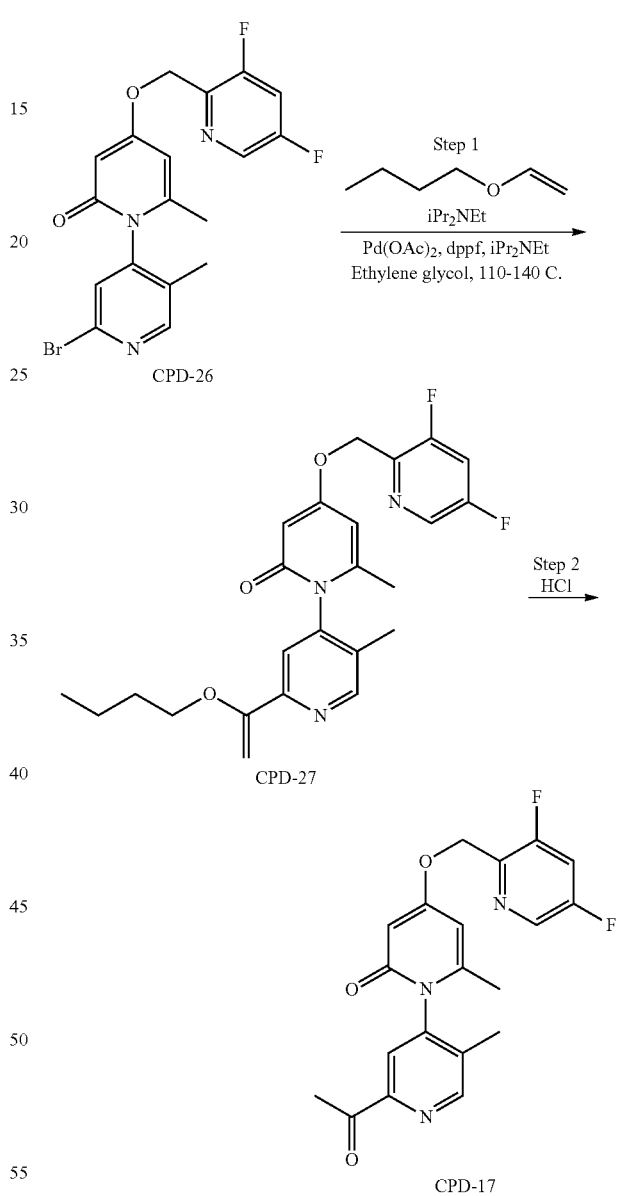

Step 1: Synthesis of 2'-(1-butoxyvinyl)-4-((3,5-difluoropyridin-2-yl)methoxy)-5',6-dimethyl-2H-[1,4'-bipyridin]-2-one (CPD-27). To a stirred suspension of 2'-bromo-4-((3,5-difluoropyridin-2-yl)methoxy)-5',6-dimethyl-2H-[1,4'-bipyridin]-2-one (CPD-26) (Example 15, Step 2, 5.0 g, 11.84 mmol), iPr$_2$NEt (4.1 mL, 23.68 mmol), butyl vinyl ether (7.7 mL, 59.21 mmol), and ethylene glycol (25 mL) under N$_2$ was warmed in an oil bath to 40° C. with stirring while bubbling N$_2$ through mixture. Solid Pd(OAc)$_2$ (0.11 g, 0.474 mmol, 4 mol %) and dppf (0.53 g, 0.947 mmol, 8 mol %) were added sequentially, and the oil bath was heated to 100° C. After a total of 15 h at 100° C., IPC-HPLC was >98% desired product. The mixture was cooled to RT and treated with 8 mL of 3 N HCl. After stirring vigorously for 30 min, the reaction was complete (HPLC). The mixture was transferred to a separatory funnel with EtOAc and water. A small amount of saturated aq. NaCl was added, and the mixture mixed well and allowed to separate. The phases were separated and the aq. extracted again w/EtOAc after neutralizing ($K_3PO_4$/aq. KOH). The combined organic extract was washed with water, and both aq. phases were back-extracted again with EtOAc. Combined organic layers vacuum filtered through a pad of silica gel. The filtrate was evaporated, and the residue chromatographed over silica gel with 0-30% 2-methyltetrahydrofuran in EtOAc. Combined desired fractions, concentrated and dried under high vacuum to afford 2'-(1-butoxyvinyl)-4-((3,5-difluoropyridin-2-yl)methoxy)-5',6-dimethyl-2H-[1,4'-bipyridin]-2-one (CPD-27) as a tan foam, 2.35 g (yield: 52%). $^1$H NMR (400 MHz, $CDCl_3$) δ ppm: 8.56 (s, 1H), 8.40 (s, 1H), 7.41 (s, 1H), 7.24-7.32 (m, 2H), 6.04 (s, 1H), 5.96 (s, 1H), 5.44 (s, 1H), 5.19 (s, 2H), 4.36 3.84-3.91 (m, 2H), 2.11 (s, 3H), 1.85 (s, 3H), 1.72-1.80 (m, 2H), 1.42-1.51 (m, 2H), 0.96 (t, J=7.3 Hz, 3H); MS (ES) m/z 386.29 (M+H).

Step 2: Synthesis of 2'-acetyl-4-((3,5-difluoropyridin-2-yl)methoxy)-5',6-dimethyl-2H-[1,4'-bipyridin]-2-one (CPD-17). To a stirred suspension of 2'-(1-butoxyvinyl)-4-((3,5-difluoropyridin-2-yl)methoxy)-5',6-dimethyl-2H-[1,4'-bipyridin]-2-one (CPD-27) (Example 20, Step 1, 2.0 g, 5 mmol) was added 2-methyltetrahydrofuran followed by 3N HCl to ~pH 2. The resulting mixture was stirred vigorously at RT for 30 min, whereupon the reaction was complete. The acid was neutralized with sat'd $KHCO_3$ ($CO_2$ off-gassing), and the product was extracted into two portions of EtOAc. The combined organic phase was washed twice with water, then filtered through a pad of silica gel, eluting with EtOAc. Combined desired fraction and concentrated, then further dried on a high vacuum line to afford 2'-acetyl-4-((3,5-difluoropyridin-2-yl)methoxy)-5',6-dimethyl-2H-[1,4'-bipyridin]-2-one (CPD-17) as a light yellow, free-flowing foam, 1.46 g (yield: 70%)$^1$H NMR (400 MHz, $CDCl_3$) δ ppm: 8.68 (s, 1H), 8.40 (s, 1H), 7.81 (s, 1H), 7.30-7.36 (m, 1H), 6.03 (s, 1H), 5.97 (s, 1H), 5.19 (s, 2H), 2.72 (s, 3H), 2.20 (s, 3H), 1.83 (s, 3H): MS (ES) m/z 386.29 (M+H).

Example 21: Alternative Preparation of 2'-acetyl-4-((3,5-difluoropyridin-2-yl)methoxy)-5',6-dimethyl-2H-[1,4'-bipyridin]-2-one (CDP-17) from CPD-26

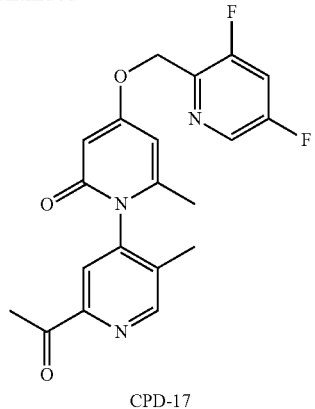

CPD-17

To a stirred suspension of 2'-bromo-4-((3,5-difluoropyridin-2-yl)methoxy)-5',6-dimethyl-2H-[1,4'-bipyridin]-2-one (CPD-26) (Example 15, Step 2, 5.0 g, 11.84 mmol), was added $iPr_2NEt$ (4.1 mL, 23.68 mmol), hydroxyethyl vinyl ether (5.3 mL, 59.2 mmol), NMP (13 mL), and water (13 mL) under $N_2$. The mixture was warmed with stirring to 45° C. while bubbling $N_2$ through mixture. Solid $Pd(OAc)_2$ (0.08 g, 0.36 mmol, 3 mol %) nd 1,3-bis(diphenylphosphino)propane (dppp) (0.29 g, 0.71 mmol, 6 mol %) were added sequentially, and the oil bath was heated to 95° C. for 24 h until the IPC-HPLC was 91.8% desired product. The mixture was cooled resulting in a clear, light brown solution. The mixture was diluted with 2-methyltetrahydrofuran and treated with 3 N HCl to ~pH 2 and stirred vigorously at RT for 30 min, IPC-HPLC indicated no starting material remained. The acid was neutralized with sat'd $KHCO_3$ ($CO_2$ off-gassing), and the product was extracted into two portions of EtOAc. The combined organic phase was washed twice with water, then filtered through a pad of silica gel, eluting with EtOAc. Combined desired fractions, concentrated and dried on high vacuum to afford 2'-acetyl-4-((3,5-difluoropyridin-2-yl)methoxy)-5',6-dimethyl-2H-[1,4'-bipyridin]-2-one (CDP-17) as a light yellow, free-flowing foam, 3.8 g (yield: 70%). $^1$H NMR (400 MHz, $CDCl_3$) δ ppm: 8.68 (s, 1H), 8.40 (s, 1H), 7.81 (s, 1H), 7.30-7.36 (m, 1H), 6.03 (s, 1H), 5.97 (s, 1H), 5.19 (s, 2H), 2.72 (s, 3H), 2.20 (s, 3H), 1.83 (s, 3H): MS (ES) m/z 386.26 (M+H).

Example 22: Alternative Preparation of 2'-acetyl-3-chloro-4-((3,5-difluoropyridin-2-yl)methoxy)-5',6-dimethyl-2H-[1,4'-bipyridin]-2-one (CPD-18) from CPD-28

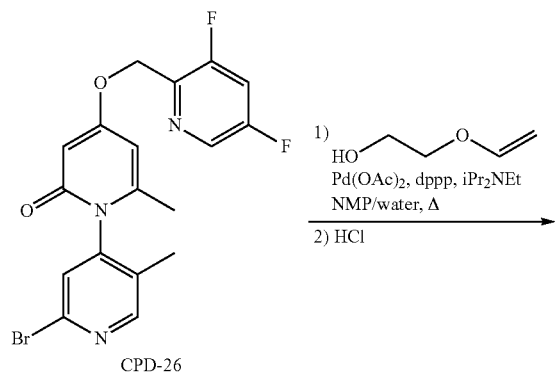

CPD-26

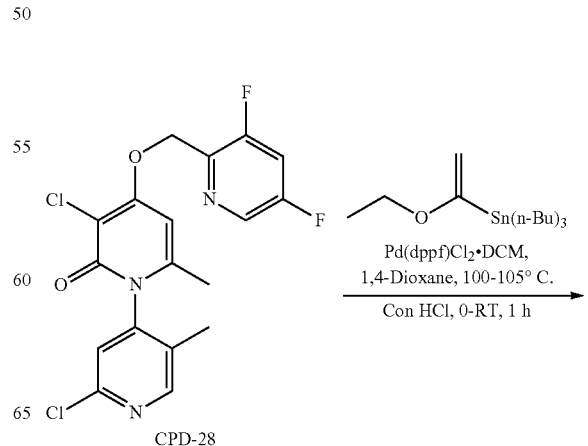

CPD-28

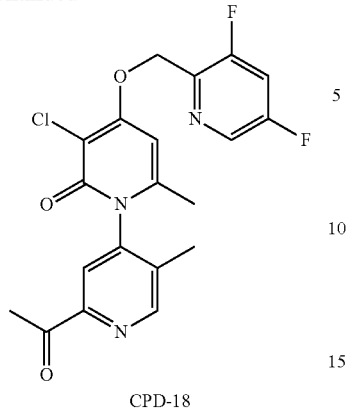

CPD-18

To a stirred suspension of 2',3-dichloro-4-((3,5-difluoropyridin-2-yl)methoxy)-5',6-dimethyl-2H-[1,4'-bipyridin]-2-one (CPD-28) (Example 40, 1 g, 2.43 mmol, 1 eq) in 1,4-dioxane (7.5 ml, 7.5 vol). Tributyl-(1-ethoxyvinyl)stannane (1.228 g, 3.640 mmol, 1.5 eq) was added at rt under argon atmosphere. Reaction mass was degassed with argon for 10 minutes. Copper iodide (23.13 mg, 0.121 mmol, 0.05 eq) and Pd(dppf)Cl$_2$-DCM complex (79.47 mg, 0.0973 mmol, 0.04 eq) were added under argon atmosphere. Reaction mass was degassed with argon for 5 minutes. The reaction mixture was heated in oil bath at 100-105° C. for 16 h, IPC-LCMS was 86% complete. Reaction mixture was cooled to rt, diluted with 1,4-dioxane (5 ml), filtered through celite and washed with 1,4-dioxane. The combined organic layer was concentrated to 50%, cooled to 0-5° C. 36% HCl (1 ml, 1 vol) was added slowly below 5° C. and reaction mass was stirred for 1 h. Reaction mass was solidified slowly, it was diluted with petroleum ether and filtered. The solid was suspended in DCM (20 ml), cooled to 0-5° C. and basified with 20% NaOH (aq) solution. Separated the two layers and aqueous layer was again extracted with DCM (10 ml). The combined organic layer was dried over Na$_2$SO$_4$ and evaporated to afford crude compound. The crude compound was purified by column chromatography using 100-200 mesh silica gel, combined desired fraction, concentrated and dried under high vacuum to afford 2'-acetyl-3-chloro-4-((3,5-difluoropyridin-2-yl)methoxy)-5',6-dimethyl-2H-[1,4'-bipyridin]-2-one (CPD-18) as an off-white solid, 800 mg (yield: 78%). $^1$H-NMR (400 MHz, DMSO-d6) δ ppm: 8.70 (s, 1H), 8.40 (d, 1H, J=2.4 Hz), 7.78 (s, 1H), 7.34 (m, 1H), 6.37 (s, 1H), 5.41 (d, 2H, J=1.6 Hz), 2.73 (s, 3H), 2.18 (s, 3H), 1.93 (s, 3H); MS (ES) m/z 420.14 (M+H).

Example 23: Alternative Preparation of 2'-acetyl-3-chloro-4-((3,5-difluoropyridin-2-yl)methoxy)-5',6-dimethyl-2H-[1,4'-bipyridin]-2-one (CPD-18) from CPD-28

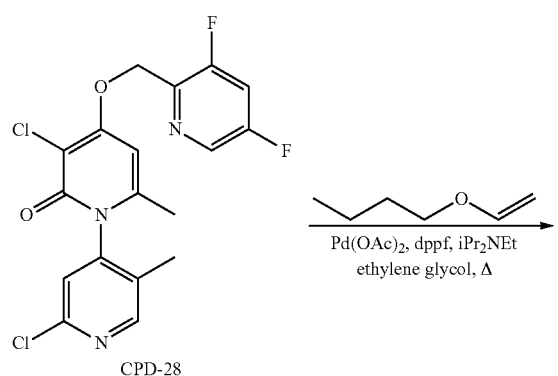

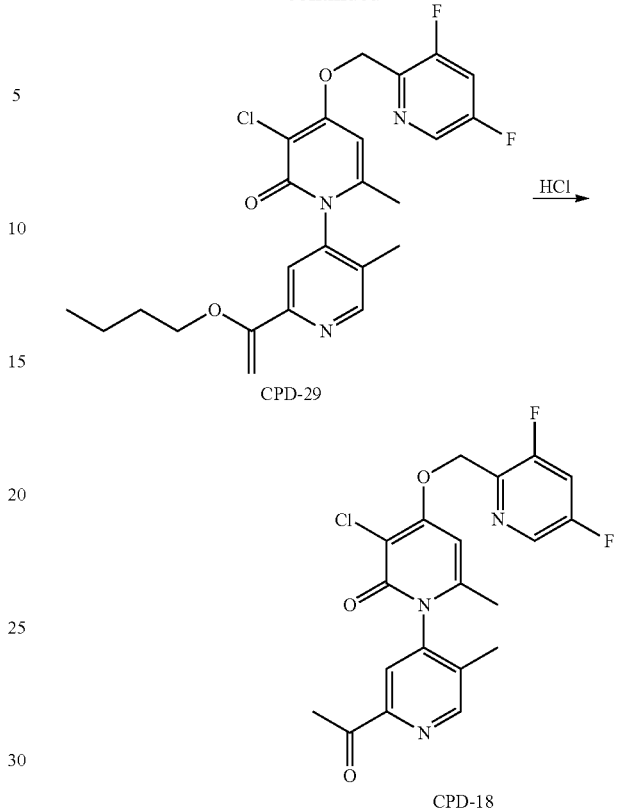

CPD-29

CPD-18

Step 1: Synthesis of 2'-(1-butoxyvinyl)-3-chloro-4-((3,5-difluoropyridin-2-yl)methoxy)-5',6-dimethyl-2H-[1,4'-bipyridin]-2-one (CPD-29). To a stirred suspension of 2',3-dichloro-4-((3,5-difluoropyridin-2-yl)methoxy)-5',6-dimethyl-2H-[1,4'-bipyridin]-2-one (CPD-28) (Example 40, 5.0 g, 12.13 mmol) was added iPr$_2$NEt (4.2 mL, 24.26 mmol), butyl vinyl ether (1.9 mL, 14.56 mmol, 1.2 equiv), and ethylene glycol (25 mL). The mixture was warmed in an oil bath to 35° C. with stirring while bubbling N$_2$ through mixture. Solid Pd(OAc)$_2$ (0.14 g, 0.606 mmol, 5 mol %) and dppf (0.67 g, 1.21 mmol, 10 mol %) were charged to the mixture sequentially, and the bath was heated to 115° C. for 9 h the mixture was cooled to RT and partitioned between water and EtOAc. The aq. phase was extracted again with EtOAc, and the combined organic phase washed twice with water, filtered through a pad of silica gel, eluting with EtOAc. Combined desired fractions, concentrated and dried under high vacuum to afford 2'-(1-butoxyvinyl)-3-chloro-4-((3,5-difluoropyridin-2-yl)methoxy)-5',6-dimethyl-2H-[1,4'-bipyridin]-2-one (CPD-29) as a tan foam. No further purification was performed and the material was carried onto Step 2. $^1$H-NMR (400 MHz, DMSO-d6) δ ppm: 8.55 (s, 1H), 8.38 (s, 1H), 7.37 (s, 1H), 7.28-7.36 (m, 1H), 6.35 (s, 1H), 5.44 (s, 1H), 5.38 (s, 2H), 4.36 (s, 1H), 3.84-3.91 (m, 2H), 2.07 (s, 3H), 1.93 (s, 3H), 1.70-1.78 (m, 2H), 1.40-1.49 (m, 2H), 0.94 (t, J=7.3 Hz, 3H); MS (ES) m/z 476.10 (M+H).

Step 2: Synthesis of 2'-acetyl-3-chloro-4-((3,5-difluoropyridin-2-yl)methoxy)-5',6-dimethyl-2H-[1,4'-bipyridin]-2-one (CPD-18). The mixture from Step 1 containing 2'-(1-butoxyvinyl)-3-chloro-4-((3,5-difluoropyridin-2-yl)methoxy)-5',6-dimethyl-2H-[1,4'-bipyridin]-2-one (CPD-29) (Step 1) at RT was treated with 8 mL of 3 N HCl. After stirring vigorously for 30 min, IPC-HPLC shows no starting material remaining. The mixture was partitioned between EtOAc and brine. The aqueous phase was extracted again w/EtOAc after neutralizing (K₃PO₄/aq. KOH). The combined organic extract was washed with water, and both aq. phases were back-extracted again with EtOAc. All of the organic phases were combined and vacuum filtered through a pad of silica gel. The filtrate was evaporated, and the residue chromatographed over silica gel with 0-30% 2-methytetrahydrofuran in EtOAc. Combined desired fractions, concentrated and dried under high vacuum to afford 2'-acetyl-3-chloro-4-((3,5-difluoropyridin-2-yl)methoxy)-5',6-dimethyl-2H-[1,4'-bipyridin]-2-one (CPD-18) as a light tan foam, 2.35 g (yield: 52%). $^1$H-NMR (400 MHz, DMSO-d6) δ ppm: 8.70 (s, 1H), 8.40 (d, 1H, J=2.4 Hz), 7.78 (s, 1H), 7.34 (m, 1H), 6.37 (s, 1H), 5.41 (d, 2H, J=1.6 Hz), 2.73 (s, 3H), 2.18 (s, 3H), 1.93 (s, 3H); MS (ES) m/z 420.14 (M+H).

Example 24: Alternative Preparation of 2'-acetyl-3-chloro-4-((3,5-difluoropyridin-2-yl)methoxy)-5',6-dimethyl-2H-[1,4'-bipyridin]-2-one (CPD-18) from CPD-30

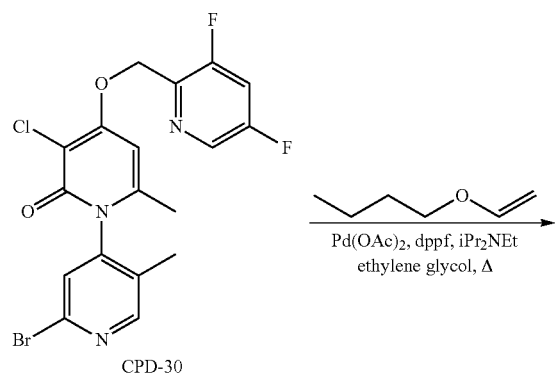

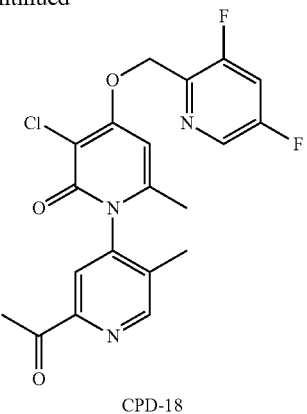

CPD-18

Step 1: Synthesis of 2'-(1-butoxyvinyl)-3-chloro-4-((3,5-difluoropyridin-2-yl)methoxy)-5',6-dimethyl-2H-[1,4'-bipyridin]-2-one (CPD-29). To a stirred suspension of 2'-bromo-3-chloro-4-((3,5-difluoropyridin-2-yl)methoxy)-5',6-dimethyl-2H-[1,4'-bipyridin]-2-one (CPD-30) (Example 37, 7.0 g, 15.33 mmol) was added iPr₂NEt (5.3 mL, 30.66 mmol), hydroxyethyl vinyl ether (56.9 mL, 76.64 mmol), NMP (18 mL) and water (18 mL). The mixture was warmed with stirring to 45° C. while bubbling N₂ through mixture. Solid Pd(OAc)₂ (0.1 g, 0.46 mmol, 3 mol %) and 1,3-bis(diphenylphosphino)propane (dppp) (0.38 g, 0.92 mmol, 6 mol %) were added sequentially, and the oil bath was heated to 92° C. Heating at 92-94° C. was continued for 28 h, with the reaction progress being monitored by HPLC and TLC. Conversion was very slow initially, so small additional charges of Pd(OAc)₂ were added after about 3 and 21 h of heating. The reaction was terminated after 28 h of heating, having never been homogeneous. the mixture was cooled to RT and partitioned between water and EtOAc. The aqueous phase was extracted again with EtOAc, and the combined organic phase washed twice with water, filtered through a pad of silica gel, eluting with EtOAc. Combined desired fractions, concentrated and dried under high vacuum to afford 2'-(1-butoxyvinyl)-3-chloro-4-((3,5-difluoropyridin-2-yl)methoxy)-5',6-dimethyl-2H-[1,4'-bipyridin]-2-one (CPD-29) as a tan foam, 1.03 g (yield: 15%). No further purification was performed and the material was carried onto Step 2. $^1$H-NMR (400 MHz, DMSO-d6) δ ppm: 8.55 (s, 1H), 8.38 (s, 1H), 7.37 (s, 1H), 7.28-7.36 (m, 1H), 6.24 (s, 1H), 5.44 (s, 1H), 5.38 (s, 2H), 4.32 (s, 1H), 3.83-3.90 (m, 2H), 2.07 (s, 3H), 1.92 (s, 3H), 1.70-1.77 (m, 2H), 1.40-1.49 (m, 2H), 0.93 (t, J=7.3 Hz, 3H); MS (ES) m/z 476.08 (M+H).

Step 2: Synthesis of 2'-acetyl-3-chloro-4-((3,5-difluoropyridin-2-yl)methoxy)-5',6-dimethyl-2H-[1,4'-bipyridin]-2-one (CPD-18). The stirred mixture of 2'-(1-butoxyvinyl)-3-chloro-4-((3,5-difluoropyridin-2-yl)methoxy)-5',6-dimethyl-2H-[1,4'-bipyridin]-2-one (CPD-29) (Step 1) was treated at rt with 8 mL of 3 N HCl. After stirring vigorously for 30 min, IPC-HPLC showed no sm remaining). The mixture was partitioned between EtOAc and brine. The aqueous layer was extracted again w/EtOAc after neutralizing (K₃PO₄/aq. KOH). The combined organic extract was washed with water, and both aq. phases were back-extracted again with EtOAc. All of the organic phases were combined and vacuum filtered through a pad of silica gel. The filtrate was evaporated, and the residue chromatographed over silica gel with 0-30% 2-methytetrahydrofuran in EtOAc. Combined desired fractions, concentrated and dried under high vacuum to afford 2'-acetyl-3-chloro-4-((3,5-difluoropyridin-2-yl)methoxy)-5',6-dimethyl-2H-[1,4'-bipyridin]-2-one (CPD-18) as an off-white solid, 1.2 g (yield: 75%). $^1$H-NMR (400 MHz, DMSO-d6) δ ppm: 8.70 (s, 1H), 8.40 (d, 1H, J=2.4 Hz), 7.78 (s, 1H), 7.34 (m, 1H), 6.37 (s, 1H), 5.41 (d, 2H, J=1.6 Hz), 2.73 (s, 3H), 2.18 (s, 3H), 1.93 (s, 3H); MS (ES) m/z 420.14 (M+H).

Example 25: Alternative Preparation of 2'-acetyl-3-chloro-4-((3,5-difluoropyridin-2-yl)methoxy)-5',6-dimethyl-2H-[1,4'-bipyridin]-2-one (CPD-18) from CPD-30

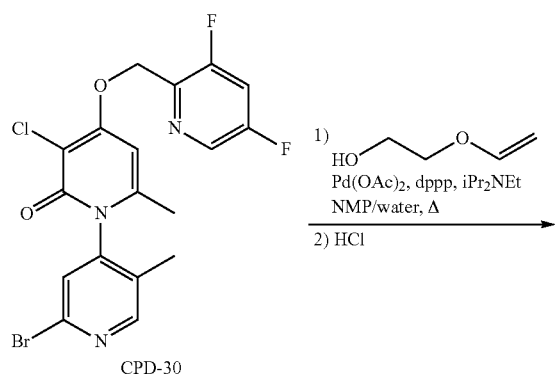

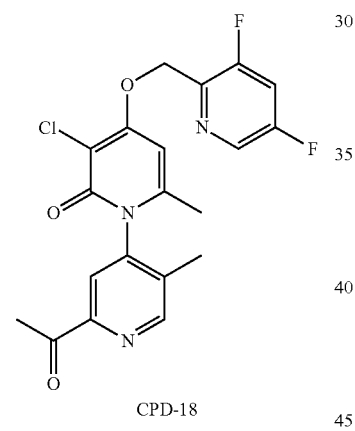

To a stirred suspension of 2'-bromo-3-chloro-4-((3,5-difluoropyridin-2-yl)methoxy)-5',6-dimethyl-2H-[1,4'-bipyridin]-2-one (CPD-30) (Example 37, 7.0 g, 15.33 mmol), iPr$_2$NEt (5.3 mL, 30.66 mmol), hydroxyethyl vinyl ether (56.9 mL, 76.64 mmol), NMP (18 mL) and water (18 mL) were charged to a RB flask fitted with a stir bar and condenser, and under N$_2$. The mixture was warmed with stirring to 45° C. while bubbling N$_2$ through mixture. Solid Pd(OAc)$_2$ (0.1 g, 0.46 mmol, 3 mol %) and dppp (0.38 g, 0.92 mmol, 6 mol %) were added sequentially, and the oil bath was heated to 92° C. Heating at 92-94° C. was continued for 28 h, with the reaction progress being monitored by HPLC and TLC. Conversion was very slow initially, so small additional charges of Pd(OAc)$_2$ were added after about 3 and 21 h of heating. The reaction was terminated after 28 h of heating, having never been homogeneous. The mixture was cooled and diluted with 2-methyltetrahydrofuran and treated with 3 N HCl to ~pH 2 and stirred vigorously at RT for 30 min. The acid was neutralized with sat'd KHCO$_3$ (CO$_2$ off-gassing), and the product was extracted into two portions of EtOAc. The combined organic phase was washed twice with water, then filtered through a pad of silica gel, eluting with EtOAc. Combined desired fractions, concentrated and dried on high vacuum to afford 2'-acetyl-3-chloro-4-((3,5-difluoropyridin-2-yl)methoxy)-5',6-dimethyl-2H-[1,4'-bipyridin]-2-one (CPD-18) as an off-white solid, 1.4 g (yield: 20%). $^1$H-NMR (400 MHz, DMSO-d6) δ ppm: 8.70 (s, 1H), 8.40 (d, 1H, J=2.4 Hz), 7.78 (s, 1H), 7.34 (m, 1H), 6.38 (s, 1H), 5.42 (d, 2H, J=1.6 Hz), 2.73 (s, 3H), 2.19 (s, 3H), 1.92 (s, 3H); MS (ES) m/z 420.12 (M+H).

Example 26: Alternative Preparation of methyl 3-chloro-4-((3,5-difluoropyridin-2-yl)methoxy)-5',6-dimethyl-2-oxo-2H-[1,4'-bipyridine]-2'-carboxylate (CDP-05) from CPD-28

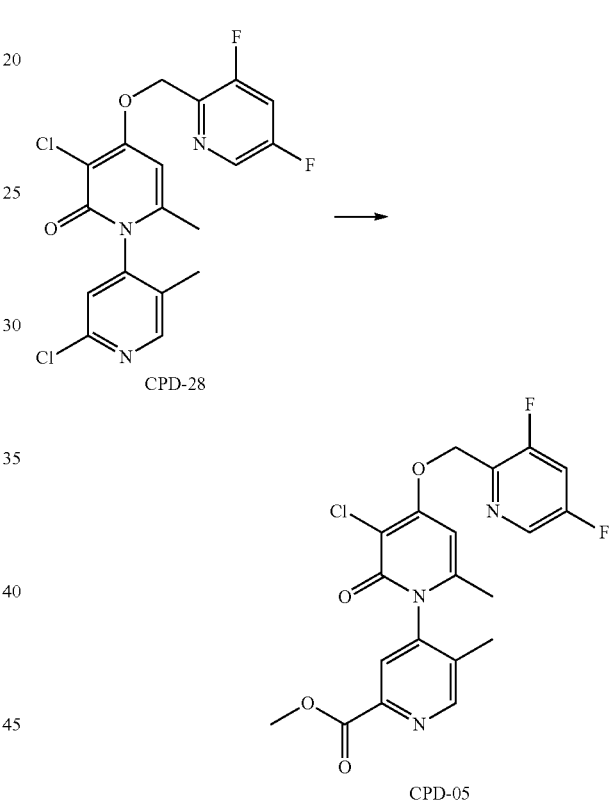

To a stirred suspension of 2',3-dichloro-4-((3,5-difluoropyridin-2-yl)methoxy)-5',6-dimethyl-2H-[1,4'-bipyridin]-2-one (CPD-28) (Example 41, 50.0 g, 1.0 eq.) in methanol (400 mL, 8.0 vol.) was added TEA (36.8 g, 3.0 eq.) at 25-30° C. and purged with Argon gas for 30 min. Then added and Pd(dppf)Cl$_2$ (2.4 g, 0.05 eq.) and purged with argon gas for 30 min. Applied CO pressure 60-70 psi (5 Kg) and released pressure. Again pressurized with CO pressure 75-100 psi (7 Kg) and slowly heated reaction mass to 90-95° C. and maintained at the same temperature for 16 h. The progress of the reaction was monitored by TLC/IPC-HPLC. After completion of the reaction, reaction mass was cooled to room temperature and diluted with DCM (100 mL, 2 vol.) and stirred for 15-30 min. Thus the resulting reaction mass was filtered through hyflo bed. Filtrate was distilled under reduced pressure at below 55° C. to afford the crude residue added IPA (250 mL, 5.0 vol.) at 25-35° C. and stirred for 10-12 h and filtered the solid, washed with IPA (50 mL, 1 vol.). After drying under vacuum at below 50° C. to afford methyl 3-chloro-4-((3,5-difluoropyridin-2-yl)methoxy)-5',6-dimethyl-2-oxo-2H-[1,4'-bipyridine]-2'-carboxylate (CPD-05) as a light brown solid, 34.39 g (yield: 66.8%), and HPLC purity 95.3%. ¹H-NMR (400 MHz, DMSO-d6) δ ppm: 8.82 (s, 1H), 8.6 (d, J=2.4 Hz, 1H), 8.13-8.07 (m, 1H), 8.03 (s, 1H), 6.81 (s, 1H), 5.48 (d, J=1.6 Hz, 2H), 3.89 (s, 3H), 1.92 (s, 3H), 1.81 (s, 3H); MS (ES) m/z 436.10 (M+H).

Example 27: Alternative Preparation of methyl 3-chloro-4-((3,5-difluoropyridin-2-yl)methoxy)-5',6-dimethyl-2-oxo-2H-[1,4'-bipyridine]-2'-carboxylate (CDP-05) from CPD-30

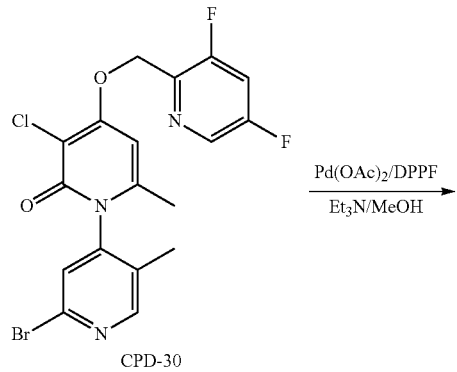

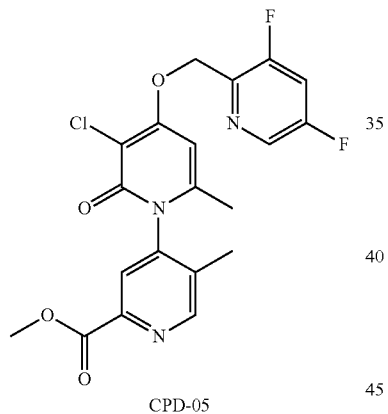

To a stirred solution of 2'-bromo-3-chloro-4-((3,5-difluoropyridin-2-yl)methoxy)-5',6-dimethyl-2H-[1,4'-bipyridin]-2-one (CPD-30) (Example 38, 3 g, 6.593 mmol, 1 eq) in dry methanol (45 ml, 15 vol) in a clean steel bomb was added dppf (182 mg, 0.329 mmol, 0.05 eq) and TEA (2 g, 19.78 mmol, 3 eq) at rt under argon atmosphere. Reaction mass was degassed with argon for 10 minutes followed by the addition of Pd(OAc)₂ (73.9 mg, 0.329 mmol, 0.05 eq) under argon atmosphere. Reaction mass was degassed with argon for 5 minutes. Steel bomb was closed and pressurized with CO gas (100 psi) and released. Again pressurized with CO gas (100 psi) and the reaction mixture was magnetically stirred and heated in oil bath to 80-85° C. for 18 h. The reaction was monitored by IPC-LCMS which showed ~93.1% desired mass. Reaction mixture was cooled to rt, filtered on celite bed, concentrated filtrate to afford 2.2 µm crude product. Celite bed was taken in rbf and suspended in 20% MeOH/DCM (100 ml) and stirred for 30 min and filtered. Filtrate was concentrated under reduced pressure to afford (200 mg) solid. Combined solid was taken in ethyl acetate (25 ml), stirred for 30 min then filtered and dried to afford methyl 3-chloro-4-((3,5-difluoropyridin-2-yl)methoxy)-5',6-dimethyl-2-oxo-2H-[1,4'-bipyridine]-2'-carboxylate (CPD-05) as a light brown solid, 2.2 µm (yield: 78%). ¹H-NMR (400 MHz, DMSO-d6) δ ppm: 8.59 (d, J=2.4 Hz, 1H), 8.82 (s, 1H), 8.12-8.02 (m, 2H), 7.80 (s, 1H), 6.72 (s, 1H), 5.47 (s, 2H), 3.89 (s, 3H), 2.08 (s, 3H), 1.92 (s, 3H); MS (ES) m/z 435.90 (M+H).

Example 28: Alternative Preparation of 3-chloro-4-((3,5-difluoropyridin-2-yl)methoxy)-N-methoxy-N,5',6-trimethyl-2-oxo-2H-[1,4'-bipyridine]-2'-carboxamide (CDP-16) from CPD-28

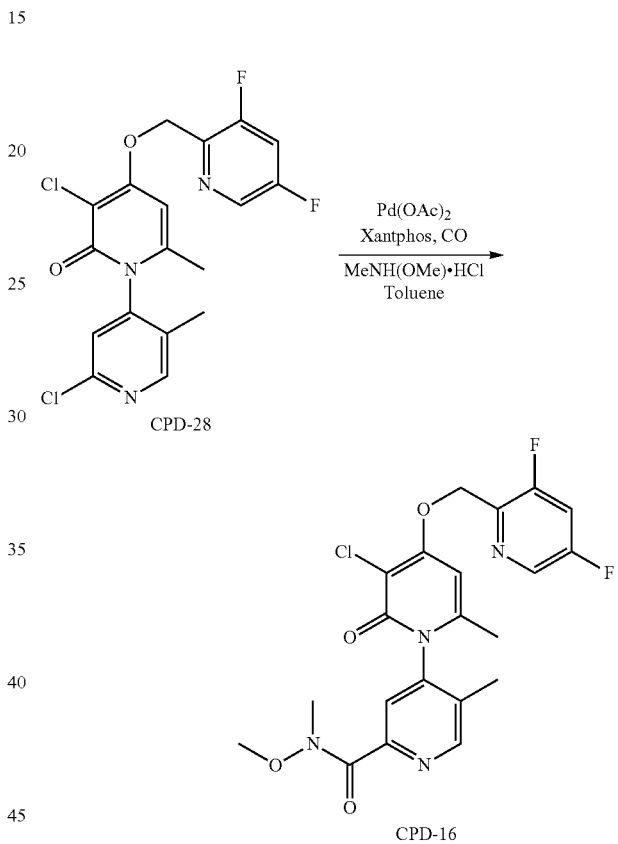

To a stirred suspension of 2',3-dichloro-4-((3,5-difluoropyridin-2-yl)methoxy)-5',6-dimethyl-2H-[1,4'-bipyridin]-2-one (CPD-28) (Example 41, 500 mg, 1.2165 mmol, 1 eq) in toluene (12.5 mL, 25 vol) in a steel bomb was added N,O-dimethylhydroxylamine hydrochloride (237.2 mg, 2.433 mmol, 2 eq), xantphos (28.1 mg, 0.048 mmol, 0.04 eq), and K₃PO₄ (796.6 mg, 3.649 mmol, 3 eq) at rt under argon atmosphere. Reaction mass was degassed with argon for 10 minutes, then Pd(OAc)₂ (10.92 mg, 0.0486 mmol, 0.04 eq) was added under argon atmosphere. The reaction mass was again degassed with argon for 5 minutes. Steel bomb was closed and filled with CO gas (200 psi), the reaction mixture was magnetically stirred and heated in oil bath to 120° C. for 3.5 days, IPC-LCMS showed 68.38% of desired material. Reaction mixture was cooled to rt, diluted with EtOAc and filtered through celite bed. Filtrate was concentrated and dried under high vacuum to afford 3-chloro-4-((3,5-difluoropyridin-2-yl)methoxy)-N-methoxy-N,5',6-trimethyl-2-oxo-2H-[1,4'-bipyridine]-2'- carboxamide (CPD-16) as a light brown solid, 248 mg (yield: 45%). MS (ES) m/z 465.21 (M+H).

Example 29: Alternative Preparation of 3-chloro-4-((3,5-difluoropyridin-2-yl)methoxy)-N-methoxy-N,5',6-trimethyl-2-oxo-2H-[1,4'-bipyridine]-2'-carboxamide (CDP-16) from CPD-30

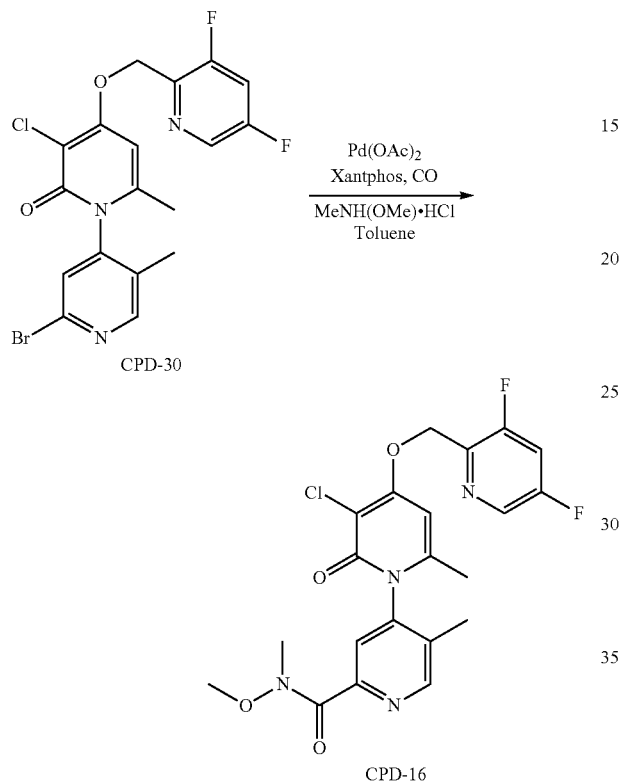

To a stirred suspension of 2'-bromo-3-chloro-4-((3,5-difluoropyridin-2-yl)methoxy)-5',6-dimethyl-2H-[1,4'-bipyridin]-2-one (CPD-30) (Example 38, 500 mg, 1.098 mmol, 1 eq) in a steel bomb in toluene (25 mL, 50 vol) was added N,O-dimethylhydroxylamine hydrochloride (214.2 mg, 2.197 mmol, 2 eq), xantphos (25.37 mg, 0.0439 mmol, 0.04 eq), and $K_3PO_4$ (719.6 mg, 3.54 mmol, 3 eq) at rt under argon atmosphere. Reaction mass was degassed with argon for 10 minutes, then Pd(OAc)$_2$ (9.86 mg, 0.0439 mmol, 0.04 eq) was added under argon atmosphere. The reaction mass was again degassed with argon for 5 minutes. Steel bomb was closed and filled with CO gas (200 psi) and degassed, the reaction mixture was magnetically stirred and heated in oil bath to 100-110° C. for 18 h. The reaction was monitored by IPC-LCMS, which showed 71.51% of desired material. Reaction mixture was cooled to rt, diluted with EtOAc and filtered through celite bed. The combined organic layer was concentrated under reduced pressure. The crude product was purified by Prep-HPLC. Combined desired fractions, concentrated under reduced pressure to remove volatile, basified with Aq. NaHCO$_3$ solution and extracted with DCM, dried over Na$_2$SO$_4$ concentrated under reduced pressure to afford 3-chloro-4-((3,5-difluoropyridin-2-yl)methoxy)-N-methoxy-N,5',6-trimethyl-2-oxo-2H-[1,4'-bipyridine]-2'-carboxamide (CPD-16) as an off-white solid, 280 mg (yield: 39.22%). $^1$H-NMR (400 MHz, DMSO-d6) δ ppm: 8.70 (s, 1H), 8.59 (d, J=2.4 Hz, 1H), 8.12-8.06 (m, 1H), 7.63 (s, 1H), 6.79 (s, 1H), 5.47 (s, 2H), 3.68 (s, 3H), 3.29 (s, 3H), 2.05 (s, 3H), 1.93 (s, 3H); MS (ES) m/z 465.16 (M+H).

Example 30: Alternative Preparation of 3-chloro-4-((3,5-difluoropyridin-2-yl)methoxy)-N-methoxy-N,5',6-trimethyl-2-oxo-2H-[1,4'-bipyridine]-2'-carboxamide (CDP-16) from CPD-15

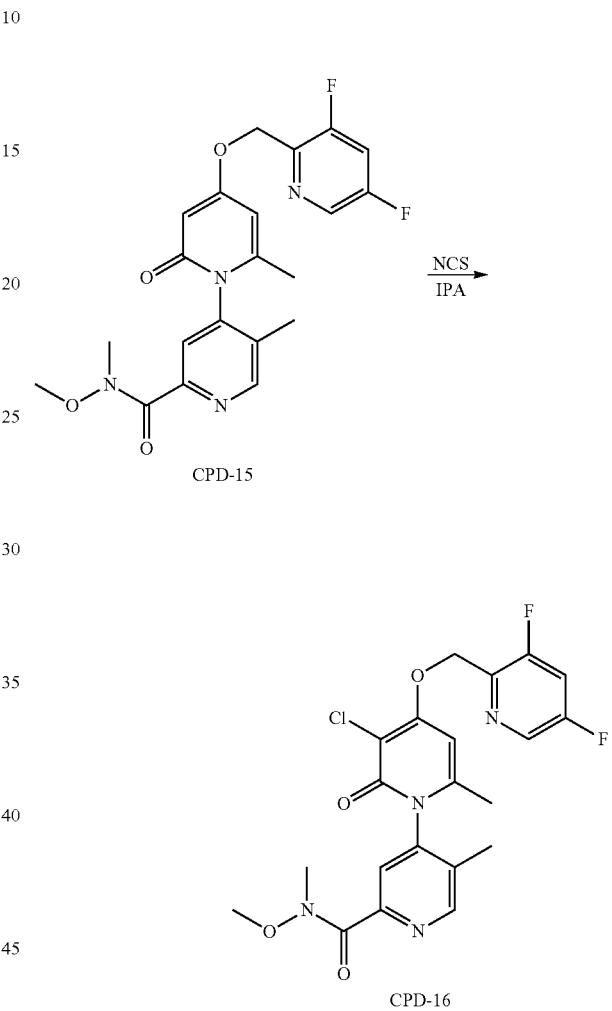

To a stirred suspension of 4-((3,5-difluoropyridin-2-yl)methoxy)-N-methoxy-N,5',6-trimethyl-2-oxo-2H-[1,4'-bipyridine]-2'-carboxamide (CPD-15) (8.5 g, 19.76 mmol) in IPA (15.0 vol.) was added dichloroacetic acid (0.25 eq.) at 25-30° C. Then heated the reaction mixture to 45-50° C., added a portion wise of N-chlorosuccinimide (1.0 eq.) to the reaction mass at 45-50° C. and heated the reaction mass further to 60-65° C. After completion of the reaction (by TLC), Cooled the reaction mass to RT, and further cooled to 0-5° C., filtered the obtained solid and washed with IPA (1 vol.) and dried to afford 3-chloro-4-((3,5-difluoropyridin-2-yl)methoxy)-N-methoxy-N,5',6-trimethyl-2-oxo-2H-[1,4'-bipyridine]-2'-carboxamide (CPD-16) as a tan solid, 4.5 g (yield: 49%) with HPLC purity 96.43%. $^1$H-NMR (400 MHz, DMSO-d6) δ ppm: 8.69 (s, 1H), 8.59 (d, J=2.4 Hz, 1H), 8.12-8.07 (m, 1H), 7.63 (s, 1H), 6.80 (s, 1H), 5.47 (s, 2H), 3.68 (s, 3H), 3.30 (s, 3H), 2.05 (s, 3H), 1.92 (s, 3H); MS (ES) m/z 465.12 (M+H).

Example 31: Preparation of 4-((3,5-difluoropyridin-2-yl)methoxy)-5',6-dimethyl-2-oxo-2H-[1,4'-bipyridine]-2'-carboxylic acid (CDP-11) from CPD-03

Example 32: Preparation of 4-((3,5-difluoropyridin-2-yl)methoxy)-5',6-dimethyl-2-oxo-2H-[1,4'-bipyridine]-2'-carboxylic acid (CDP-11) from CPD-26

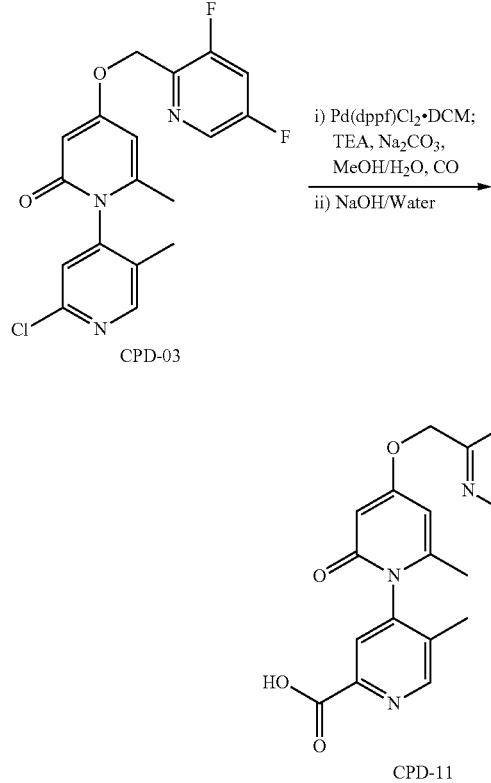

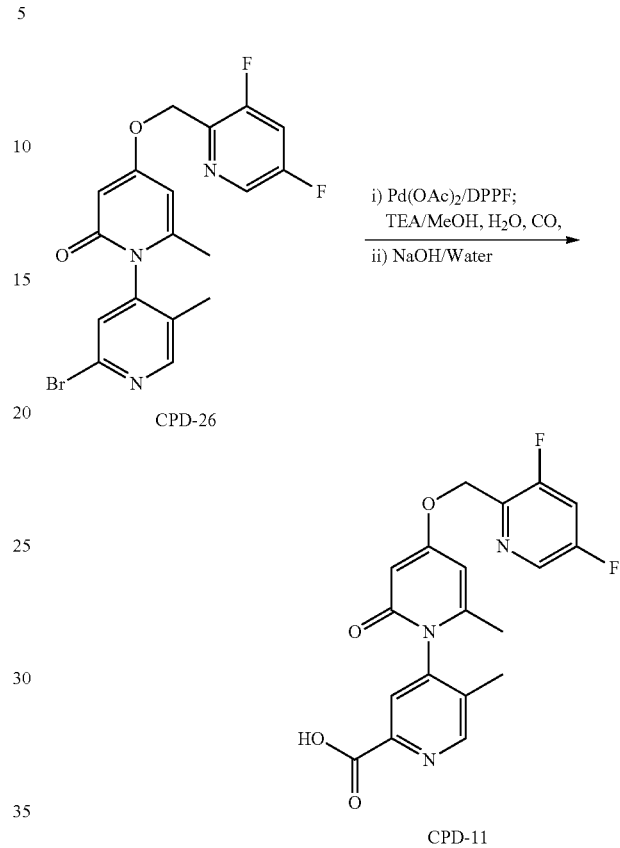

To a solution of 2'-chloro-4-((3,5-difluoropyridin-2-yl)methoxy)-5',6-dimethyl-2H-[1,4'-bipyridin]-2-one (CPD-03, Example 5, 1 g, 2.64 mmol, 1 eq) in methanol and water (20 ml, 20 vol, 9:1) in a steel bomb with magnetic stirring was added Na$_2$CO$_3$ (420.8 mg, 3.97 mmol, 1.5 eq) at rt under argon atmosphere. Reaction mass was degassed with argon for 15 minutes. Then Pd(dppf)Cl$_2$-DCM complex (108.53 mg, 0.132 mmol, 0.05 eq) was added under argon atmosphere. Reaction mass was degassed with argon for 5 minutes. Steel bomb was closed and filled with CO gas (50 psi) and released. Again filled with CO gas (100 psi) and the reaction mixture was magnetically stirred and heated in oil bath to 90-95° C. for 17 h. The reaction was monitored by IPC-LCMS until >80% desired product. Reaction mass was cooled to rt, diluted with methanol and filtered through celite bed. Filtrate was concentrated under reduced pressure and crude product was diluted with water (20 ml) and washed with ethyl acetate (2×20 ml). Aqueous layer was acidified with 1N aqueous citric acid solution and extracted with 10% MeOH/DCM. The combined organic layer was dried over Na$_2$SO$_4$ and evaporated under reduced pressure to afford 4-((3,5-difluoropyridin-2-yl)methoxy)-5',6-dimethyl-2-oxo-2H-[1,4'-bipyridine]-2'-carboxylic acid (CPD-11) as an off-white solid, 700 mg, (Yield: 71%), HPLC purity 99.36%. $^1$H-NMR (400 MHz, DMSO-d6) δ ppm: 13.24 (brs, 1H), 8.76 (s, 1H), 8.59 (d, 1H, 2.4 Hz), 8.10 (m, 1H), 7.87 (s, 1H), 6.13 (d, 1H, J=2 Hz), 6.04 (d, 1H, J=2.4 Hz), 5.24 (s, 2H), 2.08 (s, 3H), 1.82 (s, 3H); LCMS (ES) m/z 387.99 (M+H).

To a suspension of 2'-bromo-4-((3,5-difluoropyridin-2-yl)methoxy)-5',6-dimethyl-2H-[1,4'-bipyridin]-2-one (CPD-26) (Example 15, Step 2, 200 mg, 0.473 mmol, 1 eq) in methanol and water (3.6 mL: 0.4 mL, 20 vol, 9:1) was added triethylamine (0.194 mL, 1.421 mmol, 3 eq), dppf (13.1 mg, 0.0236 mmol, 0.05 eq) at rt under nitrogen atmosphere. Reaction mass was degassed with argon for 15 minutes. Then Pd(OAc)$_2$ (5.3 mg, 0.0236 mmol, 0.05 eq) was added under argon atmosphere. Reaction mass was degassed with argon for 5 minutes then the vial was placed in clean, dry Steel bomb. Steel bomb was closed and filled with CO gas (50 psi) and released. Charged with CO gas (100 psi) and the reaction mixture was magnetically stirred and heated in oil bath to 90-95° C. for 16 h. The reaction was monitored by LCMS until ~65.2% of desired mass was observed. Pressure was released, vial removed and cooled to rt. Water (0.5 mL) and NaOH (56.7 mg, 1.421 mmol, 3.0 eq) were added and reaction mixture was stirred rt for 16 h and monitored by LCMS until ~90.6% of desired mass observed. Reaction mixture was diluted with methanol and filtered through celite bed. Filtrate was concentrated under reduced pressure. The crude product was diluted with water (4 mL) and washed with ethyl acetate. Aqueous layer pH adjusted to neutral (6-7) with 1N HCl. Reaction mass was extracted with 20% MeOH/DCM. Evaporated solvent under reduced pressure to afford, 4-((3,5-difluoropyridin-2-yl)methoxy)-5',6-dimethyl-2-oxo-2H-[1,4'-bipyridine]-2'-carboxylic acid (CPD-11) as a dark brown solid, 150 mg (yield: 81.4%). $^1$H-NMR (400 MHz, DMSO-d6) δ ppm: 13.22 (brs, 1H), 8.77 (s, 1H), 8.594 (s, 1H), 8.07 (t, 1H, J=9.2 Hz), 7.87 (s, 1H), 6.13 (s, 1H), 6.04 (s, 1H), 5.24 (s, 1H), 2.08 (s, 3H), 1.98 (s, 3H); MS (ES) m/z 388.17 (M+H).

Example 33: Preparation of 3-chloro-4-((3,5-difluoropyridin-2-yl)methoxy)-5',6-dimethyl-2-oxo-2H-[1,4'-bipyridine]-2'-carboxylic acid (CDP-06) from CPD-28

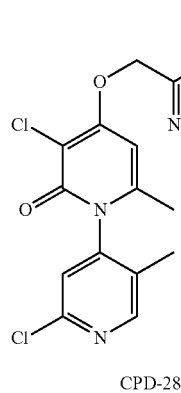

CPD-28

Pd(dppf)Cl$_2$
CO
Methanol
Water
Na$_2$CO$_3$

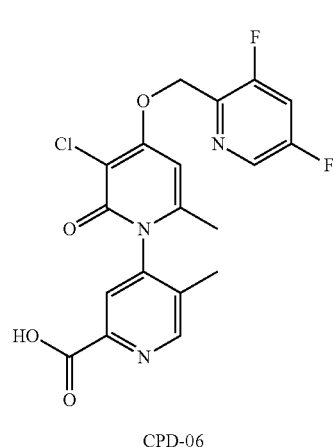

CPD-06 solid, 18.0 g (yield: 70.3%). $^1$H-NMR (400 MHz, DMSO-d6) δ ppm: 8.79 (d, J=10.0 Hz, 1H), 8.60 (d, J=2.4 Hz, 1H), 7.98 (s, 1H), 8.12-8.07 (m, 1H), 6.80 (s, 1H), 5.47 (d, J=12.0 Hz, 2H), 2.08 (s, 3H), 1.93 (s, 3H); MS (ES) m/z 422.28 (M+H).

Example 34: Preparation of 3-chloro-4-((3,5-difluoropyridin-2-yl)methoxy)-5',6-dimethyl-2-oxo-2H-[1,4'-bipyridine]-2'-carboxylic acid (CDP-06) from CPD-30

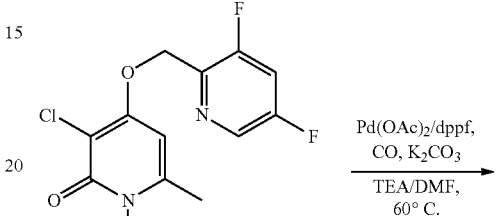

CPD-30

Pd(OAc)$_2$/dppf,
CO, K$_2$CO$_3$
TEA/DMF,
60° C.

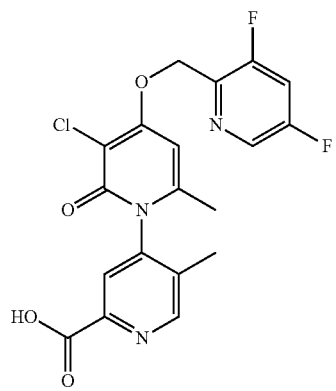

CPD-06

To a stirred suspension of 2',3-dichloro-4-((3,5-difluoropyridin-2-yl)methoxy)-5',6-dimethyl-2H-[1,4'-bipyridin]-2-one (CPD-28) (Example 41, 25.0 g, 1.0 eq.) in methanol (450 mL, 18.0 vol.) and water (50 mL, 2 vol.) was added Na$_2$CO$_3$ (9.64 g, 1.5 eq.) to the reaction mass at 25-30° C. and purged with Argon gas for 30 min. Then added and Pd(dppf)Cl$_2$ (2.4 g, 0.05 eq.) and purged with argon gas for 30 min. Then applied CO pressure 60-70 psi (5 Kg) and released CO pressure. Again pressurized with CO pressure 75-100 psi (7 Kg) and slowly heated reaction mass to 90-95° C. and maintained at the same temperature for 24 h. The Progress of the reaction was monitored by TLC/IPC-HPLC. After completion of reaction, cooled to 25-35° C. and diluted with water (75.0 mL 3.0 vol.) and stirred for 20-30 min. Then added charcoal (1.25 g, 0.05 T) to the reaction mass and heated to 50-55° C. for 1-2 h. Stopped heating and the resulting reaction mass was filtered through hyflo bed, distilled-off methanol and reaction mass was diluted with THF (125 mL, 5.0 vol.). Then the pH of the reaction mass was adjusted to 1-2 using 6N HCl (60 mL) at 10-15° C. and stirred for 2-3 h, filtered the solid and washed with water (75 mL, 3 vol.) and dried at 50° C. to afford 3-chloro-4-((3,5-difluoropyridin-2-yl)methoxy)-5',6-dimethyl-2-oxo-2H-[1,4'-bipyridine]-2'-carboxylic acid (CPD-06) as an off-white To a stirred suspension of 2'-bromo-3-chloro-4-((3,5-difluoropyridin-2-yl)methoxy)-5',6-dimethyl-2H-[1,4'-bipyridin]-2-one (CPD-30) (Example 38, 500 mg, 1.098 mmol, 1 eq) in methanol and water (9:1) in a steel bomb was added K$_2$CO$_3$ (303 mg, 2.19 mmol, 2 eq), dppf (30 mg, 0.054 mmol, 0.05 eq) at rt under argon atmosphere. Reaction mass was degassed with argon for 10 minutes. Then Pd(OAc)$_2$ (12.3 mg, 0.054 mmol, 0.05 eq), was added under argon atmosphere. Reaction mass was degassed with argon for 5 minutes. Steel bomb was closed and filled with CO gas (100 psi) and released. Again pressurized with CO gas (100 psi) and the reaction mixture was magnetically stirred and heated in oil bath to 90-95° C. for 20 h. The reaction was monitored by LCMS which showed ~79.9% desired mass. Reaction mixture was cooled to rt, diluted with methanol and filtered through celite bed. Organic layer was concentrated under reduced pressure. The crude compound was taken in RBF then acidified with 1N HCl to pH ~2. Solid was filtered and dried to afford crude desired material. It was purified by prep HPLC. Combined desired fractions, concentrated under reduced pressure and lyophilized to afford 3-chloro-4-((3,5-difluoropyridin-2-yl)methoxy)-5',6-dimethyl-2-oxo-2H-[1,4'-bipyridine]-2'-carboxylic acid (CPD-06) as an off-white solid, 200 mg (yield: 43%). ¹H-NMR (400 MHz, DMSO-d6) δ ppm: 13.3 (brs, 1H), 8.81 (s, 1H), 8.60 (d, 1H, J=2 Hz), 8.12-8.06 (m, 1H), 7.92 (s, 1H), 6.79 (s, 1H), 5.47 (s, 2H), 2.07 (s, 3H), 1.92 (s, 3H); MS (ES) m/z 422.10 (M+H).

Example 35: Preparation of 3-chloro-4-((3,5-difluoropyridin-2-yl)methoxy)-5',6-dimethyl-2-oxo-2H-[1,4'-bipyridine]-2'-carboxylic acid (CDP-06) from CPD-11

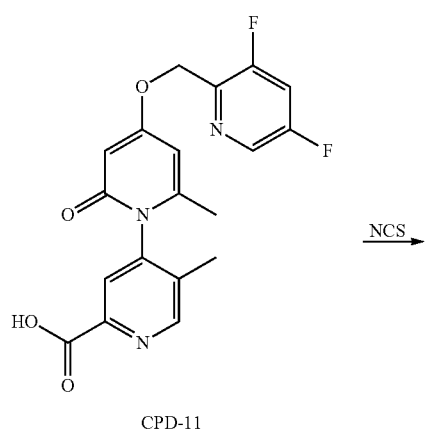

CPD-11

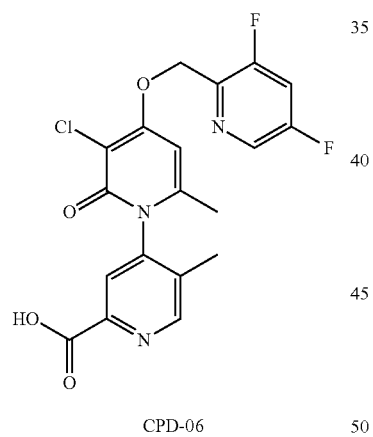

CPD-06

To a stirred suspension 4-((3,5-difluoropyridin-2-yl)methoxy)-5',6-dimethyl-2-oxo-2H-[1,4'-bipyridine]-2'-carboxylic acid (CPD-11) (Example 16, 1.0 g, 2.58 mmol) in IPA (15.0 vol.) and heated to 45-50° C. was added N-chlorosuccinimide (1.0 eq.). The temperature was raised 60-65° C. After completion of the reaction indicated by TLC, cooled the reaction mass to RT and then further cooled to 0-5° C., filtered the obtained solid, washed the with IPA (1 vol.) and dried to afford 3-chloro-4-((3,5-difluoropyridin-2-yl)methoxy)-5',6-dimethyl-2-oxo-2H-[1,4'-bipyridine]-2'-carboxylic acid (CPD-06) as an off-white solid, 0.8 g (yield: 74%). ¹H-NMR (300 MHz, DMSO-d6) δ ppm 13.2 (br s, 1H), 8.81 (s, 1H), 8.60 (d, J=2.7 Hz, 1H), 8.15-8.06 (m, 1H), 7.98 (s, 1H), 6.80 (s, 1H), 5.48 (s, 2H), 2.07 (s, 3H), 1.93 (s, 3H); LC-MS m/z 422.13 (M+H)+.

Example 36: Preparation of 4-((3,5-difluoropyridin-2-yl)methoxy)-N-methoxy-N,5',6-trimethyl-2-oxo-2H-[1,4'-bipyridine]-2'-carboxamide (CDP-15) from CPD-03

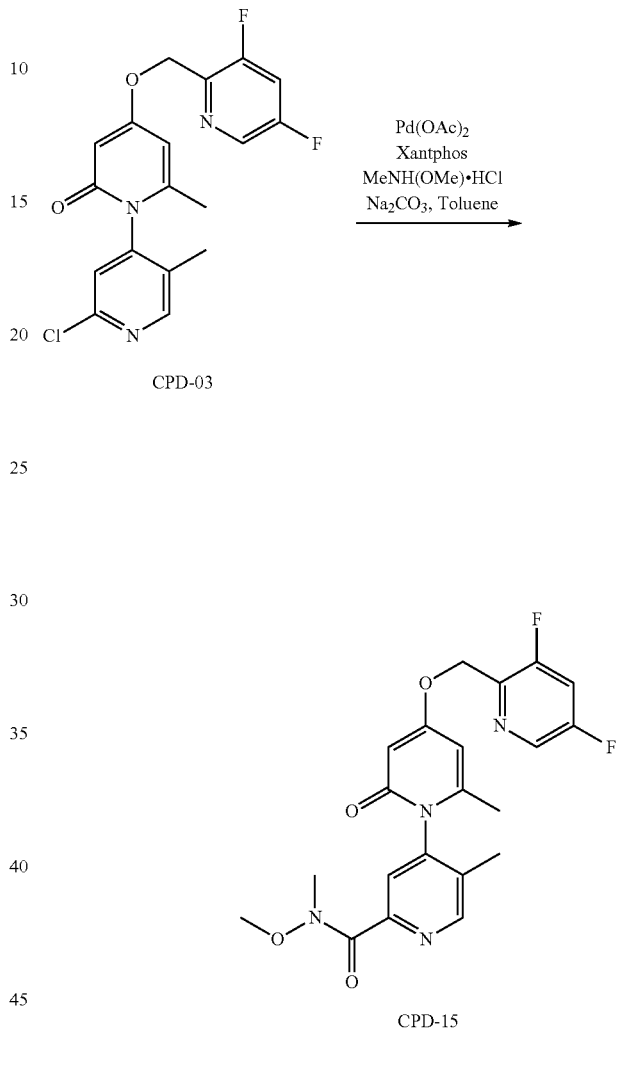

To a stirred suspension of 2'-chloro-4-((3,5-difluoropyridin-2-yl)methoxy)-5',6-dimethyl-2H-[1,4'-bipyridin]-2-one (CDP-03) (Example 5, Step 1, 5.0 g, 1.0 eq.), in Toluene (10.0 vol.), was added Na₂CO₃ (3.0 eq.). The mixture was degassed with argon gas for 30-45 min. Pd(OAc)₂ (0.02 eq.), Xantphos (0.02 eq.), and MeNH(OMe)-HCl (1.5 eq.) were added and the suspension was purged with Argon gas for 10-15 min. The temperature was slowly raised to 80° C. and maintained for 15 h under CO pressure (60-70 PSI) at the same temperature. Reaction mass was allowed to cool to RT and filtered through celite bed to obtain filtered mL's that were concentrated under reduced pressure at below 50° C. to afford 4-((3,5-difluoropyridin-2-yl)methoxy)-N-methoxy-N,5',6-trimethyl-2-oxo-2H-[1,4'-bipyridine]-2'-carboxamide (CPD-15), as a tan solid, 4.0 g (yield: 70%). ¹H-NMR (400 MHz, DMSO-d6) δ ppm: 8.65 (brs, 1H), 8.42 (d, 1H, J=2.4 Hz), 7.53 (s, 1H), 7.31 (m, 1H), 6.02 (dd, 2H, J=2.4 Hz), 5.18 (d, 2H, J=2 Hz), 3.76 (s, 3H), 3.45 (s, 3H), 2.17 (s, 3H), 1.84 (s, 3H); MS (ES) m/z 431.13 (M+H).

Example 37: Preparation of 4-((3,5-difluoropyridin-2-yl)methoxy)-N-methoxy-N,5',6-trimethyl-2-oxo-2H-[1,4'-bipyridine]-2'-carboxamide (CDP-15) from CPD-26

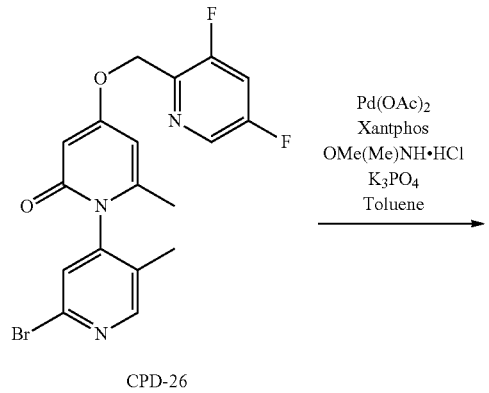

CPD-26

Pd(OAc)$_2$
Xantphos
OMe(Me)NH·HCl
K$_3$PO$_4$
Toluene

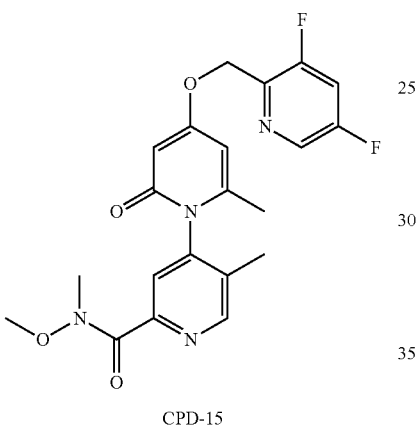

CPD-15

To a stirred suspension of 2'-bromo-4-((3,5-difluoropyridin-2-yl)methoxy)-5',6-dimethyl-2H-[1,4'-bipyridin]-2-one (CPD-26) (Example 15, Step 2, 500 mg, 1.18 mmol, 1 eq) was taken into steel bomb and suspended in toluene (15 ml, 30 vol). N,O-dimethylhydroxylamine hydrochloride (231 mg, 2.36 mmol, 2 eq), Xantphos (27.28 mg, 0.0472 mmol, 0.04 eq), K$_3$PO$_4$ (751 mg, 3.54 mmol, 3 eq) were added at rt under nitrogen atmosphere. Reaction mass was degassed with argon for 10 minutes. Then Pd(OAc)$_2$ (10.62 mg, 0.0472 mmol, 0.04 eq) was added under N$_2$ atmosphere. Reaction mass was degassed with argon for 5 minutes. Steel bomb was closed and filled with CO gas (50 Psi) and released. The reactor was charged with CO gas (50 Psi) and the reaction mixture was magnetically stirred and heated in oil bath to 100-110° C. for 16 h, IPC-LCMS showed ~65% desired mass. Reaction mixture was cooled to rt, diluted with ethyl acetate and filtered through celite bed. The combined organic layer was concentrated under reduced pressure. The crude product was purified by column chromatography over 230-400 Si-gel, using 2-3% methanol in DCM as a eluent to afford 4-((3,5-difluoropyridin-2-yl)methoxy)-N-methoxy-N,5',6-trimethyl-2-oxo-2H-[1,4'-bipyridine]-2'-carboxamide (CPD-15) as an off-white solid, 250 mg (yield: 42%). $^1$H-NMR (400 MHz, DMSO-d6) δ ppm: 8.63 (brs, 1H), 8.40 (d, 1H, J=2.4 Hz), 7.52 (s, 1H), 7.31 (m, 1H), 6.02 (dd, 2H, J=2.4 Hz), 5.19 (d, 2H, J=2 Hz), 3.76 (s, 3H), 3.44 (s, 3H), 2.17 (s, 3H), 1.86 (s, 3H); MS (ES) m/z 431.06 (M+H).

Example 38: Preparation of 2'-bromo-3-chloro-4-((3,5-difluoropyridin-2-yl)methoxy)-5',6-dimethyl-2H-[1,4'-bipyridin]-2-one (CDP-30) from CPD-26

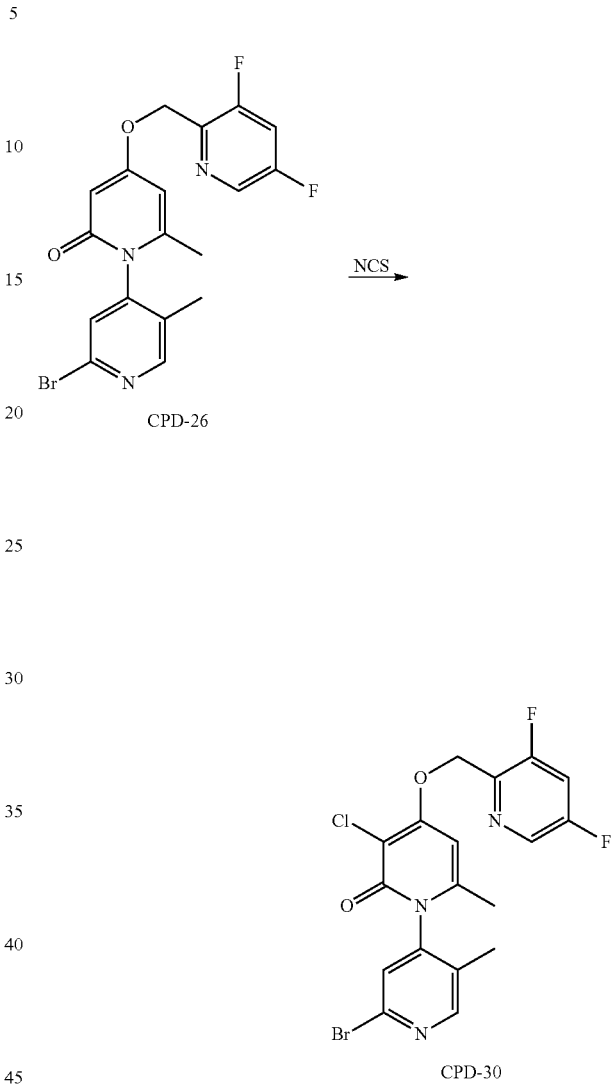

To a stirred suspension of 2'-bromo-4-((3,5-difluoropyridin-2-yl)methoxy)-5',6-dimethyl-2H-[1,4'-bipyridin]-2-one (CPD-26) (Example 15, Step 2, 10 g, 23.69 mmol, 1.0 eq) in isopropyl alcohol (150 ml, 15 vol) was added N-chlorosuccinimide (3.80 g, 28.43 mmol, 1.2 eq) at rt. Reaction mass was slowly heated to 65-70° C. for 2 h, while heating slowly clear solution was formed at 55-60° C. When temperature reached 65-70° C., solid formation was observed in the reaction. Heating was continued at 65-70° C. for 2 h. Progress of the reaction was monitored by TLC until no starting material remained, reaction mass was cooled to 55-60° C. and filtered while hot. The solid was washed with IPA (20 ml, 2 vol). Solid was dried under reduced pressure at 45° C. for 2 h to afford 2'-bromo-3-chloro-4-((3,5-difluoropyridin-2-yl)methoxy)-5',6-dimethyl-2H-[1,4'-bipyridin]-2-one (CPD-30) as an off-white solid, 5.5 g, (yield: 51%). $^1$H-NMR (400 MHz, CDCl$_3$) δ ppm: 8.42 (s, 1H), 8.397-8.391 (d, J=2.4 Hz, 1H), 7.345-7.297 (m, 1H), 7.27 (s, 1H), 6.37 (s, 1H), 5.404-5.399 (d, J=2 Hz, 2H), 2.055 (s, 3H), 1.973 (s, 3H); MS (ES) m/z 455.96 (M+H).

Example 39: Preparation of 2'-bromo-3-chloro-4-((3,5-difluoropyridin-2-yl)methoxy)-5',6-dimethyl-2H-[1,4'-bipyridin]-2-one (CDP-30) from CDP-31

Example 40: Preparation of 2'-bromo-3-chloro-4-hydroxy-5',6-dimethyl-2H-[1,4'-bipyridin]-2-one (CDP-31) from CPD-25

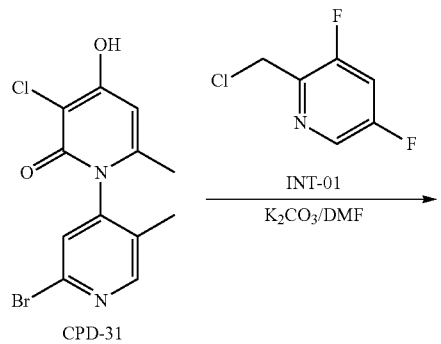

CPD-31

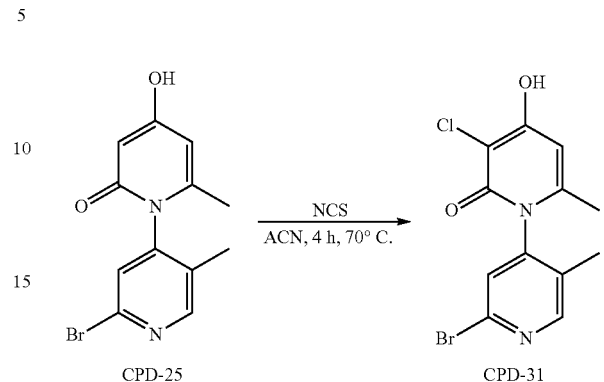

CPD-25  CPD-31

To a stirred mixture of 2'-bromo-4-hydroxy-5',6-dimethyl-2H-[1,4'-bipyridine]-2-one (CDP-25) (Example 15, Step 1, 15.0 g, 0.0508 mol, 1 eq) in DMF (255 mL, 15 vol) was added N-chlorosuccinimide (8.1 g, 0.061 mol, 1.2 eq) portion wise at 25-30° C. and then reaction mass was heated to 72° C. (oil bath) for 4 h. The reaction progress was monitored by TLC and LCMS, which showed absence of starting material and formation of products. Reaction mass was cooled to RT and water (300 mL, 20 vol) was added, stirred for 45 min and the solid was filtered. It was washed with water (75 mL, 5 vol) and dried to afford crude desired material (15.1 g). A suspension of crude desired material (15.1 g) in methanol (900 mL, 60 vol) was heated to reflux, and stirred for 45 min to get a clear solution. It was filtered through filter paper and distilled to remove methanol (80%), stirred at RT and the solid was filtered. It was washed with methanol (75 mL, 5 vol) and dried under high vacuum to afford 2'-bromo-3-chloro-4-hydroxy-5',6-dimethyl-2H-[1,4'-bipyridin]-2-one (CDP-31) as an off-white solid, 10.2 g (yield: 60.7%). $^1$H-NMR (400 MHz, DMSO-d6) δ ppm: 11.59 (s, 1H), 8.49 (s, 1H), 7.75 (s, 1H), 6.15 (s, 1H), 1.94 (s, 3H), 1.85 (s, 3H); MS (ES) m/z 329.58 (M+H).

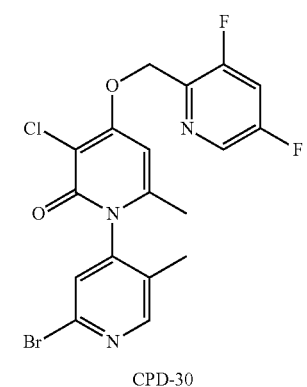

CPD-30

To a stirred solution of 2'-bromo-3-chloro-4-hydroxy-5',6-dimethyl-2H-[1,4'-bipyridin]-2-one (CDP-31) (Example 40, 15.0 g, 45.45 mmol, 1 eq.) in DMF (75 mL, 5 vol), was added K$_2$CO$_3$ (9.42 g, 68.18 mmol, 1.5 eq.) under inert atmosphere. The reaction mixture was stirred for 15 min at room temperature, then added 2-(chloromethyl)-3,5-difluoropyridine (INT-01, Example 4) (9.0 g, 54.54 mmol, 1.2 eq) in DMF (7.5 ml, 0.5 vol) (drop wise addition) at room temperature, the resulting reaction mixture was stirred at 50° C. for 7 h. The progress of the reaction was monitored by TLC and LCMS. After completion of the reaction, added ice cold water (25 vol) and stirred for 30 min, then filtered the solid and washed with water. It was dried to afford crude desired material as an off-white solid, 21.2 g. A suspension of crude desired material (21 g) in methanol (280 mL, 10 vol) was heated to reflux, stirred for 45 min to get clear solution. It was cooled and stirred at RT for 2 h and the solid was filtered. It was washed with methanol (28 mL) and dried to afford 2'-bromo-3-chloro-4-((3,5-difluoropyridin-2-yl)methoxy)-5',6-dimethyl-2H-[1,4'-bipyridin]-2-one (CDP-30) as an off-white solid, 16 g (yield: 77%). $^1$H-NMR (400 MHz, DMSO-d6) δ ppm: 8.59 (d, J=2.4 Hz, 1H), 8.52 (s, 1H), 8.09-8.08 (m, 1H), 7.80 (s, 1H), 6.92 (s, 1H), 5.47 (s, 2H), 1.95 (s, 6H); MS (ES) m/z 455.93 (M+H).

Example 41: Preparation of 2',3-dichloro-4-((3,5-difluoropyridin-2-yl)methoxy)-5',6-dimethyl-2H-[1,4'-bipyridin]-2-one (CDP-28) from CPD-03

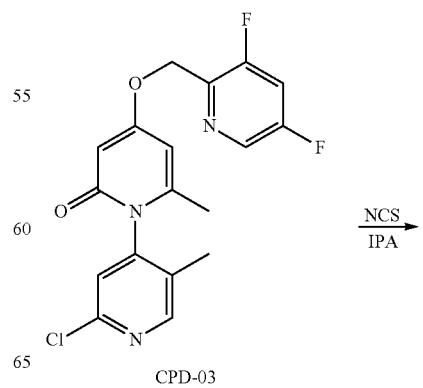

CPD-03

-continued

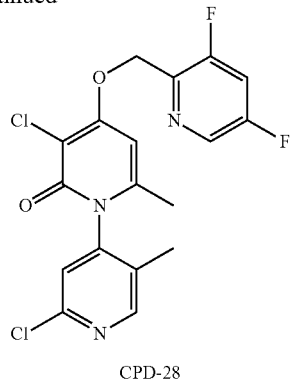

CPD-28

To a stirred suspension of 2'-chloro-4-((3,5-difluoropyridin-2-yl)methoxy)-5',6-dimethyl-2H-[1,4'-bipyridin]-2-one (CPD-03) (Example 5, 100 g, 1.0 eq.) in IPA (1500 mL, 15.0 vol.) was added dichloroacetic acid (8.53 g, 0.25 eq.) at room temperature. Then slowly heated the reaction mass to 45-50° C. and added N-chlorosuccinamide (NCS, 42.4 g, 1.2 eq.). After completion of addition of NCS, raised the temperature to 65-70° C. and maintained for 2 h, a clear solution was observed at 55-60° C. The progress of the reaction was monitored by TLC and IPC-HPLC. After completion of the reaction, cooled to 25-35° C., stirred for 1-2 h, filtered, washed with IPA (100 mL, 1.0 vol.) and dried at 45° C. for 2-3 h to afford, 2',3-dichloro-4-((3,5-difluoropyridin-2-yl)methoxy)-5',6-dimethyl-2H-[1,4'-bipyridin]-2-one (CDP-28), 89.0 g (yield: 81%) with HPLC purity 97.66%. $^1$H-NMR (400 MHz, DMSO-d$_6$) δ ppm: δ: 8.43 (s, 1H), 8.396-8.390 (d, 1H, J=2.4 Hz), 7.321-7.301 (m, 1H), 7.12 (s, 1H), 6.379 (s, 1H), 5.4.4-5.40 (d, 2H, J=1.6 Hz), 2.074 (s, 3H), 1.974 (s, 3H); MS (ES) m/z 412.07 (M+H).

Example 42: Alternative Preparation of 2'-chloro-4-hydroxy-5',6-dimethyl-2H-[1,4'-bipyridin]-2-one (CPD-02)

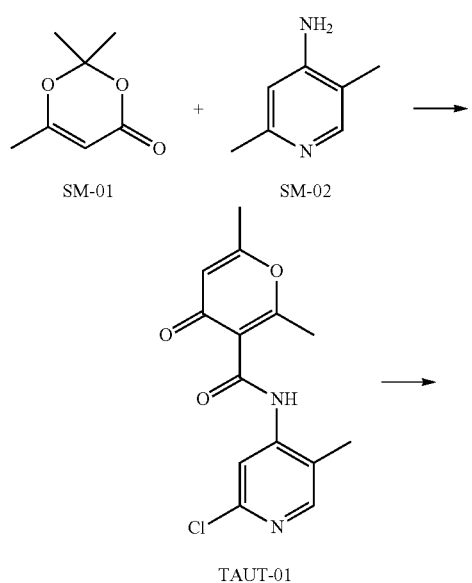

-continued

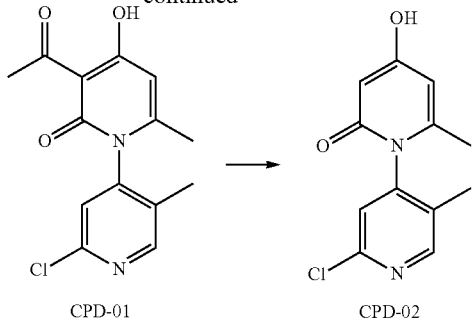

CPD-01             CPD-02

Step 1: Synthesis of N-(2-chloro-5-methylpyridin-4-yl)-2,6-dimethyl-4-oxo-4H-pyran-3-carboxamide (TAUT-01). To a stirred solution of 2-chloro-5-methylpyridin-4-amine (SM-01) (100 g, 1.0 eq.) and 2, 2, 6-trimethyl-4H-1,3-dioxin-4-one (SM-01) (400 g, 4.0 eq.) in dimethyl acetamide (500 mL, 5.0 vol.) was heated to 110-120° C. and maintained for 4-6 h. Progress of the reaction was monitored by IPC-HPLC. After completion of the reaction, cooled the reaction mass to 40-50° C., quenched with water (15 vol.). Then cooled the reaction mass to 5-10° C. and stirred for 2-3 h. The solids were filtered and washed with water (3 vol.) and dried at 50-55° C. to afford brown color solid 176 g (yield: 85.6%). Based on HPLC data, the ratio of the two compounds N-(2-chloro-5-methylpyridin-4-yl)-2,6-dimethyl-4-oxo-4H-pyran-3-carboxamide (TAUT-01): 3-acetyl-2'-chloro-4-hydroxy-5',6-dimethyl-2H-[1,4'-bipyridin]-2-one (CPD-01) are 66.2%: 31.8%. $^1$H-NMR (400 MHz, DMSO-d$_6$): δ ppm.

TAUT-01: $^1$H NMR (dmso-d6) δ 12.34 (s, 1H), 8.30 (s, 1H), 8.20 (s, 1H), 6.49 (s, 1H), 2.74 (s, 3H), 2.34 (s, 3H), 2.26 (s, 3H).

CPD-01: $^1$H NMR (dmso-d6) δ 15.74 (s, 1H), 8.51 (s, 1H), 7.66 (s, 1H), 6.24 (s, 1H), 2.54 (s, 3H), 2.01 (s, 3H), 1.93 (s, 3H), MS (ES) m/z 293.68 (M+H).

Step 2: Synthesis of 3-acetyl-2'-chloro-4-hydroxy-5',6-dimethyl-2H-[1,4'-bipyridin]-2-one (CPD-01). To a stirred suspension of N-(2-chloro-5-methylpyridin-4-yl)-2,6-dimethyl-4-oxo-4H-pyran-3-carboxamide (TAUT-01) (Step 1, 100 g, 1.0 eq.) in water (1200 mL, 12 vol.) was added 25% IPA-HCl (3.5 vol.) at 25-30° C. and stirred for 30 min. Raised the reaction mass temperature to 80-85° C. and maintained for 14-16 h. After completion of reaction (by IPC-HPLC) cooled the reaction mass temperature to 5-10° C. and stirred for 2-3 h. Filtered the solid and further purified using IPA and water ratio (1:5) at 25-30° C. and dried at 50-55° C. to afford 75.8 g of 3-acetyl-2'-chloro-4-hydroxy-5',6-dimethyl-2H-[1,4'-bipyridin]-2-one (CPD-01) as a brown colour powder, (Yield-75.8%) with HPLC purity 98.2%. $^1$H-NMR (400 MHz, DMSO-d$_6$): δ ppm 15.74 (s, 1H), 8.52 (s, 1H), 7.67 (s, 1H), 6.25 (s, 1H), 2.55 (s, 3H), 2.02 (s, 3H), 1.94 (s, 3H). MS (ES) m/z 293.62 (M+H).

Step 3: Synthesis of 2'-chloro-4-hydroxy-5',6-dimethyl-2H-[1,4'-bipyridin]-2-one (CPD-02). To a 3-acetyl-2'-chloro-4-hydroxy-5',6-dimethyl-2H-[1,4'-bipyridin]-2-one (CPD-01) (Step 2, 100 g, 1.0 eq.) was added sulfuric acid (2 vol.) at 25-30° C. and resulting suspension was heated to 110-120° C. for 4-6 h. Progress of the reaction was monitored by IPC-HPLC. After completion of the reaction, stopped heating and cooled the reaction mass to 25-30° C. Reaction mass was diluted with water (15 vol.), further cooled to 5-10° C. and pH was adjusted to 8-9 with aq. NaOH solution. Then pH of the resulting reaction mass was again adjusted to 3.5-4.5 using sat. citric acid. Thus obtained solid was filtered washed with water (3 vol.), MTBE (5 vol.), Further slurry purified by DMF (5 vol.) and water (5 vol.), dried at 50-55° C. to afford 2'-chloro-4-hydroxy-5',6-dimethyl-2H-[1,4'-bipyridin]-2-one (CPD-02) as a brown color solid 52 g (yield: 60.7%) with HPLC purity 99.3%.

$^1$H-NMR (400 MHz, DMSO-d$_6$): δ ppm 10.8 (br s, 1H), 8.47 (s, 1H), 7.55 (s, 1H), 5.97-5.96 (m, 1H), 5.57 (d, J=2.4 Hz, 1H), 1.96 (s, 3H), 1.83 (s, 3H). MS (ES) m/z 251.52 (M+H).

Example 43: Kinetic Dynamic Resolution of the Atropisomers of CPD-06

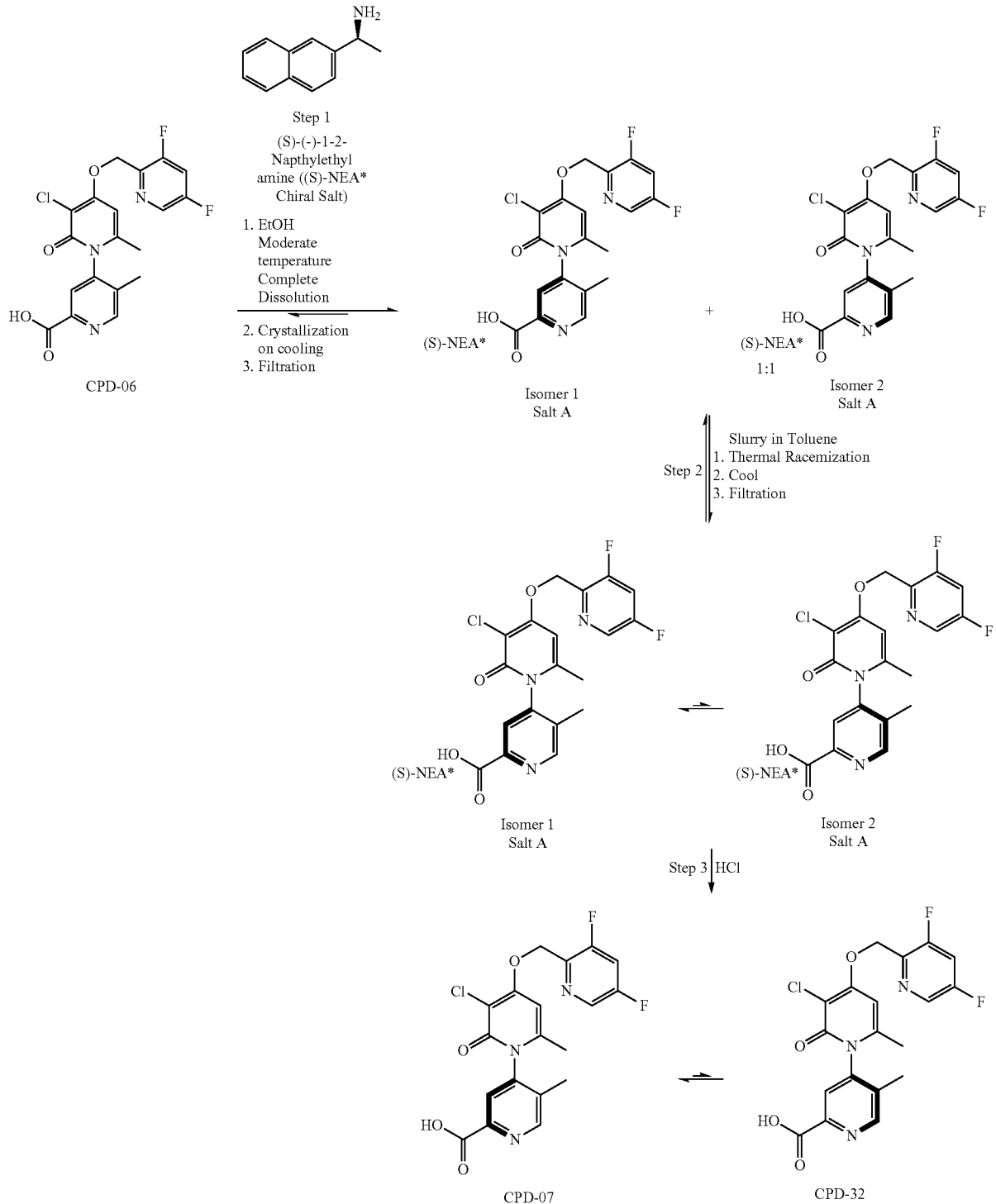

Step 1: Synthesis of (P & M) 3-chloro-4-((3,5-difluoropyridin-2-yl)methoxy)-5',6-dimethyl-2-oxo-2H-[1,4'-bipyridine]-2'-carboxylic acid (S)-1-(naphthalen-2-yl)ethan-1-aminium (Isomer 1 Salt A and Isomer 2 Salt A) salt. To a stirred suspension of 3-chloro-4-((3,5-difluoropyridin-2-yl)methoxy)-5',6-dimethyl-2-oxo-2H-[1,4'-bipyridine]-2'-carboxylic acid (CPD-06) (10 g) in Ethanol (20 vol.) in RBF and slowly heated to 25-35° C. then added (S)-(−)-1-2-Napthylethyl amine (1.0 eq.) 25-35° C. (Observation: after addition of (S)-(−)-1-2-Napthylethyl amine, clear solution was observed and immediately precipitation observed) and stirred for 24 h at 25-35° C., filtered the solid, and dried to afford a 1:1 diastereomeric salt mixture of (P & M) 3-chloro-4-((3,5-difluoropyridin-2-yl)methoxy)-5',6-dimethyl-2-oxo-2H-[1,4'-bipyridine]-2'-carboxylic acid (S)-1-(naphthalen-2-yl)ethan-1-aminium (Isomer 1 Salt A and Isomer 2 Salt A) salt as a white solid, 13.7 g (yield: 97%).

Step 2: Synthesis of (P)-3-Chloro-4-((3,5-difluoropyridin-2-yl)methoxy)-5',6-dimethyl-2-oxo-2H-[1,4'-bipyridine]-2'-carboxylic acid (S)-1-(naphthalen-2-yl)ethan-1-aminium (Isomer 1 Salt A). The 1:1 diastereomeric salt mixture of (P & M) 3-chloro-4-((3,5-difluoropyridin-2-yl)methoxy)-5',6-dimethyl-2-oxo-2H-[1,4'-bipyridine]-2'-carboxylic acid (S)-1-(naphthalen-2-yl)ethan-1-aminium (Isomer 1 Salt A and Isomer 2 Salt A) salt (Step 1) was taken in toluene (20.0 vol.) and slowly heated to 120-130° C. and the suspension was maintained for 96 h. The IPC-Chiral HPLC shows 96.66%. Reaction was cooled to RT and the suspension was filtered and washed solid with MTBE and dried under vacuum to afford (P)-3-Chloro-4-((3,5-difluoropyridin-2-yl)methoxy)-5',6-dimethyl-2-oxo-2H-[1,4'-bipyridine]-2'-carboxylic acid (S)-1-(naphthalen-2-yl)ethan-1-aminium (Isomer 1 Salt A) as a white solid. Material was used as is for Step 3.

Step 3: Synthesis of (P)-3-chloro-4-((3,5-difluoropyridin-2-yl)methoxy)-5',6-dimethyl-2-oxo-2H-[1,4'-bipyridine]-2'-carboxylic acid (CPD-07). The resulting chiral amine salt, (P)-3-Chloro-4-((3,5-difluoropyridin-2-yl)methoxy)-5',6-dimethyl-2-oxo-2H-[1,4'-bipyridine]-2'-carboxylic acid (S)-1-(naphthalen-2-yl)ethan-1-aminium (Isomer 1 Salt A) (Step 2, 13.0 g) was dissolved in water (6.0 mL) and basified with 2N NaOH to pH ~12 and extracted with MTBE (2×10.0 vol.). The resulting MTBE layer containing the amine was distilled to afford (S)-(−)-1-2-Napthylethyl amine with 97.41% of HPLC purity. The aqueous layer was acidified to pH ~2 with 2N HCl and solid precipitation was observed. The precipitated solid was filtered, washed and dried under vacuum to afford (P)-3-Chloro-4-((3,5-difluoropyridin-2-yl)methoxy)-5',6-dimethyl-2-oxo-2H-[1,4'-bipyridine]-2'-carboxylic acid (CPD-07) as an off-white solid, 9.36 g (yield=72%) with 98.53% of HPLC purity and 99.77% of chiral HPLC purity. $^1$H-NMR (300 MHz, DMSO-d6): δ ppm 13.35 (br s, 1H), 8.80 (s, 1H), 8.60 (d, 1H, J=2.4 Hz), 8.07-8.12 (m, 1H), 7.97 (s, 1H), 6.80 (s, 1H), 5.47 (d, 2H, J=1.6 Hz), 2.08 (s, 3H), 1.93 (s, 3H). MS (ES) m/z 422.12 (M+H).

Example 44: Chiral Purification of CPD-20 Via Simulated Moving Bed (SMB) Chromatography CPD-20 was screened for chiral purification by Simulated Moving Bed (SMB) chromatography. The separation was conducted with parameters found in Table 4. The final separation operating pressure was 9 bar. The separation of racemic CPD-20 to obtain each atropisomer was demonstrated using Chiralpak® IB-N, 20 m, as the stationary phase and 50/50 DCM/ACN v/v as the mobile phase on a benchtop SMB unit. The SMB unit is equipped with 8 columns of 10 cm in length and 1 cm in diameter. The atropisomers were separated into two process streams, the raffinate (Formula (P)-I) and the extract (Formula (M)-I). Compound Formula (P)-I was recovered in the raffinate stream.

TABLE 4

| | SMB Parameters | | | | | | | |
| --- | --- | --- | --- | --- | --- | --- | --- | --- |
| | | | | | Eluent | | Chiral Purity (%) | |
| Run (Cycle#) | Zone 1 | Extract | F | Raffinate | flow rate | Period | Extract | Raffinate |
| Start (0) | 9.9 | 7.3 | 0.6 | 1.8 | 8.5 | 2.73 | 97.9 | 100 |
| End (345) | 8.5 | 5.9 | 0.6 | 1.8 | 7.2 | 2.83 | 99.9 | 100 |

Feed Preparation: A feed solution was prepared using CPD-20. A total of 40.3 grams of crude feed were dissolved to 0.8 liter with 50/50, DCM/ACN. The solution was tested against a known standard to determine the concentration; 50 g/l.

Example 45: Kinetic Dynamic Resolution of the Atropisomers of CPD-06 in n-Butanol

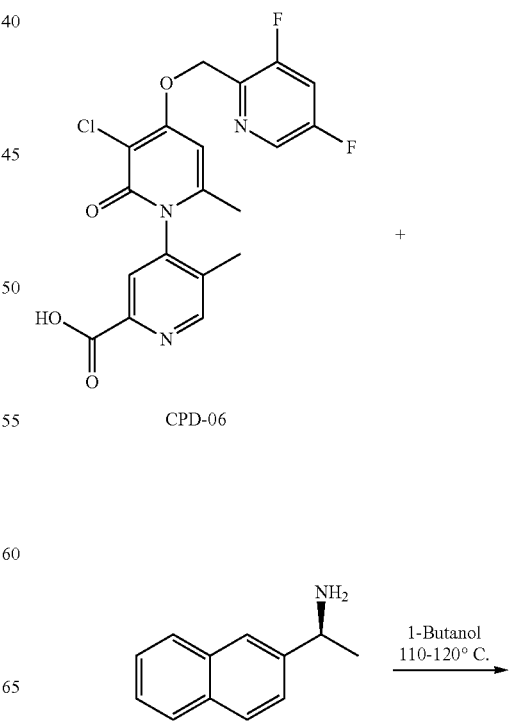

161
-continued

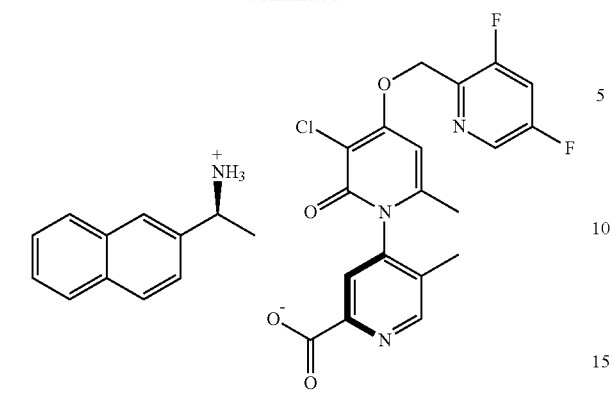

Isomer 1
Salt A

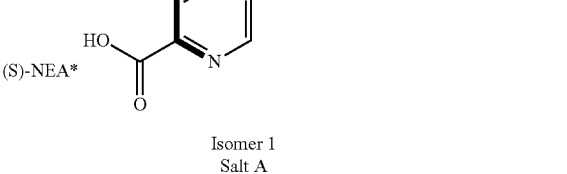

Isomer 1
Salt A

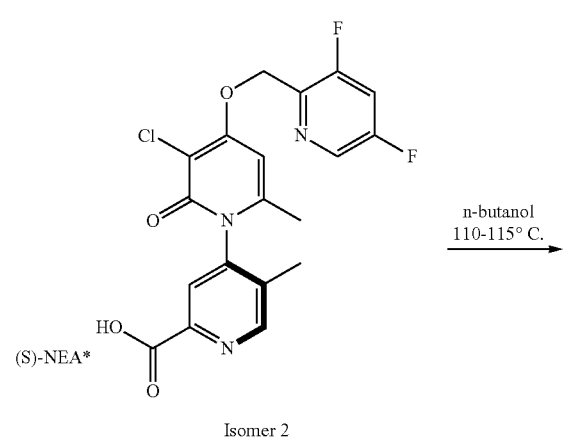

Isomer 2
Salt A

162
-continued

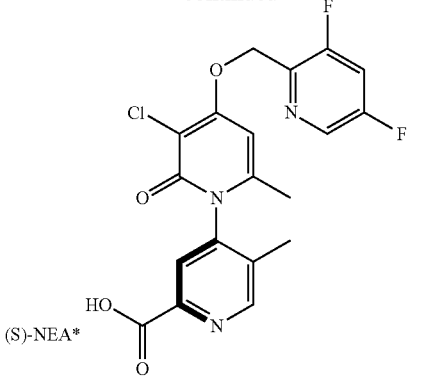

Isomer 1
Salt A

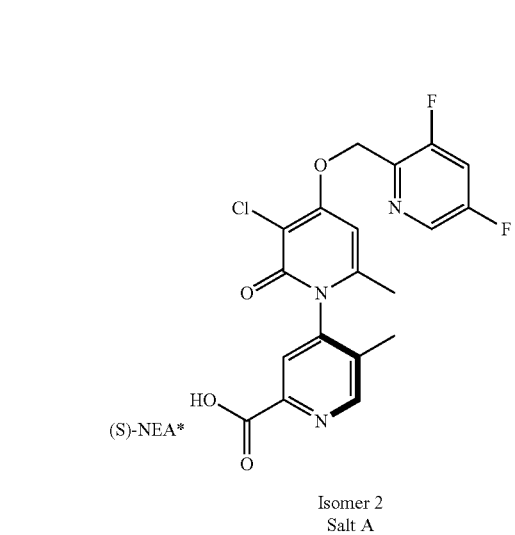

Isomer 2
Salt A

Synthesis of (P & M) 3-chloro-4-((3,5-difluoropyridin-2-yl)methoxy)-5',6-dimethyl-2-oxo-2H-[1,4'-bipyridine]-2'-carboxylic acid (S)-1-(naphthalen-2-yl)ethan-1-aminium (Isomer 1 Salt A and Isomer 2 Salt A) To the stirred suspension of (P & M) 3-chloro-4-((3,5-difluoropyridin-2-yl)methoxy)-5',6-dimethyl-2-oxo-2H-[1,4'-bipyridine]-2'-carboxylic acid HPLC chiral purity (Isomer 1: Isomer 2, 98.7%:1.3%) (Example 43 Step 1, 1.0 eq.) in 1-butanol (15.0 vol.) was added (S)-2-Napthylethyl amine (1.0 eq.) at 25-35° C. The reaction mixture was slowly heated to 110-115° C. and stirred for 40 hours at 110-115° C. The progress of the resolution was monitored by chiral HPLC. After completion of the resolution, the reaction mixture was cooled to 25-35° C., stirred for 3-4 hours at 25-35° C. Filtered the solid and dried the solid under vacuum below 45° C. to afford (P & M) 3-chloro-4-((3,5-difluoropyridin-2-yl)methoxy)-5',6-dimethyl-2-oxo-2H-[1,4'-bipyridine]-2'-carboxylic acid (S)-1-(naphthalen-2-yl)ethan-1-aminium chiral HPLC purity (Isomer 1 Salt A: Isomer 2 Salt A, 99.3%:0.70%), 5.5 g (yield: 78.3%). $^1$H-NMR (400 MHz, DMSO-d6): δ ppm 8.66 (s, 1H), 8.60 (d, J=2.0 Hz, 1H), 8.09 (td, J=2.4, 10.0 Hz, 1H), 7.96-7.88 (m, 6H), 7.78 (s, 1H), 7.63 (d, J=7.0 Hz, 1H), 7.52 (t, J=3.6 Hz, 3H), 6.77 (s, 1H), 5.41 (s, 2H), 4.46 (brs, 1H), 2.02 (s, 3H), 1.91 (s, 3H), 1.53 (d, J=6.4 Hz, 3H). MS(ES) m/z 422.28 (M+H).

Example 46: Alternative preparation of 3-chloro-4-((3,5-difluoropyridin-2-yl)methoxy)-5',6-dimethyl-2-oxo-2H-[1,4'-bipyridine]-2'-carboxylic Acid (CDP-06) from CPD-28

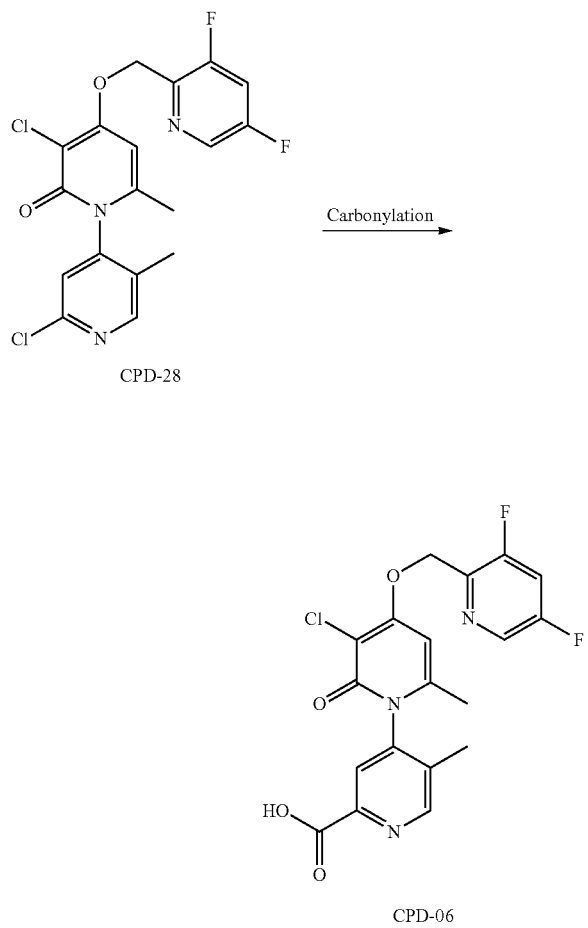

To a stirred suspension of 2',3-dichloro-4-((3,5-difluoropyridin-2-yl)methoxy)-5',6-dimethyl-2H-[1,4'-bipyridin]-2-one (CPD-28) (Example 41, 76.0 g, 1.0 eq.) in acetonitrile (8.0 vol.) and water (4.0 vol.). Then purged with argon gas for 30 min. and was added Li2CO3 (3.0 eq.) followed by Pd(dppf)Cl$_2$ (0.5 mol. %.) to the reaction mass and purged with argon gas for 30 min. Then applied CO pressure 40-45 PSI (3.0 Kg) and released CO pressure. Again, applied CO pressure 100 PSI (5.0 Kg) and slowly heated to 75° C. and stirred for 48 h. The progress of the reaction was monitored by TLC/IPC-HPLC, after reaction completion the reaction was cooled to 25-30° C. and de-gas with argon. Unloaded the reaction mass and added water (5.0 vol.) and adjusted pH to 14 with 2N NaOH solution. Then reaction mass was washed with MTBE (3×5.0 vol.) and aqueous layers were filtered through high flow bed. The pH of filtered mL's was adjusted to 1-2 with 6N HCl and stirred for 1-2 h at 25-30° C. Filtered the solid, washed with water (10.0 vol.) followed by IPA (1.0 vol.) and dried under vacuum to afford 67.5 g (yield: 86.80%) 3-chloro-4-((3,5-difluoropyridin-2-yl)methoxy)-5',6-dimethyl-2-oxo-2H-[1,4'-bipyridine]-2'-carboxylic acid (CPD-06) as an off-white solid with HPLC purity of 98.49%. $^1$H-NMR (400 MHz, DMSO-d6) δ ppm: 13.35 (br s, 1H), 8.80 (s, 1H), 8.60 (d, 1H, J=2.4 Hz), 8.07-8.12 (m, 1H), 7.97 (s, 1H), 6.80 (s, 1H), 5.47 (d, 2H, J=1.6 Hz), 2.08 (s, 3H), 1.93 (s, 3H). MS (ES) m/z 422.28 (M+H).

Example 47: Alternative preparation of (P & M) 3-chloro-4-((3,5-difluoropyridin-2-yl)methoxy)-5',6-dimethyl-2-oxo-2H-[1,4'-bipyridine]-2'-carboxylic acid (S)-1-(naphthalen-2-yl)ethan-1-aminium (Isomer 1 Salt A and Isomer 2 Salt A) Salt

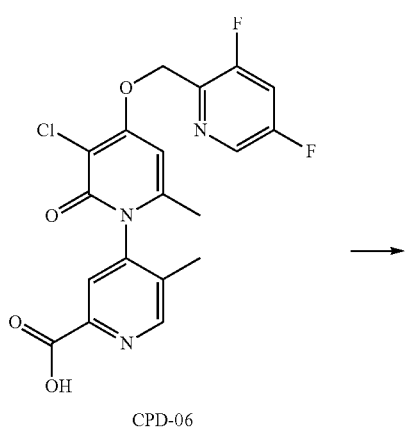

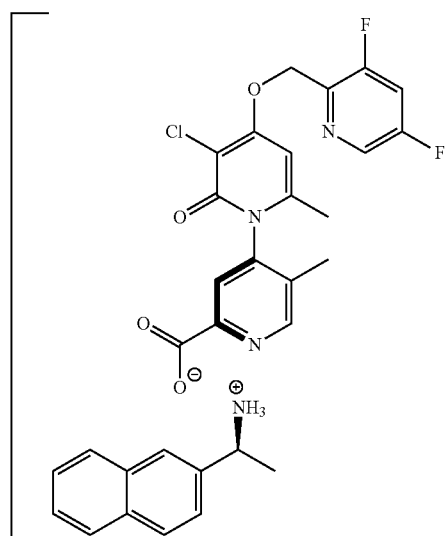

Isomer 1
Salt A

+

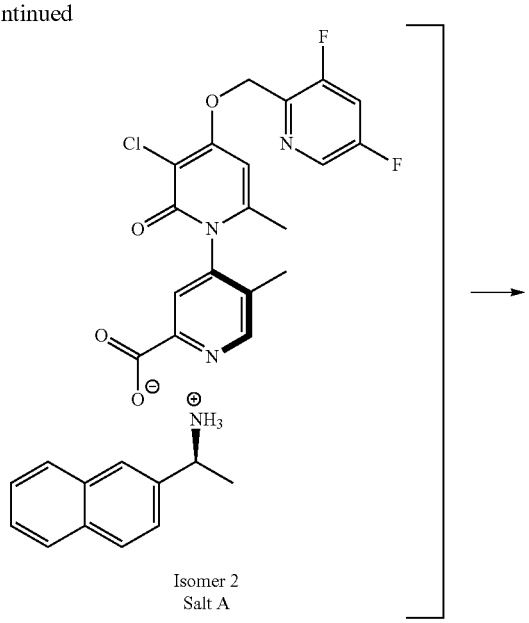

Isomer 2
Salt A

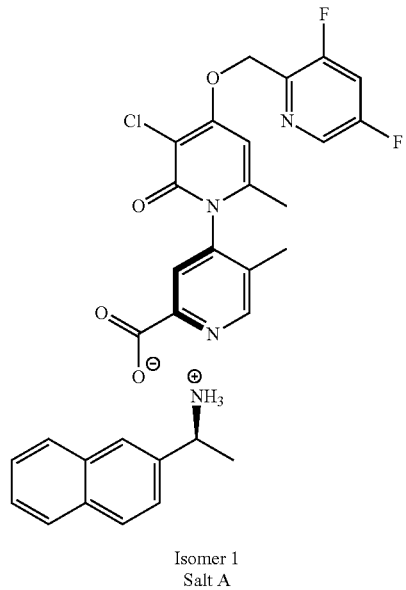

Isomer 1
Salt A

A stirred suspension of 3-chloro-4-((3,5-difluoropyridin-2-yl)methoxy)-5',6-dimethyl-2-oxo-2H-[1,4'-bipyridine]-2'-carboxylic acid (CPD-06) (25 g, 1.0 eq.) in 5% of DMSO: anisole (7.04 vol.) was slowly heated to 110-115° C. Then slowly added 3-chloro-4-((3,5-difluoropyridin-2-yl)methoxy)-5',6-dimethyl-2-oxo-2H-[1,4'-bipyridine]-2'-carboxylic acid (0.025 eq., Seed HPLC chiral purity Isomer I, Isomer 2, 99.91%:0.09%) to the reaction mass and stirred for 10-15 min. followed by the addition (S)-2-Napthylethyl amine (1.04 eq., 4.05 g) in DMSO: anisole (14 vol., 60 mL) using syringe pump with flow rate (35 mL per 1 h) for 20 h. The progress of reaction was monitored by Chiral HPLC and stirred for 64 h. Cooled to 25-30° C. and stirred for 1-2 h. Filtered the solid, washed with ethanol (10 vol.) and dried under vacuum to afford 32.07 g (yield: 91.6%) of (P & M) 3-chloro-4-((3,5-difluoropyridin-2-yl)methoxy)-5',6-dimethyl-2-oxo-2H-[1,4'-bipyridine]-2'-carboxylic acid (S)-1-(naphthalen-2-yl)ethan-1-aminium (Isomer 1 Salt A and Isomer 2 Salt A) salt. The salt (32 g) was added to water (10 vol.) and pH was adjusted to 12-14 with 2.0 N NaOH solution and aqueous layers were washed with MTBE (3×5 vol.). Then pH of the aqueous layer was adjusted to 0.5-1.0 with 6.0 N HCl and the resulting precipitated solid was stirred for 2-5 h. Filtered the solid and washed with IPA (1 vol.) and dried under vacuum to afford free acid 19.0 g (yield: 83.5%) of (P)-3-Chloro-4-((3,5-difluoropyridin-2-yl)methoxy)-5',6-dimethyl-2-oxo-2H-[1,4'-bipyridine]-2'-carboxylic acid (CPD-07) as an off-white solid, with 99.62% of HPLC purity and HPLC chiral purity (Isomer 1: Isomer 2, 99.41%:0.59%). $^1$H-NMR (400 MHz, DMSO-d6): δ ppm 13.35 (br s, 1H), 8.80 (s, 1H), 8.60 (d, 1H, J=2.4 Hz), 8.07-8.12 (m, 1H), 7.97 (s, 1H), 6.80 (s, 1H), 5.47 (d, 2H, J=1.6 Hz), 2.08 (s, 3H), 1.93 (s, 3H). MS (ES) m/z 422.12 (M+H).

Example 48: Alternative preparation of (P)-3-Chloro-4-((3,5-difluoropyridin-2-yl)methoxy)-N-methoxy-N,5',6-trimethyl-2-oxo-2H-[1,4'-bipyridine]-2'-carboxamide (CPD-08)

Example 49: Alternative preparation of (P)-2'-Acetyl-3-chloro-4-((3,5-difluoropyridin-2-yl)methoxy)-5',6-dimethyl-2H-[1,4'-bipyridin]-2-one (CPD-09)

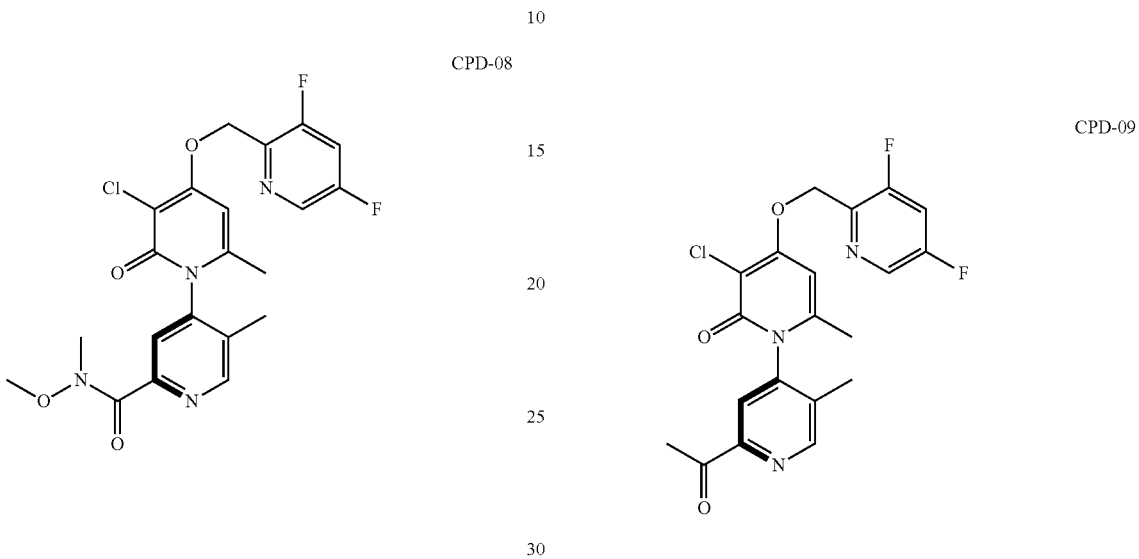

To a stirred suspension of (P)-3-Chloro-4-((3,5-difluoropyridin-2-yl)methoxy)-5',6-dimethyl-2-oxo-2H-[1,4'-bipyri-dine]-2'-carboxylic acid (CPD-07) (117.0 g, 1.0 eq, Isomer I, Isomer 2, 97.86%:2.14%) in DCM (8 vol.) at −5 to 0° C. was added 1-Ethyl-3-(3-dimethylaminopropyl)carbodiimide (EDC•HCl (1.1 eq.)) at −5 to 0° C., and it was stirred for 5-10 min. TEA (1.0 eq.) was added at 0-5° C., and the mixture was stirred for 10-20 min. Then N, O-dimethyl hydroxylamine hydrochloride (1.5 eq.) was added at −5 to 0° C. followed by the addition of TEA (1.25 eq) at −5 to 0° C. and stirred for 1-2 h, the progress of the reaction was monitored by TLC and IPC-HPLC. After completion of the reaction ice-cold water (20.0 vol.) was added and reaction was allowed to warm to 25-35° C., stirred for 10 min. and separated DCM layer. Aqueous later was extracted with DCM (2×5 vol.) and combined DCM layers were washed with water (5 vol.), dried with $Na_2SO_4$. The DCM layer was completely distilled and Co-distilled with MTBE (3×3 vol.) followed by residue precipitation with MTBE (5 vol.) and stirred for 2-3 h. Filtered the solid, washed with MTBE (1 vol.) and dried to afford 121.0 g (yield: 93.86%) of (P)-3-Chloro-4-((3,5-difluoropyridin-2-yl)methoxy)-N-methoxy-N,5',6-trimethyl-2-oxo-2H-[1,4'-bipyridine]-2'-carboxamide with HPLC purity 99.13% along with HPLC Chiral purity (Isomer 1: Isomer 2, 97.14%:2.86%). $^1$H-NMR (400 MHz, DMSO-d6): δ ppm 8.70 (s, 1H), 8.59 (d, 1H, J=2.4 Hz), 8.04-8.12 (m, 1H), 7.63 (s, 1H), 6.79 (s, 1H), 5.47 (d, 2H, J=1.6 Hz), 3.67 (s, 3H), 3.29 (s, 3H), 2.04 (s, 3H), 1.93 (s, 3H); MS (ES) m/z 465.31 (M+H).

To a stirred solution of (P)-3-Chloro-4-((3,5-difluoropyridin-2-yl)methoxy)-N-methoxy-N,5',6-trimethyl-2-oxo-2H-[1,4'-bipyridine]-2'-carboxamide (CPD-08) (115.0 g, Isomer 1: Isomer 2 (97.14%:2.86%) in dry THF (42 vol.) was slowly added MeMgCl (1.2 eq.; 3M solution in THF) at −10° C. to 0° C. and stirred for 1-1 h. Then the reaction mass temperature was raised to 0-5° C. and maintained for 1 h. The progress of the reaction was monitored by TLC and IPC-HPLC. After completion the reaction was quenched with 10% aq. ammonium chloride solution (10 vol.). The organic layer was distilled under vacuum at below 40° C. Water (2 vol.) was added and the reaction was stirred for 2-4 h at 25-30° C. The solid was filtered, washed with water (5 vol.) followed by IPA (1.0 vol.) and dried under vacuum at below 40° C. to afford 94.18 g (yield: 90.7%) of (P)-2'-Acetyl-3-chloro-4-((3,5-difluoropyridin-2-yl)methoxy)-5',6-dimethyl-2H-[1,4'-bipyridin]-2-one with HPLC purity 96.61% and HPLC chiral purity (Isomer 1: Isomer 2, 98.06%:1.94%). $^1$H-NMR (400 MHz, DMSO-d6): δ ppm 8.83 (s, 1H), 8.59 (d, 1H, J=2.4 Hz), 8.05-8.14 (m, 1H), 7.89 (s, 1H), 6.79 (s, 1H), 5.47 (d, 2H, J=1.6 Hz), 2.66 (s, 3H), 2.09 (s, 3H), 1.91 (s, 3H); MS (ES) m/z 420.08 (M+H).

Example 50: Alternative preparation of (P)-(E)-3-Chloro-4-((3,5-difluoropyridin-2-yl)methoxy)-2'-(3-(dimethyl-amino)acryloyl)-5',6-dimethyl-2H-[1,4'-bipyridin]-2-one (CPD-10)

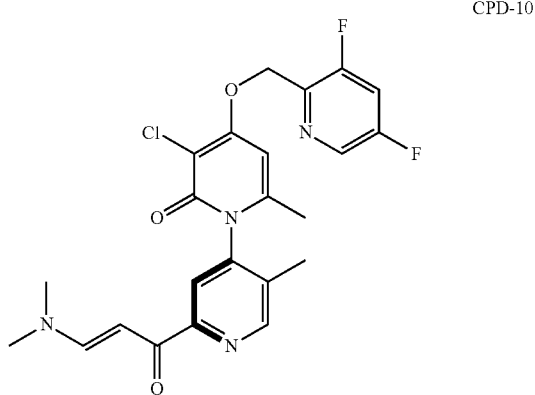

CPD-10

To a stirred solution of (P)-2'-Acetyl-3-chloro-4-((3,5-difluoropyridin-2-yl)methoxy)-5',6-dimethyl-2H-[1,4'-bipyridin]-2-one (CPD-09) (5.5 g, 1.0 eq., Isomer 1: Isomer 2, 95.28%: 4.72%), was added N,N-dimethyl-formamide dimethyl acetal (DMF-DMA (6.0 eq.)) and DMF (1.0 vol.) at 25-35° C. The reaction mass was slowly heated to 50-55° C. and maintained for at that temperature for 24 h. Progress of the reaction was monitored by TLC and IPC-HPLC. After completion of reaction, heating was stopped and the mixture was cooled to 25-35° C. and stirred for 1-2 h. Filtered solid and washed with EtOAc (2.0 vol.) and dried under vacuum at below 40° C. to afford 4.6 g (yield: 74.0%) of (P)-(E)-3-Chloro-4-((3,5-difluoropyridin-2-yl)methoxy)-2'-(3-(dimethyl-amino)acryloyl)-5',6-dimethyl-2H-[1,4'-bipyridin]-2-one with HPLC 98.74%, and HPLC chiral purity (Isomer 1: Isomer 2 (99.92%:0.08%). $^1$H-NMR (400 MHz, DMSO-d6): δ ppm 8.71 (s, 1H), 8.60 (d, 1H, J=2.4 Hz), 8.04-8.12 (m, 1H), 7.80-7.86 (m, 2H), 6.78 (s, 1H), 6.37 (d, 1H, J=12.8 Hz), 5.47 (d, 2H, J=1.6 Hz), 3.19 (s, 3H), 2.94 (s, 3H), 2.05 (s, 3H), 1.91 (s, 3H); MS (ES) m/z 475.36 (M+H).

Example 51: Alternative preparation of (P)-3-Chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one (Formula P-(I))

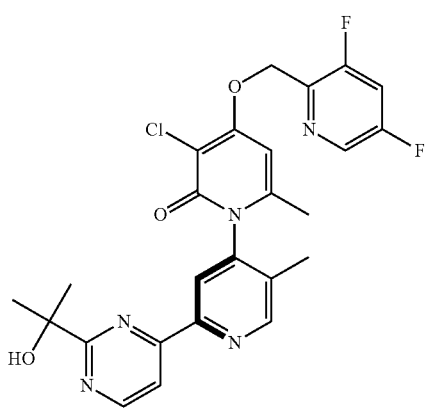

Formula (P)-I

To a stirred solution of (P)-(E)-3-Chloro-4-((3,5-difluoropyridin-2-yl)methoxy)-2'-(3-(dimethyl-amino)acryloyl)-5',6-dimethyl-2H-[1,4'-bipyridin]-2-one (CPD-10) (4.0 g, 1.0 eq., Isomer 1: Isomer 2, 99.85%:0.15%) in DMF (6.0 vol.) was added portion wise K$_2$CO$_3$ (2.5 eq.). followed by the addition of 2-hydroxy-2-methylpropionamidine HCl (INT-02) (3.0 eq.) at 25-35° C. The reaction mass was slowly warmed to 45-50° C. and was stirred at that temperature for 40 h. Progress of the reaction was monitored by TLC/IPC HPLC. After the reaction was completed, it was cooled to 25-35° C., diluted with water (15 vol.), and stirred for 1-2 h, further cooled to 0-10° C. and stirred for 3-4 h. The solid was filtered, washed with water (2.0 vol.). Then solid was dissolved in DCM (10.0 vol.) and charged activated carbon (0.5 T) and stirred for 1-2 h at 35-40° C. Filtered the Reaction mass on Hi-flow bed washed with DCM (2.0 vol.). Distilled the Filtered mL's under vacuum at below 40° C., co-distilled with IPA (2.0 vol.) and charged IPA (19.0 vol.) then heated to 72-77° C., stirred for 1-2 h at 72-77° C. Slowly cooled to 25-30° C. and further cool to 7-15° C., stirred for 2-4 h. Filtered the solid and dried under vacuum at below 40° C. to afford 2.58 g (yield: 60.0%) (P)-3-Chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one, with HPLC purity 99.65% and HPLC chiral purity (Isomer 1: Isomer 2) (98.86%: 1.14%).

Example 52: Crystallization of (P)-3-Chloro-4-((3,5-difluoropyridin-2-yl)methoxy)-2'-(2-(2-hydroxypropan-2-yl)pyrimidin-4-yl)-5',6-dimethyl-2H-[1,4'-bipyridin]-2-one (Formula P-(I))

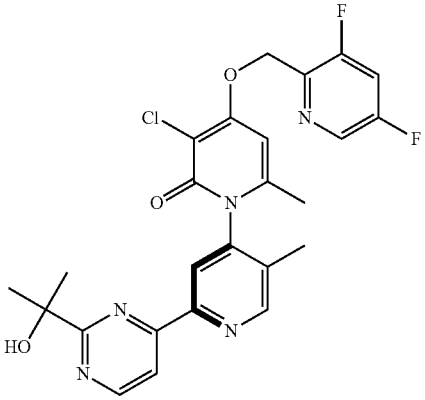

Formula (P)-I

To a stirred suspension of (P)-3-Chloro-4-((3,5-difluoropyridin-2-yl)methoxy)-2'-(2-(2-hydroxy-propan-2-yl)-pyrimidin-4-yl)-5',6-dimethyl-2H-[1,4'-bipyridin]-2-one (Formula P-(I)) (1.0 g, 1.0 eq., Isomer 1: Isomer 2 (98.86%: 1.14%) in IPA (19.0 vol.) was stirred for 1 h at 72-77° C. Seed material (Formula P-(I)) (0.25 g, 0.05 w/w times) was then added at 72-77° C. Heating was stopped and the mixture was allowed to cool to 25-35° C. After stirring for 24 h the solid was filtered. The solid was washed with IPA (2.0 vol.), and it was dried at below 40° C. to afford 0.8 g (yield: 80%) of (P)-3-Chloro-4-((3,5-difluoropyridin-2-yl)methoxy)-2'-(2-(2-hydroxypropan-2-yl)-pyrimidin-4-yl)-5',6-dimethyl-2H-[1,4'-bipyridin]-2-one with HPLC purity 99.52% and HPLC chiral purity (Isomer 1: Isomer 2, 99.65%:0.35%). $^1$H-NMR (400 MHz, DMSO-d$_6$): δ ppm 8.97 (d, 1H, J=5.2 Hz), 8.86 (s, 1H), 8.69 (s, 1H), 8.61 (d, 1H, J=2.4 Hz), 8.24 (d, 1H, J=5.2 Hz), 8.06-8.14 (m, 1H), 6.84 (s, 1H), 5.49 (d, 2H, J=1.2 Hz), 5.25 (s, 1H), 2.10 (s, 3H), 1.98 (s, 3H), 1.04 (s, 3H), 1.03 (s, 3H); MS (ES) m/z 514.37 (M+H).

What is claimed is:

1. A process for the preparation of CPD-30 having the structure:

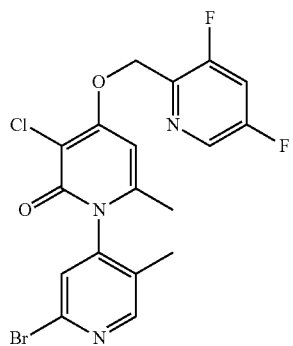

CPD-30 comprising contacting the compound

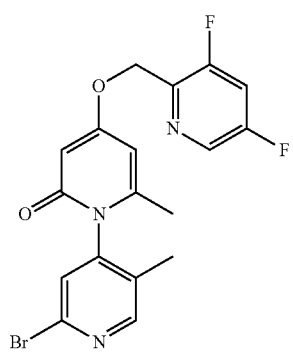

CPD-26 with a chlorination reagent to form CPD-30.

2. A process for the preparation of CPD-30 having the structure:

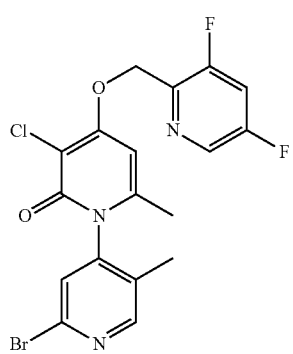

CPD-30

(a) contacting the compound

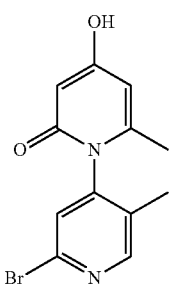

CPD-25 with a chlorination reagent to form the compound

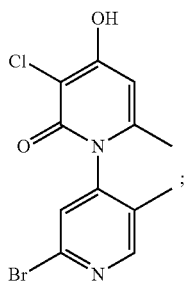

CPD-31 and
(b) contacting the compound CPD-31 with the compound

INT-01 and a base to form the compound CPD-30.

3. A process for the preparation of CPD-18 having the structure:

comprising the steps of

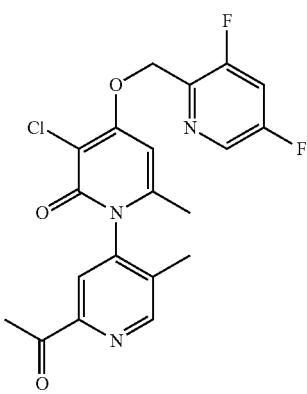

CPD-18

(a) contacting the compound

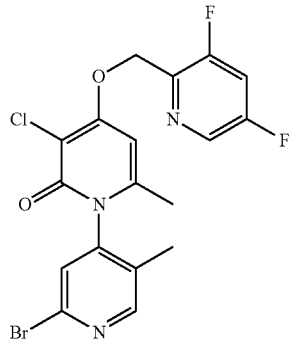
CPD-30 with butyl vinyl ether in the presence of a palladium catalyst, a phosphorus reagent, and a base to form the compound

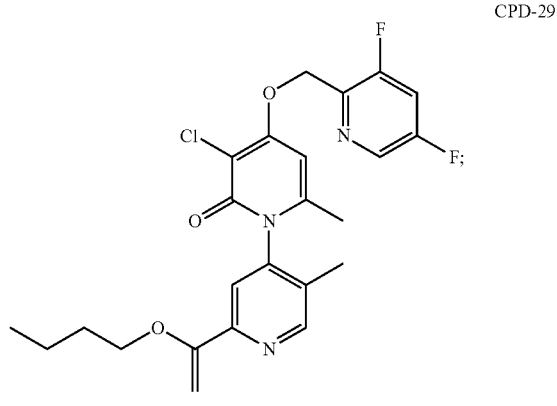 [SMILES: C=C(OCCCC)c1cc(-n2c(C)cc(OCc3ncc(F)cc3F)c(Cl)c2=O)c(C)cn1]
CPD-29 and
(b) contacting CPD-29 with an acid to form CPD-18.

4. A process for the preparation of CPD-18 having the structure:

comprising the steps of

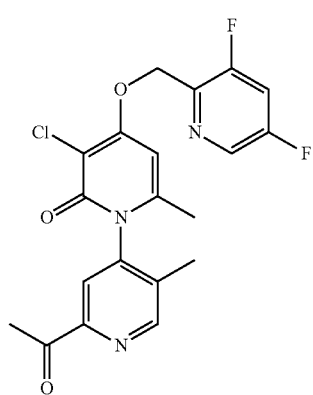
CPD-18

(a) contacting the compound

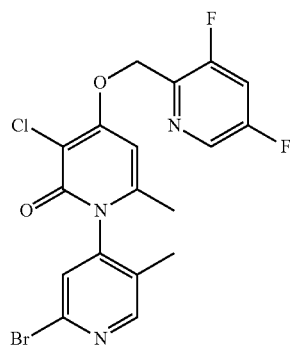
CPD-30 with hydroxyethyl vinyl ether in the presence of a palladium catalyst, a phosphorus reagent, and a base to form a mixture; and
(b) contacting the mixture of (a) with an acid to form the compound CPD-18.

5. A process for the preparation of CPD-18 having the structure:

comprising the steps of

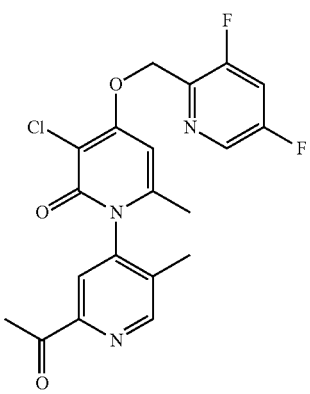
CPD-18

(a) contacting the compound

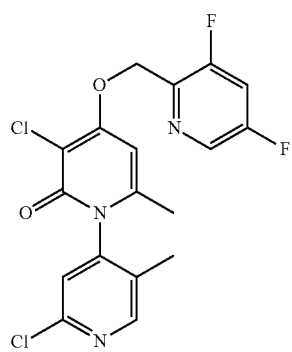
CPD-28 with a vinyl tin reagent in the presence of a palladium catalyst to form a mixture; and
(b) contacting the mixture of (a) with an acid to form the compound CPD-18.

6. A process for the preparation of CPD-18 having the structure:

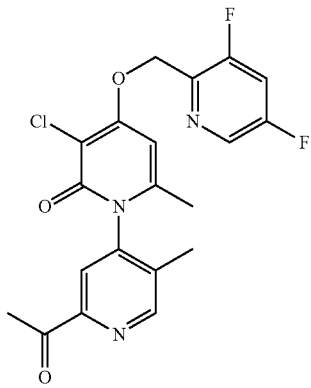
CPD-18 comprising the steps of (a) contacting the compound

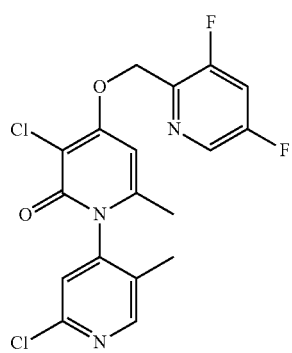
CPD-28 with butyl vinyl ether in the presence of a palladium catalyst, a phosphorus reagent, and a base to form the compound

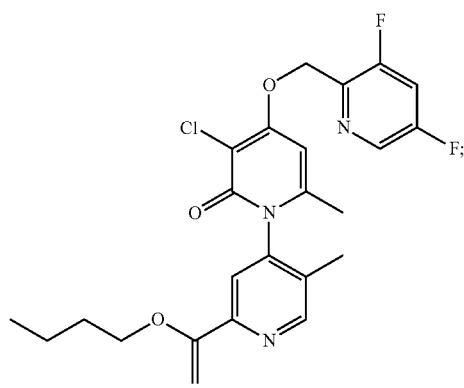
CPD-29 and (b) contacting CPD-28 with an acid to form CPD-18.

7. A compound, or a salt thereof, or a co-crystal thereof, selected from the group consisting of:

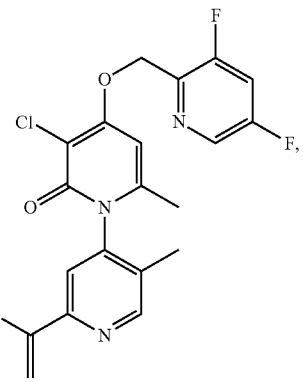
CPD-29

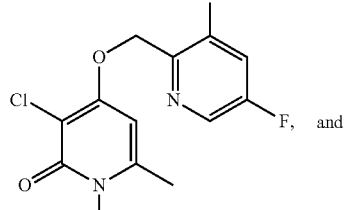
CPD-30 and

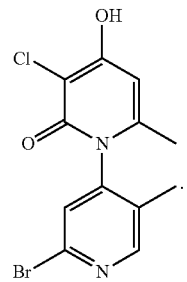
CPD-31

8. The compound of claim 7, or a co-crystal thereof, wherein the compound is:

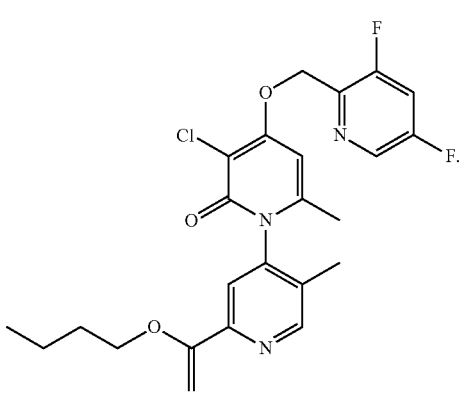
CPD-29

9. The compound of claim 7, or a co-crystal thereof, wherein the compound is:

10. The compound of claim 7, or a co-crystal thereof, wherein the compound is:
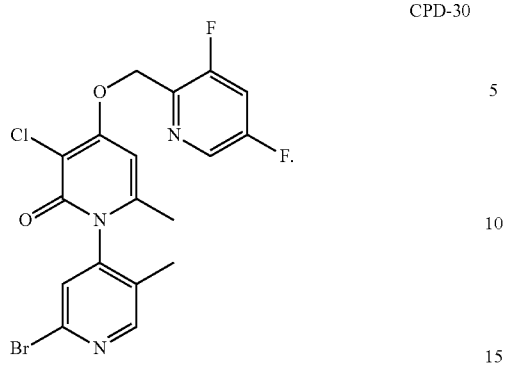
CPD-30
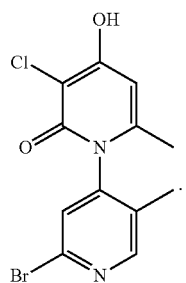
CPD-31
* * * * *